(12) United States Patent
David et al.

(10) Patent No.: US 12,060,350 B2
(45) Date of Patent: Aug. 13, 2024

(54) THERAPEUTIC COMPOUNDS AND METHODS OF USE THEREOF

(71) Applicant: REGENTS OF THE UNIVERSITY OF MINNESOTA, Minneapolis, MN (US)

(72) Inventors: Sunil A. David, Minneapolis, MN (US); Yupeng Li, Minneapolis, MN (US); Michael Brush, Minneapolis, MN (US); Kathryn Trautman, Minneapolis, MN (US); Collin Gustafson, Minneapolis, MN (US); Daniel Maurer, Minneapolis, MN (US); Balaji Pathakumari, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 843 days.

(21) Appl. No.: 17/256,933

(22) PCT Filed: Jun. 28, 2019

(86) PCT No.: PCT/US2019/039940
§ 371 (c)(1),
(2) Date: Dec. 29, 2020

(87) PCT Pub. No.: WO2020/009946
PCT Pub. Date: Jan. 9, 2020

(65) Prior Publication Data
US 2021/0269438 A1 Sep. 2, 2021

Related U.S. Application Data

(60) Provisional application No. 62/693,322, filed on Jul. 2, 2018.

(51) Int. Cl.
C07D 471/04 (2006.01)
A61K 39/39 (2006.01)
(Continued)

(52) U.S. Cl.
CPC ............ *C07D 471/04* (2013.01); *A61K 39/39* (2013.01); *A61K 47/545* (2017.08); *A61K 47/61* (2017.08);
(Continued)

(58) Field of Classification Search
CPC .................................................. C07D 471/04
See application file for complete search history.

(56) References Cited
U.S. PATENT DOCUMENTS
5,519,138 A 5/1996 Ries et al.
6,696,076 B2 2/2004 Tomai et al.
(Continued)

FOREIGN PATENT DOCUMENTS
EP 1487485 B1 12/2010
WO 2003094836 A2 11/2003
(Continued)

OTHER PUBLICATIONS
Yoo, E. "Hyaluronic Acid Conjugates of TLR7/8 Agonists for Targeted Delivery to Secondary Lymphoid Tissue", Bioconjugate Chem 29 (8), 2741-2754 (2018).
(Continued)

Primary Examiner — Golam M Shameem
(74) Attorney, Agent, or Firm — Viksnins Harris Padys Malen LLP

(57) ABSTRACT

The invention provides a compound of formula (I) or a salt thereof, wherein $R^1$, $R^2$, $R^3$ and $R^4$ have any of the values described in the specification, as well as compositions comprising a compound of formula (I). The compounds are useful as immunostimulatory agents.

15

16

(Continued)

-continued

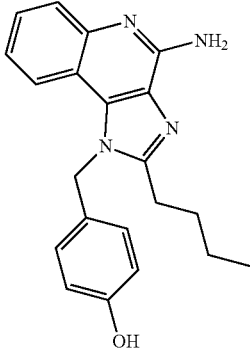

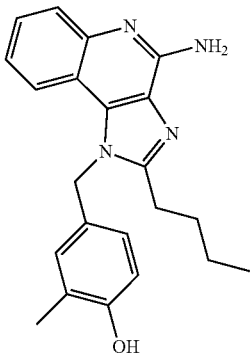

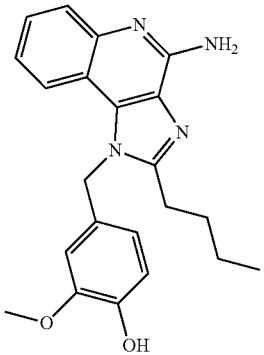

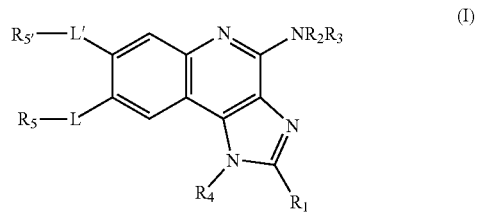

14 Claims, 8 Drawing Sheets

(51) Int. Cl.
    *A61K 47/54*     (2017.01)
    *A61K 47/61*     (2017.01)
    *A61K 47/69*     (2017.01)
    *C07F 9/6561*     (2006.01)
    *A61K 39/00*     (2006.01)
(52) U.S. Cl.
    CPC ........ *A61K 47/6923* (2017.08); *C07F 9/6561* (2013.01); *A61K 2039/55511* (2013.01)

(56) References Cited

U.S. PATENT DOCUMENTS

| | | |
|---|---|---|
| 7,091,214 B2 | 8/2006 | Hays et al. |
| 7,879,844 B2 | 2/2011 | Inoue et al. |
| 8,658,666 B2 | 2/2014 | Ride et al. |
| 8,728,486 B2 | 5/2014 | David et al. |
| 9,034,226 B2 | 5/2015 | Betz et al. |
| 9,034,336 B2 | 5/2015 | Ferguson et al. |
| 9,441,005 B2 | 9/2016 | David et al. |
| 9,884,866 B2 | 2/2018 | Ferguson et al. |
| 10,730,871 B2 | 8/2020 | Ferguson |
| 11,279,701 B2 | 3/2022 | Ferguson |
| 2006/0188913 A1 | 8/2006 | Krieg et al. |
| 2007/0213356 A1 | 9/2007 | Merrill et al. |
| 2008/0213308 A1 | 9/2008 | Valiante et al. |
| 2010/0021394 A1 | 1/2010 | Yu |
| 2012/0276050 A1 | 11/2012 | Choong et al. |
| 2014/0212442 A1 | 7/2014 | Ferguson et al. |
| 2016/0068533 A1 | 3/2016 | Ferguson et al. |
| 2017/0260184 A1 | 9/2017 | David et al. |
| 2018/0134701 A1 | 5/2018 | David et al. |

FOREIGN PATENT DOCUMENTS

| | | |
|---|---|---|
| WO | 2006031878 A2 | 3/2006 |
| WO | 2006091394 A2 | 8/2006 |
| WO | 2007109810 A2 | 9/2007 |
| WO | 2007109813 A1 | 9/2007 |
| WO | 2013033345 A1 | 3/2013 |
| WO | 2017184746 A1 | 10/2017 |

OTHER PUBLICATIONS

Ali, G., et al., "Input of Isosteric and Bioisosteric Approach in Drug Design", 20 pages (2013).
Bachmann, M., et al., "Vaccine delivery: a matter of size, geometry, kinetics and molecular patterns", Nature Reviews 10, 787-796 (2010).
Beesu, M., et al., "Identification of High-Potency Human TLR8 and Dual TLR7/TLR8 Agonists in Pyrimidine-2,4-diamines", J. Med. Chem. 60, 2084-2098 (2017).
Beesu, M., et al., "Structure-Based Design of Human TLR8-Specific Agonists with Augmented Potency and Adjuvanticity", Journal of Medicinal Chemistry 58, 7833-7849 (2015).

(56) References Cited

OTHER PUBLICATIONS

Cai, S., et al., "Intralymphatic chemotherapy using a hyaluronan-cisplatin conjugate", J. Surg Res. 147(2), 247-252 (2008).
Cai, S., et al., "Pharmacokinetics and Disposition of a Localized Lymphatic Polymeric Hyaluronan Conjugate of Cisplatin in Rodents", J. Pharm. Sci 99(6), 2664-2671 (2010).
Cariuk, P, et al., "Correlations of PDE-4 Inhibition Between Enzymes of Smooth Muscle and Inflammatory Cell Sources", Cell Biochemistry and Biophysics 28, 219-249 (1998).
Coffman, RL, et al., "Vaccine adjuvants: putting innate immunity to work", Immunity 33, 492-503 (2010).
Dianat, S, et al., "Quinoline-based imidazole-fused heterocycles as new inhibitors of 15-lipoxygenase", Journal of Enzyme Inhibition and Medicinal Chemistry 31(53), 205-209 (2016).
Dockrell, DH, et al., "Imiquimod and resiquimod as novel immunomodulators", Journal of Antimicrobial Chemotherapy 48, 751-755 (2001).
Dudek, A, et al., "First in Human Phase I Trial of 852A, a Novel Systemic Toll-like Receptor 7 Agonist, to Activate Innate Immune Responses in Patients with Advanced Cancer", Clin. Cancer Res., 13, 23, 7119-7125 (2007).
Edwards, AD, et al., "Toll-like receptor expression in murine DC subsets: lack of TLR7 expression by CD8 alpha+ DC correlates with unresponsiveness to imidazoquinolines", Eur J Immunol 33 (4), 827-833 (2003).
Fallacara, A., et al., "Hyaluronic Acid Fillers in Soft Tissue Regeneration", Facial Plastic Surgery 33, 87-96 (2017).
Federal Registry, vol. 75(169), 3 pages (2010).
Ferguson, D, "Selective Activation of Toll-like Receptor 7 and 8 in the Design of Cancer Vaccines, Discovery on Target, Immunomodulatory Small Molecules", 15th Annual Discovery on Target, Boston, MA, Sep. 25, 2017.
Gibson, SJ, et al., "Plasmacytoid dendritic cells produce cytokines and mature in response to the TLR7 agonists, imiquimod and resiquimod", Cell Immunol. 218 (1-2), 74-86 (2002).
Gill, VL, et al., "Use of imiquimod 5% cream (Aldara) in cats with multicentric squamous cell carcinoma in situ: 12 cases (2002-2005)", Vet Comp Oncol., 6 (1), 55-64 (2008).
Gupta, R., "Aluminum compounds as vaccine adjuvants", Advanced Drug Delivery Reviews 32(3), 155-172 (1998).
He, W., et al., "Efficacy and safety of intraarticular hyaluronic acid and corticosteroid for knee osteoarthritis: A meta-analysis", International Journal of Surgery 39, 95-103 (2017).
Ingale, S., et al., "Robust immune responses elicited by a fully synthetic three-component vaccine", Nat Chem Biol. 3 (10), 663-667 (2007).
Jackson, D. G., "Biology of the lymphatic marker LYVE-1 and applications in research into lymphatic trafficking and lymphangiogenesis", APMIS 112, 526-538 (2004).
Jackson, D. G., et al., "Immunological functions of hyaluronan and its receptors in the lymphatics", Immunol. Rev. 230, 216-231 (2009).
Jiang, D., et al., "Hyaluronan as an Immune Regulator in Human Diseases", Physiol Rev. 91(1), 221-264 (2011).
Kastenmuller, K., et al., "Protective T cell immunity in mice following protein-TLR7/8 agonist-conjugate immunization requires aggregation, type I IFN, and multiple DC subsets", J Clin Invest 121 (5), 1782-1796 (2011).
Krishnamachari, Y., et al., "Innovative strategies for co-delivering antigens and CpG oligonucleotides", Adv Drug Delivery Rev. 61 (3), 205-217 (2009).
Lan, T, et al., "Stabilized immune modulatory RNA compounds as agonists of Toll-like receptors 7 and 8", PNAS, 104, 34, 13750-13755 (2007).
Larson, P, et al., "Design and Synthesis of N1-Modified Imidazoquinoline Agonists for Selective Activation of Toll-like Receptors 7 and 8", ACS Med Chem Lett, DOI: 10.1021/acsmedchemlett.7b00256, published on Web Oct. 16, 2017.
Liao, S., et al., "Lymphatic System: An Active Pathway for Immune Protection", Semin Cell Dev Biol. 38, 83-89 (2015).
Liu, H., et al., "Structure-based Programming of Lymph Node Targeting in Molecular Vaccines", Nature 507(7493), 519-522 (2014).
Lu, H., et al., "Treatment failure of a TLR-7 agonist occurs due to self-regulation of acute inflammation and can be overcome by IL-10 blockade", J Immunol 184, 5360-5367 (2010).
Mero, A., et al., "Hyaluronic Acid Bioconjugates for the Delivery of Bioactive Molecules", Polymers 6, 346-369 (2014).
Misra, S., et al., "HA/CD44 interactions as potential targets for cancer therapy", FEBS J. 278(9), 1429-1443 (2011).
Nierkens, S., et al., "In vivo colocalization of antigen and CpG [corrected] within dendritic cells is associated with the efficacy of cancer immunotherapy", Cancer Res. 68 (13), 5390-5396 (2008).
Nuhn, L., et al., "pH-degradable imidazoquinoline-ligated nanogels for lymph node-focused immune activation", Proc. Natl. Acad. Sci. USA 113, 8098-8103 (2016).
Pal, I., et al., "The role of the lymphatic system in vaccine trafficking and immune response", Advanced Drug Delivery Reviews 63, 909-922 (2011).
Patent Cooperation Treaty, International Searching Authority, Search Report and Written Opinion for PCT/US2019/039940, 17 pages, dated Sep. 30, 2019.
Philbin, V, et al., "Immunostimulatory Activity of Toll-Like Receptor 8 Agonists Towards Human Leucocytes: Basic Mechanisms and Translational Opportunities", Biochem Soc Trans 35 (Pt 6), 1485-1491 (2007).
Reddy, S., et al., "Exploiting lymphatic transport and complement activation in nanoparticle vaccines", Nature Biotechnology 25, 1159-1164 (2007).
Schatné, C. E., et al., "Chemical modifications of hyaluronic acid for the synthesis of derivatives for a broad range of biomedical applications", Carbohydrate Polymers 85(3), 469-489 (2011).
Schiaffo, CE, et al., "Structure-activity relationship analysis of imidazoquinolines with Toll-like receptors 7 and 8 selectivity and enhanced cytokine induction", J Med Chem 57 (2), 339-347 (2014).
Shi, CE, et al., "Discovery of Imidazoquinolines with Toll-Like Receptor 7/8 Independent Cytokine Induction", ACS Med. Chem. Lett. 3, 501-504 (2012).
Shukla, NM, et al., "Structure—Activity Relationships in Human Toll-Like Receptor 7-Active Imidazoquinoline Analogues", J. Med. Chem. 53, 4450-4465 (2010).
Swartz, M., et al., "Lymphatic drainage function and its immunological implications: From dendritic cell homing to vaccine design", Seminars in Immunology 20, 147-156 (2008).
Tan, P., et al., "Non-aesthetic indications for periocular hyaluronic acid filler treatment: a review", Brit. J. Ophthal doi: 10.1136/bjophthalmol-2017-310525, (2017).
Temmerman, M., et al., "Particulate vaccines: on the quest for optimal delivery and immune response", Drug Discovery Today 16(13-14), 569-582 (2011).
Waeckerie-Men, Y., et al., "Lymph node targeting of BCG vaccines amplifies CD4 and CD8 T-cell responses and protection against *Mycobacterium tuberculosis*", Vaccine, 31(7), 1057-1064 (2013).
Wang, C., et al., "Lymphatic-targeted cationic liposomes: A robust vaccine adjuvant for promoting long-term immunological memory", Vaccine 32, 5475-5483 (2014).
Wu, JJ, et al., "Resiquimod: a new immune response modifier with potential as a vaccine adjuvant for Th1 immune responses", Antiviral Res 64, 79-83 (2004).
Yoo, E., et al., "Determinants of Activity at Human Toll-like Receptors 7 and 8: Quantitative Structure-Activity Relationship (QSAR) of Diverse Heterocyclic Scaffolds", Journal of Medicinal Chemistry 57, 7955-7970 (2014).
Yoo, E, "Exploration of Toll-like Receptor 7 and 8 Agonists as Potential Vaccine Adjuvants", Thesis, Retrieved from the Internet at https://pdfs.semanticscholar.org/780b/f87d0a02c580064fa3f70d4d561963952d29.pdf, pp. 33 pages (Apr. 16, 2015).

21

22

23

24

THERAPEUTIC COMPOUNDS AND METHODS OF USE THEREOF

CROSS-REFERENCE TO RELATED APPLICATIONS

This application claims the benefit of U.S. Provisional Application Ser. No. 62/693,322 filed Jul. 2, 2018. The entire content of the application referenced above is hereby incorporated by reference herein.

GOVERNMENT FUNDING

This invention was made with government support under HSN272201400056C awarded by the National Institutes of Health. The government has certain rights in the invention.

BACKGROUND OF THE INVENTION

The lymphatic system provides for unidirectional transport of transudative interstitial fluid and proteins exiting microcirculation due to hydrostatic pressure, and returning them back to the intravascular compartment. Lymphatic fluid drains via afferent lymphatic vessels into regional lymph nodes, which are highly organized secondary lymphoid tissues specialized in immune surveillance of the contents of lymph (Liao, S. et al. *Semin. Cell Dev. Biol.* 2015, 38, 83-89). Immune cells located in specialized zones within lymph nodes not only respond to antigens arriving from distal sites of infection, but also receive and orchestrate appropriate immune responses to migrating antigen presenting cells (APCs) bearing antigenic epitopes. This is of particular relevance in immunization, wherein peripheral APCs such as dendritic cells (DCs) and macrophages capture antigens from the injection site, and then migrate into the lymphoid tissues to trigger downstream T and B-lymphocyte activation as well as memory cell differentiation (Swartz, M. A. et al. *Semin. Immunol.* 2008, 20, 147-156). The lymph nodes also contain a large number of resident APCs, which can actively process antigens and serve as a major reservoir for long-lived memory B cells and central memory T cells, therefore playing a crucial role in generating long-term immunological memory (Waeckerle-Men, Y. et al. *Vaccine* 2013, 31, 1057-1064 and Pal, I. et al. *Adv. Drug Deliv. Rev.* 2011, 63, 909-922).

The flow of interstitial fluid also brings fragments of extracellular matrix (ECM) macromolecules into lymph (Jiang, D. et al. *Physiol. Rev.* 2011, 91, 221 and Jackson, D. G. et al. *Immunol. Rev.* 2009, 230, 216-231). Important among the constituents of ECM is hyaluronic acid (hyaluronan, HA), a linear glycosaminoglycan polymer with a molecular weight that can reach $10^7$ Daltons, and composed of repeating polymeric disaccharides of D-glucuronic acid (GlcUA) and N-acetyl glucosamine (GlcNAc) linked by β-1,4 and β-1,3 glycosidic bonds (Schante, C. E. et al. *Carbohyd. Polym.* 2011, 85, 469-489). Depending on the molecular size, HA can interact with several cognate HA-recognizing molecules (Mero, A. et al. *Polymers* 2014, 6, 346-369) important among which are CD44, a single chain, transmembrane glycoprotein expressed on leukocytes that traffic through the lymphatics (Misra, S. et al. *FEBSJ.* 2011, 278, 1429-1443), as well as lymphatic vessel endothelial hyaluronan receptor-1 (LYVE-1), which is expressed almost exclusively on lymphatic endothelium (Jackson, D. G. et al. *APMIS,* 2004, 112, 526-538). CD44-HA interaction is known to be involved in a variety of cellular functions, including cell-cell interactions, receptor-mediated internalization/degradation of HA, and cell migration. LYVE-1 participates in HA-mediated leukocyte trafficking, adhesion, and transmigration (Jackson, D. G. et al. *Immunol. Rev.* 2009, 230, 216-231).

The efficient delivery of antigen/adjuvant has been a major challenge in the development of subunit vaccines, and enhancing vaccine delivery to secondary lymphoid organs might be a promising approach for improving vaccine efficacy (Swartz, M. A. et al. *Semin. Immunol.* 2008, 20, 147-156, Wang, C. et al. *Vaccine* 2014, 32, 5475-5483 and Liu, H. et al. *Nature* 2014, 507, 519-522). Several studies have addressed enhanced or targeted delivery of antigens to secondary lymphoid tissue, including the use of depot-forming adjuvants (Gupta, R. K. et al. *Adv. Drug Deliv. Rev.* 1998, 32, 155-172), nanoparticulate carriers that are preferentially internalized by APCs (Bachmann, M. F. et al. *Nat. Rev. Immunol.* 2010, 10, 787-796; De Temmerman, M. L. et al. *Drug Discov. Today* 2011, 16, 569-582 and Reddy, S. T. et al. *Nat. Biotechnol.* 2007, 25, 1159-1164), or intralymphatic immunization (Waeckerle-Men, Y. et al. *Vaccine* 2013, 31, 1057-1064), but strategies that could use well-defined molecular conjugates would be more attractive. We envisioned that we could take advantage of the characteristics of HA, a natural biopolymer with an excellent clinical track record (Tan, P. et al. *Brit. J. Ophthal.* 2017, doi: 10.1136/bjophthalmol-2017-310525; He, W. W. et al. *Int. J. Surg.* 2017, 39, 95-103 and Fallacara, A. et al. *Facial Plast. Surg.* 2017, 33, 87-96)-biodegradability, biocompatibility, high potential loading and, importantly, its known propensity for trafficking to lymph nodes (Cai, S. et al. *J. Pharm. Sci.* 2010, 99, 2664-2671 and Cai, S. et al. *J. Surg. Res.* 2008, 147, 247-252). We hypothesized that covalently coupled conjugates of HA bearing TLR7/TLR8 agonists, which we have previously demonstrated to induce prominent Th1-biased responses (Beesu, M. et al. *J. Med. Chem.* 2017, 60, 2084-2098; Beesu, M. et al. *J. Med. Chem.* 2015, 58, 7833-7849; Yoo, E. et al. *J. Med. Chem.* 2014, 57, 7955-7970 and Nuhn, L. et al. *Proc. Natl. Acad. Sci. USA.* 2016, 113, 8098-8103) could facilitate targeted delivery of these adjuvants to secondary lymphoid tissue while also minimizing systemic exposure of these small molecules with molecular properties that portend a large volume of distribution.

There is currently a need for compounds possessing TLR7 and TLR8 activity, and bearing functional groups that can allow chemical transformation, including conjugation to biomolecules.

SUMMARY OF THE INVENTION

This invention provides novel imidazoquinoline analogues possessing TLR7 and TLR8 activity, and bearing functional groups that allow chemical transformation, including conjugation to biomolecules. Accordingly the invention provides a compound of formula (I):

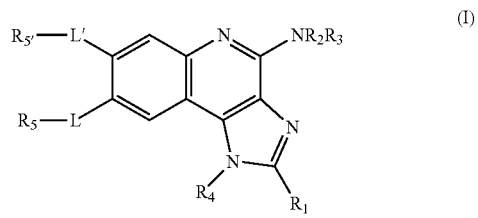

wherein:
- $R_1$ is H, $(C_1\text{-}C_6)$alkyl, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkanoyloxy, or $(C_3\text{-}C_6)$cycloalkyl, wherein any $(C_1\text{-}C_6)$alkyl, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkanoyloxy, or $(C_3\text{-}C_6)$cycloalkyl, is optionally substituted with one or more groups independently selected from hydroxy, halo, oxo, $(C_3\text{-}C_5)$cycloalkyl, and $(C_1\text{-}C_6)$alkoxy;
- each $R_2$ and $R_3$ is independently H, or $(C_1\text{-}C_6)$alkyl that is optionally substituted with one or more groups independently selected from hydroxy, halo, $(C_3\text{-}C_5)$cycloalkyl, and $(C_1\text{-}C_6)$alkoxy;
- $R_4$ is $(C_1\text{-}C_6)$alkyl that is substituted with aryl, wherein the aryl is substituted with one $-OR^z$ and is optionally substituted with one or more groups independently selected from the group consisting of halogen, $(C_3\text{-}C_5)$cycloalkyl, $-OR^h$, isothiocyanate, $-NR^aR^b$, $-NR^cC(=O)R^d$, $-NR^cC(=S)-NR^fR^g$, and $(C_1\text{-}C_6)$alkyl optionally substituted with one or more groups independently selected from the group consisting of halogen, $(C_3\text{-}C_5)$cycloalkyl, $-OR^h$, isothiocyanate, $-NR^aR$, $-NR^cC(=O)R^d$, and $-NR^cC(=S)-NR^fR^g$;
- L is absent or is a divalent, branched or unbranched hydrocarbon chain, having from 1 to 20 carbon atoms, wherein one or more (e.g. 1, 2, 3, or 4) of the carbon atoms is optionally replaced by a non-peroxide ($-O-$);
- $R_5$ is H, an activated group, or $NR^xR^y$;
- L' is absent or is a divalent, branched or unbranched hydrocarbon chain, having from 1 to 20 carbon atoms, wherein one or more (e.g. 1, 2, 3, or 4) of the carbon atoms is optionally replaced by a non-peroxide ($-O-$);
- $R_{5'}$ is H, an activated group, or $NR^xR^y$;
- provided that either $-L-R_5$ taken together or $-L'-R_{5'}$ taken together is H;
- each $R^a$ and $R^b$ is independently selected from the group consisting of H, $(C_1\text{-}C_6)$alkyl, $(C_3\text{-}C_6)$cycloalkyl, $(C_1\text{-}C_6)$alkoxy and X-Y; or $R^a$ and $R^b$ together with the nitrogen to which they are attached form a aziridino, azetidino, morpholino, piperazino, pyrrolidino or piperidino;
- each $R^c$ and $R^d$ is independently selected from the group consisting of H, $(C_1\text{-}C_6)$alkyl, $(C_3\text{-}C_6)$cycloalkyl, and $(C_1\text{-}C_6)$alkoxy;
- each $R^e$ is independently selected from the group consisting of H, $(C_1\text{-}C_6)$alkyl, $(C_3\text{-}C_6)$cycloalkyl, and $(C_1\text{-}C_6)$alkoxy;
- each $R^f$ and $R^g$ is independently selected from the group consisting of H, $(C_3\text{-}C_6)$cycloalkyl, $(C_1\text{-}C_6)$alkoxy and $(C_1\text{-}C_6)$alkyl that is optionally substituted with $NR^kR^m$; or R and $R^g$ together with the nitrogen to which they are attached form a aziridino, azetidino, morpholino, piperazino, pyrrolidino or piperidino;
- each $R^k$ and $R^m$ is independently selected from the group consisting of H, $(C_1\text{-}C_6)$alkyl, and $(C_3\text{-}C_6)$cycloalkyl; or $R^k$ and $R^m$ together with the nitrogen to which they are attached form a aziridino, azetidino, morpholino, piperazino, pyrrolidino or piperidino;
- each $R^z$ and $R^h$ is independently selected from the group consists of H, $(C_1\text{-}C_6)$alkyl, $(C_2\text{-}C_6)$alkenyl, $(C_2\text{-}C_6)$alkynyl, $(C_3\text{-}C_5)$cycloalkyl $-P(=O)OH)_2$, or W—Z;
- $R^x$ is H;
- $R^y$ is a residue of hyaluronic acid;
- each W is independently a linking group or is absent;
- each Z is independently Z is an antigen;
- each X is independently a linking group or is absent; and
- each Y is independently a residue of hyaluronic acid;
- or a salt thereof.

The invention provides a pharmaceutical composition comprising a compound of formula I, or a pharmaceutically acceptable salt thereof, and a pharmaceutically acceptable excipient.

The invention provides a method for stimulating immune activity in an animal comprising administering a compound of formula I, or a pharmaceutically acceptable salt thereof, to the animal.

The invention provides a method for immunizing a host comprising, administering to the host, 1) an antigen and 2) a compound of formula I, or a pharmaceutically acceptable salt thereof.

The invention provides a compound of formula I, or a pharmaceutically acceptable salt thereof, for use in medical therapy.

The invention provides a compound of formula I, or a pharmaceutically acceptable salt thereof, for stimulating immune activity.

The invention provides a use of a compound of formula I, or a pharmaceutically acceptable salt thereof, to prepare a medicament for stimulating immune activity in an animal.

The invention provides a composition comprising an antigen and a compound of formula I, or a pharmaceutically acceptable salt thereof.

The invention provides a self-adjuvanting vaccine comprising a compound of formula I, or a pharmaceutically acceptable salt thereof linked to an antigen.

The invention provides a probe comprising a compound of formula I, or a pharmaceutically acceptable salt thereof, wherein Z is a detectable group.

Certain compounds of the invention may be particularly useful because they may be selective for TLR7 over other toll-like receptors, such as, for example, TLR8.

Certain compounds of the invention may be particularly useful because they selectively activate TLR7 or TLR8 or alternate receptors (such as the inflammasome) in triggering the productions of specific cytokines.

DETAILED DESCRIPTION

Figure 1:
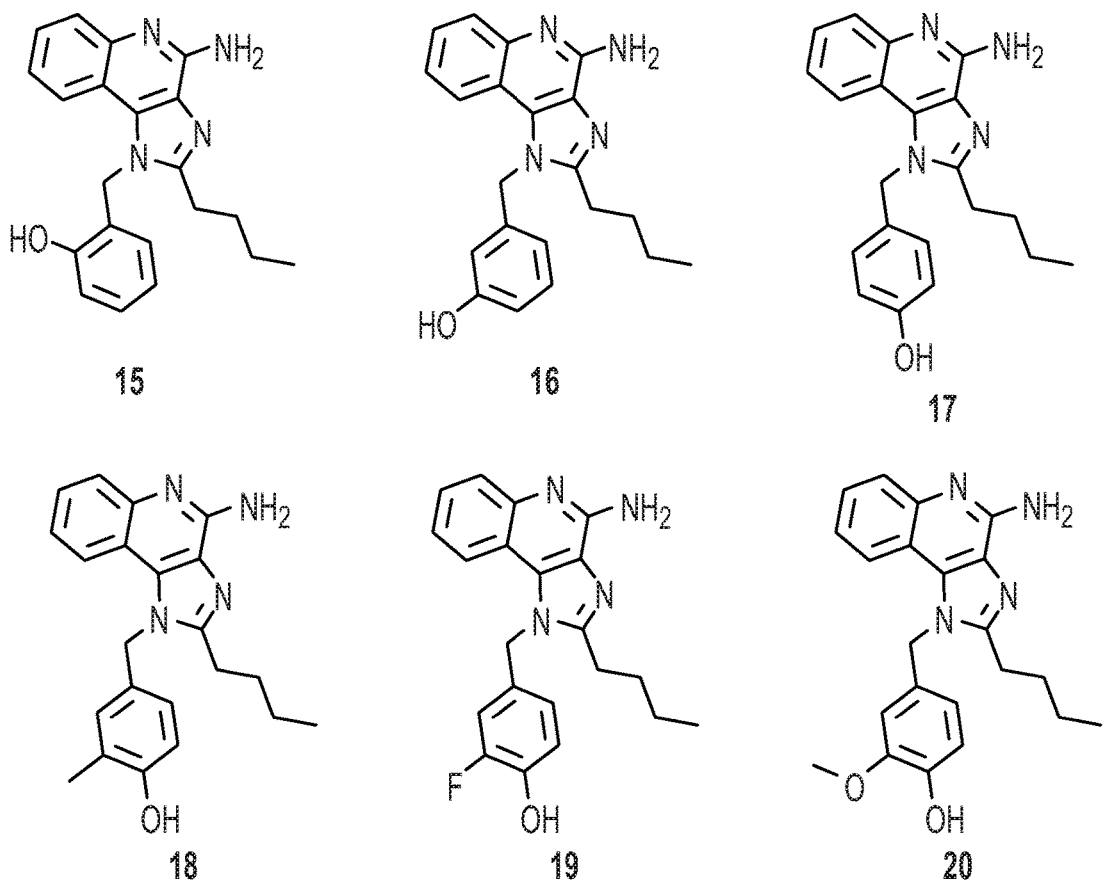
FIG. 1 shows hTLR7 and hTLR8 Agonistic activities of phenolic compounds 15-20.
Figure 1:
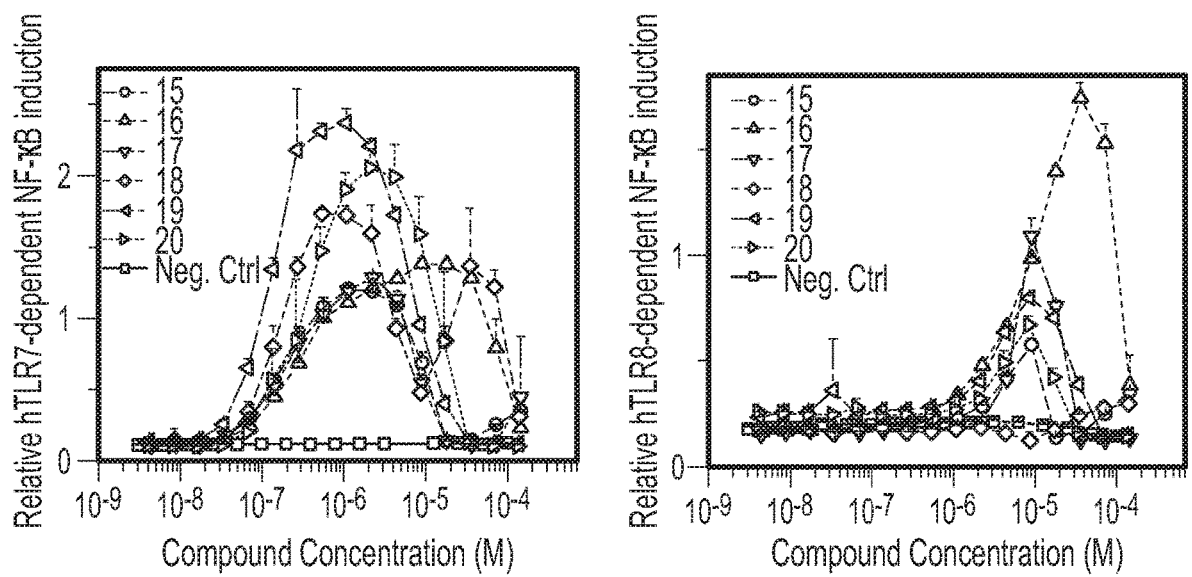
Figure 2:
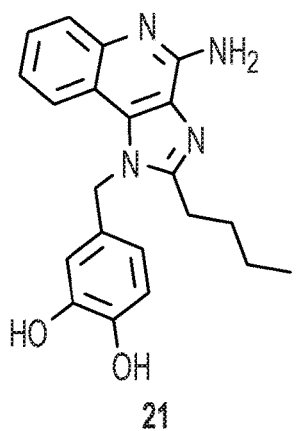
FIG. 2 shows hTLR7 and hTLR8 Agonistic activities of bis-phenolic compounds 21-24.
Figure 2:
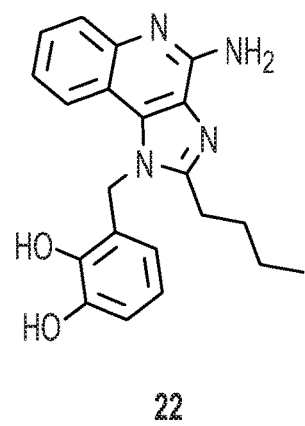
Figure 2:
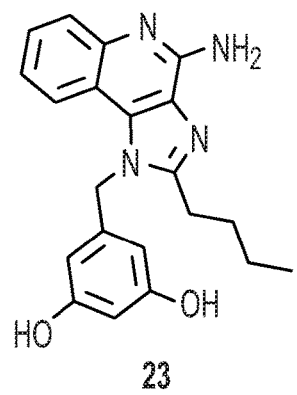
Figure 2:
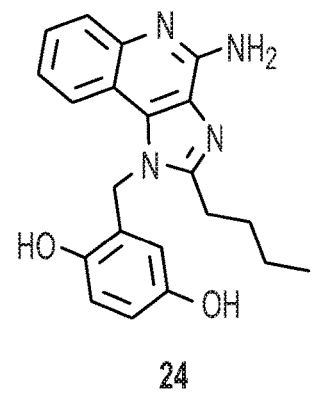
Figure 2:
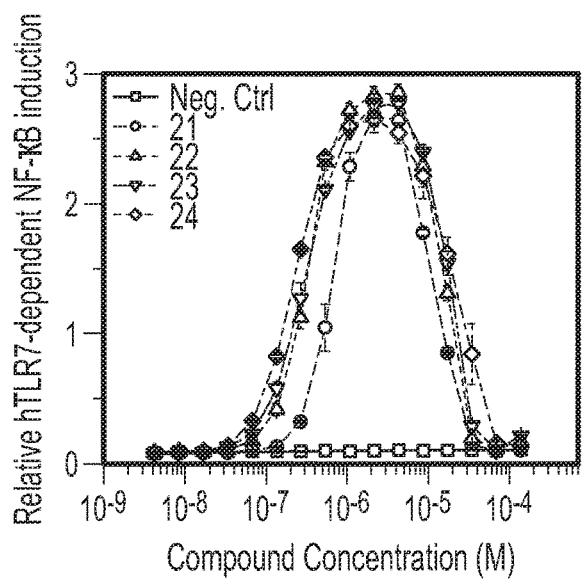
Figure 2:
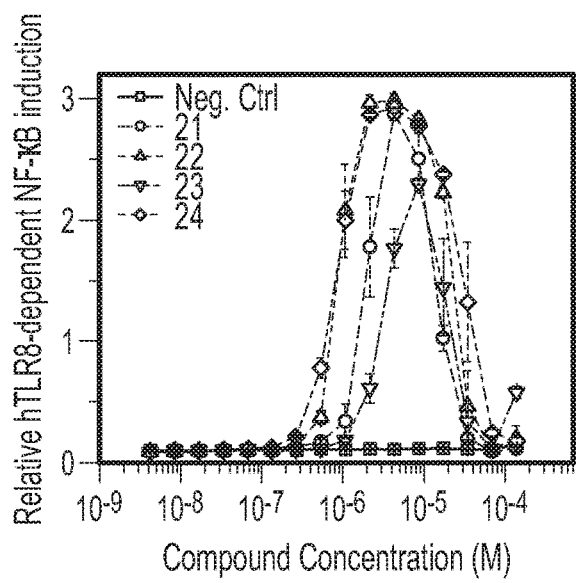
Figure 3:
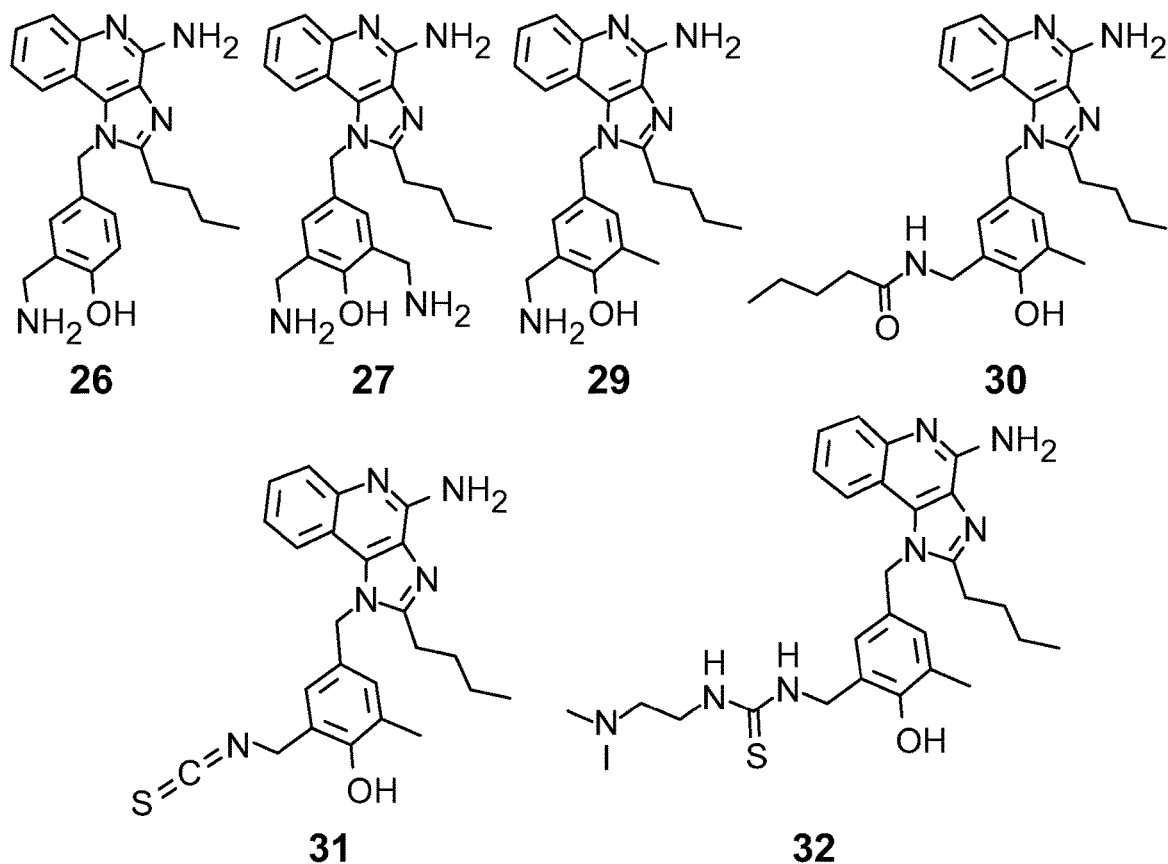
FIG. 3 shows hTLR7 and hTLR8 Agonistic activities Tscherniac-Einhorn compounds 26-27, 29-32.
Figure 3:
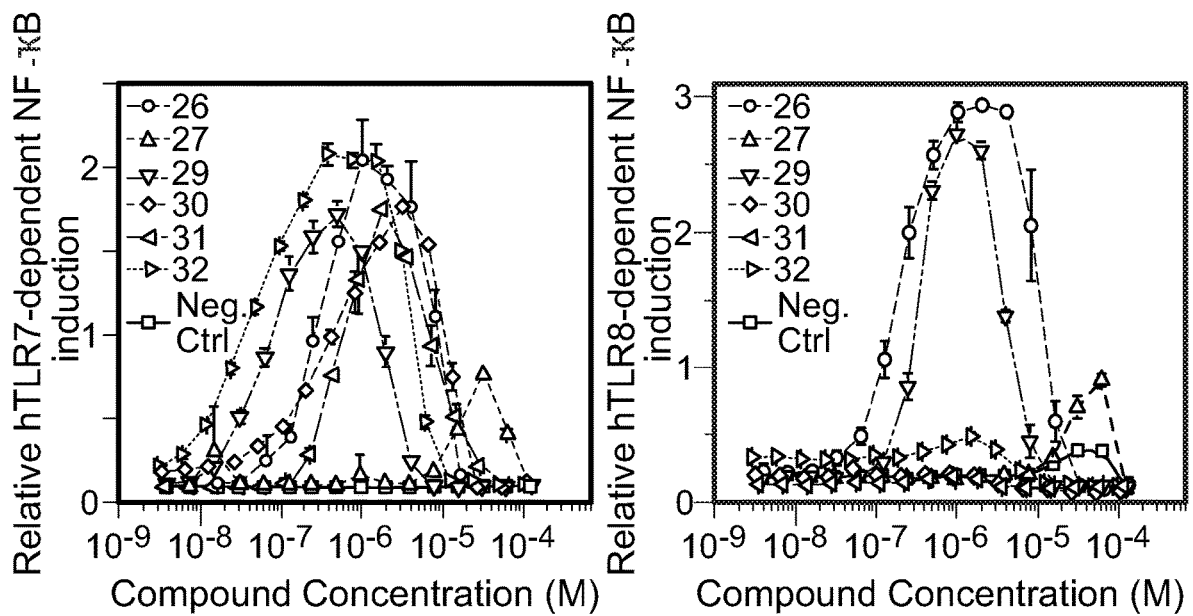
Figure 4:
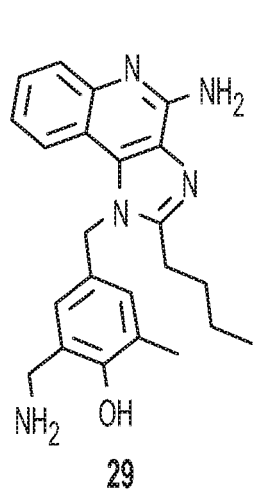
FIG. 4 shows compound 29 can induce cytokine release strongly in human whole blood.
Figure 4:
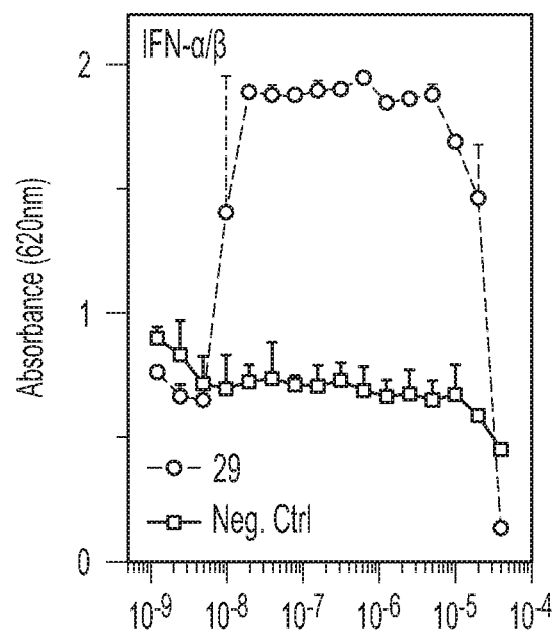
Figure 4:
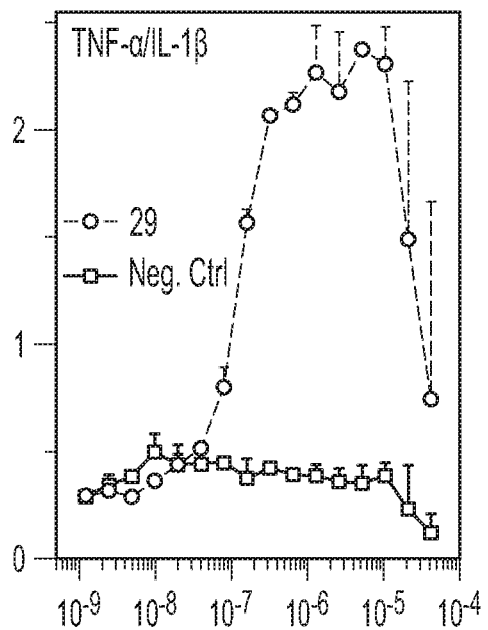
Figure 4:
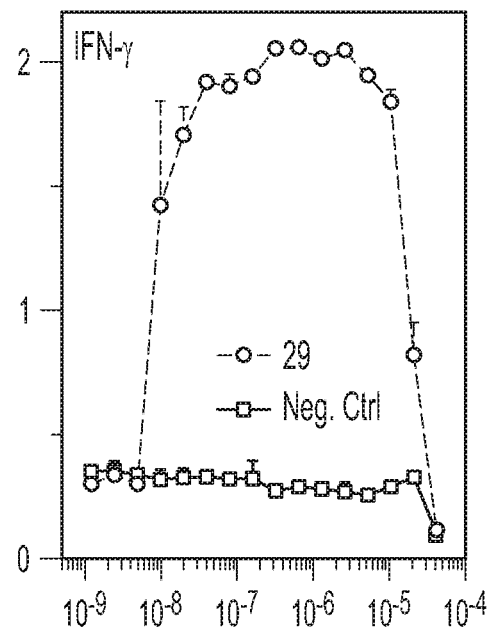
Figure 5:
FIG. 5 shows hTLR7 and hTLR8 Agonistic activities of O-alkyne compounds and related analogs.
Figure 5:
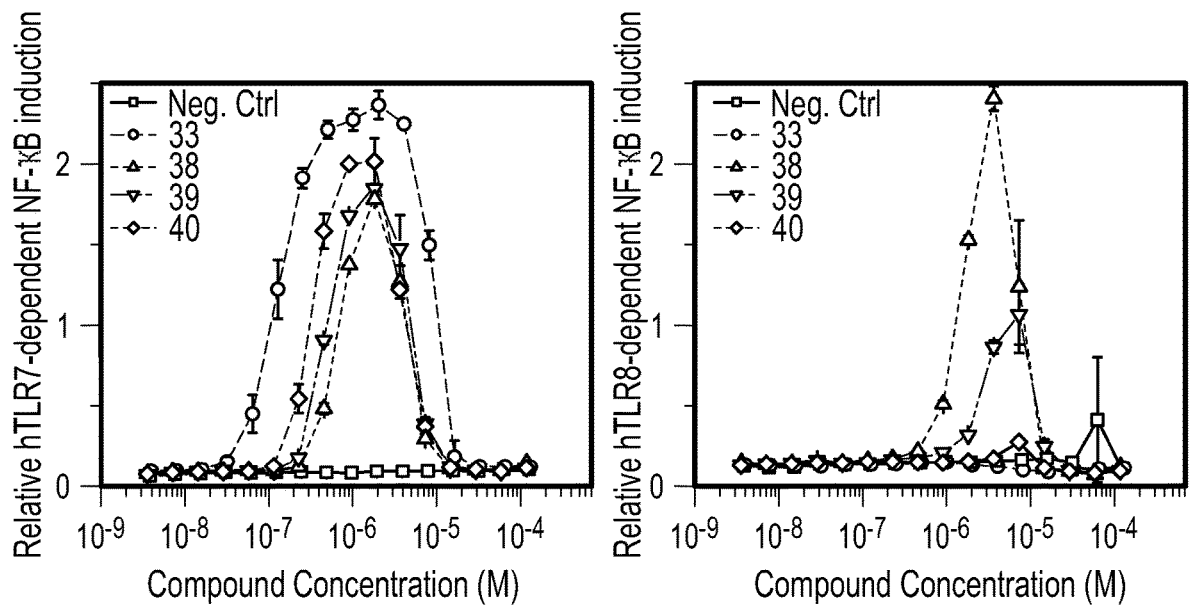
Figure 6:
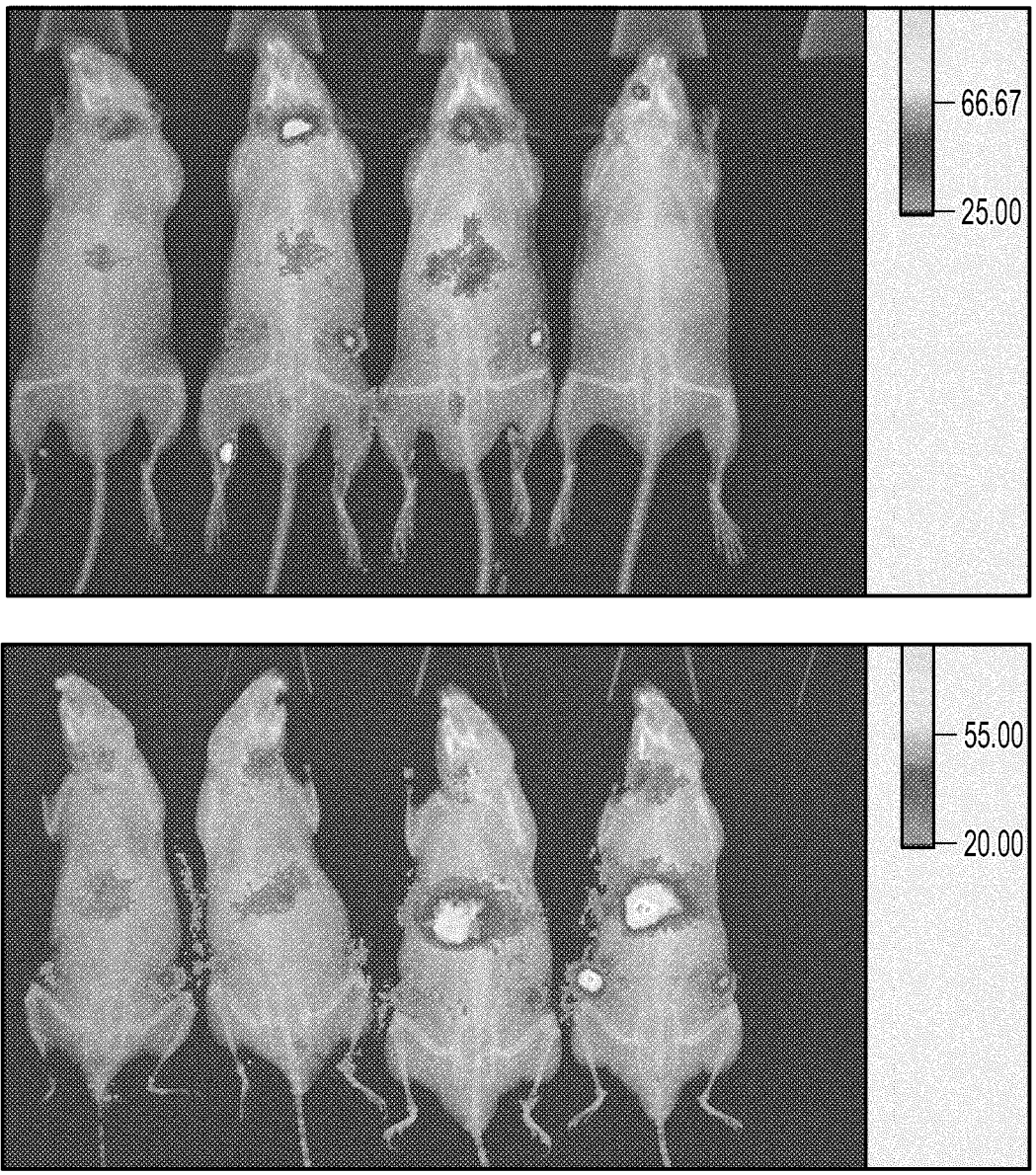
FIG. 6 shows hyaluronic acid conjugate 42 (but not 43) persists at the injection site.
Figure 7:
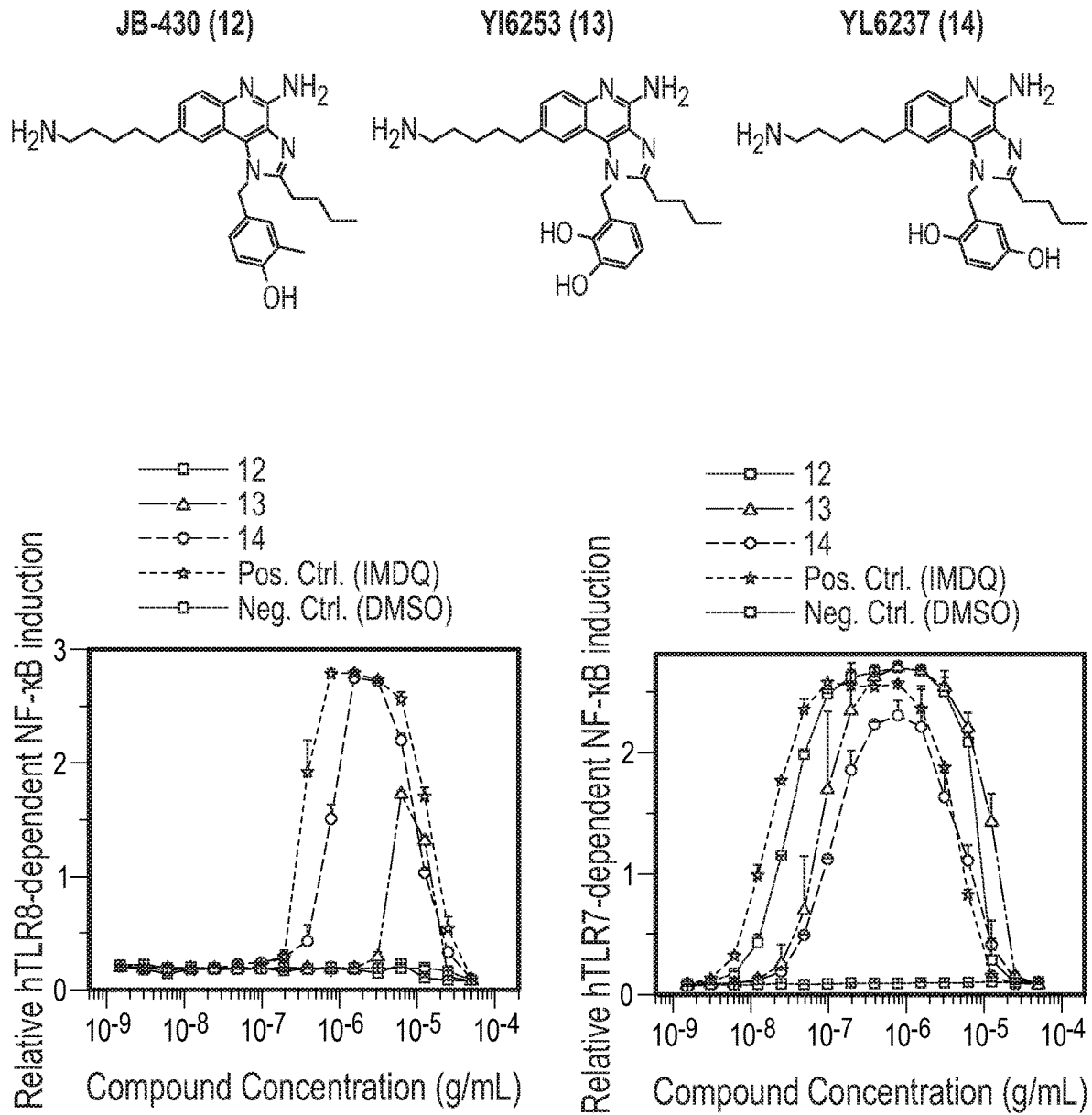
FIG. 7 shows hTLR7 and hTLR8 agonistic activity of alkylamine phenolic compounds.
Figure 8:
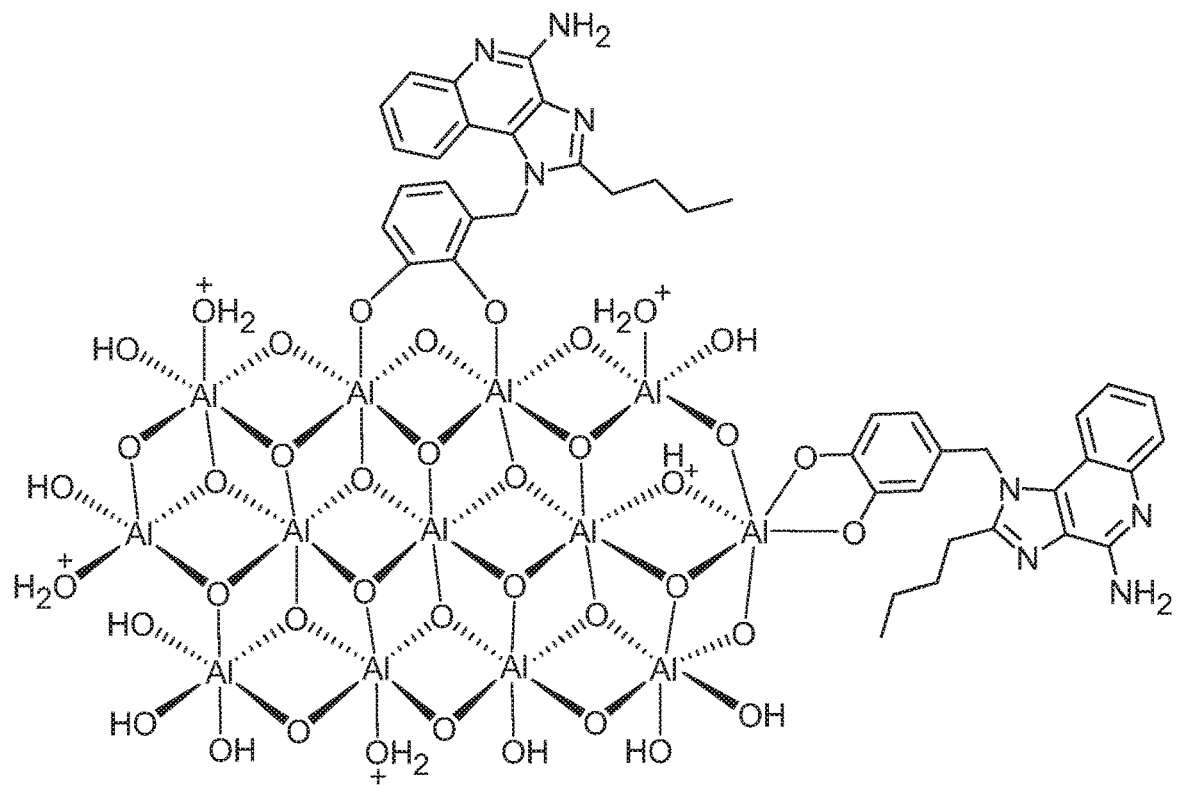
FIG. 8 illustrates complexes between nanoparticles comprising aluminum (Alhydrogel) and representative compounds of the invention.
Figure 8:
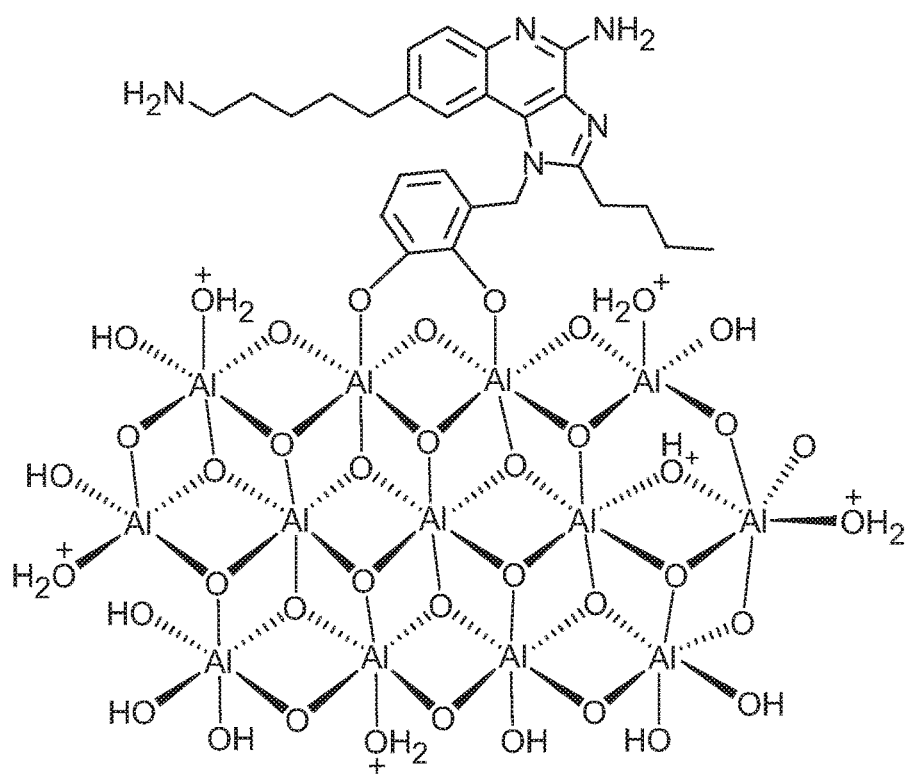

The following definitions are used, unless otherwise described: halo or halogen is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to.

The term "activated group" refers to a functional group that can be covalently coupled to a linker moiety L or to an antigen moiety. In one embodiment, the activated group is an amine, a thiol derivative, a maleimide, an isothiocyanate, an isocyanate, an N-succinimide, a leaving group (e.g. Cl, Br, I, mesyl, or tosyl), or an alkyne (e.g. an alkyne that can undergo "click chemistry" with an azides to give a 1,2,3-triazoles). In one embodiment, the activated group is an amine, a thiol derivative, a maleimide, an isothiocyanate, an isocyanate, an N-succinimide, or an alkyne (e.g. an alkyne that can undergo "click chemistry" with an azides to give a 1,2,3-triazoles). In one embodiment, $R^5$ is $NH_2$, a thiol derivative (—SH), a maleimide, an isothiocyanate, an isocyanate, chloro, bromo, or an N-succinimide. In one embodiment, $R^5$ is $NH_2$, a thiol derivative (—SH), a maleimide, an isothiocyanate, an isocyanate, or an N-succinimide. In one embodiment, $R^5$ is an alkyne that can undergo "click chemistry" with an azides to give a 1,2,3-triazole. In one embodiment, $R^5$ is a $(C_1-C_6)$alkyne. In one embodiment, $R^{5'}$ $NH_2$, a thiol derivative (—SH), a maleimide, an isothiocyanate, an isocyanate, chloro, bromo, or an N-succinimide. In one embodiment, $R^{5'}$ is $NH_2$, a thiol derivative (—SH), a maleimide, an isothiocyanate, an isocyanate, or an N-succinimide. In one embodiment, $R^{5'}$ is an alkyne that can undergo "click chemistry" with an azide to give a 1,2,3-triazole. In one embodiment, $R^5$ is a $(C_1-C_6)$alkyne.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples include $(C_1-C_8)$alkyl, $(C_2-C_8)$alkyl, $C_1-C_6$alkyl, $(C_2-C_6)$alkyl and $(C_3-C_6)$alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and and higher homologs and isomers.

The term "alkenyl" refers to an unsaturated alkyl radical having one or more double bonds. Examples of such unsaturated alkyl groups include vinyl, 2-propenyl, crotyl, 2-isopentenyl, 2-(butadienyl), 2,4-pentadienyl, 3-(1,4-pentadienyl) and the higher homologs and isomers.

The term "alkynyl" refers to an unsaturated alkyl radical having one or more triple bonds. Examples of such unsaturated alkyl groups ethynyl, 1- and 3-propynyl, 3-butynyl, and higher homologs and isomers.

The term "alkoxy" refers to an alkyl groups attached to the remainder of the molecule via an oxygen atom ("oxy").

The term "alkylthio" refers to an alkyl groups attached to the remainder of the molecule via a thio group.

The term "cycloalkyl" refers to a saturated or partially unsaturated (non-aromatic) all carbon ring having 3 to 8 carbon atoms (i.e., $(C_3-C_8)$carbocycle). The term also includes multiple condensed, saturated all carbon ring systems (e.g., ring systems comprising 2, 3 or 4 carbocyclic rings). Accordingly, carbocycle includes multicyclic carbocyles such as a bicyclic carbocycles (e.g., bicyclic carbocycles having about 3 to 15 carbon atoms, about 6 to 15 carbon atoms, or 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). Non-limiting examples of cycloalkyls include cyclopropyl, cyclobutyl, cyclopentyl, cyclohexyl, bicyclo[2.2.1]heptane, pinane, and adamantane.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed carbon ring systems (e.g., ring systems comprising 2, 3 or 4 rings) having about 9 to 20 carbon atoms in which at least one ring is aromatic and wherein the other rings may be aromatic or not aromatic (i.e., cycloalkyl. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, indanyl, naphthyl, 1, 2, 3, 4-tetrahydronaphthyl, anthracenyl, and the like.

The term "heterocycle" refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from cycloalkyl, aryl, and heterocycle to form the multiple condensed ring system. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. In one embodiment the term heterocycle includes a 3-15 membered heterocycle. In one embodiment the term heterocycle includes a 3-10 membered heterocycle. In one embodiment the term heterocycle includes a 3-8 membered heterocycle. In one embodiment the term heterocycle includes a 3-7 membered heterocycle. In one embodiment the term heterocycle includes a 3-6 membered heterocycle. In one embodiment the term heterocycle includes a 4-6 membered heterocycle. In one embodiment the term heterocycle includes a 3-10 membered monocyclic or bicyclic heterocycle comprising 1 to 4 heteroatoms. In one embodiment the term heterocycle includes a 3-8 membered monocyclic or bicyclic heterocycle heterocycle comprising 1 to 3 heteroatoms. In one embodiment the term heterocycle includes a 3-6 membered monocyclic heterocycle comprising 1 to 2 heteroatoms. In one embodiment the term heterocycle includes a 4-6 membered monocyclic heterocycle comprising 1 to 2 heteroatoms. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one imidazolidine, pyrazolidine, butyrolactam, valerolactam, imidazolidinone, hydantoin, dioxolane, phthalimide, and 1,4-dioxane.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from cycloalkyl, aryl, heterocycle, and heteroaryl. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, triazolyl, tetrazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, and quinazolyl.

The term "alkoxycarbonyl" as used herein refers to a group (alkyl)-O—C(=O)—, wherein the term alkyl has the meaning defined herein.

The term "alkanoyloxy" as used herein refers to a group (alkyl)-C(=O)—O—, wherein the term alkyl has the meaning defined herein.

As used herein, the term "heteroatom" is meant to include oxygen (O), nitrogen (N), sulfur (S) and silicon (Si).

As used herein a wavy line ∿ that intersects a bond in a chemical structure indicates the point of attachment of the bond that the wavy bond intersects in the chemical structure to the remainder of a molecule.

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder, such as, for example, the development or spread of cancer. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention, The phrase "therapeutically effective amount" or "effective amount" includes but is not limited to an amount of a compound of the that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" as used herein refers to humans, higher non-human primates, rodents, domestic, cows, horses, pigs, sheep, dogs and cats. In one embodiment, the mammal is a human. The term "patient" as used herein refers to any animal including mammals. In one embodiment, the patient is a mammalian patientIn one embodiment, the patient is a human patient.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein). An amino acid can be linked to the remainder of a compound of formula I through the carboxy terminus, the amino terminus, or through any other convenient point of attachment, such as, for example, through the sulfur of cysteine.

The term saccharide includes monosaccharides, disaccharides, trisaccharides and polysaccharides. The term includes glucose, sucrose fructose and ribose, as well as deoxy sugars such as deoxyribose and the like. Saccharide derivatives can conveniently be prepared as described in International Patent Applications Publication Numbers WO 96/34005 and 97/03995. A saccharide can conveniently be linked to the remainder of a compound of formula I through an ether bond.

The term "peptide" describes a sequence of 2 to 25 amino acids (e.g. as defined hereinabove) or peptidyl residues. The sequence may be linear or cyclic. For example, a cyclic peptide can be prepared or may result from the formation of disulfide bridges between two cysteine residues in a sequence. A peptide can be linked to the remainder of a compound of formula I through the carboxy terminus, the amino terminus, or through any other convenient point of attachment, such as, for example, through the sulfur of a cysteine. Preferably a peptide comprises 3 to 25, or 5 to 21 amino acids. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right.

As used herein, the term "moiety" means a chemical group on a compound or capable of being coupled to a compound that includes a functional group/subunit. As used herein, a "moiety" may include a compound with a specific function that is a part of a larger compound or capable of being coupled to a different compound to form a larger compound. For instance, a "reporter moiety" is a chemical group that includes a reporter compound (e.g., a fluorescent dye molecule) that is coupled to or adapted to be coupled to another compound.

As used herein, the term "agonist" indicates a compound that induces a receptor molecule, for instance, a ligand that binds with and activates a receptor molecule. In embodiments of the present disclosure, imidazoquinoline derived compounds of the present disclosure are ligands that can activate certain receptors in a host immune system, such as TLR 7 and TLR8, thereby inducing the receptors to generate an immunological response. Thus, in embodiments, the imidazoquinoline derived compounds of the present disclosure can be TLR7 or dual TLR7/TLR8 agonists.

As used herein, the term "adjuvant" indicates a compound that induces and/or enhances an immunological response in a host. The adjuvants of the present disclosure induce immu-nological responses by activating toll-like receptor (TLR) 7 or by activating TLR7 and TLR8. Some of the adjuvants of the present disclosure may also induce other immunological responses in the host in addition to the activation of TLR7 and/or 8, such as by stimulating interferons (IFN). In general, an "immunological response" refers to a response by the host's immune system to a stimuli, in this case, and adjuvant. Adjuvants that "enhance" an immunological response in a host induce a stronger immunological response to an antigen or other immunological stimulus in the host than would be seen by the administration of an antigen and/or stimulus alone.

The term "self-adjuvant" or "self-adjuvanting vaccine" indicates a compound and/or vaccine (e.g., an antigen that induces an immune response) where the adjuvant effect is induced by the compound itself without the need for a separate adjuvant compound. In embodiments of a self-adjuvant of the present disclosure, an adjuvant molecule is covalently coupled to an antigen. This is in contrast to an antigen and an adjuvant molecule that are physically separate from each other (e.g., not coupled), even though they may be co-administered.

The compounds disclosed herein can also exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —CH$_3$ group may be substituted with —CD$_3$.

The pharmaceutical compositions of the invention can comprise one or more excipients. When used in combination with the pharmaceutical compositions of the invention the term "excipients" refers generally to an additional ingredient that is combined with the compound of formula (I) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

The term "residue" as it applies to the residue of a compound refers to a compound that has been modified in any manner which results in the creation of an open valence wherein the site of the open valence. The open valence can be created by the removal of 1 or more atoms from the compound (e.g., removal of a single atom such as hydrogen or removal of more than one atom such as a group of atoms including but not limited to an amine, hydroxyl, methyl, amide (e.g., —C(=O)NH$_2$) or acetyl group). The open valence can also be created by the chemical conversion of a first function group of the compound to a second functional group of the compound (e.g., reduction of a carbonyl group, replacement of a carbonyl group with an amine) followed by the removal of 1 or more atoms from the second functional group to create the open valence.

Specific values listed below for radicals, substituents, and ranges, are for illustration only; they do not exclude other defined values or other values within defined ranges for the radicals and substituents. It is to be understood that two or more values may be combined. It is also to be understood that the values listed herein below (or subsets thereof) can be excluded.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, iso-propoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$ alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R^1$ is n-butyl.

A specific value for each $R^2$ and $R^3$ is hydrogen.

A specific value for $R^4$ is

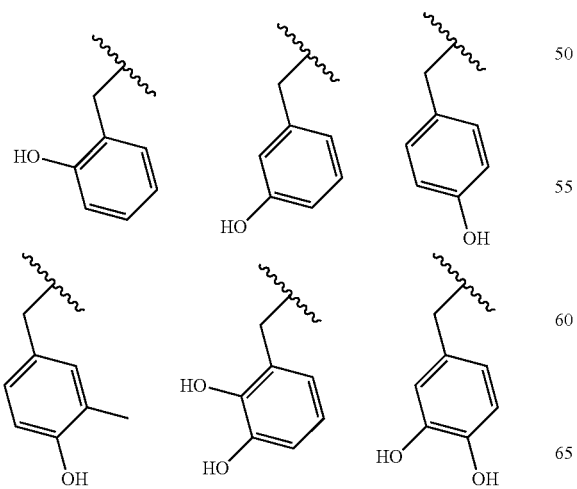

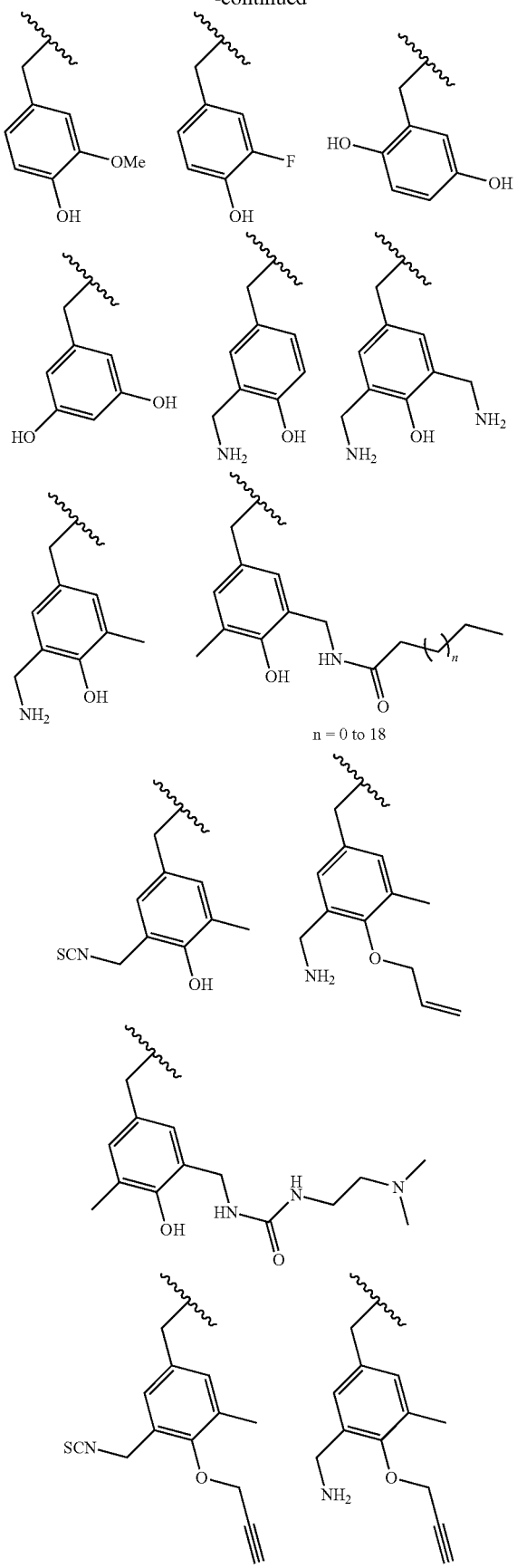

A specific value for Y, wherein Y is a residue of hyaluronic acid is

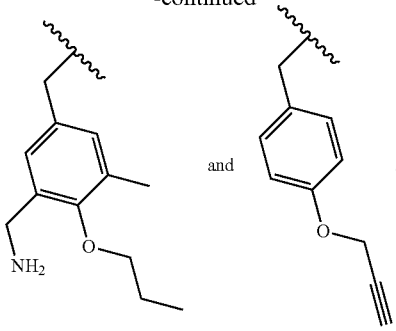

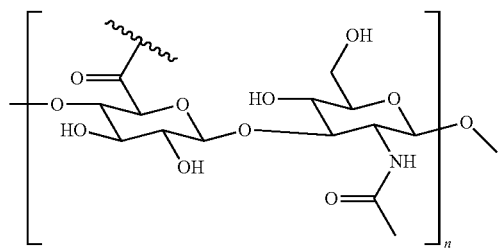

where n=1-1,000,000.

A specific value for W, wherein W is a linking group is

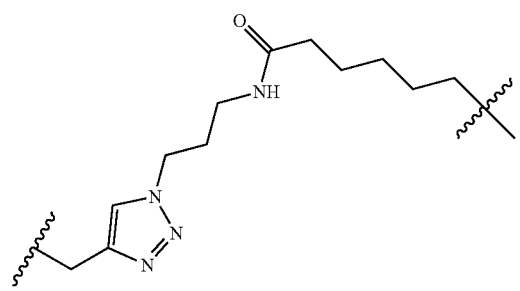

Antigen Conjugates

In one embodiment of the invention, the compound of the invention comprises one or more antigens. "Antigen" refers to a molecule capable of being recognized by the immune system and/or being capable of inducing a humoral immune response and/or cellular immune response leading to the activation of B- and/or T-lymphocytes. An antigen can have one or more epitopes (B- and/or T-cell epitopes). Antigens as used herein may also be mixtures of several individual antigens. "Antigenic determinant" refers to that portion of an antigen that is specifically recognized by either B- or T-lymphocytes. B-lymphocytes responding to antigenic determinants produce antibodies, whereas T-lymphocytes respond to antigenic determinants by proliferation and establishment of effector functions critical for the mediation of cellular and/or humoral immunity. A viral antigen refers to an antigen with multiple antigenicities that is protein in nature, strain-specific, and closely associated with the virus particle. A viral antigen is a protein encoded by the viral genome. A viral protein is an antigen specified by the viral genome that can be detected by a specific immunological response. In one embodiment, Z is a viral antigen. In one embodiment, the virus is a flavivirus. In one embodiment, the virus is an alphavirus. In one embodiment, the virus is a betaherpesvirinae. In one embodiment, the virus is selected from the group consisting of west nile virus, yellow fever virus, dengue fever virus, HIV virus, or chikungunya virus.

In one embodiment, the antigen is a bacterial antigen, which is a moiety that is found on the surfaces of a bacterial organism. In one embodiment, Z is a bacterial antigen. In one embodiment, the bacteria is a gram-positive bacteria or a gram-negative bacteria.

In one embodiment, the antigen is a cancer antigen, which is a moiety that is found on the surfaces of a cancer cell. In one embodiment, Z is an antigen for a cancer.

In one embodiment, the compound of formula (I) is a compound of formula (Ib)

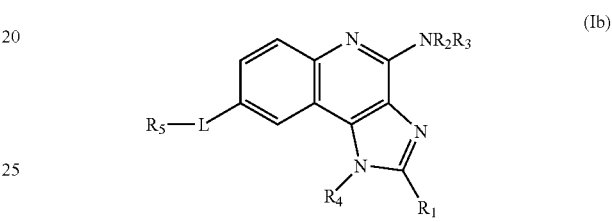

(Ib)

wherein:

$R_1$ is H, $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_1-C_6)$alkanoyloxy, or $(C_3-C_6)$cycloalkyl, wherein any $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_1-C_6)$alkanoyloxy, or $(C_3-C_6)$cycloalkyl, is optionally substituted with one or more groups independently selected from hydroxy, halo, oxo, $(C_3-C_5)$cycloalkyl, and $(C_1-C_6)$alkoxy;

each $R_2$ and $R_3$ is independently H, or $(C_1-C_6)$alkyl that is optionally substituted with one or more groups independently selected from hydroxy, halo, $(C_3-C_5)$cycloalkyl, and $(C_1-C_6)$alkoxy;

$R_4$ is $(C_1-C_6)$alkyl that is substituted with aryl, wherein the aryl is substituted with one —$OR^z$ and is optionally substituted with one or more groups independently selected from the group consisting of halogen, $(C_3-C_5)$cycloalkyl, —$OR^h$, isothiocyanate, —$N^aR^b$, —$NR^cC(=O)R^d$, —$NR^eC(=S)$—$NR^fR^g$, and $(C_1-C_6)$alkyl optionally substituted with one or more groups independently selected from the group consisting of halogen, $(C_3-C_5)$cycloalkyl, —$OR^h$, isothiocyanate, —$NR^aR^b$, —$NR^cC(=O)R^d$, and —$NR^cC(=S)$—$NR^fR^g$;

L is absent or is a divalent, branched or unbranched hydrocarbon chain, having from 1 to 8 carbon atoms, wherein one or more (e.g. 1, 2, 3, or 4) of the carbon atoms is optionally replaced by a non-peroxide (—O—);

$R_5$ is H or an activated group;

each $R^a$ and $R^b$ is independently selected from the group consisting of H, $(C_1-C_6)$alkyl, $(C_3-C_6)$cycloalkyl, $(C_1-C_6)$alkoxy and X-Y; or $R^a$ and $R^b$ together with the nitrogen to which they are attached form a aziridino, azetidino, morpholino, piperazino, pyrrolidino or piperidino;

each $R^c$ and $R^d$ is independently selected from the group consisting of H, $(C_1-C_6)$alkyl, $(C_3-C_6)$cycloalkyl, and $(C_1-C_6)$alkoxy;

each $R^c$ is independently selected from the group consisting of H, $(C_1-C_6)$alkyl, $(C_3-C_6)$cycloalkyl, and $(C_1-C_6)$alkoxy;

each $R^f$ and $R^g$ is independently selected from the group consisting of H, $(C_3-C_6)$cycloalkyl, $(C_1-C_6)$alkoxy and $(C_1-C_6)$alkyl that is optionally substituted with $NR^kR^m$; or R and $R^g$ together with the nitrogen to which they are attached form a aziridino, azetidino, morpholino, piperazino, pyrrolidino or piperidino;

each $R^k$ and $R^m$ is independently selected from the group consisting of H, $(C_1-C_6)$alkyl, and $(C_3-C_6)$cycloalkyl; or $R^k$ and $R^m$ together with the nitrogen to which they are attached form a aziridino, azetidino, morpholino, piperazino, pyrrolidino or piperidino;

at least one of $R^z$ and $R^b$ is present and is W—Z and each of any remaining $R^z$ and $R^h$ is independently selected from the group consists of H, $(C_1-C_6)$alkyl, $(C_2-C_6)$alkenyl, $(C_2-C_6)$alkynyl, $(C_3-C_5)$cycloalkyl —P(=O)OH$)_2$, or W—Z;

each W is independently a linking group or is absent;

each Z is independently Z is an antigen;

each X is independently a linking group or is absent; and each Y is independently a residue of hyaluronic acid;

or a salt thereof.

Hyaluronic Acid Conjugates

In one embodiment, the compound of formula (I) is a compound of formula (Ia):

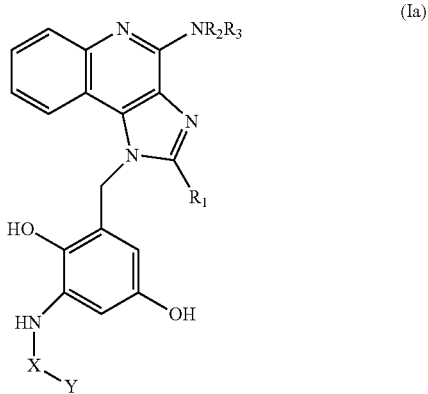

(Ia)

wherein:

$R_1$ is H, $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_1-C_6)$alkanoyloxy, or $(C_3-C_6)$cycloalkyl, wherein any $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_1-C_6)$alkanoyloxy, or $(C_3-C_6)$cycloalkyl, is optionally substituted with one or more groups independently selected from hydroxy, halo, oxo, $(C_3-C_5)$cycloalkyl, and $(C_1-C_6)$alkoxy;

each $R_2$ and $R_3$ is independently H, or $(C_1-C_6)$alkyl that is optionally substituted with one or more groups independently selected from hydroxy, halo, $(C_3-C_5)$cycloalkyl, and $(C_1-C_6)$alkoxy;

X is a linking group or is absent; and

Y is a residue of hyaluronic acid;

or a salt thereof.

In one embodiment, the compound of formula (I) is a compound of formula (Iu):

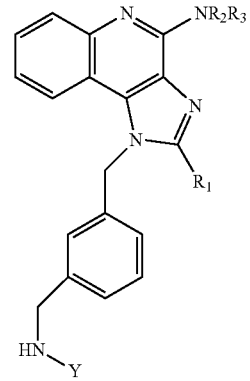

(Iu)

wherein:

$R_1$ is H, $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_1-C_6)$alkanoyloxy, or $(C_3-C_6)$cycloalkyl, wherein any $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_1-C_6)$alkanoyloxy, or $(C_3-C_6)$cycloalkyl, is optionally substituted with one or more groups independently selected from hydroxy, halo, oxo, $(C_3-C_5)$cycloalkyl, and $(C_1-C_6)$alkoxy;

each $R_2$ and $R_3$ is independently H, or $(C_1-C_6)$alkyl that is optionally substituted with one or more groups independently selected from hydroxy, halo, $(C_3-C_5)$cycloalkyl, and $(C_1-C_6)$alkoxy;

the benzyl ring is substituted with one —OR$^z$ and is optionally substituted with one or more groups independently selected from the group consisting of halogen, $(C_3-C_8)$cycloalkyl, —OR$^h$, isothiocyanate, —NR$^a$R$^b$, —NR$^c$C(=)R$^d$, —NR$^c$C(=S)—NRfRg, and $(C_1-C_6)$alkyl optionally substituted with one or more groups independently selected from the group consisting of halogen, $(C_3-C_5)$cycloalkyl, —OR$^h$, isothiocyanate, —NR$^a$R$^b$, —NR$^c$C(=)R$^d$, and —NR$^c$C(=S)—NR$^f$R$^g$;

each $R^a$ and $R^b$ is independently selected from the group consisting of H, $(C_1-C_6)$alkyl, $(C_3-C_6)$cycloalkyl, $(C_1-C_6)$alkoxy and X-Y; or $R^a$ and $R^b$ together with the nitrogen to which they are attached form a aziridino, azetidino, morpholino, piperazino, pyrrolidino or piperidino;

each $R^c$ and $R^d$ is independently selected from the group consisting of H, $(C_1-C_6)$alkyl, $(C_3-C_6)$cycloalkyl, and $(C_1-C_6)$alkoxy;

each R is independently selected from the group consisting of H, $(C_1-C_6)$alkyl, $(C_3-C_6)$cycloalkyl, and $(C_1-C_6)$alkoxy;

each $R^f$ and $R^g$ is independently selected from the group consisting of H, $(C_3-C_6)$cycloalkyl, $(C_1-C_6)$alkoxy and $(C_1-C_6)$alkyl that is optionally substituted with $NR^kR^m$; or $R^f$ and $R^g$ together with the nitrogen to which they are attached form a aziridino, azetidino, morpholino, piperazino, pyrrolidino or piperidino;

each $R^h$ is independently selected from the group consists of H, $(C_1-C_6)$alkyl, $(C_2-C_6)$alkenyl, $(C_2-C_6)$alkynyl, $(C_3-C_5)$cycloalkyl —P(=O)OH$)_2$, or W—Z;

each $R^z$ is independently selected from the group consists of H, $(C_1-C_6)$alkyl, $(C_2-C_6)$alkenyl, $(C_2-C_6)$alkynyl, $(C_3-C_5)$cycloalkyl —P(=O)OH$)_2$, or W—Z;

each W is independently a linking group or is absent;

each Z is independently Z is an antigen; and

Y is a residue of hyaluronic acid;

or a salt thereof.

In one embodiment, the compound of formula (I) is a compound of formula (Iv):

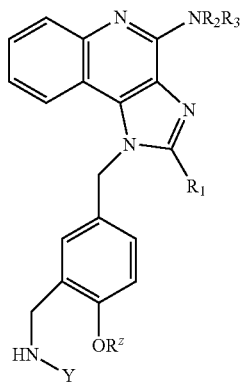

(Iv)

wherein:
R$_1$ is H, (C$_1$-C$_6$)alkyl, (C$_2$-C$_6$)alkenyl, (C$_2$-C$_6$)alkynyl, (C$_1$-C$_6$)alkanoyl, (C$_1$-C$_6$)alkoxycarbonyl, (C$_1$-C$_6$)alkanoyloxy, or (C$_3$-C$_6$)cycloalkyl, wherein any (C$_1$-C$_6$)alkyl, (C$_2$-C$_6$)alkenyl, (C$_2$-C$_6$)alkynyl, (C$_1$-C$_6$)alkanoyl, (C$_1$-C$_6$)alkoxycarbonyl, (C$_1$-C$_6$)alkanoyloxy, or (C$_3$-C$_6$)cycloalkyl, is optionally substituted with one or more groups independently selected from hydroxy, halo, oxo, (C$_3$-C$_5$)cycloalkyl, and (C$_1$-C$_6$)alkoxy;

each R$_2$ and R$_3$ is independently H, or (C$_1$-C$_6$)alkyl that is optionally substituted with one or more groups independently selected from hydroxy, halo, (C$_3$-C$_8$)cycloalkyl, and (C$_1$-C$_6$)alkoxy;

the benzyl ring is optionally substituted with one or more groups independently selected from the group consisting of halogen, (C$_3$-C$_5$)cycloalkyl, —OR$^h$, isothiocyanate, —NR$^a$R$^b$, —NR$^c$C(=O)R$^d$, —NR$^c$C(=S)—NR$^f$R$^g$, and (C$_1$-C$_6$)alkyl optionally substituted with one or more groups independently selected from the group consisting of halogen, (C$_3$-C$_5$)cycloalkyl, —OR$^h$, isothiocyanate, —NR$^a$R$^b$, —NR$^c$C(=O)R$^d$, and —NR$^c$C(=S)—NR$^f$R$^g$;

each R$^a$ and R$^b$ is independently selected from the group consisting of H, (C$_1$-C$_6$)alkyl, (C$_3$-C$_6$)cycloalkyl, (C$_1$-C$_6$)alkoxy and X-Y; or R$^a$ and R$^b$ together with the nitrogen to which they are attached form a aziridino, azetidino, morpholino, piperazino, pyrrolidino or piperidino;

each R$^c$ and R$^d$ is independently selected from the group consisting of H, (C$_1$-C$_6$)alkyl, (C$_3$-C$_6$)cycloalkyl, and (C$_1$-C$_6$)alkoxy;

each R is independently selected from the group consisting of H, (C$_1$-C$_6$)alkyl, (C$_3$-C$_6$)cycloalkyl, and (C$_1$-C$_6$)alkoxy;

each R$^f$ and R$^g$ is independently selected from the group consisting of H, (C$_3$-C$_6$)cycloalkyl, (C$_1$-C$_6$)alkoxy and (C$_1$-C$_6$)alkyl that is optionally substituted with NR$^k$R$^m$; or R and R$^g$ together with the nitrogen to which they are attached form a aziridino, azetidino, morpholino, piperazino, pyrrolidino or piperidino;

each R$^h$ is independently selected from the group consists of H, (C$_1$-C$_6$)alkyl, (C$_2$-C$_6$)alkenyl, (C$_2$-C$_6$)alkynyl, (C$_3$-C$_5$)cycloalkyl —P(=O)OH)$_2$, or W—Z;

each R$^z$ is independently selected from the group consists of H, (C$_1$-C$_6$)alkyl, (C$_2$-C$_6$)alkenyl, (C$_2$-C$_6$)alkynyl, (C$_3$-C$_5$)cycloalkyl —P(=O)OH)$_2$, or W—Z;

each W is independently a linking group or is absent;
each Z is independently Z is an antigen; and
Y is a residue of hyaluronic acid;
or a salt thereof.

In one embodiment, the compound of formula (I) is a compound of formula (Iw):

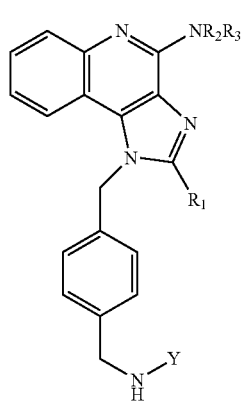

(Iw)

wherein:
R$_1$ is H, (C$_1$-C$_6$)alkyl, (C$_2$-C$_6$)alkenyl, (C$_2$-C$_6$)alkynyl, (C$_1$-C$_6$)alkanoyl, (C$_1$-C$_6$)alkoxycarbonyl, (C$_1$-C$_6$)alkanoyloxy, or (C$_3$-C$_6$)cycloalkyl, wherein any (C$_1$-C$_6$)alkyl, (C$_2$-C$_6$)alkenyl, (C$_2$-C$_6$)alkynyl, (C$_1$-C$_6$)alkanoyl, (C$_1$-C$_6$)alkoxycarbonyl, (C$_1$-C$_6$)alkanoyloxy, or (C$_3$-C$_6$)cycloalkyl, is optionally substituted with one or more groups independently selected from hydroxy, halo, oxo, (C$_3$-C$_5$)cycloalkyl, and (C$_1$-C$_6$)alkoxy;

each R$_2$ and R$_3$ is independently H, or (C$_1$-C$_6$)alkyl that is optionally substituted with one or more groups independently selected from hydroxy, halo, (C$_3$-C$_5$)cycloalkyl, and (C$_1$-C$_6$)alkoxy;

the benzyl ring is substituted with one —OR$^z$ and is optionally substituted with one or more groups independently selected from the group consisting of halogen, (C$_3$-C$_5$)cycloalkyl, —OR$^h$, isothiocyanate, —NR$^a$R$^b$, NR$^c$C(=O)R$^d$, —NR$^c$C(=S)—NRR and (C$_1$-C$_6$)alkyl optionally substituted with one or more groups independently selected from the group consisting of halogen, (C$_3$-C$_5$)cycloalkyl, —OR$^h$, isothiocyanate, —NR$^a$R$^b$, —NR$^c$C(=)R$^d$, and —NR$^c$C(=S)—NR$^f$R$^g$;

each R$^a$ and R$^b$ is independently selected from the group consisting of H, (C$_1$-C$_6$)alkyl, (C$_3$-C$_6$)cycloalkyl, (C$_1$-C$_6$)alkoxy and X-Y; or R$^a$ and R$^b$ together with the nitrogen to which they are attached form a aziridino, azetidino, morpholino, piperazino, pyrrolidino or piperidino;

each R$^c$ and R$^d$ is independently selected from the group consisting of H, (C$_1$-C$_6$)alkyl, (C$_3$-C$_6$)cycloalkyl, and (C$_1$-C$_6$)alkoxy;

each R is independently selected from the group consisting of H, (C$_1$-C$_6$)alkyl, (C$_3$-C$_6$)cycloalkyl, and (C$_1$-C$_6$)alkoxy;

each R$^f$ and R$^g$ is independently selected from the group consisting of H, (C$_3$-C$_6$)cycloalkyl, (C$_1$-C$_6$)alkoxy and (C$_1$-C$_6$)alkyl that is optionally substituted with NR$^k$R$^m$; or R$^f$ and R$^g$ together with the nitrogen to which they are attached form a aziridino, azetidino, morpholino, piperazino, pyrrolidino or piperidino;

each $R^h$ is independently selected from the group consists of H, $(C_1-C_6)$alkyl, $(C_2-C_6)$alkenyl, $(C_2-C_6)$alkynyl, $(C_3-C_5)$cycloalkyl —P(=O)OH)$_2$, or W—Z;

each $R^z$ is independently selected from the group consists of H, $(C_1-C_6)$alkyl, $(C_2-C_6)$alkenyl, $(C_2-C_6)$alkynyl, $(C_3-C_5)$cycloalkyl —P(=O)OH)$_2$, or W—Z;

each W is independently a linking group or is absent;

each Z is independently Z is an antigen; and

Y is a residue of hyaluronic acid;

or a salt thereof.

In one embodiment, the compound of formula (I) is a compound of formula (Ix):

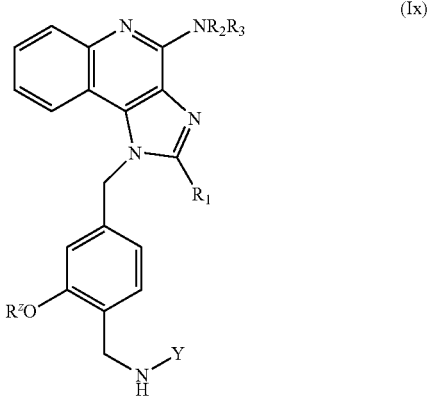

wherein:

$R_1$ is H, $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_1-C_6)$alkanoyloxy, or $(C_3-C_6)$cycloalkyl, wherein any $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_1-C_6)$alkanoyloxy, or $(C_3-C_6)$cycloalkyl, is optionally substituted with one or more groups independently selected from hydroxy, halo, oxo, $(C_3-C_5)$cycloalkyl, and $(C_1-C_6)$alkoxy;

each $R_2$ and $R_3$ is independently H, or $(C_1-C_6)$alkyl that is optionally substituted with one or more groups independently selected from hydroxy, halo, $(C_3-C_5)$cycloalkyl, and $(C_1-C_6)$alkoxy;

the benzyl ring is optionally substituted with one or more groups independently selected from the group consisting of halogen, $(C_3-C_5)$cycloalkyl, —O$R^h$, isothiocyanate, —N$R^aR^b$, —N$R^cC(=O)R^d$, —N$R^cC(=S)$—N$R^fR^g$, and $(C_1-C_6)$alkyl optionally substituted with one or more groups independently selected from the group consisting of halogen, $(C_3-C_5)$cycloalkyl, —O$R^h$, isothiocyanate, —N$R^aR^b$, —N$R^cC(=O)R^d$, and —N$R^cC(=S)$—N$R^fR^g$;

each $R^a$ and $R^b$ is independently selected from the group consisting of H, $(C_1-C_6)$alkyl, $(C_3-C_6)$cycloalkyl, $(C_1-C_6)$alkoxy and X-Y; or $R^a$ and $R^b$ together with the nitrogen to which they are attached form a aziridino, azetidino, morpholino, piperazino, pyrrolidino or piperidino;

each $R^c$ and $R^d$ is independently selected from the group consisting of H, $(C_1-C_6)$alkyl, $(C_3-C_6)$cycloalkyl, and $(C_1-C_6)$alkoxy;

each $R^e$ is independently selected from the group consisting of H, $(C_1-C_6)$alkyl, $(C_3-C_6)$cycloalkyl, and $(C_1-C_6)$alkoxy;

each $R^f$ and $R^g$ is independently selected from the group consisting of H, $(C_3-C_6)$cycloalkyl, $(C_1-C_6)$alkoxy and $(C_1-C_6)$alkyl that is optionally substituted with NR$^k$R$^m$; or R and $R^g$ together with the nitrogen to which they are attached form a aziridino, azetidino, morpholino, piperazino, pyrrolidino or piperidino;

each $R^h$ is independently selected from the group consists of H, $(C_1-C_6)$alkyl, $(C_2-C_6)$alkenyl, $(C_2-C_6)$alkynyl, $(C_3-C_5)$cycloalkyl —P(=O)OH)$_2$, or W—Z;

each $R^z$ is independently selected from the group consists of H, $(C_1-C_6)$alkyl, $(C_2-C_6)$alkenyl, $(C_2-C_6)$alkynyl, $(C_3-C_5)$cycloalkyl —P(=O)OH)$_2$, or W—Z;

each W is independently a linking group or is absent;

each Z is independently Z is an antigen; and

Y is a residue of hyaluronic acid;

or a salt thereof.

Hyaluronic acid is a polymer of disaccharides, themselves composed of D-glucuronic acid and N-acetyl-D-glucosamine, linked via alternating β-(1-4) and β-(1-3) glycosidic bonds.

Hyaluronic acid can be 25,000 disaccharide repeats in length. Polymers of hyaluronic acid can range in size from 5,000 to 20,000,000 Da in vivo. The average molecular weight in human synovial fluid is 3-4 million Da, and hyaluronic acid purified from human umbilical cord is 3,140,000 Da. Hyaluronic acid also contains silicon, ranging between 350 μg/g to 1900 μg/g depending on location in the organism.

In one embodiment the residue of hyaluronic acid, n is greater than 1.

In one embodiment the residue of hyaluronic acid, n is greater than 10.

In one embodiment the residue of hyaluronic acid, n is greater than 50.

In one embodiment the residue of hyaluronic acid, n is greater than 100.

In one embodiment the residue of hyaluronic acid, n is greater than 1000.

In one embodiment the residue of hyaluronic acid, n is greater than 5000.

In one embodiment the residue of hyaluronic acid, n is greater than 50,000.

In one embodiment the residue of hyaluronic acid, n is greater than 100,000.

In one embodiment the residue of hyaluronic acid, n is less than 100,000.

In one embodiment the residue of hyaluronic acid, n is less than 250,000.

In one embodiment the residue of hyaluronic acid, n is less than 500,000.

In one embodiment the residue of hyaluronic acid, n is less than 1,000,000.

Phosphates

In one embodiment of the invention, the compound is a compound of formula (Ic)

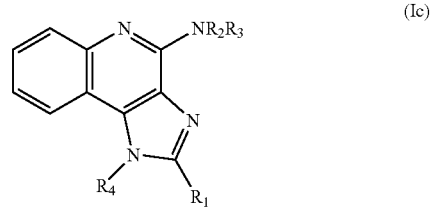

wherein:

R₁ is H, $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_1-C_6)$alkanoyloxy, or $(C_3-C_6)$cycloalkyl, wherein any $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_1-C_6)$alkanoyloxy, or $(C_3-C_6)$cycloalkyl, is optionally substituted with one or more groups independently selected from hydroxy, halo, oxo, $(C_3-C_5)$cycloalkyl, and $(C_1-C_6)$alkoxy;

each R₂ and R₃ is independently H, or $(C_1-C_6)$alkyl that is optionally substituted with one or more groups independently selected from hydroxy, halo, $(C_3-C_5)$cycloalkyl, and $(C_1-C_6)$alkoxy;

R₄ is benzyl, wherein the phenyl ring of the benzyl is substituted with one —OR$^z$ and is optionally substituted with one or more groups independently selected from the group consisting of halogen, $(C_3-C_8)$cycloalkyl, —OR$^h$, isothiocyanate, —N$^a$R$^b$, —NR$^c$C(=O)R$^d$, —NR$^c$C(=S)—NR$^f$R$^g$, and $(C_1-C_6)$alkyl optionally substituted with one or more groups independently selected from the group consisting of halogen, $(C_3-C_5)$cycloalkyl, —OR$^h$, isothiocyanate, —NR$^a$R$^b$, —NR$^c$C(=O)R$^d$, and —NR$^c$C(=S)—NR$^f$R$^g$;

each R$^a$ and R$^b$ is independently selected from the group consisting of H, $(C_1-C_6)$alkyl, $(C_3-C_6)$cycloalkyl, and $(C_1-C_6)$alkoxy; or R$^a$ and R$^b$ together with the nitrogen to which they are attached form a aziridino, azetidino, morpholino, piperazino, pyrrolidino or piperidino; each R$^c$ and R$^d$ is independently selected from the group consisting of H, $(C_1-C_6)$alkyl, $(C_3-C_6)$cycloalkyl, and $(C_1-C_6)$alkoxy;

each R is independently selected from the group consisting of H, $(C_1-C_6)$alkyl, $(C_3-C_6)$cycloalkyl, and $(C_1-C_6)$alkoxy;

each R$^f$ and R$^g$ is independently selected from the group consisting of H, $(C_3-C_6)$cycloalkyl, $(C_1-C_6)$alkoxy and $(C_1-C_6)$alkyl that is optionally substituted with NR$^k$R$^m$; or R$^f$ and R$^g$ together with the nitrogen to which they are attached form a aziridino, azetidino, morpholino, piperazino, pyrrolidino or piperidino;

each R$^k$ and R$^m$ is independently selected from the group consisting of H, $(C_1-C_6)$alkyl, and $(C_3-C_6)$cycloalkyl; or R$^k$ and R$^m$ together with the nitrogen to which they are attached form a aziridino, azetidino, morpholino, piperazino, pyrrolidino or piperidino; R$^z$ is —P(=O)OH)₂;

each R$^h$ is independently selected from the group consists of H, $(C_1-C_6)$alkyl, $(C_2-C_6)$alkenyl, $(C_2-C_6)$alkynyl, $(C_3-C_5)$cycloalkyl —P(=O)OH)₂, or W—Z;

W is a linking group or is absent;

Z is an antigen;

X is a linking group or is absent; and

Y is a residue of hyaluronic acid;

or a salt thereof.

In one embodiment of the invention, the compound is a compound of formula

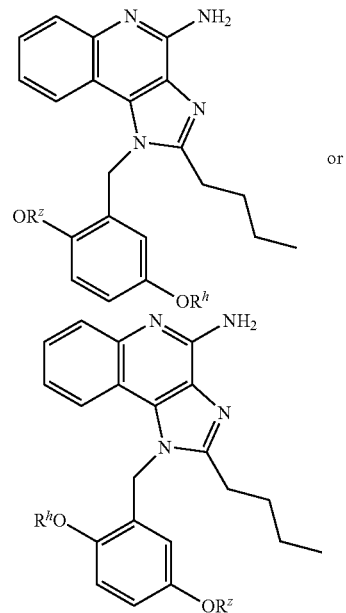

or wherein:

R$^z$ is —P(=O)OH)₂;

each R$^b$ is independently selected from the group consists of H, $(C_1-C_6)$alkyl, $(C_2-C_6)$alkenyl, $(C_2-C_6)$alkynyl, $(C_3-C_5)$cycloalkyl —P(=O)OH)₂, or W—Z;

W is a linking group or is absent;

Z is an antigen;

X is a linking group or is absent; and

Y is a residue of hyaluronic acid;

or a salt thereof.

Aluminum Complexes

Alum, is an adjuvant used in vaccines for humans. It includes a range of salts of aluminum precipitated under basic conditions, usually aluminum sulfate mixed with sodium or potassium hydroxide plus a variable amount of phosphate. The relative proportions determine the size, charge, and solubility of the resulting alum. Alum has been a component of many vaccines for decades and has an excellent safety record.

In one embodiment the invention provides a composition comprising a compound of formula I and a nanoparticle comprising aluminum hydroxide.

In one embodiment the invention provides a composition comprising one or more particles comprising aluminum and one or more compounds of formula (Id):

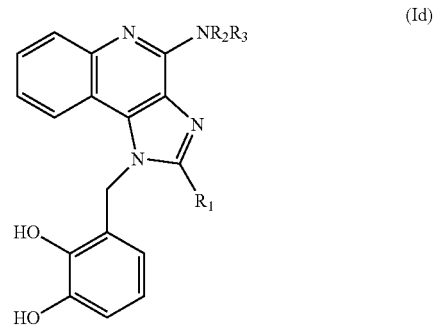

wherein:
R$_1$ is H, (C$_1$-C$_6$)alkyl, (C$_2$-C$_6$)alkenyl, (C$_2$-C$_6$)alkynyl, (C$_1$-C$_6$)alkanoyl, (C$_1$-C$_6$)alkoxycarbonyl, (C$_1$-C$_6$)alkanoyloxy, or (C$_3$-C$_6$)cycloalkyl, wherein any (C$_1$-C$_6$)alkyl, (C$_2$-C$_6$)alkenyl, (C$_2$-C$_6$)alkynyl, (C$_1$-C$_6$)alkanoyl, (C$_1$-C$_6$)alkoxycarbonyl, (C$_1$-C$_6$)alkanoyloxy, or (C$_3$-C$_6$)cycloalkyl, is optionally substituted with one or more groups independently selected from hydroxy, halo, oxo, (C$_3$-C$_5$)cycloalkyl, and (C$_1$-C$_6$)alkoxy; and
each R$_2$ and R$_3$ is independently H, or (C$_1$-C$_6$)alkyl that is optionally substituted with one or more groups independently selected from hydroxy, halo, (C$_3$-C$_5$)cycloalkyl, and (C$_1$-C$_6$)alkoxy;
or a salt thereof.

In one embodiment the invention provides a composition comprising one or more particles comprising aluminum and one or more compounds of formula (Iy):

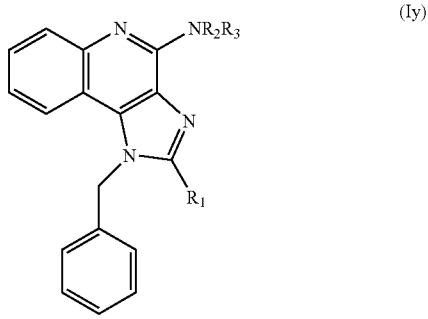

(Iy)

wherein:
R$_1$ is H, (C$_1$-C$_6$)alkyl, (C$_2$-C$_6$)alkenyl, (C$_2$-C$_6$)alkynyl, (C$_1$-C$_6$)alkanoyl, (C$_1$-C$_6$)alkoxycarbonyl, (C$_1$-C$_6$)alkanoyloxy, or (C$_3$-C$_6$)cycloalkyl, wherein any (C$_1$-C$_6$)alkyl, (C$_2$-C$_6$)alkenyl, (C$_2$-C$_6$)alkynyl, (C$_1$-C$_6$)alkanoyl, (C$_1$-C$_6$)alkoxycarbonyl, (C$_1$-C$_6$)alkanoyloxy, or (C$_3$-C$_6$)cycloalkyl, is optionally substituted with one or more groups independently selected from hydroxy, halo, oxo, (C$_3$-C$_8$)cycloalkyl, and (C$_1$-C$_6$)alkoxy;
each R$_2$ and R$_3$ is independently H, or (C$_1$-C$_6$)alkyl that is optionally substituted with one or more groups independently selected from hydroxy, halo, (C$_3$-C$_5$)cycloalkyl, and (C$_1$-C$_6$)alkoxy; and
the benzyl ring is substituted with one or two hydroxy groups;
or a salt thereof.

In one embodiment, the one or more particles comprising aluminum are nanoparticles. In one embodiment, the nanoparticles have a diameter of about 1 to about 100 nm. In one embodiment, the composition comprises a plurality of nanoparticles and a pluraliry of compounds of formula (Id). In one embodiment, the compounds of formula (Id) are associated with nanoparticles through coordination bonds. In one embodiment, the nanoparticles and the compounds of formula (Id) form a colloidal suspension in a liquid. In one embodiment, the liquid comprises water. In one embodiment, the invention provides a pharmaceutical composition comprising one or more particles comprising aluminum, one or more compounds of formula (Id), and a pharmaceutically acceptable excipient.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Linkers

As described herein, an antigen residue or a hyaluronic acid residue can be bonded (connected) to the remainder of the targeted conjugate agent through an optional linker. In one embodiment the linker is absent (e.g., the targeting element can be bonded (connected) directly to the remainder of the targeted conjugate). The linker can be variable provided the targeting conjugate functions as described herein. The linker can vary in length and atom composition and for example can be branched or non-branched or cyclic or a combination thereof. The linker may also modulate the properties of the targeted conjugate such as but not limited to solubility, stability and aggregation.

Since the linkers used in the targeted conjugates (e.g., linkers comprising polyethylene glycol (PEG)) can be highly variable, it is possible to use different sizes and types of targeting elements and still maintain the desired and/or optimal pharmacokinetic profile for the targeted conjugate.

In one embodiment the linker is —CH$_2$(CH$_2$N$_3$CH$_2$)$_3$NHC(=O)(CH$_2$)$_3$—.

In one embodiment the linker is —(CH$_2$)$_s$—; wherein s is 1, 2, 3, 4, 5, 6, 7, 8, 9, or 10.

In one embodiment the linker is —((CH$_2$)$_t$—O—(CH$_2$))$_q$—; wherein each t is independently 1,2,3, or 4, and q is 1, 2, 3, 4, 5, 6, 7, 8, 9, or 10.

In one embodiment L is absent; R$_5$ is H; L' is a divalent, branched or unbranched hydrocarbon chain, having from 1 to 20 carbon atoms, wherein one or more (e.g. 1, 2, 3, or 4) of the carbon atoms is optionally replaced by a non-peroxide (—O—); and R$_{5'}$ is H, an activated group, or NR$^x$R$^y$.

In one embodiment L is a divalent, branched or unbranched hydrocarbon chain, having from 1 to 20 carbon atoms, wherein one or more (e.g. 1, 2, 3, or 4) of the carbon atoms is optionally replaced by a non-peroxide (—O—); R$_5$ is H, an activated group, or NR$^Y$; L' is absent; and R$_{5'}$ is H.

In one embodiment L is absent; R$_5$ is H; L' is a divalent, branched or unbranched hydrocarbon chain, having from 1 to 20 carbon atoms, wherein one or more (e.g. 1, 2, 3, or 4) of the carbon atoms is optionally replaced by a non-peroxide (—O—); and R$_5$— is an activated group or N$_x$R$_y$.

In one embodiment L is a divalent, branched or unbranched hydrocarbon chain, having from 1 to 20 carbon atoms, wherein one or more (e.g. 1, 2, 3, or 4) of the carbon atoms is optionally replaced by a non-peroxide (—O—); R$_5$ is an activated group or NR$^Y$; L' is absent; and R$_{5'}$ is H.

In one embodiment L is absent; R$_5$ is H; L' is a divalent, branched or unbranched hydrocarbon chain, having from 1 to 20 carbon atoms; and R$_{5'}$ is an activated group or NR$^x$R$^y$.

In one embodiment L is a divalent, branched or unbranched hydrocarbon chain, having from 1 to 20 carbon atoms; $R_5$ is an activated group or $NR^xR^y$; L' is absent; and $R_{5'}$ is H.

In one embodiment L is absent; $R_5$ is H; L' is a divalent, branched or unbranched hydrocarbon chain, having from 1 to 20 carbon atoms, wherein one or more (e.g. 1, 2, 3, or 4) of the carbon atoms is replaced by a non-peroxide (—O—); and $R_{5'}$— is an activated group or $NR^xR^y$.

In one embodiment L is a divalent, branched or unbranched hydrocarbon chain, having from 1 to 20 carbon atoms, wherein one or more (e.g. 1, 2, 3, or 4) of the carbon atoms is replaced by a non-peroxide (—O—); $R_5$ is an activated group or $NR^xR^y$; L' is absent; and $R_{5'}$ is H.

The invention will now be illustrated by the following non-limiting examples.

EXAMPLES

Example 1. General Procedure for the Synthesis of Phenolic Compounds 15-24

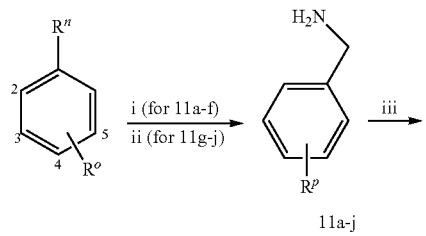

1: $R^n$ = CN, $R^o$ = 2-OH
2: $R^n$ = CN, $R^o$ = 3-OH
3: $R^n$ = CN, $R^o$ = 4-OH
4: $R^n$ = CN, $R^o$ = 3-Me, 4-OH
5: $R^n$ = CN, $R^o$ = 3-F, 4-OH
6: $R^n$ = CN, $R^o$ = 3-OME, 4-OH
7: $R^n$ = CHO, $R^o$ = 3-OH, 4-OH
8: $R^n$ = CHO, $R^o$ = 2-OH, 3-OH
9: $R^n$ = CHO, $R^o$ = 3-OH, 5-OH
10: $R^n$ = CHO, $R^o$ = 2-OH, 5-OH

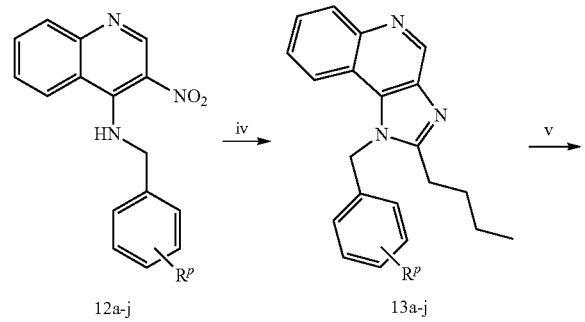

11-14a: $R^p$ = 2-OMOM
11-14b: $R^p$ = 3-OMOM
11-14c: $R^p$ = 4-OMOM
11-14d: $R^p$ = 3-Me, 4-OMOM
11-14e: $R^p$ = 3-F, 4-OMOM
11-14f: $R^p$ = 3-OMe, 4-OMOM
11-14g: $R^p$ = 3-OMOM, 4-OMOM
11-14h: $R^p$ = 2-OMOM, 3-OMOM
11-14i: $R^p$ = 3-OMOM, 5-OMOM
11-14j: $R^p$ = 2-OMOM, 5-OMOM

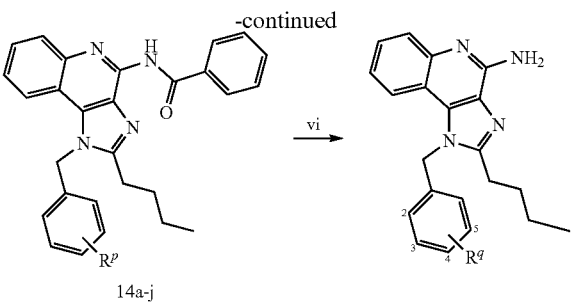

15: $R^q$ = 2-OH
16: $R^q$ = 3-OH
17: $R^q$ = 4-OH
18: $R^q$ = 3-Me, 4-OH
19: $R^q$ = 3-F, 4-OH
20: $R^q$ = 3-OMe, 4-OH
21: $R^q$ = 3-OH, 4-OH
22: $R^q$ = 2-OH, 3-OH
23: $R^q$ = 3-OH, 5-OH
24: $R^q$ = 2-OH, 5-OH

Reagents and conditions: (i) (a) chloromethyl methyl ether, DIPEA, DCM, rt, 8 h, (b) 1N LiAlH₄ in THF, THF, 65° C., 1 h; (ii) (a) chloromethyl methyl ether, DIPEA, DCM, rt, 8 h,
(b) hydroxylamine hydrochloride, NaOAc, EtOH, 65° C., 1 h, (c) 1N LiAlH₄ in THF, THF, 65° C, 1 h;
(iii) 4-chloro-3-nitroquinoline, DIPEA, DCM, rt, 12 h; (iv) (a) Pt/C, 50 psi H₂, EtOAc, 1 h,
(b) valeroyl chloride, THF, DIPEA, rt, 15 min, (c) CaO, MeOH, 65° C., 12 h;
(v) (a) m-CPBA, DCM/MeOH/CHCl₃, rt, 1 h, (b) benzoyl isocyanate, DCM, rt, 15 min;
(vi) (a) NaOMe, MeOH, 65° C., 1 h, (b) 4N HCl in dioxane, rt, 1 h.

Benzyl amine was prepared by reducing hydroxybenzonitrile or benzaldehyde oxime (starting from dihydroxybenzaldehyde) with lithium aluminum hydride. This amine intermediate was then reacted with 4-chloro-3-nitroquinoline, followed by hydrogenation under the catalysis of 10% platinum on carbon. Valeroyl chloride was used to cyclize imidazoquinoline ring in the presence of calcium oxide. Oxidation of nitro atom of quinoline ring helped introducing 4-amine group by using benzoyl isocyanate. Final phenolic compounds can be obtained by deprotecting methoxymethyl ether group and benzoyl group sequentially. Reaction details are illustrated below by describing the synthesis of representative compound 18.

(4-(Methoxymethoxy)-3-methylphenyl)methanamine (11d). To the solution of 4-hydroxy-3-methylbenzonitrile (1.06 g, 8 mmol) and N,N-diisopropylethylamine (2.78 mL, 16 mmol) in DCM (15 mL), chloromethyl methyl ether (0.912 mL, 12 mmol) was slowly added at rt while stirring. After completion (8 h), the solvent was evaporated and target compound was isolated through flash column chromatography (10% EtOAc/Hexanes) as a colorless oil (1.34 g, yield=95%). ¹H NMR (500 MHz, Chloroform-d) δ 7.45 (d, J=8.6 Hz, 1H), 7.43 (s, 1H), 7.10 (d, J=8.5 Hz, 1H), 5.25 (s, 2H), 3.48 (s, 3H), 2.25 (s, 3H). ¹³C NMR (126 MHz, CDCl₃) δ 158.9, 134.4, 131.8, 128.8, 119.4, 113.8, 104.7, 94.2, 56.4, 16.3. MS (ESI-TOF) for C₁₀H₁₁NO₂ [M+H]⁺ calculated 178.0863; found 178.0873. To the solution of obtained colorless oil 4-(methoxymethoxy)-3-methylbenzonitrile (1.30 g, 7.4 mmol) in 10 mL THF, a 1N lithium aluminum hydride solution in THF (18.5 mL, 18.5 mmol) was added slowly. After stirring at reflux for 1 h, the reaction mixture was quenched slowly with the addition of 1N NaOH in an ice bath. The precipitate was subsequently filtered off through celite. The filtrate was extracted with DCM and brine and evaporated under vacuum. The target compound 11d was isolated through flash column chromatography (8% MeOH/DCM) as a yellow oil (1.11 g, yield=84%). $^1$H NMR (500 MHz, Chloroform-d) δ 7.11 (s, 1H), 7.07 (d, J=8.4 Hz, 1H), 7.00 (d, J=8.2 Hz, 1H), 5.19 (s, 2H), 3.78 (s, 2H), 3.48 (s, 3H), 2.25 (s, 3H). $^{13}$C NMR (126 MHz, CDCl$_3$) δ 154.4, 136.7, 129.9, 127.7, 125.5, 114.1, 94.7, 56.1, 46.1, 16.5. MS (ESI-TOF) for C$_{10}$H$_{15}$NO$_2$ [M+H]$^+$ calculated 182.1176; found 182.1154, 165.0907, 135.0804.

N-(4-(Methoxymethoxy)-3-methylbenzyl)-3-nitroquinolin-4-amine (12d). To the solution of 11d (1.13 g, 6.24 mmol) and DIPEA (1.63 mL, 9.36 mmol) in 15 mL DCM was added 4-chloro-3-nitroquinoline (1.30 g, 6.24 mmol). The reaction was stirred at rt for 12 h. After completion, the solvent was evaporated and target compound 12d was isolated through flash column chromatography (70% EtOAc/Hexanes) as a yellow solid (2.14 g, yield=97%). $^1$H NMR (500 MHz, Chloroform-d) δ 9.79 (s, 1H), 9.39 (s, 1H), 8.32 (d, J=8.5 Hz, 1H), 8.02 (d, J=8.3 Hz, 1H), 7.78 (t, J=7.5 Hz, 1H), 7.46 (t, J=7.7 Hz, 1H), 7.17 (d, J=8.7 Hz, 2H), 7.09 (d, J=8.2 Hz, 1H), 5.23 (s, 2H), 5.01 (d, J=5.2 Hz, 2H), 3.50 (s, 3H), 2.27 (s, 3H). $^{13}$C NMR (126 MHz, CDCl$_3$) δ 155.7, 151.0, 150.8, 147.6, 132.8, 130.6, 130.0, 129.8, 128.6, 127.1, 126.3, 126.1, 125.6, 119.4, 114.4, 94.5, 56.3, 52.9, 16.6. MS (ESI-TOF) for C$_{19}$H$_{19}$N$_3$O$_4$ M+H]$^+$ calculated 354.1448; found 354.1476.

2-Butyl-J-(4-(methoxymethoxy)-3-methylbenzyl)-JH-imidazo[4,5-c]quinoline (13d). Compound 12d (2.33 g, 6.60 mmol) was dissolved in EtOAc (25 mL). A catalytic amount of 10% wt Pt/C was added to the reaction mixture, which was subjected to hydrogenation at 50 psi hydrogen for 1 h. The desired reduced product was filtered and concentrated as a red oil which can be used directly to the next step (2.11 g, yield=99%). $^1$H NMR (500 MHz, Chloroform-d) δ 8.50 (s, 1H), 7.97 (d, J=8.2 Hz, 1H), 7.75 (d, J=8.3 Hz, 1H), 7.46 (t, J=7.5 Hz, 1H), 7.41 (t, J=7.5 Hz, 1H), 7.17 (s, 1H), 7.14 (d, J=8.7 Hz, 1H), 7.02 (d, J=8.1 Hz, 1H), 5.20 (s, 2H), 4.29 (s, 2H), 3.74 (s, 2H), 3.49 (s, 3H), 2.24 (s, 3H). $^{13}$C NMR (126 MHz, CDCl$_3$) δ 155.0, 144.6, 143.8, 135.5, 133.0, 131.4, 130.6, 130.1, 128.0, 126.4, 126.1, 125.9, 124.0, 120.2, 114.2, 94.6, 56.2, 50.7, 16.5. MS (ESI-TOF) for C$_{19}$H$_{21}$N$_3$O$_2$ [M+H]$^+$ calculated 324.1707; found 324.1756. To the solution of obtained red oil (2.11 g, 6.53 mmol) and DIPEA (2.84 mL, 16.33 mmol) in 15 mL THF, was added valeroyl chloride (790 μL, 6.66 mmol) dropwise. After addition, the reaction was stirred at rt for 15 min. Upon completion of the reaction, the solvent was evaporated and desired pentanamide was isolated through flash column chromatography (5% MeOH/DCM) as a yellow solid (2.64 g, yield=99%). $^1$H NMR (500 MHz, Chloroform-d) δ 8.66 (s, 1H), 7.97 (d, J=8.2 Hz, 1H), 7.88 (d, J=8.4 Hz, 1H), 7.59 (t, J=7.5 Hz, 1H), 7.46 (s, 1H), 7.41 (t, J=7.5 Hz, 1H), 7.09 (s, 1H), 7.06 (d, J=8.0 Hz, 1H), 7.01 (d, J=8.0 Hz, 1H), 5.19 (s, 2H), 4.66 (s, 1H), 4.47 (s, 2H), 3.48 (s, 3H), 2.27 (t, J=7.5 Hz, 2H), 2.23 (s, 3H), 1.73-1.57 (m, 2H), 1.43-1.28 (m, 2H), 0.89 (t, J=7.2 Hz, 3H). $^{13}$C NMR (126 MHz, CDCl$_3$) δ 173.0, 155.1, 149.8, 147.6, 145.6, 132.5, 130.0 (2C, overlapped), 128.9, 128.2, 125.8, 125.5, 122.0, 121.8, 117.3, 114.3, 94.6, 56.2, 51.4, 36.7, 27.8, 22.6, 16.5, 13.9. MS (ESI-TOF) for C$_{24}$H$_{29}$N$_3$O$_3$ [M+H]$^+$ calculated 408.2282; found 408.2327. To the solution of obtained yellow solid pentanamide (2.46 g, 6.04 mmol) in 25 mL methanol was added calcium oxide (in excess). The reaction mixture was allowed to stir at 65° C. for 12 h. After completion, the solvent was evaporated and target compound 13d was isolated through flash column chromatography (60% EtOAc/Hexanes) as a pale yellow solid (1.61 g, yield=68%). $^1$H NMR (500 MHz, Chloroform-d) S 9.35 (s, 1H), 8.24 (d, J=8.4 Hz, 1H), 7.98 (d, J=8.4 Hz, 1H), 7.60 (t, J=7.6 Hz, 1H), 7.44 (t, J=7.6 Hz, 1H), 6.97 (d, J=8.4 Hz, 1H), 6.84 (s, 1H), 6.79 (d, J=8.5 Hz, 1H), 5.71 (s, 2H), 5.15 (s, 2H), 3.45 (s, 3H), 2.93 (t, J=7.7 Hz, 2H), 2.16 (s, 3H), 1.90 (p, J=7.6 Hz, 2H), 1.47 (h, J=7.1 Hz, 2H), 0.96 (t, J=7.2 Hz, 3H). $^{13}$C NMR (126 MHz, CDCl$_3$) δ 156.0, 155.3, 145.1, 144.9, 136.7, 134.3, 131.0, 128.7, 128.0, 128.0, 126.8, 126.4, 124.1, 120.2, 117.8, 114.5, 94.6, 56.2, 48.6, 29.8, 27.3, 22.7, 16.6, 13.9. MS (ESI-TOF) for C$_{24}$H$_{27}$N$_3$O$_2$ [M+H]$^+$ calculated 390.2176; found 390.2193.

N-(2-Butyl-J-(4-(methoxymethoxy)-3-methylbenzyl)-JH-imidazo[4,5-c]quinolin-4-yl)benzamide (14d). To the solution of compound 13d (1.17 g, 3.01 mmol) in a mixed solvent of DCM/MeOH/CHCl$_3$ (7.5 mL/0.75 mL/7.5 mL) was added 3-chloroperbenzoic acid (1.31 g, 7.53 mmol). The reaction was heated to reflux for 1 h. After completion, the solvent was evaporated and the target oxide compound was isolated through flash column chromatography (5% MeOH/DCM) as a red solid (1.21 g, yield=99%). $^1$H NMR (500 MHz, Chloroform-d) δ 9.09 (s, 1H), 9.01 (d, J=8.7 Hz, 1H), 7.95 (d, J=8.4 Hz, 1H), 7.67 (t, J=7.8 Hz, 1H), 7.55 (t, J=7.7 Hz, 1H), 6.99 (d, J=8.4 Hz, 1H), 6.83 (s, 1H), 6.78 (d, J=8.4 Hz, 1H), 5.67 (s, 2H), 5.16 (s, 2H), 3.45 (s, 3H), 2.91 (t, J=7.7 Hz, 2H), 2.17 (s, 3H), 1.99-1.79 (m, 2H), 1.54-1.39 (m, 2H), 0.95 (t, J=7.3 Hz, 3H). $^{13}$C NMR (126 MHz, CDCl$_3$) δ 157.9, 155.5, 138.7, 136.1, 130.9, 128.9 (2C, overlapped), 127.8 (2C, overlapped), 127.7, 127.3, 124.0, 122.0, 120.6, 118.1, 114.6, 94.5, 56.2, 48.7, 29.7, 27.3, 22.7, 16.6, 13.9. MS (ESI-TOF) for C$_{24}$H$_{27}$N$_3$O$_3$ [M+H]$^+$ calculated 406.2125; found 406.2137. To the solution of obtained red oxide solid (1.50 g, 3.7 mmol) in 15 mL DCM was added benzoyl isocyanate (0.65 g, 4.4 mmol). After completion, the solvent was evaporated and the target compound was isolated through flash column chromatography (45% EtOAc/Hexanes) as a white solid (1.61 g, yield=86%). $^1$H NMR (500 MHz, Chloroform-d) δ 9.42 (s, 1H), 8.15 (s, 2H), 7.85 (d, J=6.4 Hz, 1H), 7.62-7.47 (m, 4H), 7.32 (s, 1H), 6.98 (d, J=8.2 Hz, 1H), 6.80 (d, J=10.0 Hz, 2H), 5.68 (s, 2H), 5.16 (s, 2H), 3.45 (s, 3H), 2.92 (t, J=7.5 Hz, 2H), 2.16 (s, 3H), 1.86 (s, 2H), 1.54-1.37 (m, 2H), 0.95 (t, J=7.3 Hz, 3H). $^{13}$C NMR (126 MHz, CDCl$_3$) δ 155.4, 132.0, 129.3, 128.8, 127.9, 125.0, 124.1, 114.5, 94.5, 56.2, 48.7, 30.0, 27.3, 22.8, 16.6, 13.9. MS (ESI-TOF) for C$_{31}$H$_{32}$N$_4$O$_3$ [M+H]$^+$ calculated 509.2547; found 509.2546.

4-((4-Amino-2-butyl-JH-imidazo[4,5-c]quinolin-1-yl)methyl)-2-methylphenol (18). To the solution of compound 14d (51 mg, 0.1 mmol) in methanol (2.0 mL) was added sodium methoxide (in excess). The reaction mixture was refluxed for 1 h. After completion, deprotected product was isolated through flash column chromatography as a yellow solid. This yellow solid was then dissolved into methanol (2.0 mL), and was treated with 4N HCl in dioxane (1.0 mL) at rt for 1 h. After completion, all solvents were evaporated and the resulting residue was purified through flash column chromatography (5% MeOH/DCM) as a white solid (28 mg, yield=80%). $^1$H NMR (500 MHz, DMSO-d$_6$) δ 9.32 (s, 1H), 7.82 (d, J=8.2 Hz, 1H), 7.57 (d, J=8.3 Hz, 1H), 7.34 (t, J=7.6 Hz, 1H), 7.06 (t, J=7.5 Hz, 1H), 6.81 (s, 1H), 6.67 (d, J=8.3 Hz, 1H), 6.59 (d, J=8.2 Hz, 1H), 6.54 (s, 2H), 5.68 (s, 2H), 2.88 (t, J=7.6 Hz, 2H), 2.02 (s, 3H), 1.84-1.59 (m, 2H), 1.54-1.26 (m, 2H), 0.86 (t, J=7.3 Hz, 3H). $^{13}$C NMR (126 MHz, DMSO) δ 154.7, 153.6, 151.7, 144.6, 133.0, 127.8 (2C, overlapped), 126.4, 126.4, 126.0, 124.4, 123.8, 121.0, 120.3, 114.9, 114.7, 47.7, 29.6, 26.3, 21.9, 16.1, 13.7. MS (ESI-TOF) for C$_{22}$H$_{24}$N$_4$O [M+H]$^+$ calculated 361.2023; found 361.2024.

2-((4-Amino-2-butyl-JH-imidazo[4,5-c]quinolin-1-yl)methyl)phenol (15). Intermediate 11a: it was synthesized similarly to intermediate 11d as described above. Yellow oil, yield=60% (for two steps), purified through flash column chromatography (10% MeOH/DCM). Intermediate 12a: it was synthesized similarly to intermediate 12d as described above. Yellow solid, yield=92%, purified through flash column chromatography (5% MeOH/DCM). MS (ESI-TOF) for $C_{18}H_{17}N_3O_4[M+H]^+$ calculated 340.1292; found 340.1285. Intermediate 13a: it was synthesized similarly to intermediate 13d as described above. Yellow solid, yield=32% (for three steps), purified through flash column chromatography (4% MeOH/DCM). MS (ESI-TOF) for $C_{23}H_{25}N_3O_2$ [M+H]$^+$ calculated 376.2020; found 376.2011. Intermediate 14a: it was synthesized similarly to intermediate 14d as described above. Yellow solid, yield=46% (for two steps), purified through flash column chromatography (3% MeOH/DCM). MS (ESI-TOF) for $C_{30}H_{30}N_4O_3$ [M+H]$^+$ calculated 495.2391; found 495.2378.

Compound 15: it was synthesized similarly to compound 18 as described above. White solid, yield=65% (for two steps), purified through flash column chromatography (10% MeOH/DCM). $^1$H NMR (500 MHz, DMSO-d$_6$) δ 13.86 (s, 1H), 10.28 (s, 2H), 7.85 (d, J=8.3 Hz, 1H), 7.79 (d, J=8.3 Hz, 1H), 7.62 (t, J=7.7 Hz, 1H), 7.37 (t, J=7.7 Hz, 1H), 7.11 (t, J=7.3 Hz, 1H), 6.99 (d, J=8.1 Hz, 1H), 6.62 (t, J=7.4 Hz, 1H), 6.36 (d, J=7.5 Hz, 1H), 5.75 (s, 2H), 2.97 (t, J=7.7 Hz, 2H), 2.05-1.58 (m, 2H), 1.55-1.31 (m, 2H), 0.86 (t, J=7.3 Hz, 3H). $^3$C NMR (126 MHz, DMSO) δ 157.1, 154.3, 148.8, 135.5, 133.6, 129.4, 128.8, 125.5, 124.7, 124.5, 121.3, 121.3, 119.4, 118.5, 115.3, 112.5, 44.6, 29.2, 26.2, 21.7, 13.6. MS (ESI-TOF) for $C_{21}H_{22}N_{40}$ [M+H]$^+$ calculated 347.1866; found 347.1871. 3-((4-Amino-2-butyl-JH-imidazo[4,5-c]quinolin-1-yl)methyl)phenol (16). Intermediate 11b: it was synthesized similarly to intermediate 11d as described above. Yellow oil, yield=87% (for two steps), purified through flash column chromatography (10% MeOH/DCM). $^1$H NMR (500 MHz, Chloroform-d) δ 7.25 (t, J=7.9 Hz, 1H), 6.99 (d, J=2.3 Hz, 1H), 6.96 (d, J=7.5 Hz, 1H), 6.92 (dd, J=2.2, 8.2 Hz, 1H), 5.18 (s, 2H), 3.84 (s, 2H), 3.48 (s, 3H).

Intermediate 12b: it was synthesized similarly to intermediate 12d as described above. Yellow solid, yield=90%, purified through flash column chromatography (35% EtOAc/Hexanes). $^1$H NMR (500 MHz, Chloroform-d) δ 10.02 (s, 1H), 9.43 (s, 1H), 8.32 (d, J=8.4 Hz, 1H), 8.18 (s, 1H), 7.83 (t, J=7.4 Hz, 1H), 7.51 (s, 1H), 7.37 (t, J=7.8 Hz, 1H), 7.07 (dd, J=5.3, 13.7 Hz, 3H), 5.20 (s, 2H), 5.11 (d, J=5.4 Hz, 2H), 3.49 (s, 3H). MS (ESI-TOF) for $C_{18}H_{17}N_3O_4$ [M+H]$^+$ calculated 340.1292; found 340.1221.

Intermediate 13b: it was synthesized similarly to intermediate 13d as described above. Yellow solid, yield=71% (for three steps), purified through flash column chromatography (57% EtOAc/Hexanes). $^1$H NMR (500 MHz, Chloroform-d) δ 9.35 (s, 1H), 8.31 (s, 1H), 7.95 (d, J=8.4 Hz, 1H), 7.62 (t, J=7.5 Hz, 1H), 7.45 (t, J=7.0 Hz, 1H), 7.25-7.20 (m, 1H), 6.98 (d, J=8.3 Hz, 1H), 6.76 (s, 1H), 6.63 (d, J=7.6 Hz, 1H), 5.77 (s, 2H), 5.10 (s, 2H), 3.40 (d, J=1.4 Hz, 3H), 2.95 (t, J=7.7 Hz, 2H), 1.90 (p, J=7.5, 8.0 Hz, 2H), 1.47 (m, 2H), 0.95 (t, J=7.3 Hz, 3H). MS (ESI-TOF) for $C_{23}H_{25}N_3O_2$ [M+H]$^+$ calculated 376.2020; found 376.2040.

Intermediate 14b: it was synthesized similarly to intermediate 14d as described above. Yellow solid, yield=26% (for two steps), purified through flash column chromatography (71% EtOAc/Hexanes). $^1$H NMR (500 MHz, Chloroform-d) δ 8.24 (s, 2H), 8.06 (s, 1H), 7.82 (d, J=7.7 Hz, 1H), 7.54 (d, J=5.7 Hz, 1H), 7.32 (t, J=7.4 Hz, 1H), 7.23 (d, J=8.6 Hz, 1H), 6.98 (d, J=7.6 Hz, 1H), 6.76 (d, J=7.5 Hz, 1H), 6.64 (t, J=7.5 Hz, 1H), 5.74 (s, 2H), 5.10 (s, 2H), 3.40 (s, 3H), 2.99-2.79 (m, 2H), 1.86 (s, 2H), 1.62-1.38 (m, 2H), 0.95 (t, J=7.2 Hz, 3H). MS (ESI-TOF) for $C_{30}H_{30}N_4O_3$ [M+H]$^+$ calculated 495.2391; found 495.2398.

Compound 16: it was synthesized similarly to compound 18. White solid, yield=76% (for two steps), purified through flash column chromatography (10% MeOH/DCM). $^1$H NMR (500 MHz, DMSO-d$_6$) δ 13.80 (s, 1H), 9.48 (s, 2H), 7.97 (d, J=8.3 Hz, 1H), 7.81 (s, 1H), 7.64 (t, J=7.7 Hz, 1H), 7.39 (t, J=7.7 Hz, 1H), 7.13 (t, J=7.9 Hz, 1H), 6.66 (d, J=8.1 Hz, 1H), 6.51 (d, J=7.7 Hz, 1H), 6.40 (s, 1H), 5.88 (s, 2H), 2.96 (t, J=7.7 Hz, 2H), 2.04-1.57 (m, 2H), 1.57-1.29 (m, 2H), 0.87 (t, J=7.3 Hz, 3H). $^3$C NMR (126 MHz, DMSO) δ 157.9, 157.0, 148.8, 136.9, 135.4, 133.6, 130.2, 129.5, 124.8, 124.5, 121.7, 118.5, 116.0, 114.7, 112.4, 112.1, 48.3, 29.2, 26.2, 21.7, 13.6. MS (ESI-TOF) for $C_{21}H_{22}N_4O$ [M+H]$^+$ calculated 347.1866; found 347.1868. 4-((4-Amino-2-butyl-JH-imidazo[4,5-c]quinolin-1-yl)methyl)phenol (17). Intermediate 11c: it was synthesized similarly to intermediate 11d as described above. Yellow oil, yield=64% (for two steps), purified through flash column chromatography (8% MeOH/DCM). $^1$H NMR (500 MHz, Chloroform-d) δ 7.24 (d, J=8.6 Hz, 2H), 7.01 (d, J=8.6 Hz, 2H), 5.17 (s, 2H), 3.82 (s, 2H), 3.48 (s, 3H). MS (ESI-TOF) for $C_9H_{13}NO_2$ [M+H]$^+$ calculated 168.1019 (fragment peak: 151.0759); found 151.0747 and 121.0701.

Intermediate 12c: it was synthesized similarly to intermediate 12d as described above. Yellow solid, yield=99%, purified through flash column chromatography (42% EtOAc/Hexanes). $^1$H NMR (500 MHz, DMSO-d$_6$) δ 9.39 (s, 1H), 9.03 (s, 1H), 8.54 (d, J=8.5 Hz, 1H), 7.91 (dd, J=1.1, 8.3 Hz, 1H), 7.87-7.77 (m, 1H), 7.68-7.51 (m, 1H), 7.28 (d, J=8.6 Hz, 2H), 6.99 (d, J=8.6 Hz, 2H), 5.17 (s, 2H), 4.83 (d, J=5.4 Hz, 2H), 3.36 (s, 3H). MS (ESI-TOF) for $C_{18}H_{17}N_3O_4$ [M+H]$^+$ calculated 340.1292; found 340.1296.

Intermediate 13c: it was synthesized similarly to intermediate 13d as described above. Yellow solid, yield=68% (for three steps), purified through flash column chromatography (75% EtOAc/Hexanes or 8% MeOH/DCM). $^1$H NMR (500 MHz, Chloroform-d) δ 9.35 (s, 1H), 8.31 (s, 1H), 7.98 (d, J=8.4 Hz, 1H), 7.63 (t, J=7.7 Hz, 1H), 7.47 (t, J=7.6 Hz, 1H), 7.08-6.86 (m, 4H), 5.76 (s, 2H), 5.13 (s, 2H), 3.44 (s, 3H), 3.03-2.82 (m, 2H), 2.18-1.79 (m, 2H), 1.62-1.40 (m, 2H), 0.96 (t, J=7.3 Hz, 3H). MS (ESI-TOF) for $C_{23}H_{25}N_3O_2$ [M+H]$^+$ calculated 376.2020; found 376.2010.

Intermediate 14c: it was synthesized similarly to intermediate 14d as described above. Yellow solid, yield=74% (for two steps), purified through flash column chromatography (54% EtOAc/Hexanes or 3% MeOH/DCM). $^1$H NMR (500 MHz, Chloroform-d) δ 8.23 (s, 2H), 8.07 (s, 1H), 7.83 (d, J=8.3 Hz, 1H), 7.72-7.48 (m, 4H), 7.32 (t, J=7.6 Hz, 1H), 7.09-6.87 (m, 4H), 5.72 (s, 2H), 5.13 (s, 2H), 3.45 (s, 3H), 3.16-2.65 (m, 2H), 2.10-1.72 (m, 2H), 1.66-1.36 (m, 2H), 0.95 (t, J=7.4 Hz, 3H). MS (ESI-TOF) for $C_{30}H_{30}N_4O_3$ [M+H]$^+$ calculated 495.2391; found 495.2396.

Compound 17: it was synthesized similarly to compound 18 as described above. White solid, yield=65% (for two steps), purified through flash column chromatography (12% MeOH/DCM). $^1$H NMR (500 MHz, DMSO-d) S 9.40 (s, 1H), 7.84 (d, J=8.1 Hz, 1H), 7.59 (d, J=8.2 Hz, 1H), 7.36 (t, J=7.5 Hz, 1H), 7.08 (t, J=7.5 Hz, 1H), 6.85 (d, J=8.4 Hz, 3H), 6.69 (d, J=8.5 Hz, 4H), 5.73 (s, 2H), 3.00-2.79 (m, 3H), 1.70 (p, J=7.6 Hz, 3H), 1.37 (h, J=7.4 Hz, 3H), 0.87 (t, J=7.4 Hz, 3H). $^3$C NMR (126 MHz, DMSO) δ 156.7, 153.8, 151.4, 143.8, 133.0, 126.7 (2C), 126.5, 126.5, 126.2, 125.4, 121.2, 120.3, 115.7 (2C), 114.4, 47.6, 29.6, 26.3, 21.8, 13.7. MS (ESI-TOF) for $C_{21}H_{22}N_{40}$ [M+H]$^+$ calculated 347.1866; found 347.1872.

4-((4-Amino-2-butyl-JH-imidazo[4,5-c]quinolin-1-yl)methyl)-2-fluorophenol (19). Intermediate 11e: it was synthesized similarly to intermediate 11d as described above. Colorless oil, yield=89% (for two steps), purified through flash column chromatography (7% MeOH/DCM). $^1$H NMR (500 MHz, Chloroform-d) δ 7.14 (t, J=7.4 Hz, 1H), 7.08 (d, J=11.3 Hz, 1H), 6.99 (d, J=7.8 Hz, 1H), 5.19 (s, 2H), 3.81 (s, 2H), 3.52 (s, 3H). MS (ESI-TOF) for $C_9H_{12}FNO_2$ [M+H]$^+$ calculated 186.0925 (fragment peak: 169.0665); found 169.0649 and 139.0555.

Intermediate 12e: it was synthesized similarly to intermediate 12d as described above. Yellow solid, yield=98%, purified through flash column chromatography (50% EtOAc/Hexanes). $^1$H NMR (500 MHz, Methanol-$d_4$) δ 9.19 (s, 1H), 8.44 (d, J=8.6 Hz, 1H), 8.15-7.89 (m, 1H), 7.88-7.71 (m, 1H), 7.65-7.49 (m, 1H), 7.30-7.18 (m, 2H), 7.16 (d, J=8.4 Hz, 1H), 5.22 (s, 2H), 5.03 (s, 2H), 3.49 (s, 3H).

Intermediate 13e: it was synthesized similarly to intermediate 13d as described above. Yellow solid, yield=58% (for three steps), purified through flash column chromatography (61% EtOAc/Hexanes). $^1$H NMR (500 MHz, Methanol-$d_4$) δ 9.16 (s, 1H), 8.17 (d, J=7.8 Hz, 1H), 8.13 (d, J=7.8 Hz, 1H), 7.68 (ddd, J=8.4, 7.0, 1.2 Hz, 1H), 7.55 (td, J=7.7, 7.0, 1.2 Hz, 1H), 7.16 (t, J=8.5 Hz, 1H), 6.93 (dd, J=11.7, 2.1 Hz, 1H), 6.70 (d, J=8.5 Hz, 1H), 5.93 (s, 2H), 5.15 (s, 2H), 3.43 (s, 3H), 3.15-2.92 (m, 2H), 1.82 (p, J=7.6 Hz, 2H), 1.46 (dq, J=14.8, 7.4 Hz, 2H), 0.95 (t, J=7.4 Hz, 3H). MS (ESI-TOF) for $C_{23}H_{24}FN_3O_2$ [M+H]$^+$ calculated 394.1925; found 394.1951.

Intermediate 14e: it was synthesized similarly to intermediate 14d as described above. White solid, yield=52% (for two steps), purified through flash column chromatography (61% EtOAc/Hexanes). $^1$H NMR (500 MHz, Methanol-$d_4$) δ 8.18 (s, 1H), 8.10-7.98 (m, 1H), 7.91-7.81 (m, 1H), 7.73-7.51 (m, 4H), 7.51-7.41 (m, 2H), 7.18 (t, J=8.5 Hz, 1H), 6.96 (d, J=11.7 Hz, 1H), 6.76 (d, J=8.3 Hz, 1H), 5.92 (s, 2H), 5.17 (s, 2H), 3.44 (s, 3H), 3.12-2.89 (m, 2H), 1.79 (dt, J=8.0, 15.2 Hz, 2H), 1.45 (dt, J=7.5, 14.8 Hz, 2H), 0.93 (t, J=7.4 Hz, 3H).

Compound 19: it was synthesized similarly to compound 18 as described above. White solid, yield=57% (for two steps), purified through flash column chromatography (12% MeOH/DCM). $^1$H NMR (500 MHz, Methanol-$d_4$) δ 7.86 (d, J=8.3 Hz, 1H), 7.68 (d, J=8.4 Hz, 1H), 7.46 (t, J=7.7 Hz, 1H), 7.19 (t, J=7.6 Hz, 1H), 6.85 (t, J=8.7 Hz, 1H), 6.81 (d, J=11.8 Hz, 1H), 6.63 (d, J=8.3 Hz, 1H), 5.76 (s, 2H), 2.96 (t, J=7.7 Hz, 2H), 2.28-1.64 (m, 2H), 1.60-1.37 (m, 2H), 0.94 (t, J=7.4 Hz, 3H). $^1$H NMR (500 MHz, DMSO-$d_6$) δ 9.86 (s, 1H), 7.82 (d, J=7.6 Hz, 1H), 7.68-7.51 (m, 1H), 7.46-7.26 (m, 1H), 7.19-7.04 (m, 1H), 6.99-6.82 (m, 2H), 6.78 (s, 2H), 6.65-6.48 (m, 1H), 5.75 (s, 2H), 3.02-2.70 (m, 2H), 1.70 (p, J=7.6 Hz, 2H), 1.37 (h, J=7.4 Hz, 2H), 0.87 (t, J=7.4 Hz, 3H). $^3$C NMR (126 MHz, DMSO-$d_6$) δ 153.9, 151.3, 151.0 (d, J=242.4 Hz), 144.1, 144.0, 133.0, 127.8 (d, J=5.4 Hz), 126.7, 126.2, 125.3, 121.6 (d, J=3.0 Hz), 121.3, 120.2, 118.2, 114.3, 113.7 (d, J=19.3 Hz), 47.2, 29.6, 26.2, 21.8, 13.7. MS (ESI-TOF) for $C_{21}H_{21}FN_4O$ [M+H]$^+$ calculated 365.1772; found 365.1779.

4-((4-Amino-2-butyl-JH-imidazo[4,5-c]quinolin-1-yl)methyl)-2-methoxyphenol (20). Intermediate 11f: it was synthesized similarly to intermediate 11d as described above. Yellow oil, yield=61% (for five steps), purified through flash column chromatography (5% MeOH/DCM). $^1$H NMR (500 MHz, Chloroform-d) δ 7.11 (d, J=8.2 Hz, 1H), 6.90 (d, J=1.9 Hz, 1H), 6.82 (dd, J=8.2, 1.9 Hz, 1H), 5.21 (s, 2H), 3.89 (s, 3H), 3.82 (s, 2H), 3.52 (s, 3H).

Intermediate 12f: it was synthesized similarly to intermediate 12d as described above. Yellow solid, yield=87%, purified through flash column chromatography (52% EtOAc/Hexanes). $^1$H NMR (500 MHz, Chloroform-d) δ 9.81 (s, 1H), 9.40 (s, 1H), 8.31 (d, J=8.1 Hz, 1H), 8.15-8.00 (m, 1H), 7.91-7.71 (m, 1H), 7.56-7.38 (m, 1H), 7.19 (d, J=8.2 Hz, 1H), 6.94 (dd, J=8.2, 2.0 Hz, 1H), 6.91 (d, J=1.9 Hz, 1H), 5.26 (s, 2H), 5.05 (d, J=5.5 Hz, 2H), 3.89 (s, 3H), 3.53 (s, 3H). MS (ESI-TOF) for $C_{19}H_{19}N_3O_5$[M+H]$^+$ calculated 370.1397; found 370.1419.

Intermediate 13f: it was synthesized similarly to intermediate 13d as described above. Yellow solid, yield=68% (for three steps), purified through flash column chromatography (78% EtOAc/Hexanes). $^1$H NMR (500 MHz, Chloroform-d) δ 9.36 (s, 1H), 8.41-8.15 (m, 1H), 8.08-7.86 (m, 1H), 7.61 (ddd, J=8.3, 7.0, 1.3 Hz, 1H), 7.45 (ddd, J=8.3, 7.0, 1.3 Hz, 1H), 7.07 (d, J=8.3 Hz, 1H), 6.61 (d, J=2.0 Hz, 1H), 6.53 (dd, J=8.3, 2.0 Hz, 1H), 5.74 (s, 2H), 5.18 (s, 2H), 3.70 (s, 3H), 3.48 (s, 3H), 3.08-2.66 (m, 2H), 1.90 (p, J=7.7 Hz, 2H), 1.48 (h, J=7.4 Hz, 2H), 0.96 (t, J=7.4 Hz, 3H). MS (ESI-TOF) for $C_{24}H_{27}N_3O_3$ [M+H]$^+$ calculated 406.2125; found 406.2177.

Intermediate 14f: it was synthesized similarly to intermediate 14d as described above. Yellow solid, yield=91% (for two steps), purified through flash column chromatography (4% MeOH/DCM). MS (ESI-TOF) for $C_{31}H_{32}N_4O_4$ [M+H]$^+$ calculated 525.2496; found 525.2468.

Compound 20: it was synthesized similarly to compound 18 as described above. White solid, yield=61% (for two steps), purified through flash column chromatography (12% MeOH/DCM). $^1$H NMR (500 MHz, DMSO-$d_6$) δ 9.03 (s, 1H), 7.92 (d, J=8.2 Hz, 1H), 7.67 (d, J=8.3 Hz, 1H), 7.56 (s, OH), 7.47 (t, J=7.6 Hz, 1H), 7.22 (t, J=7.6 Hz, 1H), 6.86 (s, 1H), 6.66 (d, J=8.1 Hz, 1H), 6.23 (d, J=8.1 Hz, 1H), 5.76 (s, 2H), 3.69 (s, 3H), 2.93 (t, J=7.7 Hz, 3H), 1.91-1.57 (m, 2H), 1.38 (q, J=7.4 Hz, 3H), 0.87 (t, J=7.3 Hz, 3H). $^3$C NMR (126 MHz, MeOD) δ 157.5, 151.6, 149.8, 147.6, 140.8, 136.6, 129.6, 127.8, 126.4, 124.7, 123.3, 122.4, 119.0, 116.8, 115.1, 110.4, 56.4, 49.7, 30.7, 27.8, 23.4, 14.1. MS (ESI-TOF) for $C_{22}H_{24}N_4O_2$ [M+H]$^+$ calculated 377.1972; found 377.1973.

4-((4-Amino-2-butyl-JH-imidazo[4,5-c]quinolin-1-yl)methyl)benzene-1,2-diol (21). Intermediate 11g: To a solution of starting material 7 (691 mg, 5.0 mmol) and N,N-diisopropylethylamine (2.18 mL, 12.5 mmol) in DCM (15 mL) was added chloromethyl methyl ether (949 μL, 12.5 mmol) slowly. The reaction mixture was stirred at rt for 8 h. Upon completion, the solution was evaporated to dryness and the residue was purified through flash column chromatography (23% EtOAc/Hexanes) to afford desired product as a colorless oil (670 mg, yield=59%). $^1$H NMR (500 MHz, Chloroform-d) δ 9.87 (s, 1H), 7.68 (s, 1H), 7.51 (d, J=8.3 Hz, 1H), 7.29 (d, J=8.3 Hz, 1H), 5.33 (s, 2H), 5.30 (s, 2H), 3.53 (d, J=2.4 Hz, 6H). To the solution of obtained colorless oil (670 mg, 2.96 mmol) in ethanol (5.0 mL) were added hydroxylamine hydrochloride (309 mg, 4.44 mmol) and sodium acetate (728 mg, 8.88 mmol). The reaction mixture was stirred at 65° C. for 1 h. After completion, the solvent was evaporated and desired oxime intermediate was isolated through flash column chromatography (22% EtOAc/Hexanes) as a yellow solid. This solid was then dissolved into 5.0 mL THF. To this solution, 4.44 mL $^1$N lithium aluminum hydride in THF was added slowly. The reaction was stirred at 65° C. for 1 h. Upon completion, method was added to quench excess lithium aluminum hydride. Flash column chromatography (4% MeOH/DCM) can afford desired product 11g as a colorless oil (400 mg, yield=59%). $^1$H NMR (500 MHz, Chloroform-d) δ 7.12 (d, J=6.8 Hz, 2H), 6.91 (d, J=8.3 Hz, 1H), 5.24 (s, 2H), 5.21 (s, 2H), 3.53 (s, 3H), 3.52 (s, 3H). MS (ESI-TOF) for $C_{11}H_{17}NO_4$ [M+H]$^+$ calculated 228.1230 (fragment peak: 211.0970); found 211.0942 and 135.0428.

Intermediate 12g: it was synthesized similarly to intermediate 12d as described above. Yellow solid, yield=99%, purified through flash column chromatography (4% MeOH/DCM). $^1$H NMR (500 MHz, Chloroform-d) δ 9.78 (s, 1H), 9.40 (s, 1H), 8.31 (d, J=8.5 Hz, 1H), 8.02 (d, J=8.3 Hz, 1H), 7.78 (t, J=7.6 Hz, 1H), 7.47 (t, J=7.7 Hz, 1H), 7.22-7.14 (m, 2H), 7.01 (d, J=8.3 Hz, 1H), 5.26 (s, 2H), 5.24 (s, 2H), 5.03 (d, J=5.4 Hz, 2H), 3.53 (s, 3H), 3.51 (s, 3H). MS (ESI-TOF) for $C_{20}H_{21}N_3O_6$ [M+H]$^+$ calculated 400.1503; found 400.1552.

Intermediate 13g: it was synthesized similarly to intermediate 13d as described above. Yellow solid, yield=53% (for three steps), purified through flash column chromatography (4% MeOH/DCM). $^1$H NMR (500 MHz, Chloroform-d) δ 9.33 (s, 1H), 8.22 (d, J=8.4 Hz, 1H), 7.94 (d, J=8.4 Hz, 1H), 7.58 (t, J=7.7 Hz, 1H), 7.42 (t, J=7.6 Hz, 1H), 7.02 (d, J=8.4 Hz, 1H), 6.97 (s, 1H), 6.48 (d, J=8.4 Hz, 1H), 5.67 (s, 2H), 5.15 (s, 2H), 5.11 (s, 2H), 3.45 (s, 3H), 3.38 (s, 3H), 3.01-2.76 (m, 2H), 1.88 (p, J=7.7 Hz, 2H), 1.45 (h, J=7.4 Hz, 2H), 0.94 (t, J=7.4 Hz, 3H). MS (ESI-TOF) for $C_{25}H_{29}N_3O_4$ [M+H]$^+$ calculated 436.2231; found 436.2233.

Intermediate 14g: it was synthesized similarly to intermediate 14d as described above. Yellow solid, yield=86% (for two steps), purified through flash column chromatography (4% MeOH/DCM). $^1$H NMR (500 MHz, Methanol-d$_4$) δ 8.18 (d, J=6.7 Hz, 2H), 8.10 (d, J=7.2 Hz, 1H), 8.05 (d, J=8.4 Hz, 1H), 7.86 (d, J=7.5 Hz, 1H), 7.68-7.51 (m, 4H), 7.49-7.38 (m, 1H), 7.06 (d, J=8.4 Hz, 1H), 6.95 (s, 1H), 6.62 (d, J=8.4 Hz, 1H), 5.87 (s, 2H), 5.13 (s, 2H), 5.05 (s, 2H), 3.43 (s, 3H), 3.31 (s, 3H, overlapped), 3.15-2.84 (m, 2H), 1.77 (p, J=7.7 Hz, 2H), 1.44 (h, J=7.4 Hz, 2H), 0.92 (t, J=7.3 Hz, 3H). MS (ESI-TOF) for $C_{32}H_{34}N_4O_5$ [M+H]$^+$ calculated 555.2602; found 555.2600.

Compound 21: it was synthesized similarly to compound 18 as described above. Yellow solid, yield=60% (for two steps), purified through flash column chromatography (12% MeOH/DCM). $^1$H NMR (500 MHz, Methanol-d$_4$) δ 8.06 (d, J=8.3 Hz, 1H), 7.75 (d, J=8.3 Hz, 1H), 7.66 (t, J=7.8 Hz, 1H), 7.44 (t, J=7.8 Hz, 1H), 6.73 (d, J=8.1 Hz, 1H), 6.48 (s, 1H), 6.42 (d, J=8.1 Hz, 1H), 5.78 (s, 2H), 3.01 (t, J=7.6 Hz, 2H), 2.42-1.65 (m, 2H), 1.63-1.28 (m, 2H), 0.96 (t, J=7.4 Hz, 3H). $^{13}$C NMR (126 MHz, MeOD) δ 159.1, 150.3, 147.4, 146.4, 137.7, 135.3, 131.0, 127.3, 126.5, 125.5, 123.3, 119.5, 118.0, 117.0, 114.3, 113.6, 49.8, 30.4, 27.8, 23.3, 14.1. MS (ESI-TOF) for $C_{21}H_{22}N_4O_2$ [M+H]$^+$ calculated 363.1816; found 363.1818.

3-((4-Amino-2-butyl-JH-imidazo[4,5-c]quinolin-1-yl) methyl)benzene-1,2-diol (22). Intermediate 11h: it was synthesized similarly to intermediate 11g as described above. Yellow oil, yield=46% (for three steps), purified through flash column chromatography (8% MeOH/DCM). $^1$H NMR (500 MHz, Chloroform-d) δ 7.09 (d, J=7.9 Hz, 1H), 7.04 (t, J=7.8 Hz, 1H), 7.00 (d, J=7.2 Hz, 1H), 5.19 (s, 2H), 5.15 (s, 2H), 3.94 (s, 2H), 3.59 (s, 3H), 3.50 (s, 3H).

Intermediate 12h: it was synthesized similarly to intermediate 12d as described above. Yellow solid, yield=79%, purified through flash column chromatography (1% MeOH/DCM). $^1$H NMR (500 MHz, Chloroform-d) δ 9.76 (s, 1H), 9.39 (s, 1H), 8.29 (d, J=8.4 Hz, 1H), 8.01 (d, J=8.1 Hz, 1H), 7.77 (t, J=7.3 Hz, 1H), 7.45 (t, J=7.2 Hz, 1H), 7.22-7.16 (m, 1H), 7.09 (d, J=7.9 Hz, 1H), 7.06 (d, J=7.5 Hz, 1H), 5.23 (s, 2H), 5.16 (s, 2H), 5.14 (s, 2H), 3.52 (s, 3H), 3.39 (s, 3H). MS (ESI-TOF) for $C_{20}H_{21}N_3O_6$ [M+H]$^+$ calculated 400.1503; found 400.1505.

Intermediate 13h: it was synthesized similarly to intermediate 13d as described above. Yellow solid, yield=61% (for three steps), purified through flash column chromatography (5% MeOH/DCM). $^1$H NMR (500 MHz, Chloroform-d) δ 9.36 (s, 1H), 8.23 (d, J=8.4 Hz, 1H), 7.97 (d, J=8.4 Hz, 1H), 7.59 (t, J=7.6 Hz, 1H), 7.43 (t, J=7.6 Hz, 1H), 7.10 (d, J=8.2 Hz, 1H), 6.82 (t, J=8.0 Hz, 1H), 6.02 (d, J=7.8 Hz, 1H), 5.91 (s, 2H), 5.35 (s, 2H), 5.26 (s, 2H), 3.69 (s, 3H), 3.55 (s, 3H), 3.04-2.74 (m, 2H), 1.89 (p, J=7.7 Hz, 2H), 1.46 (h, J=7.4 Hz, 2H), 0.95 (t, J=7.4 Hz, 3H). MS (ESI-TOF) for $C_{25}H_{29}N_3O_4$ [M+H]$^+$ calculated 436.2231; found 436.2216.

Intermediate 14h: it was synthesized similarly to intermediate 14d as described above. Yellow solid, yield=90% (for two steps), purified through flash column chromatography (4% MeOH/DCM). $^1$H NMR (500 MHz, Chloroform-d) δ 9.41 (s, 1H), 8.23 (s, 1H), 8.09 (s, 1H), 7.85 (s, 1H), 7.82 (d, J=7.7 Hz, 1H), 7.62-7.45 (m, 4H), 7.39-7.29 (m, 1H), 7.11 (d, J=8.1 Hz, 1H), 6.84 (t, J=8.0 Hz, 1H), 6.03 (d, J=7.8 Hz, 1H), 5.88 (s, 2H), 5.34 (s, 2H), 5.26 (s, 2H), 3.69 (s, 3H), 3.55 (s, 3H), 2.91 (s, 2H), 2.01-1.79 (m, 2H), 1.54-1.37 (m, 2H), 0.94 (t, J=7.3 Hz, 3H). MS (ESI-TOF) for $C_{32}H_{34}N_4O_5$ [M+H]$^+$ calculated 555.2602; found 555.2621.

Compound 22: it was synthesized similarly to compound 18 as described above. Yellow solid, yield=53% (for two steps), purified through flash column chromatography (10% MeOH/DCM). $^1$H NMR (500 MHz, Methanol-d$_4$) δ 7.82 (d, J=8.3 Hz, 1H), 7.66 (d, J=8.3 Hz, 1H), 7.42 (t, J=7.7 Hz, 1H), 7.15 (t, J=7.6 Hz, 1H), 6.72 (d, J=7.9 Hz, 1H), 6.47 (t, J=7.9 Hz, 1H), 5.83 (d, J=7.7 Hz, 1H), 5.78 (s, 2H), 2.98 (t, J=7.7 Hz, 2H), 2.11-1.63 (m, 2H), 1.57-1.35 (m, 2H), 0.94 (t, J=7.3 Hz, 3H). $^{13}$C NMR (126 MHz, MeOD) δ 159.2, 150.3, 146.6, 144.0, 137.8, 135.2, 130.9, 126.4, 125.5, 123.1, 122.7, 120.9, 119.4, 117.0, 116.0, 114.4, 46.0, 30.4, 27.8, 23.3, 14.1. MS (ESI-TOF) for $C_{21}H_{22}N_4O_2$[M+H]$^+$ calculated 363.1816; found 363.1822.

5-((4-Amino-2-butyl-JH-imidazo[4,5-c]quinolin-1-yl) methyl)benzene-1,3-diol (23). Intermediate 11i: it was synthesized similarly to intermediate 11g as described above. Colorless oil, yield=36% (for three steps), purified through flash column chromatography (8% MeOH/DCM). $^1$H NMR (500 MHz, Chloroform-d) δ 6.66 (s, 2H), 6.62 (s, 1H), 5.16 (s, 4H), 3.81 (s, 2H), 3.48 (s, 6H). MS (ESI-TOF) for $C_{11}H_{17}NO_4$ [M+H]$^+$ calculated 228.1230 (fragment peak: 211.0970); found 228.1224, 211.0969.

Intermediate 12i: it was synthesized similarly to intermediate 12d as described above. Yellow solid, yield=99%, purified through flash column chromatography (1% MeOH/DCM). $^1$H NMR (500 MHz, Chloroform-d) δ 9.83 (s, 1H), 9.40 (s, 1H), 8.26 (d, J=8.5 Hz, 1H), 8.02 (d, J=8.3 Hz, 1H), 7.77 (t, J=7.6 Hz, 1H), 7.45 (t, J=7.6 Hz, 1H), 6.85-6.54 (m, 3H), 5.16 (s, 4H), 5.03 (d, J=5.7 Hz, 2H), 3.48 (s, 6H). MS (ESI-TOF) for $C_{20}H_{21}N_3O_6$ [M+H]$^+$ calculated 400.1503; found 400.1491.

Intermediate 13i: it was synthesized similarly to intermediate 13d as described above. Yellow solid, yield=67% (for three steps), purified through flash column chromatography (7% MeOH/DCM). $^1$H NMR (500 MHz, Chloroform-d) δ 9.35 (s, 1H), 8.25 (s, 1H), 7.96 (d, J=8.9 Hz, 1H), 7.64-7.58 (m, 1H), 7.48-7.42 (m, 1H), 6.67 (s, 1H), 6.37 (s, 2H), 5.72 (s, 2H), 5.05 (s, 4H), 3.38 (s, 6H), 3.10-2.77 (m, 2H), 1.97-1.84 (m, 2H), 1.51-1.43 (m, 2H), 0.96 (t, J=7.3 Hz, 3H). MS (ESI-TOF) for $C_{25}H_{29}N_3O_4$ [M+H]$^+$ calculated 436.2231; found 436.2233.

Intermediate 14i: it was synthesized similarly to intermediate 14d as described above. Yellow solid, yield=79% (for two steps), purified through flash column chromatography (6% MeOH/DCM). $^1$H NMR (500 MHz, Chloroform-d) δ 8.44 (s, 1H), 8.09 (s, 1H), 8.02 (d, J=7.8 Hz, 1H), 7.87 (d, J=7.9 Hz, 1H), 7.84-7.76 (m, 1H), 7.59-7.45 (m, 4H), 7.29 (s, 1H), 6.66 (s, 1H), 6.35 (s, 2H), 5.66 (s, 2H), 5.04 (s, 4H), 3.36 (s, 6H), 3.01-2.67 (m, 2H), 2.09-1.72 (m, 2H), 1.56-1.37 (m, 2H), 0.93 (t, J=7.4 Hz, 3H). MS (ESI-TOF) for $C_{32}H_{34}N_4O_5$ [M+H]$^+$ calculated 555.2602; found 555.2623.

Compound 23: it was synthesized similarly to compound 18 as described above. White solid, yield=52% (for two steps), purified through flash column chromatography (10% MeOH/DCM). $^1$H NMR (500 MHz, Methanol-d$_4$) δ 8.03 (d, J=8.3 Hz, 1H), 7.75 (d, J=8.4 Hz, 1H), 7.67 (t, J=7.8 Hz, 1H), 7.45 (t, J=7.8 Hz, 1H), 6.18 (s, 1H), 5.98 (s, 2H), 5.78 (s, 2H), 3.01 (t, J=7.6 Hz, 2H), 2.44-1.74 (m, 2H), 1.68-1.41 (m, 2H), 0.96 (t, J=7.3 Hz, 3H). $^{13}$C NMR (126 MHz, MeOD) δ 160.7 (2C), 159.2, 150.4, 138.5, 137.8, 135.3, 131.0, 126.5, 125.6, 123.2, 119.5, 114.3, 104.8 (2C), 103.1, 50.0, 30.3, 27.8, 23.3, 14.1. $^{13}$C NMR (126 MHz, DMSO) δ 159.0 (2C), 157.1, 148.8, 137.5, 135.5, 133.6, 129.5, 124.8, 124.4, 121.7, 118.4, 112.4, 103.3 (2C), 101.7, 48.3, 29.2, 26.2, 21.7, 13.7. MS (ESI-TOF) for $C_{21}H_{22}N_4O_2$ [M+H]$^+$ calculated 363.1816; found 363.1819.

2-((4-Amino-2-butyl-JH-imidazo[4,5-c]quinolin-1-yl)methyl)benzene-1,4-diol (24). Intermediate 11j: it was synthesized similarly to intermediate 11g as described above. Yellow oil, yield=63% (for three steps), purified through flash column chromatography (10% MeOH/DCM). $^1$H NMR (500 MHz, Chloroform-d) δ 7.03 (d, J=8.9 Hz, 1H), 7.00 (d, J=2.5 Hz, 1H), 6.91 (dd, J=2.6, 8.9 Hz, 1H), 5.17 (s, 2H), 5.12 (s, 2H), 3.89 (s, 2H), 3.48 (s, 3H), 3.47 (s, 3H).

Intermediate 12j: it was synthesized similarly to intermediate 12d as described above. Yellow solid, yield=73%, purified through flash column chromatography (2% MeOH/DCM). $^1$H NMR (500 MHz, Chloroform-d) δ 9.78 (s, 1H), 9.37 (s, 1H), 8.29 (d, J=8.4 Hz, 1H), 8.02 (d, J=8.3 Hz, 1H), 7.78 (t, J=7.6 Hz, 1H), 7.48 (t, J=7.7 Hz, 1H), 7.14 (d, J=8.9 Hz, 1H), 7.04 (d, J=2.6 Hz, 1H), 7.00 (dd, J=2.8, 8.9 Hz, 1H), 5.16 (s, 2H), 5.10 (s, 2H), 5.03 (d, J=5.7 Hz, 2H), 3.46 (s, 3H), 3.43 (s, 3H). MS (ESI-TOF) for $C_{20}H_{21}N_3O_6$ [M+H]$^+$ calculated 400.1503; found 400.1493.

Intermediate 13j: it was synthesized similarly to intermediate 13d as described above. Yellow solid, yield=84% (for three steps), purified through flash column chromatography (5% MeOH/DCM). $^1$H NMR (500 MHz, Chloroform-d) δ 9.36 (s, 1H), 8.24 (d, J=8.5 Hz, 1H), 7.90 (d, J=8.4 Hz, 1H), 7.59 (t, J=7.5 Hz, 1H), 7.41 (t, J=7.6 Hz, 1H), 7.16 (d, J=8.9 Hz, 1H), 6.94 (dd, J=2.7, 9.1 Hz, 1H), 6.12 (d, J=2.3 Hz, 1H), 5.76 (s, 2H), 5.32 (s, 2H), 4.82 (s, 2H), 3.59 (s, 3H), 3.18 (s, 3H), 3.03-2.70 (m, 2H), 1.91 (p, J=7.7 Hz, 2H), 1.53-1.42 (m, 2H), 0.96 (t, J=7.4 Hz, 3H). MS (ESI-TOF) for $C_{25}H_{29}N_3O_4$ [M+H]$^+$ calculated 436.2231; found 436.2243.

Intermediate 14j: it was synthesized similarly to intermediate 14d as described above. Yellow solid, yield=69% (for two steps), purified through flash column chromatography (3% MeOH/DCM). $^1$H NMR (500 MHz, Chloroform-d) δ 9.45 (s, 1H), 8.17 (s, 3H), 7.77 (d, J=8.1 Hz, 1H), 7.64-7.45 (m, 4H), 7.29 (d, J=6.7 Hz, 1H), 7.16 (d, J=9.0 Hz, 1H), 6.94 (dd, J=2.6, 9.0 Hz, 1H), 6.14 (d, J=2.3 Hz, 1H), 5.73 (s, 2H), 5.32 (s, 2H), 4.83 (s, 2H), 3.59 (s, 3H), 3.19 (s, 3H), 3.06-2.81 (m, 2H), 1.87 (h, 2H), 1.47 (h, J=7.4 Hz, 2H), 0.95 (t, J=7.4 Hz, 3H). MS (ESI-TOF) for $C_{32}H_{34}N_4O_5$ [M+H]$^+$ calculated 555.2602; found 555.2591.

Compound 24: it was synthesized similarly to compound 18 as described above. White solid, yield=51% (for two steps), purified through flash column chromatography (10% MeOH/DCM). $^1$H NMR (500 MHz, Methanol-d$_4$) δ 7.98 (d, J=8.3 Hz, 1H), 7.75 (d, J=8.3 Hz, 1H), 7.65 (t, J=7.8 Hz, 1H), 7.42 (t, J=7.8 Hz, 1H), 6.78 (d, J=8.7 Hz, 1H), 6.58 (dd, J=8.6, 2.5 Hz, 1H), 5.83 (d, J=2.3 Hz, 1H), 5.77 (s, 2H), 3.03 (t, J=7.6 Hz, 2H), 2.46-1.72 (m, 2H), 1.67-1.39 (m, 2H), 0.97 (t, J=7.4 Hz, 3H). $^{13}$C NMR (126 MHz, MeOD) δ 159.2, 151.8, 150.3, 148.5, 137.7, 135.2, 131.0, 126.5, 125.6, 123.0, 122.9, 119.5, 117.3, 116.6, 114.4, 113.1, 46.0, 30.4, 27.8, 23.3, 14.1. MS (ESI-TOF) for $C_{21}H_{22}N_4O_2$[M+H]$^+$ calculated 363.1816; found 363.1805.

Example 2. Synthetic Routes of Tscherniac-Einhorn Compounds 26-27

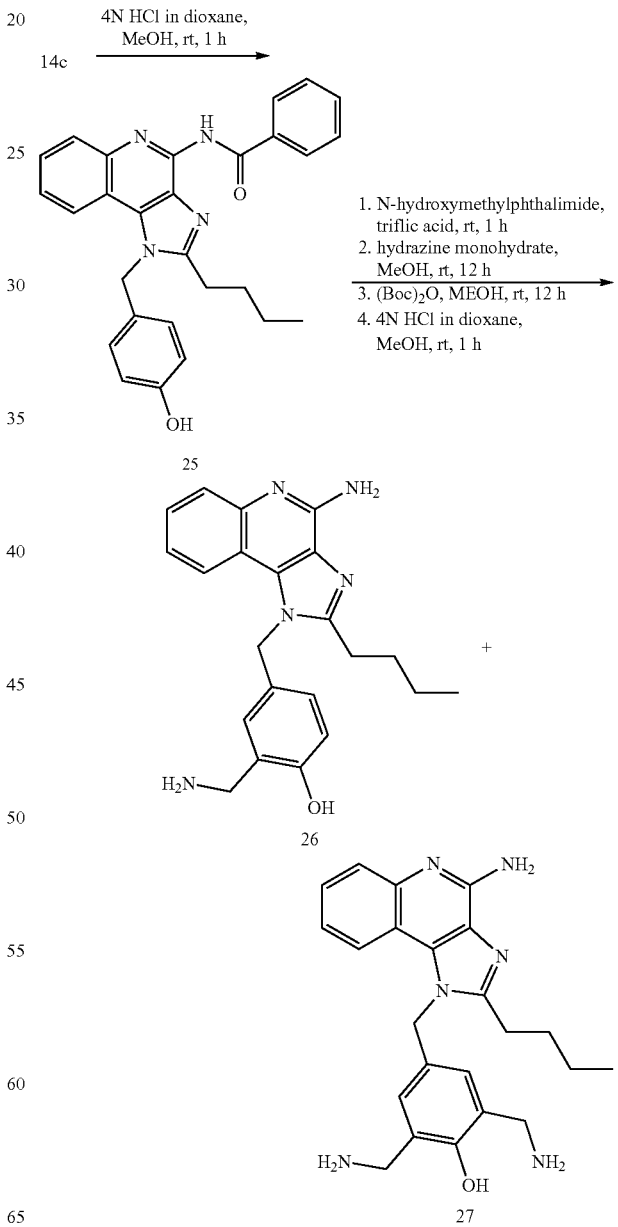

4-((4-Amino-2-butyl-JH-imidazo[4,5-c]quinolin-1-yl)methyl)-2-(aminomethyl)phenol (26). This reaction was also referred as Tscherniac-Einhorn reaction (Zaugg, H. E. et al. *Synthesis* 1970, 2,49; Chung, J. Y. L. et al. *Tetrahedron Letters* 2008, 49, 6095 and Rodriguez-Berna, G. et al. *ACS Med. Chem. Lett.* 2013, 4, 651). To the solution of compound 25 (45 mg, 0.1 mmol) in triflic acid (0.5 mL) was added N-hydroxymethylphthalimide (21 mg, 0.12 mmol) in several portions. The reaction mixture was stirred at rt for 1 h. The reaction mixture was then poured into ice water. Precipitated yellow solid was collected and purified through flash column chromatography (5% MeOH/DCM) to get rid of excess N-hydroxymethylphthalimide and other impurities. The obtained compound was dissolved into methanol (1.5 mL). Hydrazine monohydrate (48 μL, 1.0 mmol) was then added and the reaction mixture was stirred at reflux for 1 h. After completion, (Boc)$_2$O (in excess) was added with stirring at rt for overnight (12 h). The resulting mixture was evaporated and the residue was purified through flash column chromatography (10% MeOH/DCM) to afford Boc-protected product as a white solid. This white solid was dissolved into MeOH (1.0 mL) and was treated with 4N HCl in dioxane (0.5 mL) at rt for 12 h. After reaction, the solvent was evaporated and target compound was isolated through C$_{18}$ reverse phase column chromatography (18% acetonitrile/water with 0.1% TFA) as a white solid (14 mg, TFA salt, 37% for four steps). $^1$H NMR (500 MHz, Methanol-d$_4$) δ 8.01 (d, J=8.2 Hz, 1H), 7.77 (d, J=8.3 Hz, 1H), 7.65 (t, J=7.8 Hz, 1H), 7.40 (t, J=7.8 Hz, 1H), 7.02 (d, J=10.7 Hz, 2H), 6.90 (d, J=8.2 Hz, 1H), 5.86 (s, 2H), 4.02 (s, 2H), 3.00 (t, J=7.7 Hz, 2H), 1.92-1.77 (m, 2H), 1.67-1.38 (m, 2H), 0.97 (t, J=7.4 Hz, 3H). $^{13}$C NMR (126 MHz, MeOD) δ 158.9, 157.4, 150.6, 137.5, 135.5, 130.9, 129.3, 129.0, 127.3, 126.4, 125.9, 122.9, 121.8, 119.7, 117.0, 114.2, 49.6, 40.5, 30.3, 27.8, 23.4, 14.1. MS (ESI-TOF) for C$_{22}$H$_{25}$N$_5$O [M+H]$^+$ calculated 376.2132; found 376.2130.

4-((4-amino-2-butyl-1H-imidazo[4,5-c]quinolin-1-yl)methyl)-2, 6-bis(aminomethyl)phenol (27). This reaction was also referred as Tscherniac-Einhorn reaction (Zaugg, H. E. et al. *Synthesis* 1970,2,49; Chung, J. Y. L. et al. *Tetrahedron Letters* 2008, 49, 6095 and Rodriguez-Berna, G. et al. *ACS Med. Chem. Lett.* 2013, 4, 651). To the solution of compound 25 (45 mg, 0.1 mmol) in triflic acid (0.5 mL) was added N-hydroxymethylphthalimide (89 mg, 0.5 mmol). The reaction mixture was stirred at rt for 1 h. The reaction mixture was then poured into ice water. Precipitated yellow solid was collected and purified through flash column chromatography (9% MeOH/DCM) to get rid of excess N-hydroxymethylphthalimide and other impurities. The obtained yellow oil was dissolved into methanol (1.5 mL). Hydrazine monohydrate (48 μL, 1.0 mmol) was then added and the reaction mixture was stirred at reflux for 1 h. After completion, (Boc)$_2$O (in excess) was added to the reaction with stirring at rt for overnight (12 h). The resulting mixture was evaporated and the residue was purified through flash column chromatography (8% MeOH/DCM) to afford Boc-protected product as a white solid (22 mg). This white solid was dissolved into MeOH (1.0 mL) and was treated with 4N HCl in dioxane (0.5 mL) at rt for 12 h. After reaction, the solvent was evaporated and target compound was isolated through C18 reverse phase column chromatography (10% acetonitrile/water with 0.1% TFA) as a white solid (21 mg, TFA salt, 42% for four steps). $^1$H NMR (500 MHz, Methanol-d$_4$) δ 7.97 (d, J=8.2 Hz, 1H), 7.77 (d, J=8.3 Hz, 1H), 7.63 (t, J=7.7 Hz, 1H), 7.40 (t, J=7.7 Hz, 1H), 7.18 (s, 2H), 5.90 (s, 2H), 4.13 (s, 4H), 2.99 (t, J=7.6 Hz, 2H), 2.26-1.69 (m, 2H), 1.51 (h, J=7.3 Hz, 2H), 0.99 (t, J=7.3 Hz, 3H). $^3$C NMR (126 MHz, MeOD) δ 158.9, 155.4, 150.6, 137.4, 135.4, 130.9, 130.4 (2C), 129.1, 126.5, 126.0, 124.4 (2C), 122.8, 119.6, 114.1, 49.0 (2C, overlapped), 39.8, 30.2, 27.8, 23.4, 14.2. MS (ESI-TOF) for C$_{23}$H$_{28}$N$_{60}$ [M+H]$^+$ calculated 405.2397; found 405.2408.

The intermediate compound 25 was prepared as follows.

N-(2-butyl-J-(4-hydroxybenzyl)-1H-imidazo[4,5-c]quinolin-4-yl)benzamide (25). A solution of intermediate 14c (1.18 mmol, 0.58 g) in methanol (5.0 mL) was treated with 4N HCl in dioxane (3.0 mL) at rt for 1 h. After completion, the reaction mixture was evaporated to dryness. The resulting residue was purified through flash column chromatography (7% MeOH/DCM) to afford target compound as a yellow solid (0.45 g, yield=86%). H NMR (500 MHz, Chloroform-d)δ8.27 (d, J=7.5 Hz, 2H), 8.17 (d, J=8.4 Hz, 1H), 8.03 (d, J=8.4 Hz, 1H), 7.81-7.64 (m, 2H), 7.59 (t, J=7.7 Hz, 2H), 7.55-7.47 (m, 1H), 6.87 (d, J=8.5 Hz, 2H), 6.78 (d, J=8.4 Hz, 2H), 5.78 (d, J=15.4 Hz, 2H), 3.49 (s, 1H), 3.30-2.69 (m, 2H), 1.95-1.70 (m, 2H), 1.55-1.34 (m, 2H), 0.89 (t, J=7.3 Hz, 3H). MS (ESI-TOF) for C$_{28}$H$_{26}$N$_4$O$_2$ [M+H]$^+$ calculated 451.2129; found 451.2109.

Example 3. Synthetic Routes of Tscherniac-Einhorn Compounds 29-30

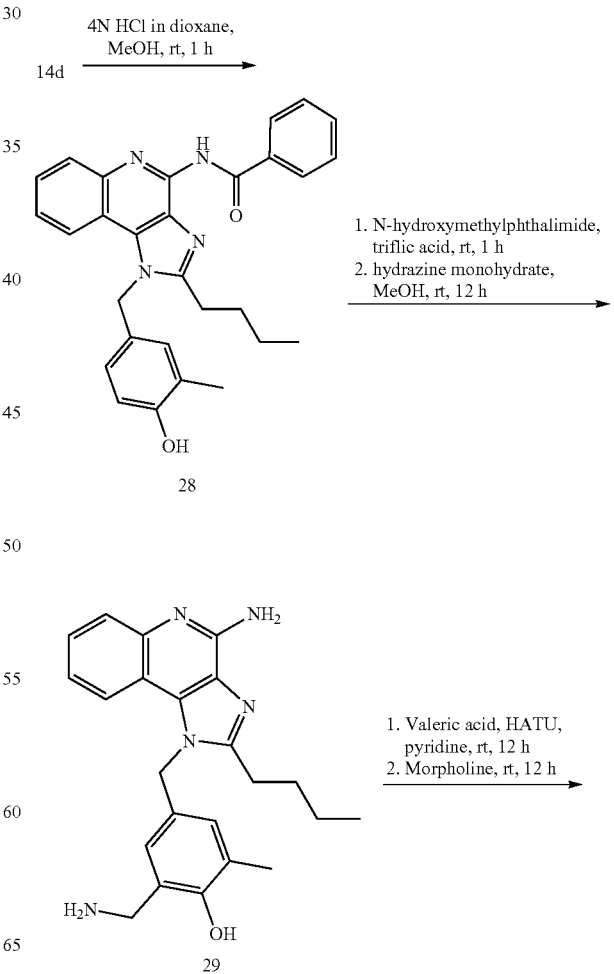

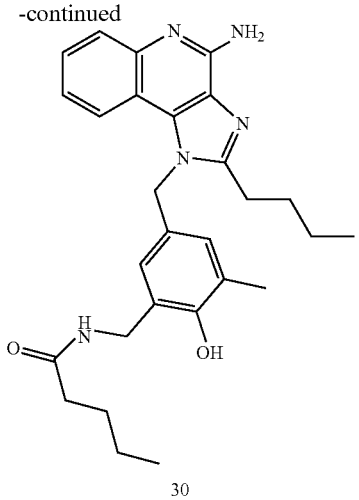

30

N-(2 Butyl-(-(4-hydroxy-3-methylbenzyl)-1H-imidazo[4,5-c]quinolin-4-yl)benzamide (28). To the solution of intermediate 14d (1.63 g, 3.20 mmol) in 5 mL methanol was added 4N HCl in dioxane (2 mL). The reaction mixture was allowed to stir at rt for 1 h. Upon completion, the reaction solution was evaporated to dryness. Resulting residue was purified through flash column chromatography (5% MeOH/DCM) to afford target compound 28 as an off-white solid (1.05 g, yield=70%). $^1$H NMR (500 MHz, DMSO-$d_6$) δ 10.79 (s, 1H), 9.32 (s, 1H), 8.13 (d, J=8.3 Hz, 1H), 8.09 (d, J=7.4 Hz, 2H), 8.00 (d, J=8.3 Hz, 1H), 7.78-7.52 (m, 4H), 7.47 (t, J=7.5 Hz, 1H), 6.85 (s, 1H), 6.69 (d, J=8.1 Hz, 1H), 6.61 (d, J=8.1 Hz, 1H), 5.80 (s, 2H), 2.93 (t, J=7.5 Hz, 2H), 2.03 (s, 3H), 1.84-1.58 (m, 2H), 1.51-1.29 (m, 2H), 0.85 (t, J=7.1 Hz, 3H). $^{13}$C NMR (126 MHz, DMSO) δ 165.7, 155.3, 154.8, 144.8, 142.8, 135.0, 134.1, 131.9, 131.4, 129.0, 128.5 (2C), 128.0 (2C), 127.9, 126.9, 126.1, 125.4, 124.5, 123.8, 120.6, 116.9, 114.9, 47.8, 29.5, 26.3, 21.8, 16.1, 13.6. MS (ESI-TOF) for $C_{29}H_{28}N_4O_2$ [M+H]$^+$ calculated 465.2285; found 465.2296.

4-((4-Amino-2-butyl-1H-imidazo[4,5-c]quinolin-1-yl)methyl)-2-(aminomethyl)-6-methylphenol (29). This reaction was also referred as Tscherniac-Einhorn reaction (Zaugg, H. E. et al. *Synthesis* 1970, 2, 49; Chung, J. Y. L. et al. *Tetrahedron Letters* 2008, 49, 6095 and Rodriguez-Berna, G. et al. *ACS Med. Chem. Lett.* 2013, 4, 651). To the solution of compound 28 (46 mg, 0.1 mmol) in triflic acid (0.5 mL) was added N-hydroxymethylphthalimide (35 mg, 0.2 mmol). The reaction mixture was stirred at rt for 1 h. After completion, the reaction mixture was poured into ice water. Precipitated yellow solid was collected and dissolved into methanol (1.5 mL). Hydrazine monohydrate (0.5 mL) was then added and the reaction mixture was stirred at reflux for 1 h. After completion, solvents were evaporated and the resulting residue was purified through flash column chromatography (22% MeOH/DCM) to afford desired product 29 as a white solid (23 mg, yield=59%). $^1$H NMR (500 MHz, Methanol-$d_4$) δ 7.86 (d, J=8.2 Hz, 1H), 7.66 (d, J=8.3 Hz, 1H), 7.41 (t, J=7.7 Hz, 1H), 7.12 (t, J=7.6 Hz, 1H), 6.78 (s, 1H), 6.56 (s, 1H), 5.68 (s, 2H), 3.85 (s, 2H), 2.94 (t, J=7.7 Hz, 2H), 2.12 (s, 3H), 1.92-1.67 (m, 2H), 1.65-1.33 (m, 2H), 0.94 (t, J=7.3 Hz, 3H). $^{13}$C NMR (126 MHz, MeOD) δ 157.1, 156.0, 152.7, 145.4, 135.5, 128.7, 128.4, 127.3, 126.9, 126.8, 126.6, 125.5, 124.7, 123.3, 121.7, 115.9, 49.0 (1C, overlapped), 43.9, 30.9, 27.8, 23.4, 16.3, 14.1. MS (ESI-TOF) for $C_{23}H_{27}N_5O$ [M+H]$^+$ calculated 390.2288; found 390.2288.

N-(5-((4-Amino-2-butyl-1H-imidazo[4,5-c]quinolin-1-yl)methyl)-2-hydroxy-3-methylbenzyl)pentanamide (30). To the solution of compound 29 (39 mg, 0.1 mmol) in pyridine (1.0 mL) were added valeric acid (13 μL, 0.12 mmol) and HATU (57 mg, 0.15 mmol). The reaction mixture was stirred at rt for overnight (12 h). After completion, 0.5 mL morpholine was added to remove ester side product. After 12 h stirring at rt, the reaction mixture was evaporated to dryness. Resulting residue was purified through flash column chromatography (9% MeOH/DCM) to afford desired product as a yellow solid (32 mg, yield=68%). H NMR (500 MHz, Methanol-$d_4$)δ 7.99 (d, J=8.3 Hz, 1H), 7.71 (d, J=8.3 Hz, 1H), 7.60 (t, J=7.7 Hz, 1H), 7.36 (t, J=7.7 Hz, 1H), 6.87 (s, 1H), 6.61 (s, 1H), 5.77 (s, 2H), 4.16 (s, 2H), 2.98 (t, J=7.6 Hz, 2H), 2.15 (s, 3H), 2.08 (t, J=7.5 Hz, 2H), 1.83 (p, J=7.6 Hz, 2H), 1.54-1.40 (m, 4H), 1.25 (h, J=7.5 Hz, 2H), 0.94 (t, J=7.3 Hz, 3H), 0.86 (t, J=7.3 Hz, 3H). $^{13}$C NMR (126 MHz, MeOD) δ 177.2, 158.5, 154.6, 150.9, 137.4, 137.2, 130.4, 128.7, 128.1, 127.0, 126.9, 126.0, 125.9, 125.6, 122.8, 121.0, 114.6, 49.6, 40.2, 36.3, 30.4, 28.9, 27.8, 23.3, 23.2, 16.6, 14.1, 14.0. MS (ESI-TOF) for $C_{28}H_{35}N_5O_2$ [M+H]$^+$ calculated 474.2864; found 474.2871.

Example 4. Synthetic Routes of Tscherniac-Einhorn Compounds 31-32

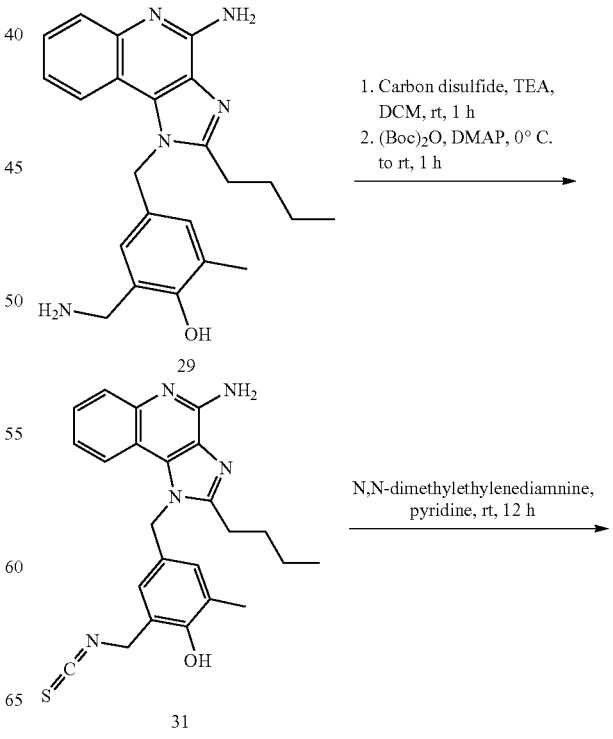

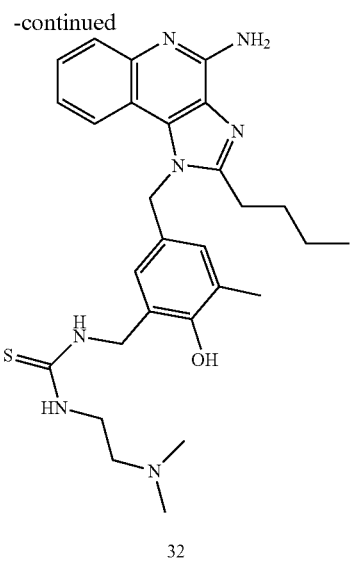

32

4-((4-Amino-2-butyl-1H-imidazo[4,5-c]quinolin-1-yl)methyl)-2-(isothiocyanatomethyl)-6-methylphenol (31). This reaction was performed with a similar procedure reported previously (Munch, H. et al. *Tetrahedron Letters* 2008, 49, 3117). To the solution of compound 29 (90 mg, 0.23 mmol) in DCM (5.0 mL) were added carbon disulfide (138 μL, 2.3 mmol) and triethylamine (96 μL, 0.69 mmol). The reaction mixture was stirred at rt for 1 h. After completion, the reaction mixture was cooled to 0° C. with ice bath. Then (Boc)$_2$O (50 mg, 0.23 mmol) and catalytic amount of DMAP were added. The reaction solution was slowly warmed to rt and stirred for 1 h. After reaction, 1.0 mL of TFA was added and the resulting reaction mixture was stirred at rt for 4 h. The reaction solution was then evaporated to dryness. Resulting residue was purified through flash column chromatography (10% MeOH/DCM) to afford desired product as a white solid (12 mg, yield=12%). $^1$H NMR (500 MHz, Methanol-d$_4$)δ 7.82 (d, J=8.2 Hz, 1H), 7.67 (d, J=8.4 Hz, 1H), 7.43 (t, J=7.7 Hz, 1H), 7.15 (t, J=7.5 Hz, 1H), 6.98 (s, 1H), 6.63 (s, 1H), 5.83 (s, 2H), 4.28 (s, 2H), 2.97 (t, J=7.6 Hz, 2H), 2.27 (s, 3H), 2.02-1.64 (m, 2H), 1.61-1.38 (m, 2H), 0.94 (t, J=7.3 Hz, 3H). $^{13}$C NMR (126 MHz, DMSO) δ 181.9, 155.3, 150.1, 146.2, 134.2, 132.4, 128.0, 127.3, 125.5, 125.1, 123.1, 120.8, 120.8, 117.7, 113.4, 47.6, 41.5, 29.3, 26.2, 21.8, 15.1, 13.7. MS (ESI-TOF) for C$_{24}$H$_{25}$N$_5$OS [M+H]$^+$ calculated 432.1853; found 432.1869.

1-(5-((4-Amino-2-butyl-JH-imidazo[4,5-c]quinolin-1-yl)methyl)-2-hydroxy-3-methylbenzyl)-3-(2-(dimethylamino)ethyl)thiourea (32). To the solution of compound 31(10 mg, 0.023 mmol) in pyridine (0.5 mL) was added N,N-dimethylenediamine (5 μL, 0.046 mmol). The reaction mixture was stirred at rt for overnight (12 h). After completion, all the solvents were evaporated and the resulting residue was purified through flash column chromatography (6% MeOH/DCM) to afford desired product as a white solid (10 mg, yield=84%). $^1$H NMR (500 MHz, Methanol-d$_4$)δ 7.88 (d, J=8.3 Hz, 1H), 7.66 (d, J=8.4 Hz, 1H), 7.43 (t, J=7.7 Hz, 1H), 7.16 (t, J=7.6 Hz, 1H), 6.85 (s, 1H), 6.67 (s, 1H), 5.71 (s, 2H), 4.55 (s, 2H), 3.45 (s, 2H), 2.95 (t, J=7.7 Hz, 2H), 2.49 (s, 2H), 2.23 (s, 6H), 2.16 (s, 3H), 1.96-1.66 (m, 2H), 1.64-1.37 (m, 2H), 0.95 (t, J=7.3 Hz, 3H). $^{13}$C NMR (126 MHz, MeOD) δ 156.3, 154.0, 152.6, 144.7, 135.6, 128.6, 128.5, 127.8, 127.3, 127.0, 126.9, 126.1, 125.5, 123.6, 121.8, 115.9, 95.4, 59.2, 56.2, 49.0 (1C, overlapped), 45.2 (2C), 42.6, 30.8, 27.9, 23.5, 16.7, 14.1. MS (ESI-TOF) for C$_{28}$H$_{37}$N$_7$OS [M+H]$^+$ calculated 520.2853; found 520.2854.

Example 5. Synthetic Route of O-Alkyne Compound 33

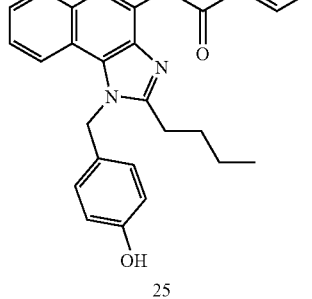

25

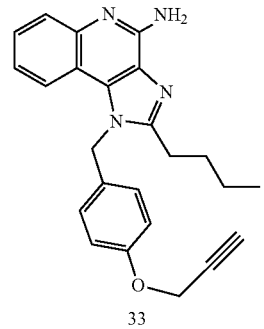

33

2-Butyl-J-(4-(prop-2-yn-1-yloxy)benzyl)-1H-imidazo[4,5-c]quinolin-4-amine (33). To the solution of compound 25 (14 mg, 0.03 mmol) and NaHCO$_3$ (3.8 mg, 0.045 mmol) in N,N-dimethylacetamide (0.5 mL) was added propargyl bromide (4 μL, 0.036 mmol). The reaction mixture was stirred at 60° C. for overnight (18 h). After completion, crude product was isolated through flash column chromatography. This crude product was then treated with sodium methoxide (in excess) in 1.0 mL methanol. This reaction mixture was stirred refluxing for 1 h. After evaporating the solvent, the residue was purified through flash column chromatography (8% MeOH/DCM) to afford desired product as a yellow solid (7 mg, yield=61%). H NMR (500 MHz, Chloroform-d) S 7.80 (d, J=8.3 Hz, 1H), 7.74 (d, J=8.2 Hz, 1H), 7.44 (t, J=7.6 Hz, 1H), 7.14 (t, J=7.4 Hz, 1H), 7.00 (d, J=8.2 Hz, 2H), 6.93 (d, J=8.2 Hz, 2H), 5.68 (s, 4H), 4.64 (s, 2H), 2.87 (t, J=7.6 Hz, 2H), 2.49 (s, 1H), 1.84-1.74 (m, 2H), 1.59-1.37 (m, 2H), 0.93 (t, J=7.2 Hz, 3H). $^{13}$C NMR (126 MHz, CDCl$_3$) δ 157.5, 154.3, 151.1, 134.2, 128.3, 127.3, 126.9 (2C), 126.8, 126.7, 122.5, 119.9, 115.8 (2C), 115.2, 78.4, 75.9, 56.0, 48.5, 30.1, 27.3, 22.7, 13.9. MS (ESI-TOF) for C$_{24}$H$_{24}$N$_4$O [M+H]$^+$ calculated 385.2023; found 385.2038.

Example 6. Synthetic Routes of O-Alkyne Compounds and Related Analogs 38-40

4N HCl in dioxane,
MeOH, rt, 1 h

13d

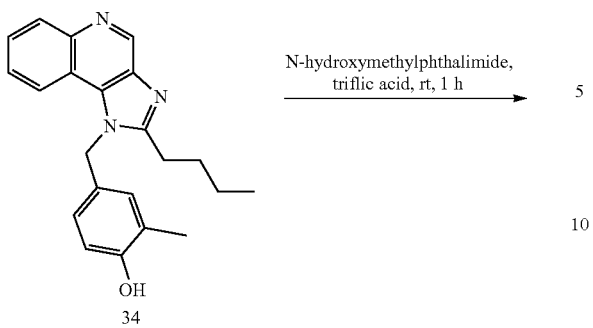

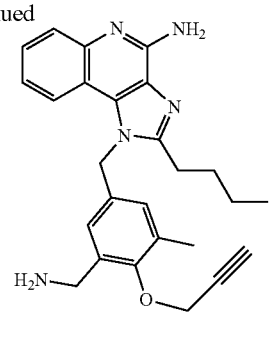

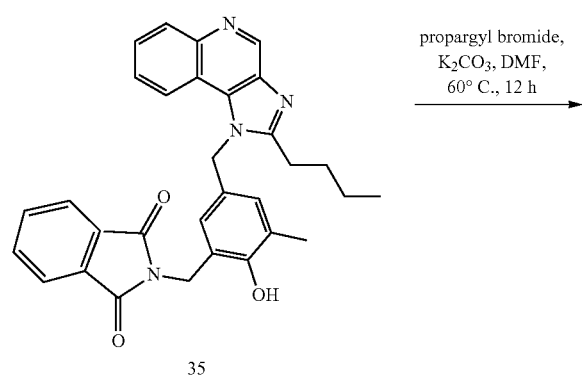

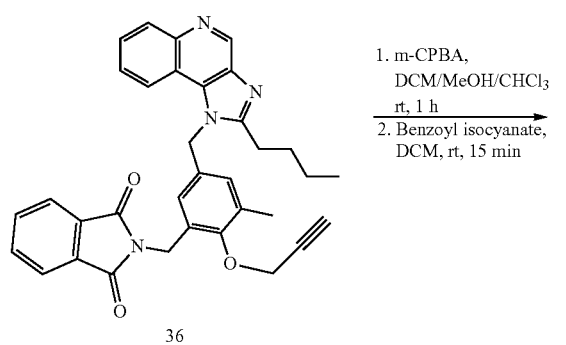

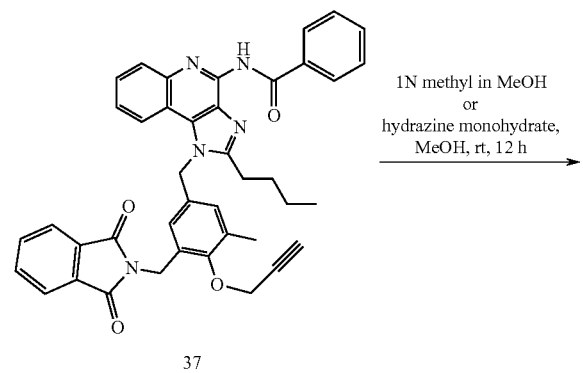

4-((2-Butyl-JH-imidazo[4,5-c]quinolin-1-yl)methyl)-2-methylphenol (34) To the solution of intermediate 13d (0.78 g, 2.0 mmol) in 3 mL methanol was added 4N HCl in dioxane (2 mL). The reaction was allowed to stir at rt for 1 h. Upon completion, the reaction mixture was evaporated to dryness. Resulting residue was purified through flash column chromatography (1% MeOH/DCM) to afford target compound as a white solid (543 mg, yield=78%). $^1$H NMR (500 MHz, Chloroform-d) δ 9.25 (s, 1H), 8.21 (d, J=8.4 Hz, 1H), 7.98 (d, J=8.2 Hz, 1H), 7.56 (t, J=7.6 Hz, 1H), 7.49-7.35 (m, 1H), 6.96 (s, 1H), 6.65 (d, J=8.3 Hz, 1H), 6.42 (s, 1H), 5.68 (s, 2H), 3.49 (s, 1H), 3.11-2.62 (m, 2H), 2.26 (s, 3H), 1.84 (p, J=7.7 Hz, 2H), 1.42 (h, J=7.3 Hz, 2H), 0.90 (t, J=7.3 Hz, 3H). $^1$H NMR (500 MHz, DMSO-d$_6$) δ 9.31 (s, 1H), 9.19 (s, 1H), 8.13 (dd, J=8.4, 17.4 Hz, 2H), 7.61 (t, J=7.6 Hz, 1H), 7.51 (t, J=7.6 Hz, 1H), 6.83 (s, 1H), 6.67 (d, J=8.3 Hz, 1H), 6.58 (d, J=8.2 Hz, 1H), 5.79 (s, 2H), 2.95 (t, J=7.5 Hz, 2H), 2.02 (s, 3H), 1.78 (p, J=7.5 Hz, 2H), 1.40 (h, J=7.4 Hz, 2H), 0.89 (t, J=7.3 Hz, 3H). $^3$C NMR (126 MHz, DMSO) δ 156.0, 154.8, 144.2, 144.0, 136.2, 133.5, 130.1, 127.9, 126.5, 126.1, 126.1, 124.5, 123.8, 120.8, 117.3, 114.9, 47.8, 29.0, 26.2, 21.8, 16.0, 13.7. MS (ESI-TOF) for $C_{22}H_{23}N_3O$ [M+H]$^+$ calculated 346.1914; found 346.1924.

2-(5-((2-Butyl-1H-imidazo[4,5-c]quinolin-1-yl)methyl)-2-hydroxy-3-methylbenzyl)isoindoline-1,3-dione (35). This reaction was also referred as Tscherniac-Einhorn reaction (Zaugg, H. E. et al. *Synthesis* 1970, 2, 49; Chung, J. Y. L. et al. *Tetrahedron Letters* 2008, 49, 6095 and Rodriguez-Berna, G. et al. *ACS Med. Chem. Lett.* 2013, 4, 651). To a solution of compound 34 (1.38 g, 4.0 mmol) in triflic acid (5.0 mL) was added N-hydroxymethylphthalimide (1.06 g, 6.0 mmol) slowly. The reaction mixture was stirred at rt for 1 h. After completion, the reaction mixture was poured on ice-water. Precipitated yellow solid was collected and purified through flash column chromatography (3% MeOH/DCM) to afford desired product as a yellow solid (1.31 g, yield=65%). $^1$H NMR (500 MHz, Chloroform-d) δ 9.36 (s, 1H), 8.44 (d, J=8.5 Hz, 1H), 8.08 (d, J=8.5 Hz, 1H), 7.87-7.78 (m, 3H), 7.79-7.72 (m, 3H), 7.63 (t, J=7.7 Hz, 1H), 6.87 (s, 1H), 6.74 (s, 1H), 5.78 (s, 2H), 4.67 (s, 2H), 3.03 (t, J=7.6 Hz, 2H), 2.17 (s, 3H), 1.94 (p, J=7.5 Hz, 2H), 1.49 (h, J=7.4 Hz, 2H), 0.96 (t, J=7.3 Hz, 3H). $^3$C NMR (126 MHz, CDCl$_3$) δ 168.9, 161.4, 153.8, 140.3, 138.3, 135.9, 135.5, 134.9(2C), 131.6, 131.0, 129.4, 129.3, 128.2, 126.6, 124.5, 124.0 (2C), 123.5, 122.8, 121.5, 116.5, 49.1, 37.2, 29.2, 27.5, 22.5, 16.7, 13.9. MS (ESI-TOF) for $C_{31}H_{28}N_4O_3$ [M+H]$^+$ calculated 505.2234; found 505.2221.

2-(5-((2-Butyl-JH-imidazo[4,5-c]quinolin-1-yl)methyl)-3-methyl-2-(prop-2-yn-1-yloxy)benzyl)isoindoline-1,3-dione (36) To a solution of compound 35(1.0 g, 2.0 mmol) and K$_2$CO$_3$ (552 mg, 4.0 mmol) in DMF (5.0 mL) was added propargyl bromide (334 μL, 3.0 mmol). The reaction mixture was stirred at 60° C. for 8 h. Upon completion, the reaction mixture was evaporated to dryness. Resulting residue was purified through flash column chromatography (6% MeOH/DCM) to afford desired product as a yellow solid (750 mg, yield=69%). H NMR (500 MHz, Chloroform-d) δ 9.24 (s, 1H), 8.13 (d, J=8.4 Hz, 1H), 7.81 (d, J=8.4 Hz, 1H), 7.73 (s, 4H), 7.51 (t, J=7.6 Hz, 1H), 7.35 (t, J=7.6 Hz, 1H), 6.73 (s, 1H), 6.70 (s, 1H), 5.63 (s, 2H), 4.92 (s, 2H), 4.68 (s, 2H), 2.86 (t, J=7.7 Hz, 2H), 2.51 (s, 1H), 2.22 (s, 3H), 1.93-1.76 (m, 2H), 1.50-1.34 (m, 2H), 0.91 (t, J=7.3 Hz, 3H). $^{13}$C NMR (126 MHz, CDCl$_3$) δ 168.0, 155.8, 154.2, 145.0, 144.7, 136.5, 134.2, 134.1, 133.0, 131.8, 131.5, 131.2, 130.9, 127.8, 126.8, 126.4, 123.6, 123.4, 120.0, 117.5, 78.9, 76.0, 60.6, 48.5, 36.8, 29.7, 27.3, 22.6, 16.8, 13.9. MS (ESI-TOF) for $C_{34}H_{30}N_4O_3$ [M+H]$^+$ calculated 543.2391; found 543.2506.

N-(2-Butyl-J-(3-((1,3-dioxoisoindolin-2-yl)methyl)-5-methyl-4-(prop-2-yn-1-yloxy)benzyl)-1H-imidazo[4,5-c]quinolin-4-yl)benzamide (37) Compound 37 was synthesized similarly to compound 14d. Yellow solid (0.7 mmol scale, 340 mg, yield=73%). $^1$H NMR (500 MHz, Chloroform-d) δ 9.36 (s, 1H), 8.13 (s, 2H), 7.85-7.66 (m, 4H), 7.66 (d, J=7.3 Hz, 1H), 7.59-7.49 (m, 3H), 7.45 (t, J=7.7 Hz, 1H), 7.21 (t, J=7.6 Hz, 1H), 6.73 (s, 1H), 6.68 (s, 1H), 5.59 (s, 2H), 4.92 (s, 2H), 4.67 (d, J=1.9 Hz, 2H), 2.85 (t, J=7.7 Hz, 2H), 2.51 (s, 1H), 2.22 (s, 3H), 1.86-1.68 (m, 2H), 1.58-1.33 (m, 2H), 0.90 (t, J=7.3 Hz, 3H). MS (ESI-TOF) for $C_{41}H_{35}N_5O_4$[M+H]$^+$ calculated 662.2762; found 662.2899.

1-(3-(Aminomethyl)-5-methyl-4-(prop-2-yn-1-yloxy) benzyl)-2-butyl-1H-imidazo[4,5-c]quinolin-4-amine (38) To the solution of compound 37 (0.34 g, 0.51 mmol) in methanol (5.0 mL) was added hydrazine monohydrate (1.0 mL). The reaction mixture was stirred at rt for overnight (12 h). Upon completion, all the solvents were evaporated and resulting residue was purified through flash column chromatography (8% MeOH/DCM) to afford crude product as a yellow solid. Further purification with reverse-phase HPLC afforded desired alkyne product as a yellow solid (165 mg, yield=76%). Side products alkene 39 and alkane 40 were also separated successfully (Menges, N. et al. *Synlett* 2014, 25, 671). An alternative method using 1N methylamine in methanol as the deprotecting reagent can afford desired alkyne product only. The reaction was performed with excess methylamine stirring at rt until completion (12 h). $^1$H NMR (500 MHz, Methanol-d$_4$) δ 7.97 (d, J=8.3 Hz, 1H), 7.78 (d, J=8.3 Hz, 1H), 7.65 (t, J=7.7 Hz, 1H), 7.40 (t, J=7.7 Hz, 1H), 7.07 (s, 1H), 7.01 (s, 1H), 5.91 (s, 2H), 4.70 (d, J=2.1 Hz, 2H), 4.19 (s, 2H), 3.03 (s, 1H), 2.99 (t, J=7.6 Hz, 2H), 2.29 (s, 3H), 1.93-1.83 (m, 2H), 1.61-1.43 (m, 2H), 0.97 (t, J=7.4 Hz, 3H). $^{13}$C NMR (126 MHz, MeOD) δ 158.9, 156.3, 150.6, 137.5, 135.4, 134.6, 133.3, 131.2, 131.0, 129.6, 126.5, 126.2, 126.0, 122.8, 119.7, 114.2, 79.5, 78.1, 61.7, 49.0 (1C, overlapped), 40.3, 30.3, 27.7, 23.3, 16.7, 14.1. MS (ESI-TOF) for $C_{26}H_{29}N_5O$ [M+H]$^+$ calculated 428.2445; found 428.2441.

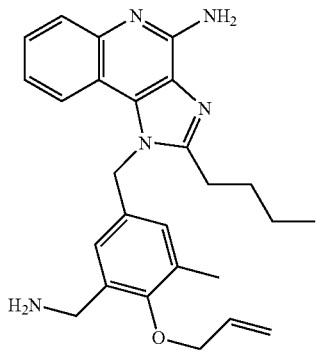

1-(4-(Allyloxy)-3-(aminomethyl)-5-methylbenzyl)-2-butyl-JH-imidazo[4,5-c]quinolin-4-amine(39) Compound 39 was separated as a white solid side product (35 mg, yield=16%)(Menges, N. et al. *Synlett* 2014, 25, 671). $^1$H NMR (500 MHz, Methanol-d$_4$) δ 7.97 (d, J=7.7 Hz, 1H), 7.78 (d, J=7.8 Hz, 1H), 7.65 (t, J=7.3 Hz, 1H), 7.40 (t, J=7.1 Hz, 1H), 7.07 (s, 1H), 6.97 (s, 1H), 6.35-6.04 (m, 1H), 5.90 (s, 2H), 5.42 (d, J=17.1 Hz, 1H), 5.27 (d, J=9.9 Hz, 1H), 4.43 (s, 2H), 4.06 (s, 2H), 2.99 (s, 2H), 2.28 (s, 3H), 1.89 (s, 2H), 1.70-1.23 (m, 2H), 0.97 (t, J=6.4 Hz, 3H). $^3$C NMR (126 MHz, MeOD) δ 158.8, 157.2, 150.6, 137.4, 135.4, 134.6, 134.5, 132.6, 131.0, 130.9, 129.0, 126.4, 126.0, 125.9, 122.7, 119.7, 118.6, 114.1, 75.5, 49.4, 39.9, 30.2, 27.7, 23.3, 16.6, 14.1. MS (ESI-TOF) for $C_{26}H_{31}N_5O$ [M+H]$^+$ calculated 430.2601; found 430.2607.

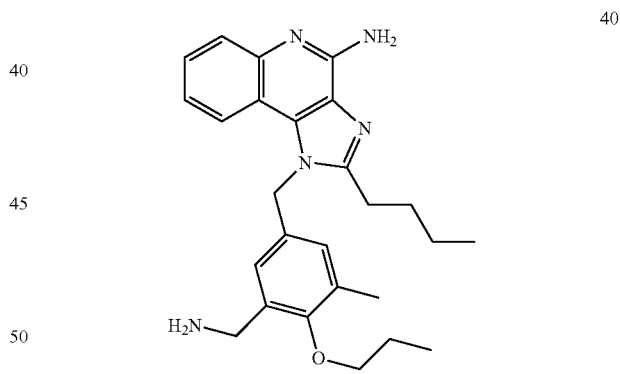

1-(3-(Aminomethyl)-5-methy-4-propoxybenzyl)-2-butyl-1H-imidazo[4,5-c]quinolin-4-amine (40) Compound 40 was separated as a white solid side product (10 mg, yield=4%) (Menges, N. et al. *Synlett* 2014, 25, 671). $^1$H NMR (500 MHz, Methanol-d$_4$)δ 7.98 (d, J=8.2 Hz, 1H), 7.78 (d, J=8.3 Hz, 1H), 7.65 (t, J=7.7 Hz, 1H), 7.40 (t, J=7.7 Hz, 1H), 7.06 (s, 1H), 6.97 (s, 1H), 5.89 (s, 2H), 4.05 (s, 2H), 3.82 (t, J=6.5 Hz, 2H), 2.99 (t, J=7.6 Hz, 2H), 2.27 (s, 3H), 1.93-1.74 (m, 4H), 1.59-1.40 (m, 2H), 1.08 (t, J=7.4 Hz, 3H), 0.97 (t, J=7.3 Hz, 3H). $^3$C NMR (126 MHz, MeOD) δ 158.9, 157.4, 150.6, 137.5, 135.5, 134.5, 132.5, 131.1, 131.0, 128.8, 126.4, 126.0, 126.0, 122.8, 119.7, 114.2, 76.5, 49.4, 39.7, 30.3, 27.7, 24.5, 23.3, 16.5, 14.1, 10.8. MS (ESI-TOF) for $C_{26}H_{33}N_5O$ [M+H]$^+$ calculated 432.2758; found 432.2771.

Example 7. Synthetic Route of O-Alkyne Compound 41

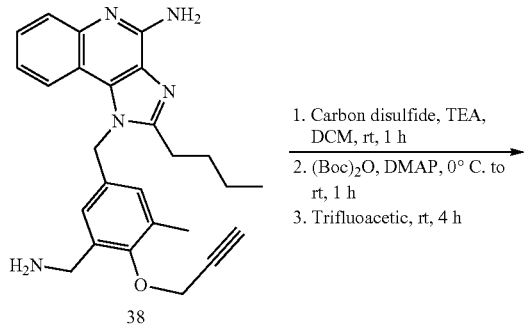

N-(2-Butyl-J-(3-((1,3-dioxoisoindolin-2-yl)methyl)-5-methyl-4-(prop-2-yn-1-yloxy)benzyl)-1H-imidazo[4,5-c]quinolin-4-yl)benzamide (41) Compound 41 was synthesized similarly to compound 31. Yellow solid (0.1 mmol scale, 30 mg, yield=64%). H NMR (500 MHz, Methanol-$d_4$) δ 7.99 (d, J=8.3 Hz, 1H), 7.74 (d, J=8.3 Hz, 1H), 7.65 (t, J=7.8 Hz, 1H), 7.42 (t, J=7.8 Hz, 1H), 7.16 (s, 1H), 6.76 (s, 1H), 5.93 (s, 2H), 4.76 (s, 2H), 4.59 (d, J=1.7 Hz, 2H), 3.02 (t, J=7.6 Hz, 2H), 2.95 (s, 1H), 2.31 (s, 3H), 2.04-1.66 (m, 2H), 1.64-1.40 (m, 2H), 0.95 (t, J=7.4 Hz, 3H). $^{13}$C NMR (126 MHz, MeOD) δ 159.0, 154.8, 150.6, 137.6, 135.4, 134.4, 133.0, 131.4, 131.0, 130.1, 126.5, 126.0, 123.4, 122.9, 119.6, 114.3, 79.5, 77.7, 61.6, 49.0 (1C, overlapped), 44.9, 30.4, 27.8, 23.3, 16.7, 14.1. MS (ESI-TOF) for $C_{27}H_{27}N_5OS$ $[M+H]^+$ calculated 470.2009; found 470.2016.

Example 8. Synthetic Route for Hyaluronic Acid Conjugate Compound 42

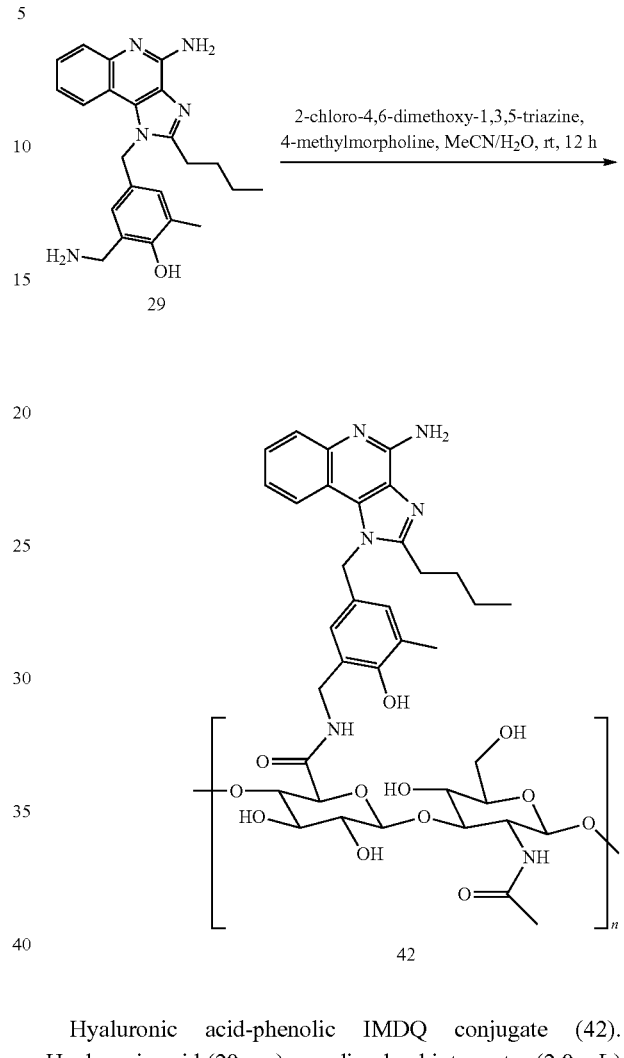

Hyaluronic acid-phenolic IMDQ conjugate (42). Hyaluronic acid (20 mg) was dissolved into water (2.0 mL) with stirring (150 rpm) at rt. This solution was cooled to 4° C. in ice bath. A mixture of 2-chloro-4,6-dimethoxy-1,3,5-triazine (8.7 mg, 0.049 mmol) and 4-methylmorpholine (5.5 μL, 0.049 mmol) in acetonitrile (1.35 mL) was added dropwise to the solution. The reaction mixture was then removed from ice and checked pH to neutral (pH=7). After 1 h stirring at rt, a solution of compound 29 (HCl salt, 2.1 mg, 0.0049 mmol) dissolved into water (0.75 mL) and acetonitrile (0.5 mL) was added dropwise. 4-Methylmorpholine (5.5 μL, 0.049 mmol) was also added. After checking pH at neutral, the reaction mixture was allowed to stir at rt for 24 h. Upon completion, the reaction mixture was injected into HPLC with size exclusion column. Eluents with small molecule 29 diagnostic UV absorbance (324 nm) were collected, combined, and concentrated with spin columns. The approximate concentration was calculated with a standard curve of UV absorbance at 324 nm of small molecule 29 to be 165.3 μg/mL.

Example 9. Synthetic Route for Hyaluronic Acid Conjugate Compound 43

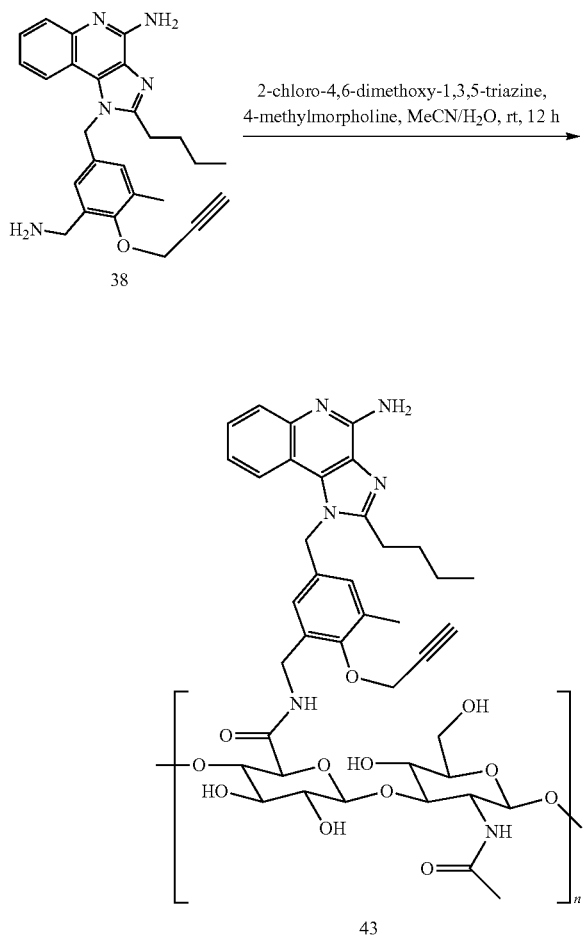

Hyaluronic acid-phenolic IMDQ (O-alkyne) conjugate (43). Hyaluronic acid (20 mg) was dissolved into water (4.0 mL) with stirring (500 rpm) at rt. This solution was cooled to 4° C. in ice bath. A mixture of 2-chloro-4,6-dimethoxy-1,3,5-triazine (8.7 mg, 0.049 mmol) and 4-methylmorpholine (5.5 µL, 0.049 mmol) in acetonitrile (2.7 mL) was added dropwise to the solution. The reaction mixture was then removed from ice and checked pH to neutral (pH=7). After 1 h stirring at rt, a solution of compound 38 (HCl salt, 25 mg, 0.059 mmol) dissolved into water (0.6 mL) and acetonitrile (0.4 mL) was added dropwise. 4-Methylmorpholine (5.5 µL, 0.049 mmol) was also added. After checking pH at neutral, the reaction mixture was allowed to stir at rt for 24 h. Upon completion, the reaction mixture was treated with Dowex 50WX8 hydrogen resin (200 mg) (resin was washed with 1.0 mL water for three times) in water (0.2 mL) with stirring at rt for 1 h. Then the reaction mixture was transferred to centrifuge tubes and spun down (5 min, 600 rpm). The supernatant was collected. The resin at the bottom was rinsed with 1 mL water for three times. All the supernatants were collected and combined with previous supernatant. The sample was then dialyzed in Slide-A-Lyzer 3500 MWCO dialysis cassettes with 0.1M sodium chloride solution for 48 h, followed by distilled water for 72 h (buffer was changed every 12 h). After dialysis, entirety of sample was transfer to a glass vial and lyophilized overnight to afford white solid. This solid was washed with 1 mL acetone for five times, and dried under high vacuum overnight as a white solid (13.2 mg, reaction yield=53%, loading yield=20%).

Example 10. Synthetic Route for Hyaluronic Acid Conjugate Compound 44

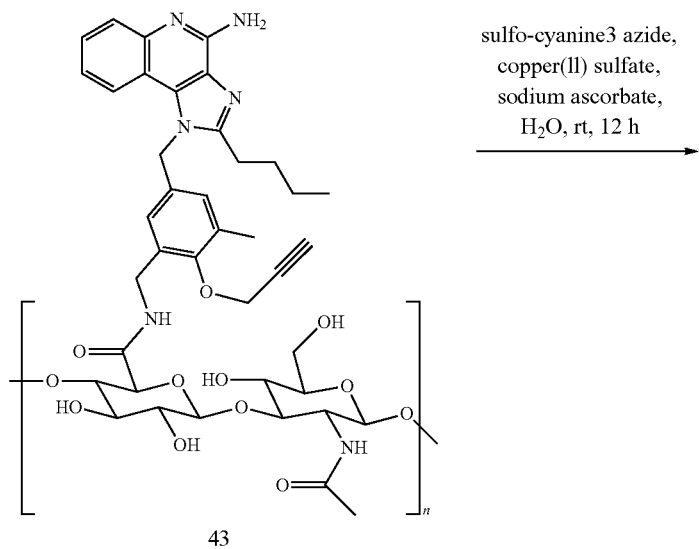

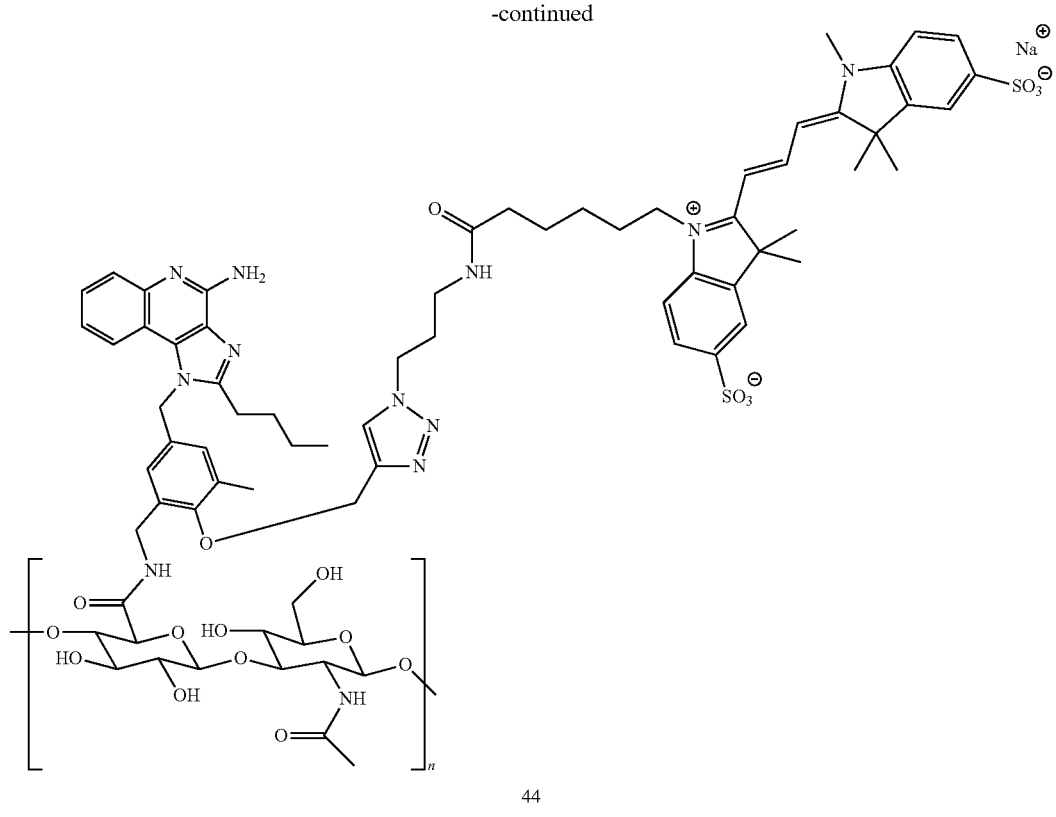

44

Hyaluronic acid-phenolic IMDQ (O-alkyne)-azide ternary conjugate (44). Compound 43 (1.28 mg) was dissolved into distilled water (1.28 mL) to prepare a 1.0 mg/mL solution (pH~5). To this solution, copper(II) sulfate (1.0 mg/mL water stock, 130 μL) and sodium ascorbate (1.0 mg/mL water stock, 260 μL) were added (pH-7), followed by adding sulfo-cyanine3 azide (Lumiprobe, Cat. #B1330) (5 mg/mL DMSO stock, 80 μL). The reaction mixture was then stirred at rt for 4 h. Upon completion, the reaction mixture was injected into HPLC with size exclusion column. Eluents with diagnostic UV absorbance (545 nm) were collected, combined, and concentrated with spin columns. The sample was finally collected as a red solution (0.5 mL) in PBS buffer.

Example 11. General Procedure for Synthesizing Alkylamine Phenolic Compounds 112-114

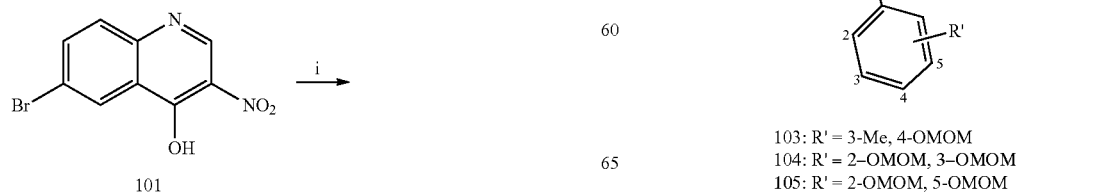

103: R' = 3-Me, 4-OMOM
104: R' = 2-OMOM, 3-OMOM
105: R' = 2-OMOM, 5-OMOM

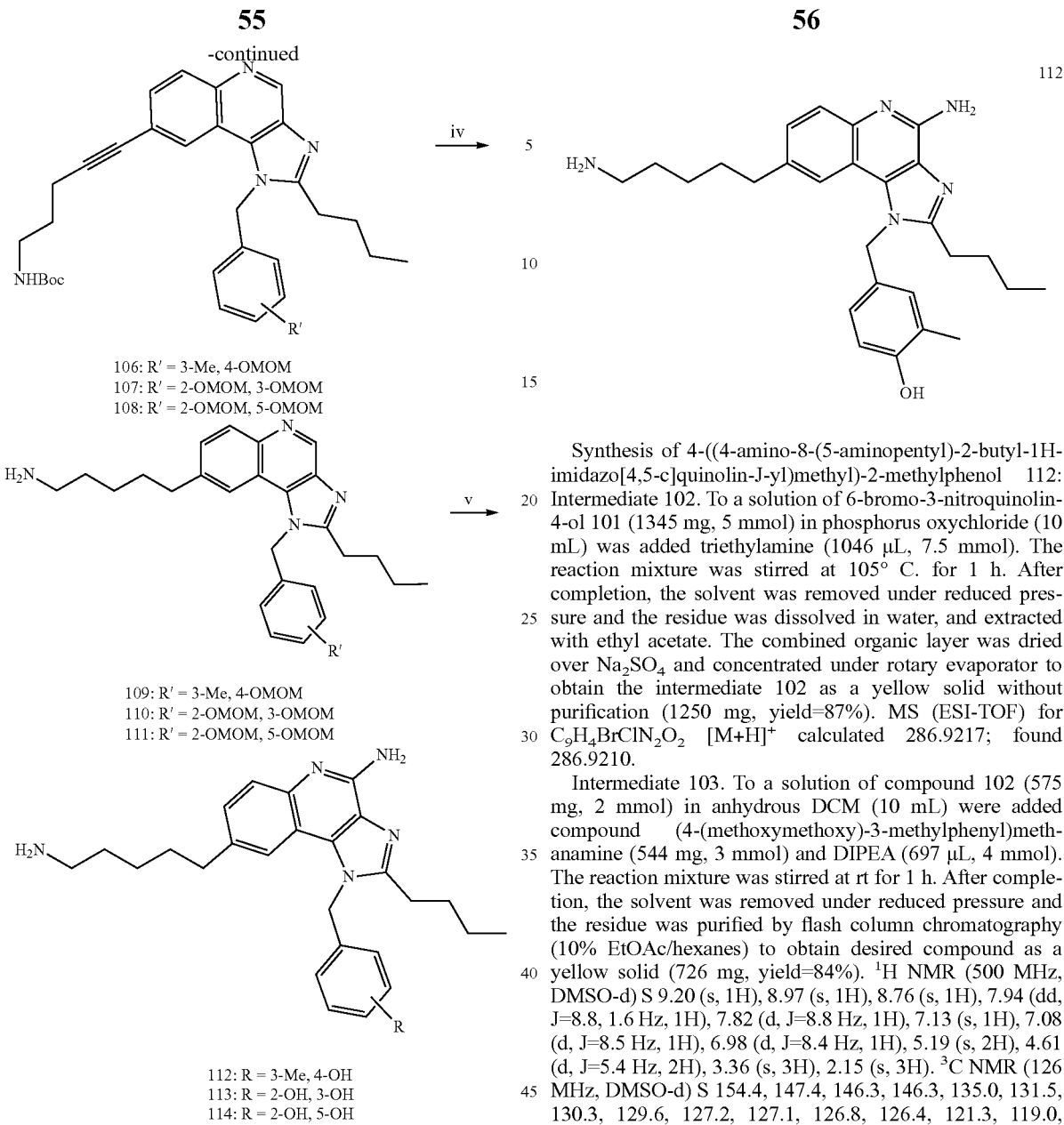

6-Bromo-4-chloro-3-nitroquinoline was prepared by chlorination with phosphorus oxychloride first. The intermediate reacted with benzylamines to give desired nitro compound. The nitro compound was hydrogenated after Sonogashira coupling with N-Boc-4-pentyne-1-amine, and then cyclized under refluxing condition with presence of calcium oxide to afford imidazolequinoline intermediate. This intermediate was oxidized and reacted with benzoyl isocyanate. After deprotecting benzoyl group and methoxymethoxy group sequentially, desired alkylamine phenolic compounds 112-114 were obtained through flash column chromatography as yellow solids.

Synthesis of 4-((4-amino-8-(5-aminopentyl)-2-butyl-1H-imidazo[4,5-c]quinolin-J-yl)methyl)-2-methylphenol 112: Intermediate 102. To a solution of 6-bromo-3-nitroquinolin-4-ol 101 (1345 mg, 5 mmol) in phosphorus oxychloride (10 mL) was added triethylamine (1046 μL, 7.5 mmol). The reaction mixture was stirred at 105° C. for 1 h. After completion, the solvent was removed under reduced pressure and the residue was dissolved in water, and extracted with ethyl acetate. The combined organic layer was dried over $Na_2SO_4$ and concentrated under rotary evaporator to obtain the intermediate 102 as a yellow solid without purification (1250 mg, yield=87%). MS (ESI-TOF) for $C_9H_4BrClN_2O_2$ [M+H]$^+$ calculated 286.9217; found 286.9210.

Intermediate 103. To a solution of compound 102 (575 mg, 2 mmol) in anhydrous DCM (10 mL) were added compound (4-(methoxymethoxy)-3-methylphenyl)methanamine (544 mg, 3 mmol) and DIPEA (697 μL, 4 mmol). The reaction mixture was stirred at rt for 1 h. After completion, the solvent was removed under reduced pressure and the residue was purified by flash column chromatography (10% EtOAc/hexanes) to obtain desired compound as a yellow solid (726 mg, yield=84%). $^1$H NMR (500 MHz, DMSO-d) S 9.20 (s, 1H), 8.97 (s, 1H), 8.76 (s, 1H), 7.94 (dd, J=8.8, 1.6 Hz, 1H), 7.82 (d, J=8.8 Hz, 1H), 7.13 (s, 1H), 7.08 (d, J=8.5 Hz, 1H), 6.98 (d, J=8.4 Hz, 1H), 5.19 (s, 2H), 4.61 (d, J=5.4 Hz, 2H), 3.36 (s, 3H), 2.15 (s, 3H). $^3$C NMR (126 MHz, DMSO-d) S 154.4, 147.4, 146.3, 146.3, 135.0, 131.5, 130.3, 129.6, 127.2, 127.1, 126.8, 126.4, 121.3, 119.0, 114.0, 93.9, 55.6, 49.9, 16.1. MS (ESI-TOF) for $C_{19}H_{18}BrN_3O_4$ [M+H]$^+$ calculated 432.0553; found 432.0557.

Intermediate 106. To a stirred solution of compound 103 (648 mg, 1.5 mmol) in anhydrous acetonitrile (10 mL) were added N-Boc-4-pentyne-1-amine (330 mg, 1.8 mmol), Pd(dppf)Cl$_2$ (122 mg, 0.15 mmol), CuI (29 mg, 0.15 mmol) and DIPEA (523 μL, 3 mmol). The reaction mixture was stirred at 60° C. under nitrogen atmosphere for 12 h. The solvent was removed under reduced pressure and the residue was purified by flash column chromatography (5% MeOH/DCM) to obtain desired compound as a yellow solid (625 mg, yield=78%). $^1$H NMR (500 MHz, DMSO-d$_6$) δ 9.26 (s, 1H), 8.96 (s, 1H), 8.58 (s, 1H), 7.84 (d, J=8.5 Hz, 1H), 7.75 (d, J=8.5 Hz, 1H), 7.13 (s, 1H), 7.08 (d, J=8.4 Hz, 1H), 6.98 (d, J=8.4 Hz, 1H), 6.90 (t, J=5.1 Hz, 1H), 5.19 (s, 2H), 4.64 (d, J=5.2 Hz, 2H), 3.36 (s, 3H), 3.07 (q, J=6.6 Hz, 2H), 2.47 (t, J=7.2 Hz, 2H), 2.15 (s, 3H), 1.68 (p, J=7.1 Hz, 2H), 1.37 (s, 9H). $^3$C NMR (126 MHz, DMSO) δ 155.6, 154.3, 147.2, 146.7, 134.4, 130.3, 129.8, 129.8, 128.0, 126.8, 126.3, 120.8, 113.9, 93.8, 91.9, 80.1, 77.5, 55.6, 50.0, 28.5, 28.2, 16.3, 16.0. MS (ESI-TOF) for $C_{29}H_{34}N_4O_6$ [M+Na]$^+$ calculated 535.2551; found, 535.2520.

Intermediate 109. To a solution of compound 106 (535 mg, 1 mmol) in anhydrous EtOAc (20 mL) was added a catalytic amount of 10% wt Pd/C. The reaction mixture was subjected to hydrogenation at 50 psi for 12 h. The reaction mixture was filtered and the filtrate was concentrated under reduced pressure. The crude product was collected as a yellow solid (290 mg, yield=57%). MS (ESI-TOF) for $C_{29}H_{40}N_4O_4$ [M+H]$^+$ calculated 509.3122; found 509.3123. To a solution of obtained yellow solid (254 mg, 0.5 mmol) and DIPEA (174 μL, 1 mmol) in THF (4.0 mL) was added valeroyl chloride (71 μL, 0.6 mmol). The reaction mixture was stirred at rt for 15 min. The solvent was removed under reduced pressure and the crude material was purified by flash column chromatography (5% MeOH/DCM) to obtain the desired product as a pale yellow solid (246 mg, yield=83%). MS (ESI-TOF) for $C_{34}H_{48}N_4O_5$[M+H]$^+$ calculated 593.3697; found 593.3656. To a solution of obtained pale yellow solid (237 mg, 0.4 mmol) in methanol (5 mL) was added excess calcium oxide. The reaction mixture was stirred at 65° C. for 12 h. The solvent was removed under reduced pressure and the residue was purified by flash column chromatography (5% MeOH/DCM) to obtain desired compound as a white solid (211 mg, yield=92%). $^1$H NMR (500 MHz, Methanol-d$_4$) δ 9.06 (s, 1H), 8.03 (d, J=8.6 Hz, 1H), 7.84 (s, 1H), 7.48 (dd, J=8.6, 1.5 Hz, 1H), 6.98 (d, J=8.5 Hz, 1H), 6.95 (s, 1H), 6.74 (dd, J=8.5, 1.8 Hz, 1H), 5.84 (s, 2H), 5.15 (s, 2H), 3.40 (s, 3H), 3.08-3.03 (m, 2H), 2.95 (t, J=7.0 Hz, 2H), 2.68 (t, J=7.5 Hz, 2H), 2.16 (s, 3H), 1.82 (p, J=7.6 Hz, 2H), 1.55-1.34 (m, 15H), 1.20 (p, J=7.6, 7.0 Hz, 2H), 0.95 (t, J=7.4 Hz, 3H). $^3$C NMR (126 MHz, MeOD) δ 158.5, 158.4, 156.4, 143.9, 143.5, 142.8, 136.9, 135.6, 129.9, 129.7, 129.5, 129.1, 125.0, 120.9, 118.6, 115.5, 95.6, 79.7, 56.3, 41.2, 36.7, 31.7, 30.9, 30.8, 28.8, 27.9, 27.2, 23.4, 16.6, 14.0. MS (ESI-TOF) for $C_{34}H_{46}N_4O_4$ [M+H]$^+$ calculated 575.3592; found 575.3535.

Compound 112. To the solution of compound 109 (92 mg, 0.16 mmol) in a mixed solvent of DCM/MeOH/CHCl$_3$ (2 mL/0.2 mL/2 mL) was added 3-chloroperbenzoic acid (68 mg, 0.40 mmol). The reaction was stirred at rt for 1 h. After completion, the solvent was evaporated and the target oxide compound was isolated through flash column chromatography (5% MeOH/DCM) as a yellow solid (80 mg, yield=85%). To the solution of obtained yellow oxide solid (42 mg, 0.12 mmol) in 3 mL DCM was added benzoyl isocyanate (22 mg, 0.14 mmol). After stirring at rt for 15 min, the solvent was evaporated. The residue was dissolved into 5 mL methanol. Sodium methoxide (in excess) was then added. The resulting mixture was stirred at 65° C. for 1 h. After completion, the solvent was evaporated and the residue was purified through flash column chromatography (3% MeOH/DCM) to afford a white soild (61 mg, yield=86%). $^1$H NMR (500 MHz, Methanol-d$_4$) δ 7.99 (d, J=7.7 Hz, 1H), 7.60 (s, 1H), 7.29 (d, J=8.5 Hz, 1H), 6.99 (d, J=8.5 Hz, 1H), 6.93 (s, 1H), 6.74 (d, J=8.4 Hz, 1H), 5.73 (s, 2H), 5.15 (s, 2H), 3.41 (s, 3H), 3.05-2.86 (m, 4H), 2.57 (t, J=7.4 Hz, 2H), 2.16 (s, 3H), 1.80 (p, J=7.6 Hz, 2H), 1.50-1.32 (m, 15H), 1.17 (p, J=7.7 Hz, 2H), 0.94 (t, J=7.3 Hz, 3H). $^3$C NMR (126 MHz, MeOD) δ 156.75, 156.41, 138.73, 136.00, 131.89, 130.37, 130.17, 129.67, 129.50, 129.07, 128.89, 126.61, 125.04, 124.11, 121.27, 115.47, 115.14, 95.55, 79.76, 56.30, 41.18, 36.38, 31.93, 30.84, 30.80, 28.79, 27.87, 27.13, 23.40, 16.57, 14.09. MS (ESI-TOF) for $C_{34}H_{47}N_5O_4$ [M+H]$^+$ calculated 590.3701; found 590.3746. To the obtained white solid (61 mg, 0.10 mmol) in methanol (2.0 mL) was added 1.0 mL 4N HCl in dioxane. The reaction mixture was stirred at rt for 1 h. After completion, all solvents were evaporated and desired product was isolated through flash column chromatography (10% MeOH/DCM) as a yellow solid (38 mg, yield=85%). $^1$H NMR (500 MHz, Methanol-d$_4$) δ 7.79 (s, 1H), 7.67 (d, J=8.4 Hz, 1H), 7.50 (d, J=8.5 Hz, 1H), 6.88 (s, 1H), 6.76-6.63 (m, 2H), 5.81 (s, 2H), 3.04 (t, J=7.5 Hz, 2H), 2.85 (t, J=7.5 Hz, 2H), 2.68 (t, J=7.4 Hz, 2H), 2.13 (s, 3H), 1.87 (p, J=7.6 Hz, 2H), 1.64-1.43 (m, 6H), 1.28-1.20 (m, 2H), 0.96 (t, J=7.3 Hz, 3H). $^3$C NMR (126 MHz, MeOD) δ 159.01, 156.53, 150.03, 140.97, 137.60, 133.51, 131.70, 129.14, 126.87, 126.75, 125.71, 125.03, 122.63, 119.38, 116.31, 114.17, 49.91, 40.69, 36.19, 31.75, 30.47, 28.45, 27.86, 26.84, 23.32, 16.35, 14.08. MS (ESI-TOF) for $C_{27}H_{35}N_5O$ [M+H]$^+$ calculated 446.2914; found 446.2969.

Compound 113-114 was Synthesized Similarly to Compound 112

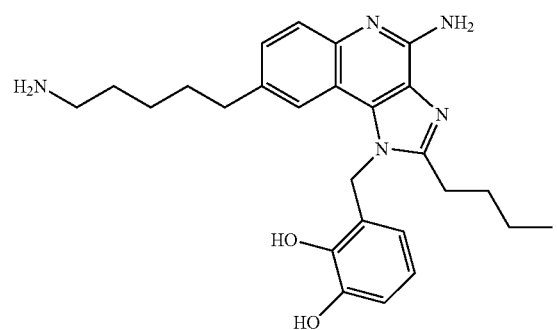

3-((4-amino-8-(5-aminopentyl)-2-butyl-1H-imidazo[4,5-c]quinolin-1-yl)methyl)benzene-1,2-diol 113: Intermediate 104. To a solution of compound 102 (1.15 g, 4 mmol) in anhydrous DCM (15 mL) were added compound (2,3-bis(methoxymethoxy)phenyl)methanamine (0.91 g, 4 mmol) and DIPEA (1.74 mL, 10 mmol). The reaction mixture was stirred at rt for 1 h. After completion, the solvent was removed under reduced pressure and the residue was purified by flash column chromatography (30% EtOAc/Hexanes) to obtain desired compound as a yellow solid (1.14 g, yield=60%). $^1$H NMR (500 MHz, Chloroform-d) δ 9.69 (s, 1H), 9.36 (s, 1H), 8.45 (d, J=1.9 Hz, 1H), 7.87 (d, J=8.9 Hz, 1H), 7.82 (dd, J=2.0, 8.9 Hz, 1H), 7.20 (dd, J=1.4, 8.2 Hz, 1H), 7.10 (t, J=7.9 Hz, 1H), 7.04 (dd, J=1.3, 7.7 Hz, 1H), 5.23 (s, 2H), 5.17 (s, 2H), 5.10 (d, J=5.7 Hz, 2H), 3.51 (s, 3H), 3.43 (s, 3H). $^3$C NMR (126 MHz, CDCl$_3$) δ 150.0, 149.9, 149.3, 147.6, 145.3, 135.7, 131.9, 131.0, 129.2, 126.9, 125.1, 121.8, 120.7, 119.0, 117.2, 99.5, 95.2, 57.5, 56.4, 48.8. MS (ESI-TOF) for $C_{20}H_{20}BrN_3O_6$ [M+H]$^+$ calculated 478.0608; found 478.0592.

Intermediate 107. To a stirred solution of compound 104 (1.14 g, 2.38 mmol) in anhydrous acetonitrile (15 mL) were added N-Boc-4-pentyne-1-amine (0.52 g, 2.86 mmol), Pd(dppf)Cl$_2$ (174 mg, 0.24 mmol), CuI (45 mg, 0.24 mmol) and DIPEA (830 μL, 4.76 mmol). The reaction mixture was stirred at 60° C. under nitrogen atmosphere for 12 h. The solvent was removed under reduced pressure and the residue was purified by flash column chromatography (46% EtOAc/Hexanes) to obtain desired compound as a yellow oil (1.24 g, yield=90%). $^1$H NMR (500 MHz, Chloroform-d) δ 9.71 (s, 1H), 9.33 (s, 1H), 8.34 (s, 1H), 7.90 (d, J=8.6 Hz, 1H), 7.72 (dd, J=1.6, 8.6 Hz, 1H), 7.19 (dd, J=1.5, 8.2 Hz, 1H), 7.09 (t, J=7.9 Hz, 1H), 7.06-7.01 (m, 1H), 5.22 (s, 2H), 5.15 (s, 2H), 5.13 (d, J=5.5 Hz, 2H), 4.75 (s, 1H), 3.51 (s, 3H), 3.41 (s, 3H), 3.28 (d, J=6.7 Hz, 2H), 2.49 (t, J=7.0 Hz, 2H), 1.81 (p, J=6.7 Hz, 2H), 1.44 (s, 9H). $^{13}$C NMR (126 MHz, CDCl$_3$) δ 156.1, 150.5, 150.1, 149.8, 147.7, 145.5, 135.4, 131.4, 130.4, 130.2, 126.9, 125.2, 122.2, 121.2, 119.4, 117.3, 99.6, 95.4, 91.3, 80.6, 57.6, 56.6, 49.1, 39.9, 29.0, 28.6, 17.1. MS (ESI-TOF) for C$_{30}$H$_{36}$N$_4$O$_5$ [M+H]$^+$ calculated 581.2606; found 581.2599.

Intermediate 110. To a solution of compound 107 (1.24 g, 2.13 mmol) in anhydrous EtOAc (20 mL) was added a catalytic amount of 10% wt Pd/C. The reaction mixture was subjected to hydrogenation at 50 psi for 12 h. The reaction mixture was filtered and the filtrate was concentrated under reduced pressure. The crude product was collected as a red oil. MS (ESI-TOF) for C$_{30}$H$_{42}$N$_4$O$_6$ [M+H]$^+$ calculated 555.3177; found 555.3146. To a solution of obtained yellow oil (1.18 g, 2.13 mmol) and DIPEA (560 μL, 3.20 mmol) in THF (10 mL) was added valeroyl chloride (266 μL, 2.24 mmol). The reaction mixture was stirred at rt for 15 min. The solvent was removed under reduced pressure and the crude material was used directly for next step. MS (ESI-TOF) for C$_{35}$H$_{46}$N$_4$O$_7$[M+H]$^+$ calculated 639.3752; found 639.3749. The solution of crude oil obtained from above step in methanol (15 mL) was then added excess calcium oxide. The reaction mixture was stirred at 65° C. for 12 h. The solvent was removed under reduced pressure and the residue was purified by flash column chromatography (68% EtOAc/Hexanes) to obtain desired compound as a yellow solid (760 mg, yield=57% for three steps). $^1$H NMR (500 MHz, Chloroform-d) δ 9.29 (s, 1H), 8.12 (d, J=8.5 Hz, 1H), 7.69 (s, 1H), 7.40 (dd, J=1.5, 8.5 Hz, 1H), 7.09 (d, J=7.9 Hz, 1H), 6.81 (t, J=8.0 Hz, 1H), 6.01 (d, J=7.6 Hz, 1H), 5.90 (s, 2H), 5.35 (s, 2H), 5.26 (s, 2H), 4.51 (s, 1H), 3.70 (s, 3H), 3.55 (s, 3H), 3.01 (d, J=6.2 Hz, 2H), 2.96-2.86 (m, 2H), 2.65 (t, J=7.4 Hz, 2H), 1.89 (p, J=7.7 Hz, 2H), 1.54-1.45 (m, 4H), 1.42 (s, 9H), 1.39-1.33 (m, 2H), 1.14 (p, J=7.3, 7.7 Hz, 2H), 0.95 (t, J=7.4 Hz, 3H). $^{13}$C NMR (126 MHz, CDCl$_3$) δ 156.0, 155.9, 149.7, 144.5, 144.2, 143.4, 140.8, 136.8, 134.1, 130.5, 130.3, 128.2, 125.4, 119.1, 118.9, 117.7, 116.3, 100.1, 95.3, 79.2, 57.8, 56.6, 45.2, 40.6, 35.9, 30.8, 29.9, 29.9, 28.6, 27.3, 26.1, 22.7, 21.2, 13.9. MS (ESI-TOF) for C$_{35}$H$_{48}$N$_4$O$_6$[M+H]$^+$ calculated 621.3647; found 621.3613.

Compound 113. To the solution of compound 110 (621 mg, 1.0 mmol) in a mixed solvent of DCM/MeOH/CHCl$_3$ (5 mL0.5 mL/5 mL) was added 3-chloroperbenzoic acid (431 mg, 2.5 mmol). The reaction was stirred at rt for 1 h. After completion, the solvent was evaporated and the target oxide compound was isolated through flash column chromatography (5% MeOH/DCM) as a red oil. MS (ESI-TOF) for C$_{35}$H$_{48}$N$_4$O$_7$[M+H]$^+$ calculated 637.3596; found 637.3609. To the solution of obtained yellow oil (637 mg, 1.0 mmol) in 5 mL DCM was added benzoyl isocyanate (177 mg, 1.2 mmol). After stirring at rt for 15 min, the solvent was evaporated and the residue was purified through flash column chromatography (71% EtOAc/Hexanes) to afford target compound as a yellow solid (0.5 g, yield=68% for two steps). MS (ESI-TOF) for C$_{42}$H$_{53}$N$_5$O$_7$ [M+H]$^+$ calculated 740.4018; found 740.4025. The obtained white solid (0.5 g, 0.68 mmol) was then dissolved into 5 mL methanol. Sodium methoxide (in excess) was then added. The resulting mixture was stirred at 65° C. for 1 h. After completion, the solvent was evaporated and the residue was purified through flash column chromatography (8% MeOH/DCM) to afford a colorless oil. MS (ESI-TOF) for C$_{35}$H$_{49}$N$_5$O$_6$ [M+H]$^+$ calculated 636.3756; found 636.3737. To the obtained oil in methanol (2 mL) was added 2.0 mL 4N HCl in dioxane. The reaction mixture was stirred at rt for 1 h. After completion, all solvents were evaporated and desired product was isolated through flash column chromatography (19% MeOH/DCM) as a yellow solid (200 mg, yield=66% for two steps). $^1$H NMR (500 MHz, Methanol-d$_4$) δ 7.73 (s, 1H), 7.64 (d, J=8.5 Hz, 1H), 7.47 (dd, J=1.2, 8.5 Hz, 1H), 6.77 (d, J=7.7 Hz, 1H), 6.51 (t, J=7.9 Hz, 1H), 5.89 (d, J=7.7 Hz, 1H), 5.81 (s, 2H), 3.14-2.97 (m, 2H), 2.96-2.80 (m, 2H), 2.68 (t, J=7.5 Hz, 2H), 1.89 (p, J=7.6 Hz, 2H), 1.62 (p, J=7.7 Hz, 2H), 1.57-1.44 (m, 4H), 1.28 (p, J=7.7 Hz, 2H), 0.98 (t, J=7.4 Hz, 3H). $^{13}$C NMR (126 MHz, MeOD) δ 159.0, 150.2, 146.6, 144.0, 140.8, 137.5, 134.0, 131.5, 125.8, 123.1, 122.3, 121.0, 119.7, 117.1, 116.0, 114.4, 45.9, 40.7, 36.1, 31.6, 30.5, 28.4, 27.8, 26.7, 23.4, 14.1. MS (ESI-TOF) for C$_{26}$H$_{33}$N$_5$O$_2$ [M+H]$^+$ calculated 448.2707; found 448.2714.

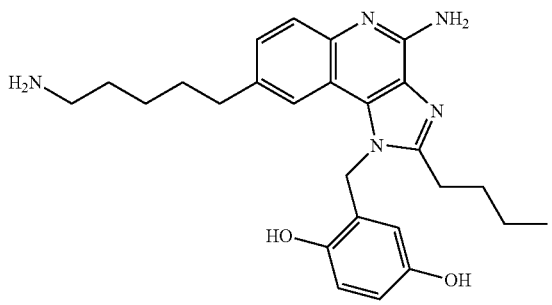

114

2-((4-amino-8-(5-aminopentyl)-2-butyl-1H-imidazo[4,5-c]quinolin-1-yl)methyl)benzene-1,4-diol 114: Intermediate 105. To a solution of compound 102 (0.77 g, 2.68 mmol) in anhydrous DCM (10 mL) were added compound (2,5-bis(methoxymethoxy)phenyl)methanamine (0.61 g, 2.68 mmol) and DIPEA (1.17 mL, 6.7 mmol). The reaction mixture was stirred at rt for 1 h. After completion, the solvent was removed under reduced pressure and the residue was purified by flash column chromatography (4% MeOH/DCM) to obtain desired compound as a yellow solid (1.05 g, yield=82%). $^1$H NMR (500 MHz, Chloroform-d) δ 9.75 (s, 1H), 9.35 (s, 1H), 8.44 (s, 1H), 7.88 (d, J=8.9 Hz, 1H), 7.83 (d, J=8.9 Hz, 1H), 7.16 (d, J=8.8 Hz, 1H), 7.04 (s, 1H), 7.01 (d, J=9.1 Hz, 1H), 5.18 (s, 2H), 5.12 (s, 2H), 4.98 (d, J=5.7 Hz, 2H), 3.46 (s, 3H), 3.45 (s, 3H). $^3$C NMR (126 MHz, CDCl$_3$) δ 152.2, 150.4, 150.3, 147.7, 142.4, 135.9, 132.0, 129.5, 127.1, 126.3, 120.9, 119.2, 117.8, 117.6, 115.8, 95.3, 95.2, 56.4, 56.1, 49.6, 0.2. MS (ESI-TOF) for C$_{20}$H$_{20}$BrN$_3$O$_6$ [M+H]$^+$ calculated 478.0608; found 478.0615.

Intermediate 108. To a stirred solution of compound 105 (1.05 g, 2.20 mmol) in anhydrous acetonitrile (15 mL) were added N-Boc-4-pentyne-1-amine (0.48 g, 2.64 mmol), Pd(dppf)Cl$_2$ (161 mg, 0.22 mmol), CuI (42 mg, 0.22 mmol) and DIPEA (766 μL, 4.40 mmol). The reaction mixture was stirred at 60° C. under nitrogen atmosphere for 12 h. The solvent was removed under reduced pressure and the residue was purified by flash column chromatography (37% EtOAc/Hexanes) to obtain desired compound as a yellow solid (1.1 g, yield=86%). $^1$H NMR (500 MHz, Chloroform-d) δ 9.76 (s, 1H), 9.32 (s, 1H), 8.32 (s, 1H), 7.90 (d, J=8.5 Hz, 1H), 7.73 (d, J=8.6 Hz, 1H), 7.14 (d, J=8.9 Hz, 1H), 7.03 (s, 1H), 7.01 (d, J=8.9 Hz, 1H), 5.16 (s, 2H), 5.11 (s, 2H), 5.01 (d, J=5.6 Hz, 2H), 4.73 (s, 1H), 3.46 (s, 3H), 3.43 (s, 3H), 3.29 (d, J=5.7 Hz, 2H), 2.51 (t, J=7.0 Hz, 2H), 1.82 (p, J=6.4 Hz, 2H), 1.44 (s, 9H). ³C NMR (126 MHz, CDCl₃) δ 156.1, 152.2, 150.8, 150.5, 149.8, 147.6, 135.5, 130.4, 130.3, 126.9, 126.7, 121.2, 119.4, 117.9, 117.7, 115.8, 95.3, 95.2, 91.4, 80.6, 56.3, 56.1, 49.9, 39.9, 29.0, 28.6, 17.2, 1.2, 0.2. MS (ESI-TOF) for $C_{30}H_{36}N_4O_5$ [M+H]⁺ calculated 581.2606; found 581.2581.

Intermediate 111. To a solution of compound 108 (1.10 g, 1.89 mmol) in anhydrous EtOAc (20 mL) was added a catalytic amount of 10% wt Pd/C. The reaction mixture was subjected to hydrogenation at 50 psi for 12 h (more catalysts may be needed for a completion of this reaction with monitoring by LC-MS). The reaction mixture was filtered and the filtrate was concentrated under reduced pressure. The crude product was collected as a yellow oil. MS (ESI-TOF) for $C_{30}H_{42}N_4O_6$ [M+H]⁺ calculated 555.3177; found 555.3131. To a solution of obtained yellow oil (1.05 g, 1.89 mmol) and DIPEA (494 µL, 2.84 mmol) in THF (5.0 mL) was added valeroyl chloride (236 µL, 1.98 mmol). The reaction mixture was stirred at rt for 15 min. The solvent was removed under reduced pressure and the crude material was used directly for next step. MS (ESI-TOF) for $C_{35}H_{46}N_4O_7$ [M+H]⁺ calculated 639.3752; found 639.3787. The solution of crude oil obtained from above step in methanol (15 mL) was then added excess calcium oxide. The reaction mixture was stirred at 65° C. for 12 h. The solvent was removed under reduced pressure and the residue was purified by flash column chromatography (95% EtOAc/Hexanes) to obtain desired compound as a yellow oil (540 mg, yield=46% for three steps). ¹H NMR (500 MHz, Chloroform-d) δ 9.28 (s, 1H), 8.12 (d, J=8.5 Hz, 1H), 7.58 (s, 1H), 7.40 (d, J=8.4 Hz, 1H), 7.17 (d, J=8.7 Hz, 1H), 6.93 (d, J=7.6 Hz, 1H), 6.09 (s, 1H), 5.74 (s, 2H), 5.32 (s, 2H), 4.80 (s, 2H), 4.52 (s, 1H), 3.59 (s, 3H), 3.15 (s, 3H), 3.02 (d, J=5.2 Hz, 2H), 2.98-2.92 (m, 2H), 2.63 (t, J=7.1 Hz, 2H), 1.90 (p, J=7.4, 7.8 Hz, 2H), 1.52-1.46 (m, 6H), 1.43 (s, 9H), 1.41-1.36 (m, 2H), 1.23-1.13 (m, 2H), 0.96 (t, J=7.2 Hz, 3H). ³C NMR (126 MHz, CDCl₃) δ 156.1, 155.9, 152.7, 149.1, 144.3, 143.5, 140.5, 136.8, 134.0, 130.5, 128.1, 126.0, 119.0, 117.7, 116.3, 115.5, 95.5, 95.1, 56.5, 55.8, 44.8, 40.6, 36.2, 30.8, 30.0, 29.9, 28.6, 27.3, 26.2, 22.7, 13.9, 0.1. MS (ESI-TOF) for $C_{35}H_{48}N_4O_6$ [M+H]⁺ calculated 621.3647; found 621.3638.

Compound 114. To the solution of compound 111 (0.48 g, 0.77 mmol) in a mixed solvent of DCM/MeOH/CHCl₃ (3 mL0.3 mL/3 mL) was added 3-chloroperbenzoic acid (0.33 g, 1.93 mmol). The reaction was stirred at rt for 1 h. After completion, the solvent was evaporated and the target oxide compound was isolated through flash column chromatography (8% MeOH/DCM) as a yellow oil. MS (ESI-TOF) for $C_{35}H_{48}N_4O_7$ [M+H]⁺ calculated 637.3596; found 637.3561. To the solution of obtained yellow oil (490 mg, 0.77 mmol) in 5 mL DCM was added benzoyl isocyanate (135 mg, 0.92 mmol). After stirring at rt for 15 min, the solvent was evaporated and the residue was purified through flash column chromatography (5% MeOH/DCM) to afford target compound as a white solid (480 mg, yield=84% for two steps). ¹H NMR (500 MHz, Methanol-d₄) δ 8.16 (d, J=6.8 Hz, 1H), 8.03 (d, J=7.7 Hz, 1H), 7.89 (d, J=7.3 Hz, 1H), 7.72-7.64 (m, 2H), 7.63-7.55 (m, 2H), 7.50-7.41 (m, 1H), 7.23 (t, J=9.7 Hz, 1H), 6.95 (t, J=8.1 Hz, 1H), 6.10 (s, 1H), 5.88 (s, 2H), 5.34 (d, J=18.4 Hz, 2H), 4.77 (d, J=9.2 Hz, 2H), 3.57 (d, J=19.5 Hz, 3H), 3.17-3.03 (m, 4H), 2.73-2.59 (m, 2H), 1.87-1.73 (m, 2H), 1.48 (d, J=59.9 Hz, 9H), 1.49-1.44 (m, 4H), 1.40-1.35 (m, 2H), 1.24-1.12 (m, 2H), 0.93 (t, J=7.3 Hz, 3H). MS (ESI-TOF) for $C_{42}H_{53}N_5O_7$ [M+H]⁺ calculated 740.4018; found 740.3980. The obtained white solid (480 mg, 0.65 mmol) was then dissolved into 5 mL methanol. Sodium methoxide (in excess) was then added. The resulting mixture was stirred at 65° C. for 1 h. After completion, the solvent was evaporated and the residue was purified through flash column chromatography (7% MeOH/DCM) to afford a colorless oil. MS (ESI-TOF) for $C_{35}H_{49}N_5O_6$ [M+H]⁺ calculated 636.3756; found 636.3714. To the obtained oil in methanol (3 mL) was added 2.0 mL 4N HCl in dioxane. The reaction mixture was stirred at rt for 1 h. After completion, all solvents were evaporated and desired product was isolated through flash column chromatography (18% MeOH/DCM) as a yellow solid (200 mg, yield=69% for two steps). ¹H NMR (500 MHz, Methanol-d₄) δ 7.73 (s, 1H), 7.66 (d, J=8.3 Hz, 1H), 7.49 (d, J=8.4 Hz, 1H), 6.83 (d, J=8.6 Hz, 1H), 6.60 (d, J=7.7 Hz, 1H), 5.84 (s, 1H), 5.76 (s, 2H), 3.05 (t, J=7.5 Hz, 2H), 2.95-2.79 (m, 2H), 2.68 (t, J=7.2 Hz, 2H), 1.89 (p, J=7.6 Hz, 2H), 1.66-1.57 (m, 2H), 1.56-1.46 (m, 4H), 1.25 (p, J=8.0 Hz, 2H), 0.98 (t, J=7.3 Hz, 3H). ³C NMR (126 MHz, MeOD) δ 159.0, 151.8, 150.1, 148.5, 140.9, 137.5, 133.9, 131.6, 125.8, 123.2, 122.3, 119.6, 117.3, 116.6, 114.3, 113.2, 46.0, 40.7, 36.2, 31.6, 30.5, 28.5, 27.8, 26.7, 23.4, 14.1. MS (ESI-TOF) for $C_{26}H_{33}N_5O_2$ [M+H]⁺ calculated 448.2707; found 448.2693.

Example 12. Representative Compounds of the Invention

Using procedures similar to those described herein, the following compounds and salts of the invention can be prepared.

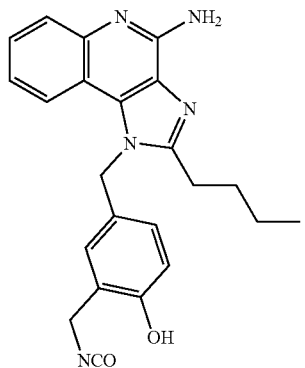

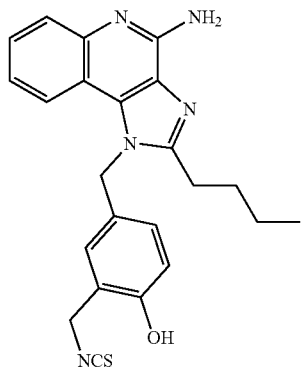

-continued
63
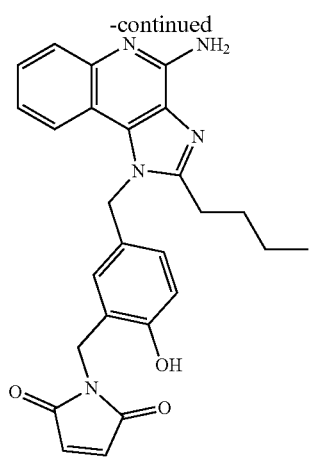
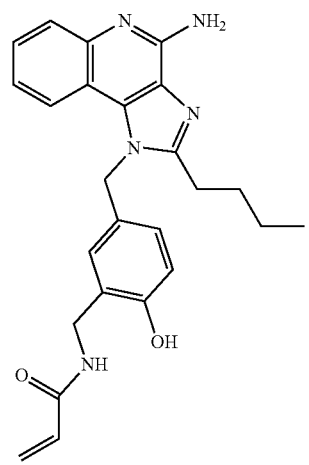
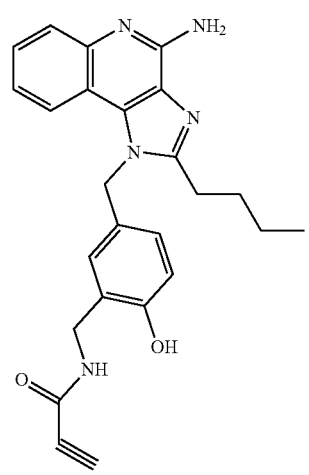
-continued
64
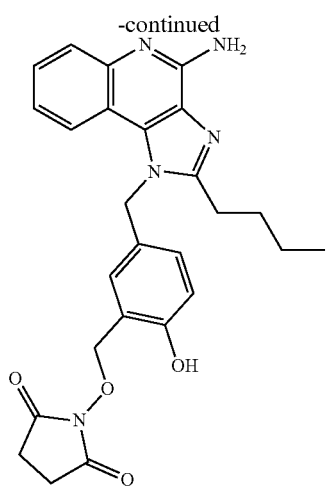
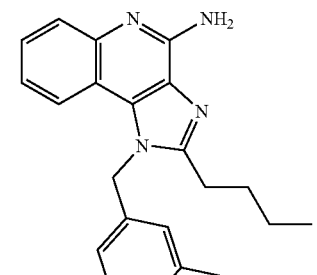
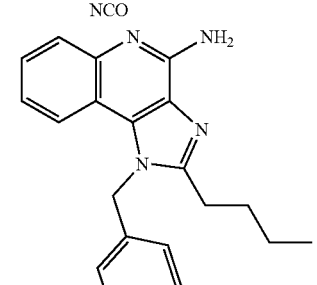
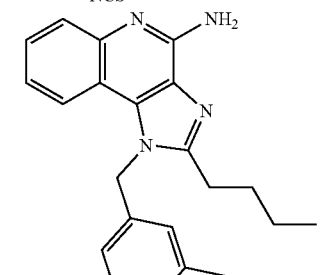
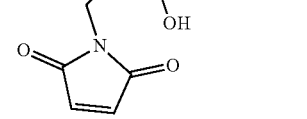

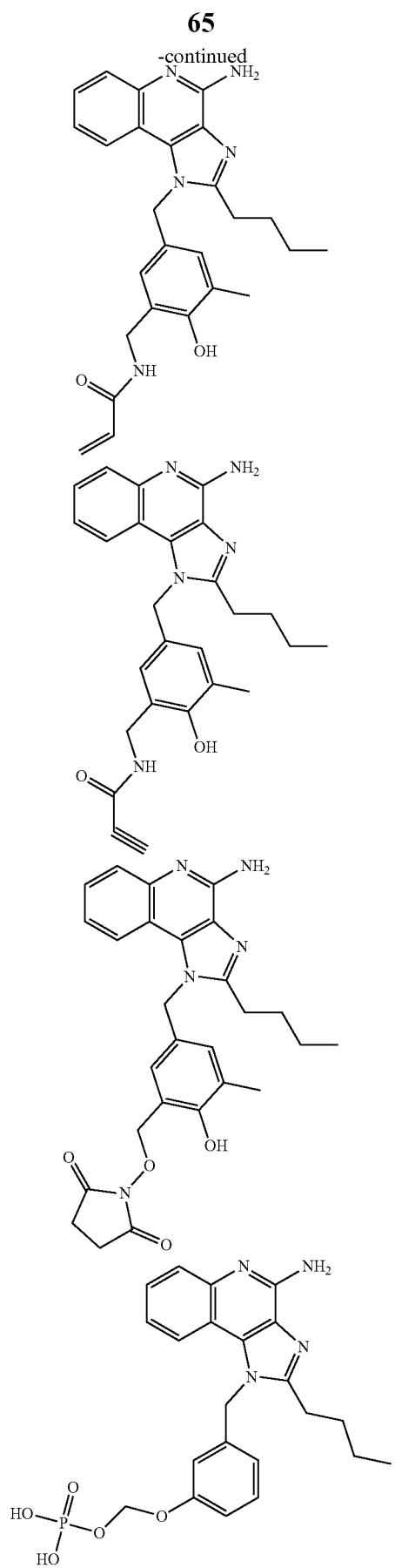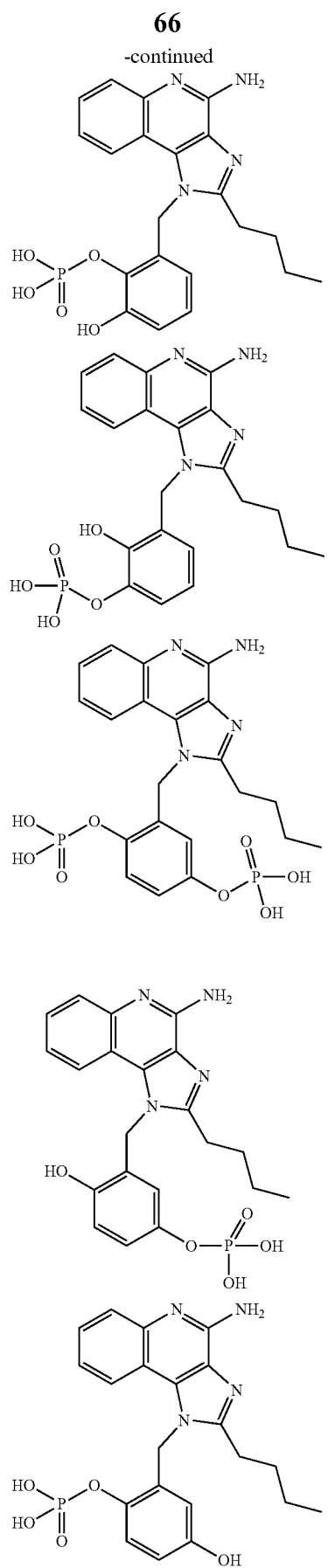

67
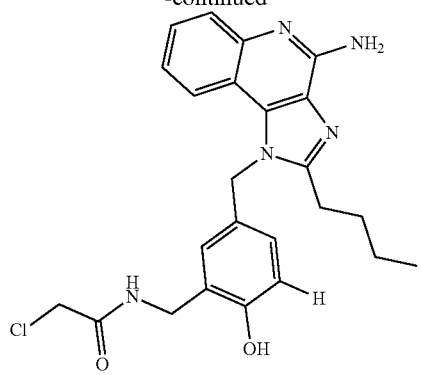
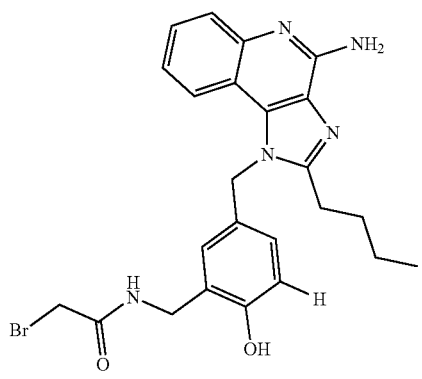
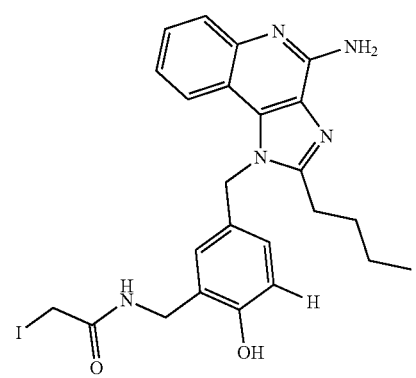
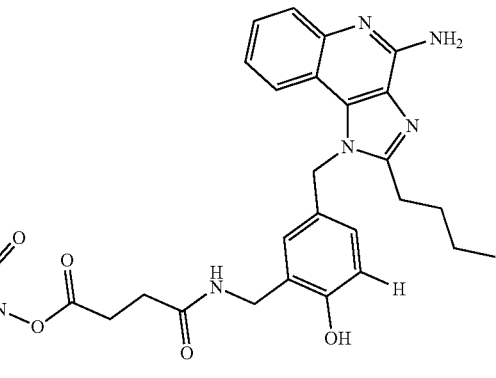
68
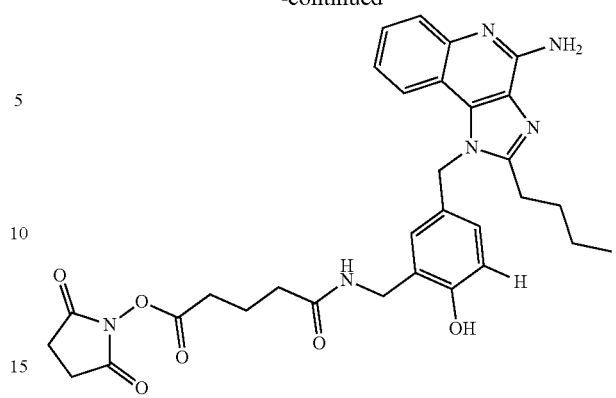
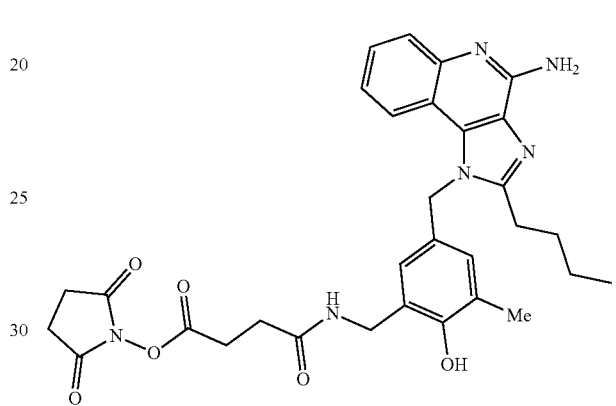
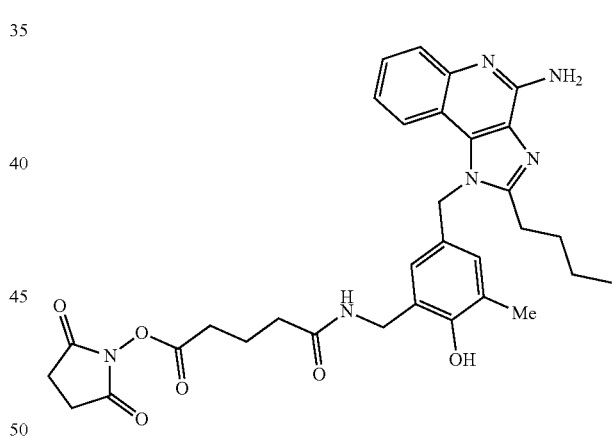
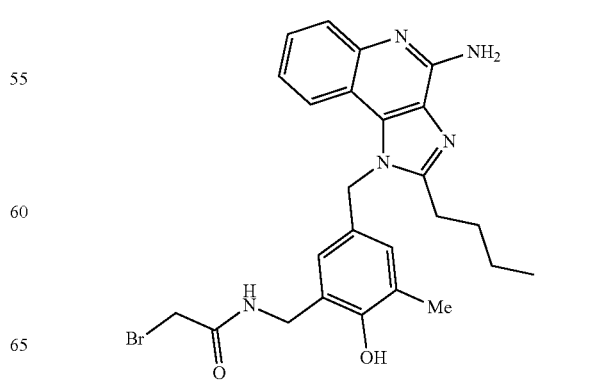

-continued
69
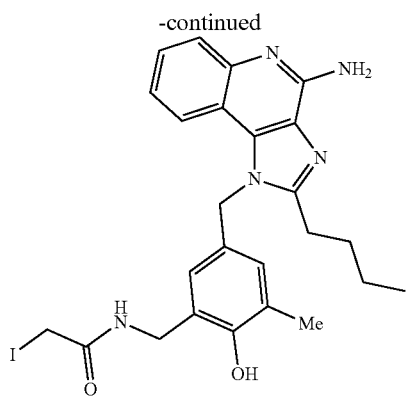
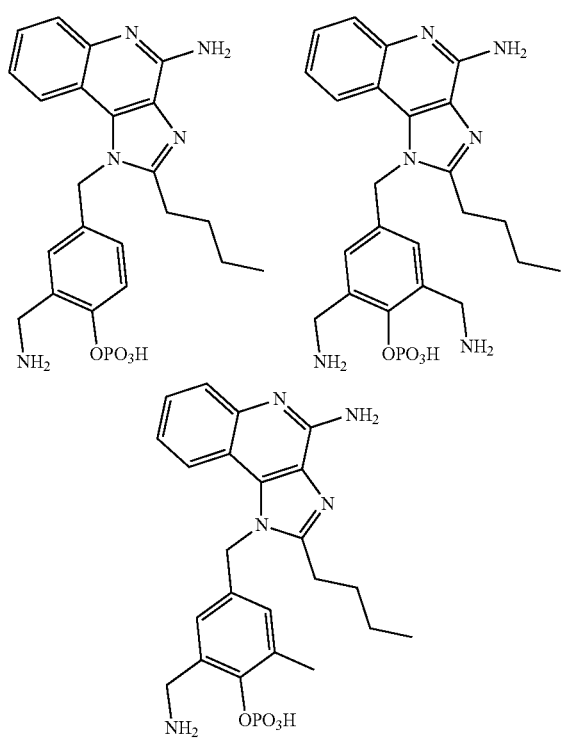
70
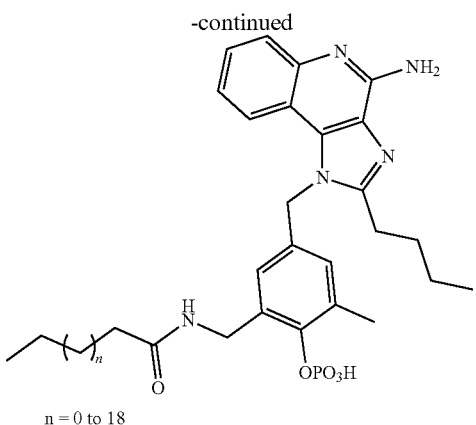
n = 0 to 18
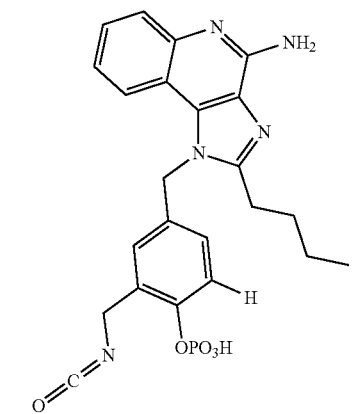

71
-continued
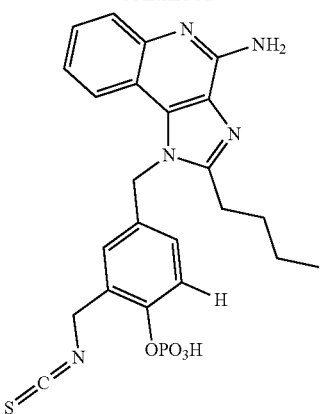
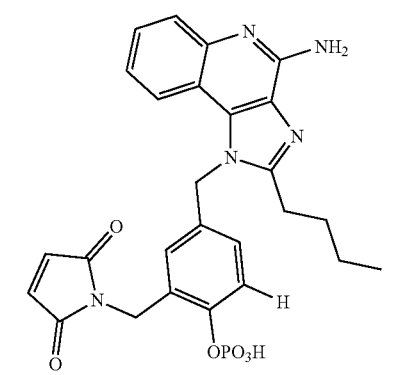
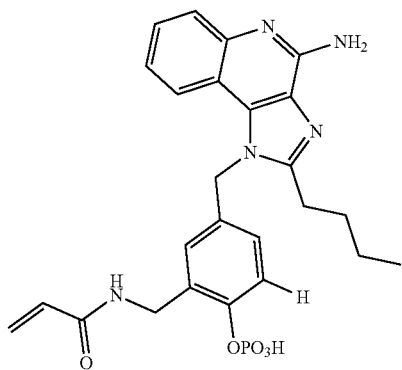
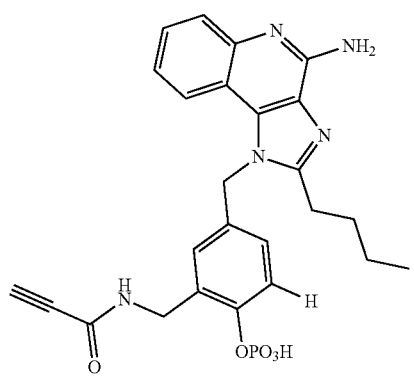
72
-continued
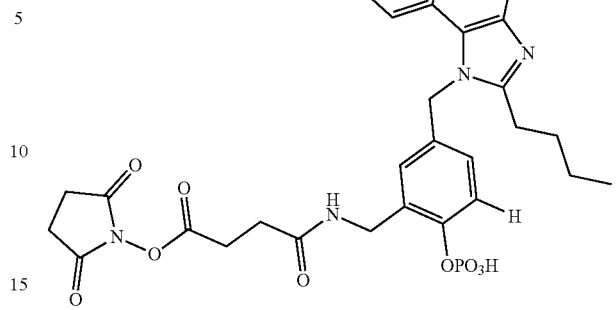
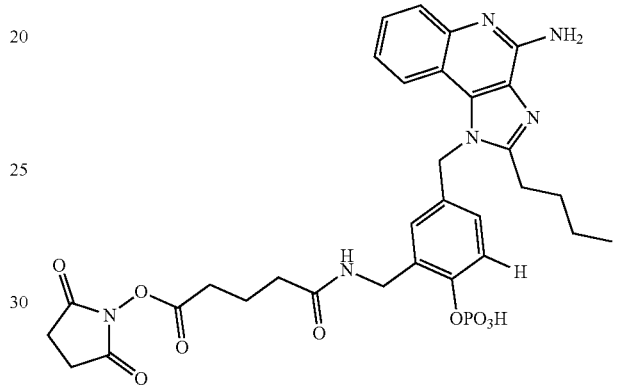
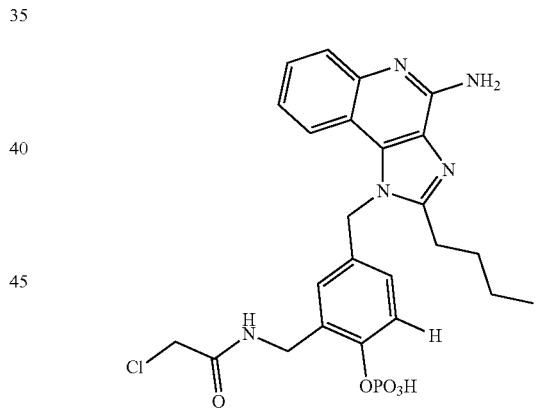
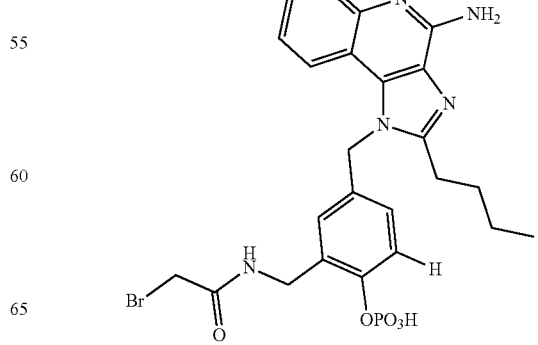

73
-continued
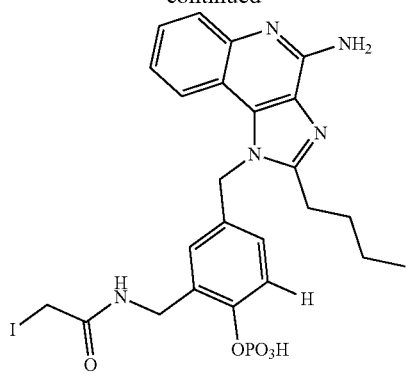
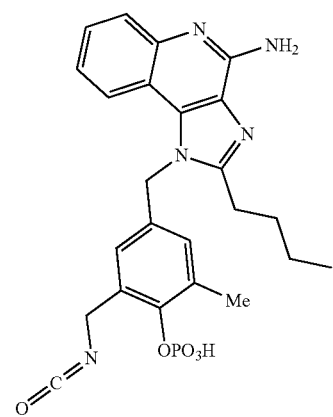
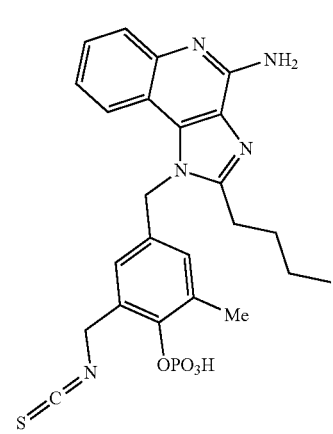
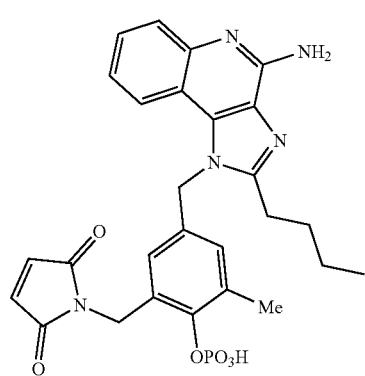
74
-continued
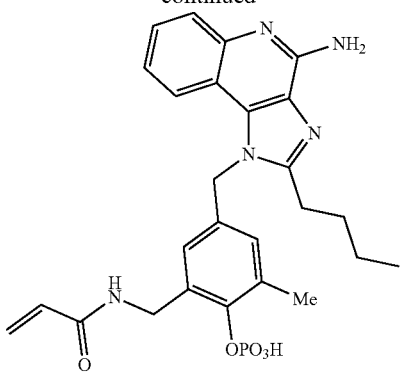
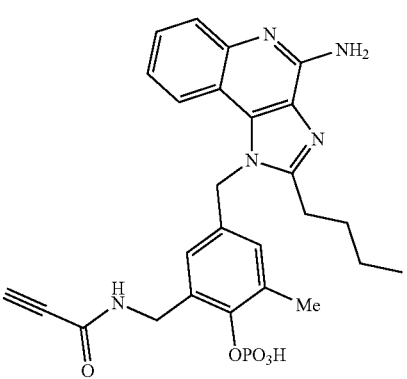
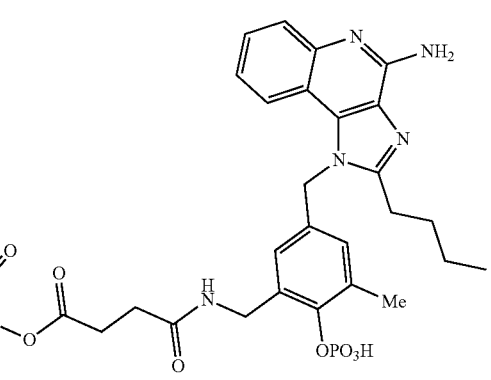
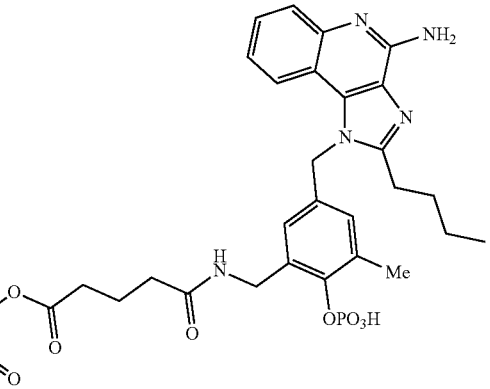

75
-continued
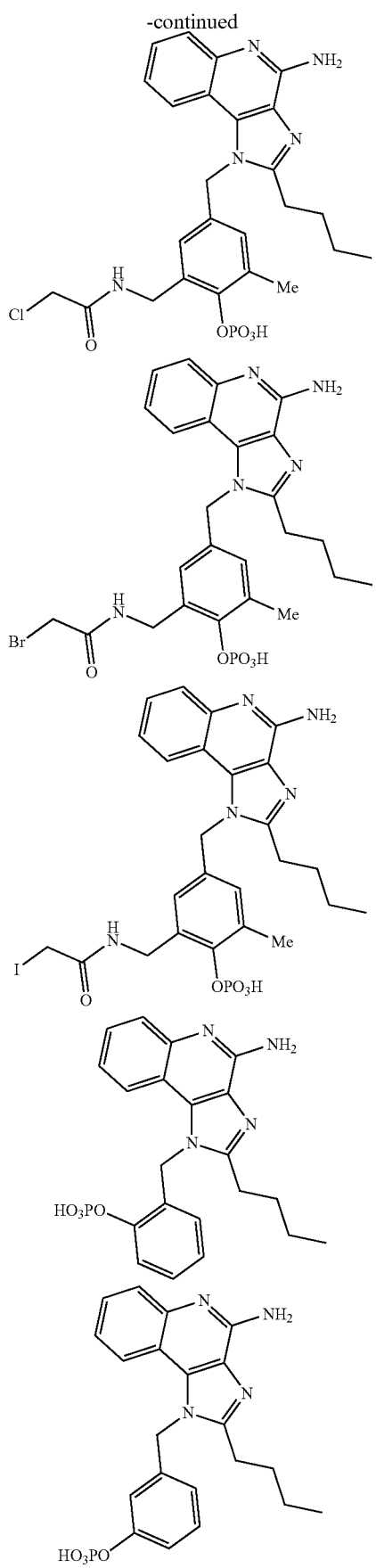
76
-continued
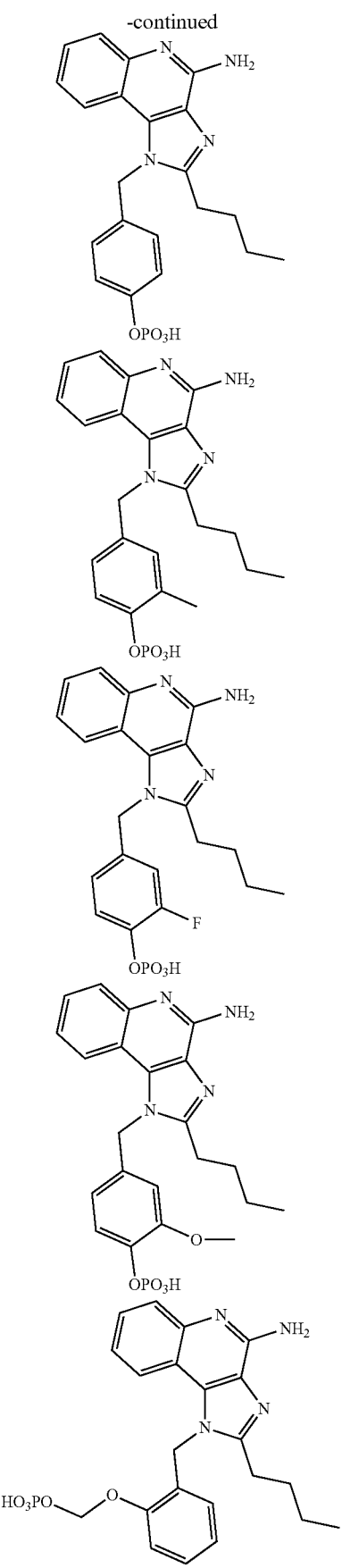

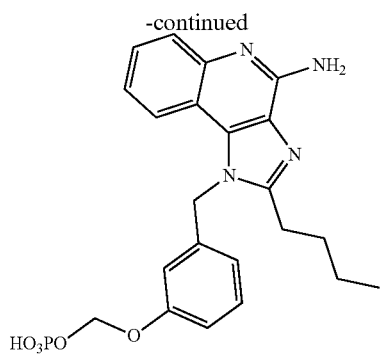
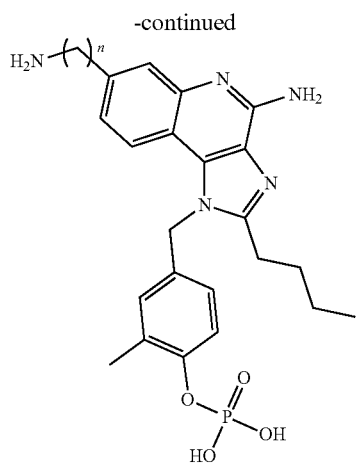
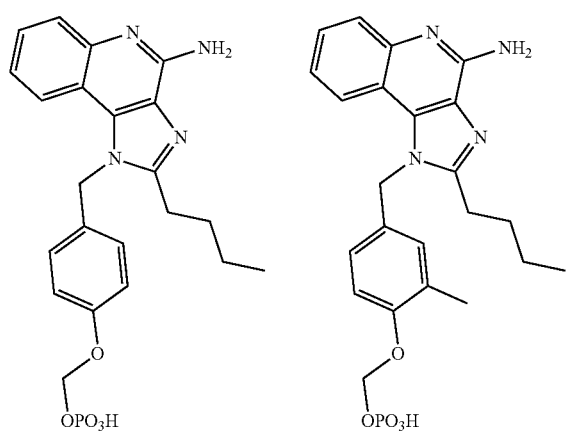
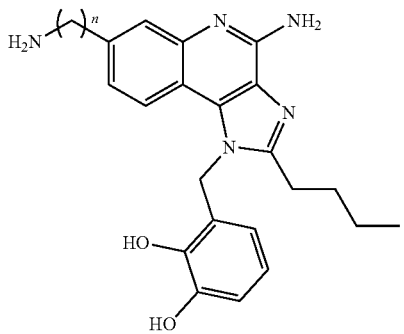
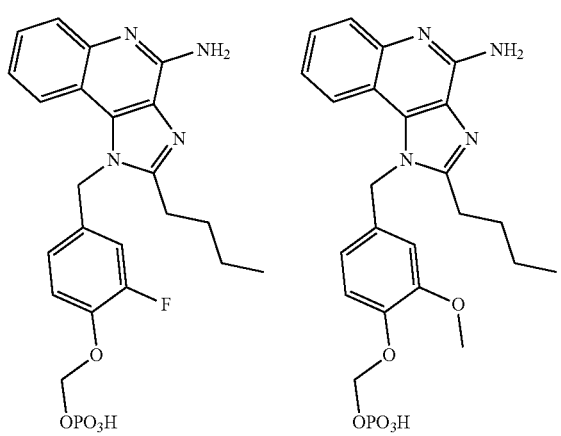
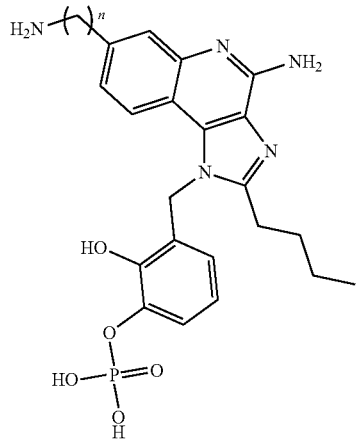
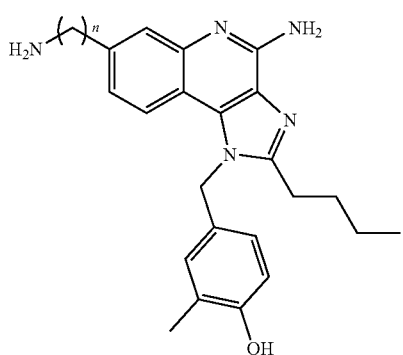
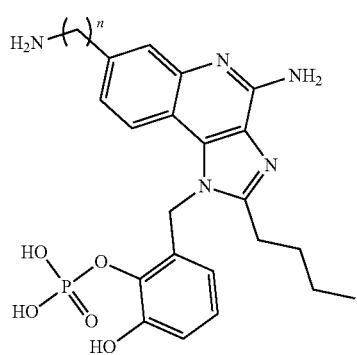

79
-continued
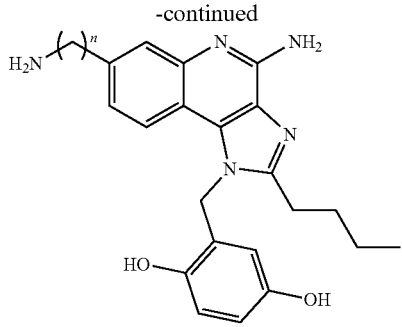
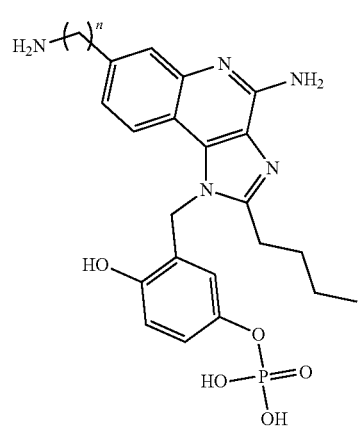
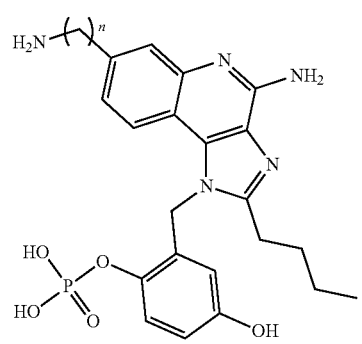
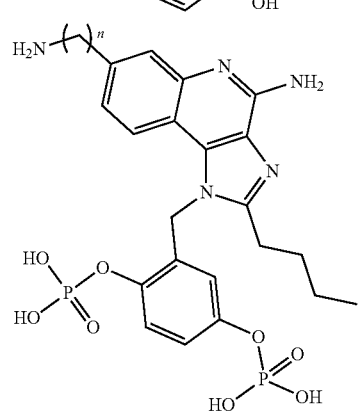
80
-continued
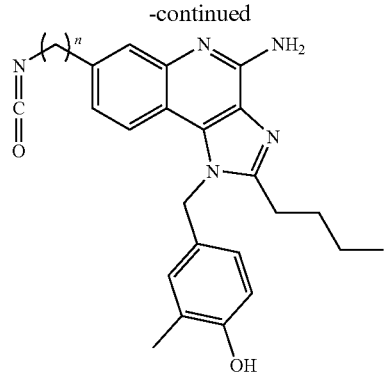
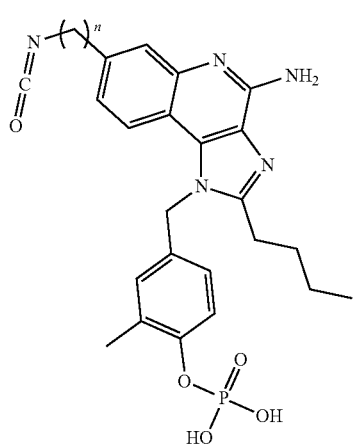
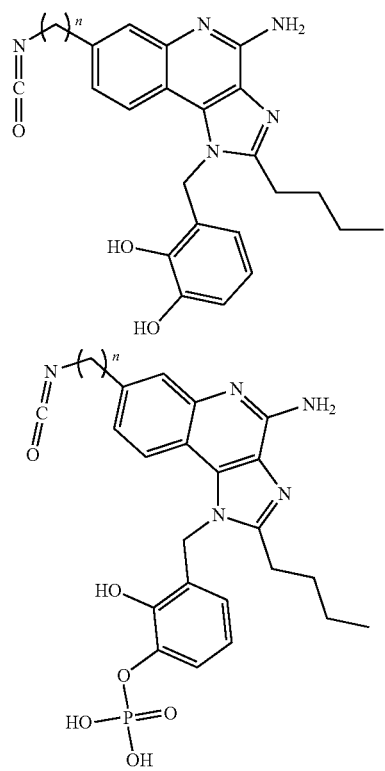

81
-continued
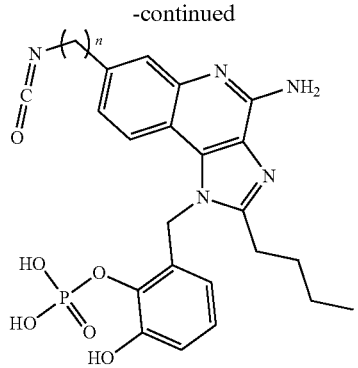
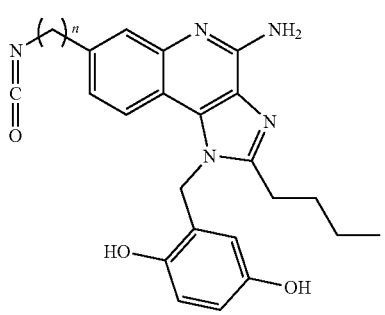
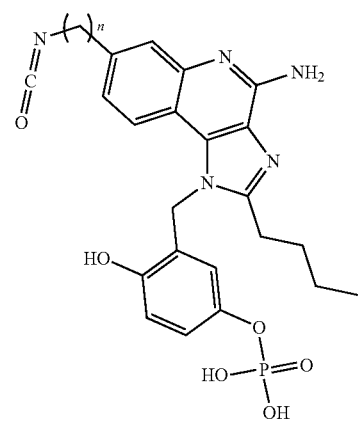
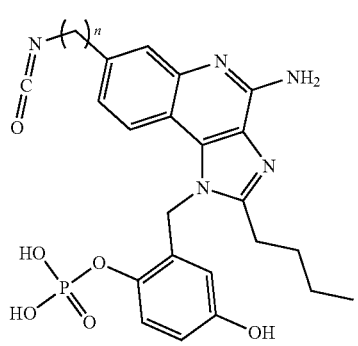
82
-continued
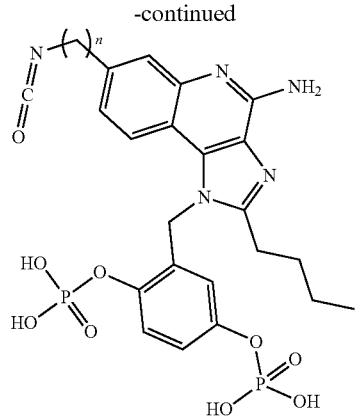
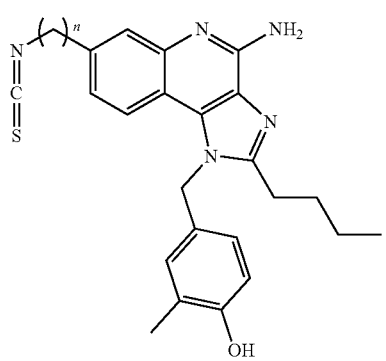
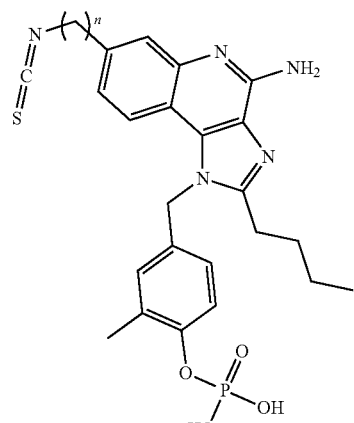
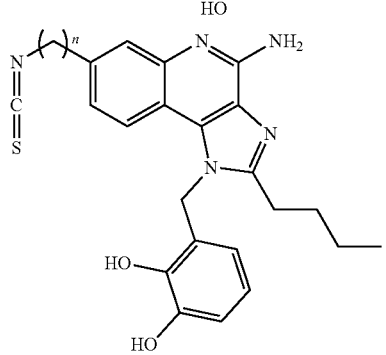

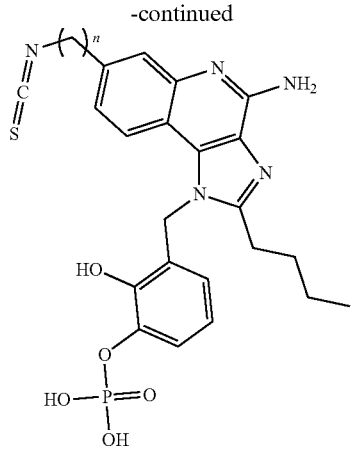
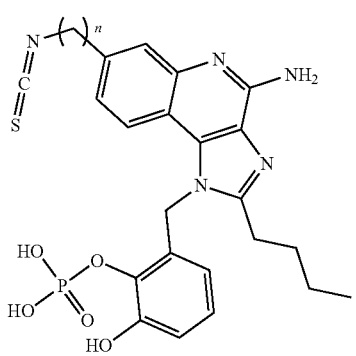
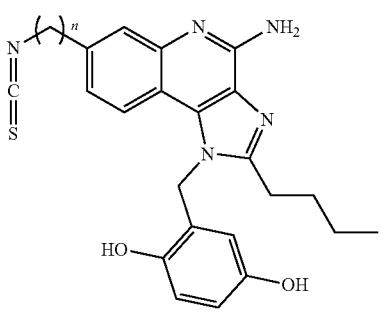
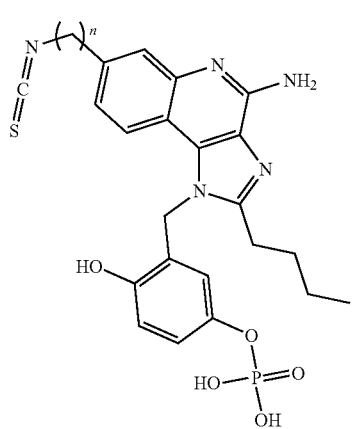
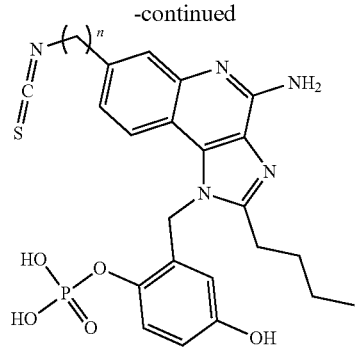
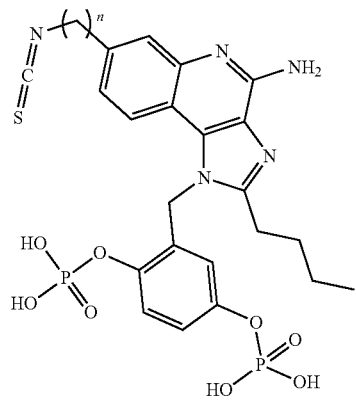
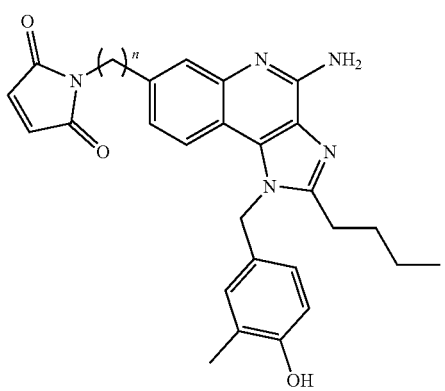
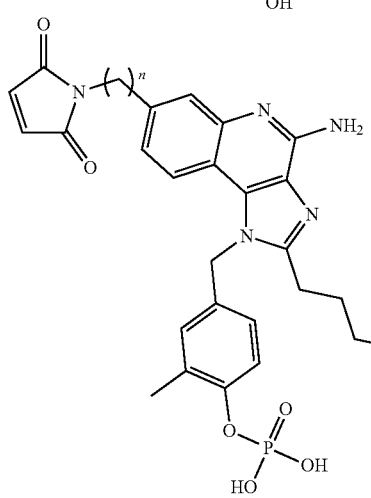

85
-continued
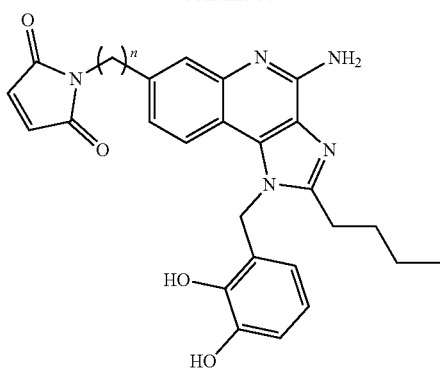
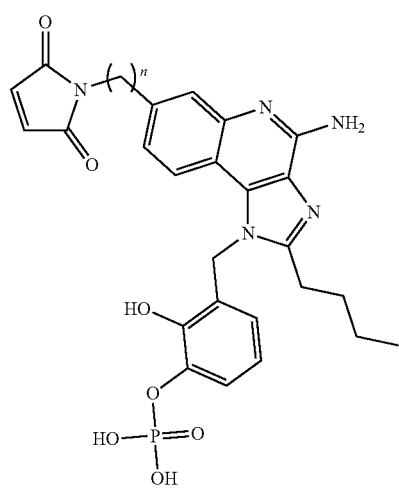
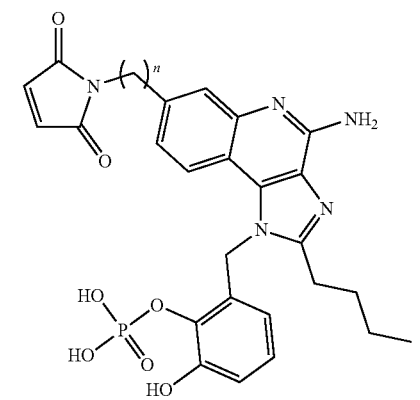
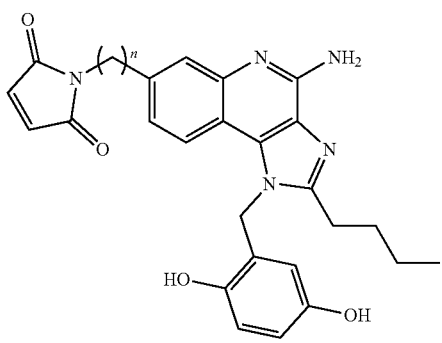
86
-continued
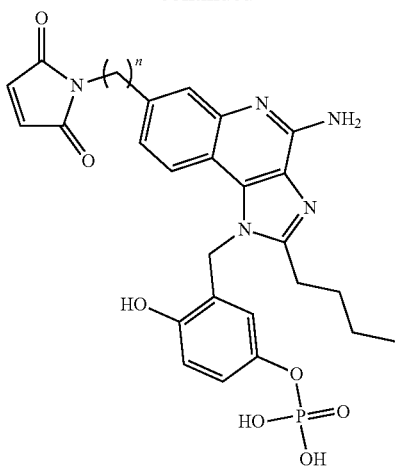
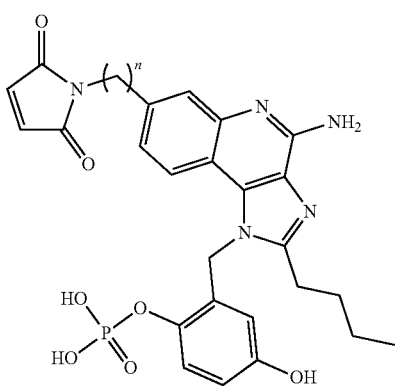
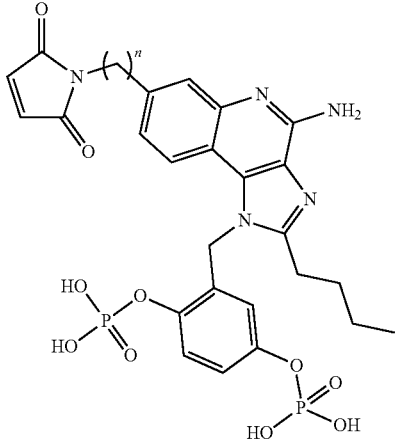
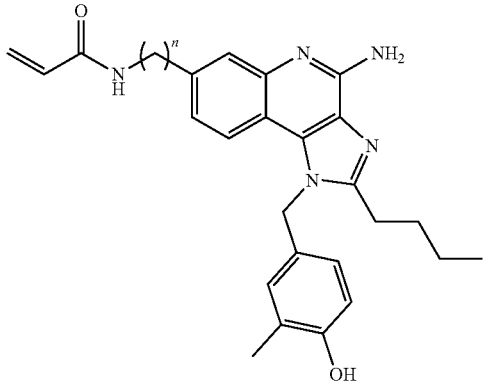

-continued
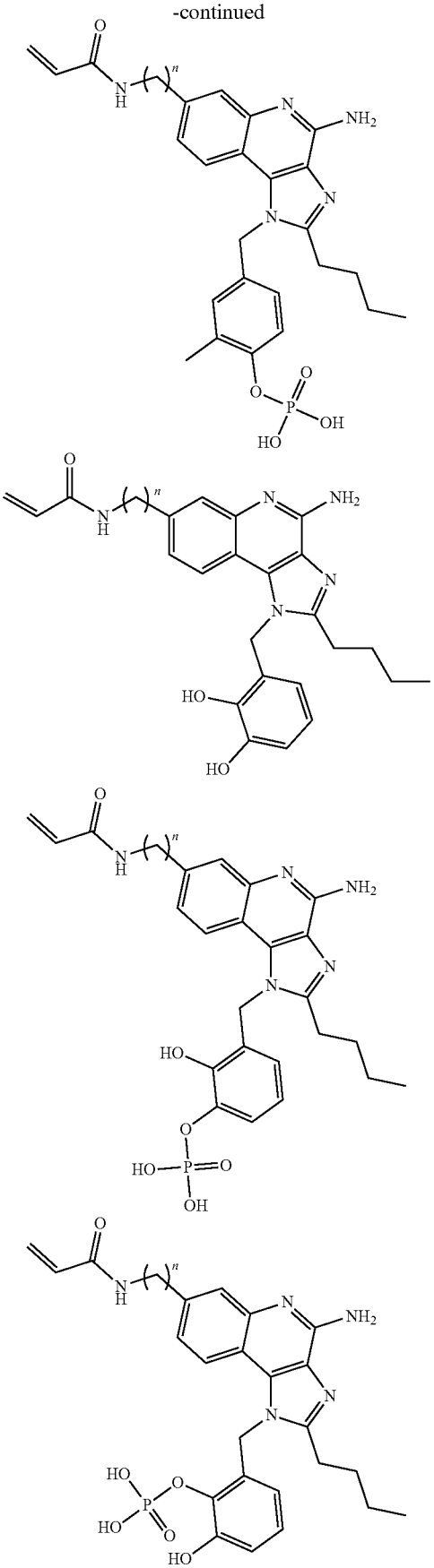
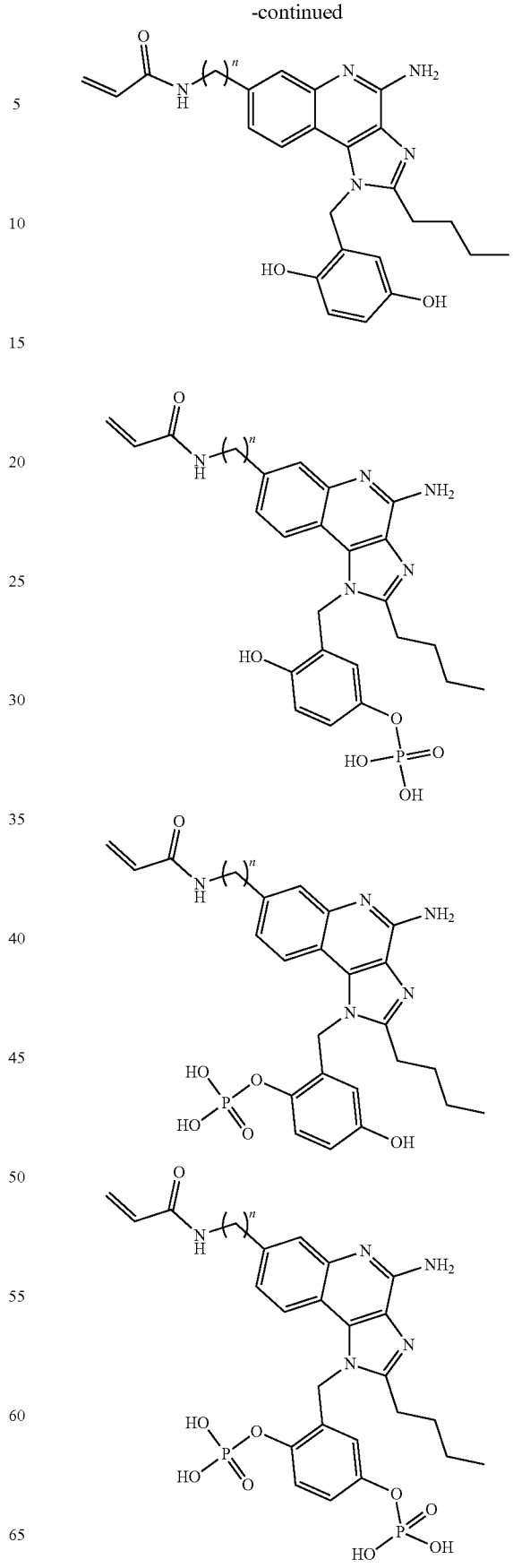

-continued
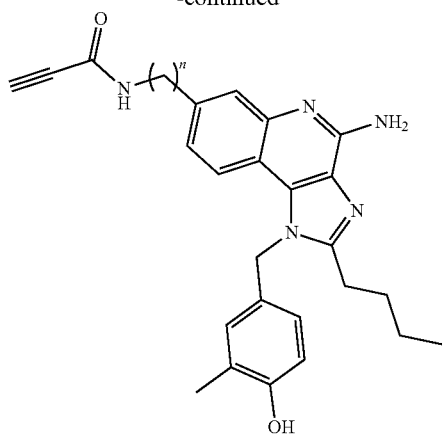
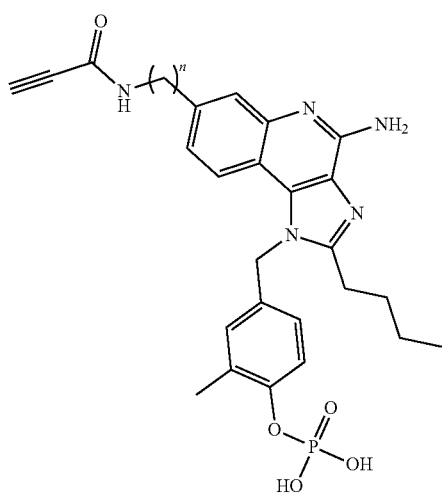
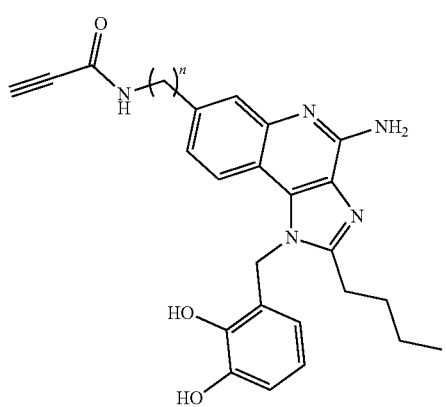
-continued
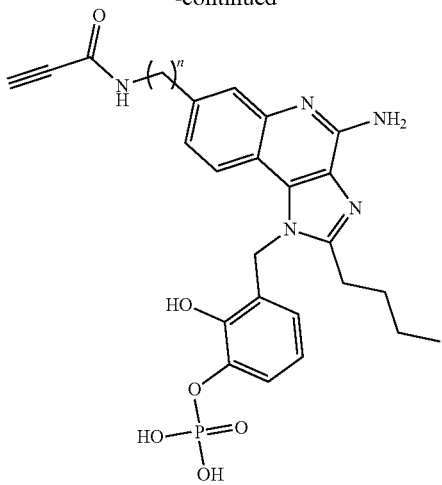
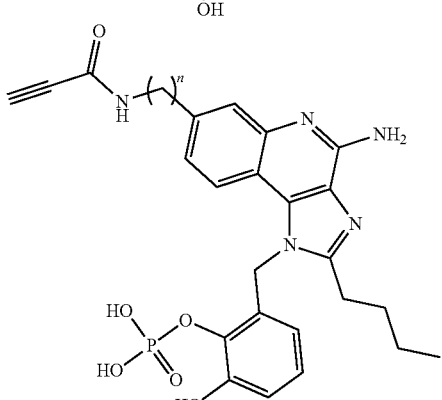
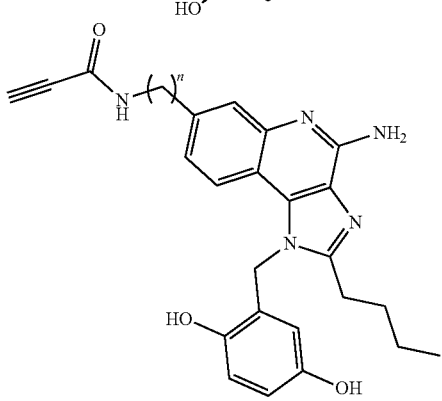
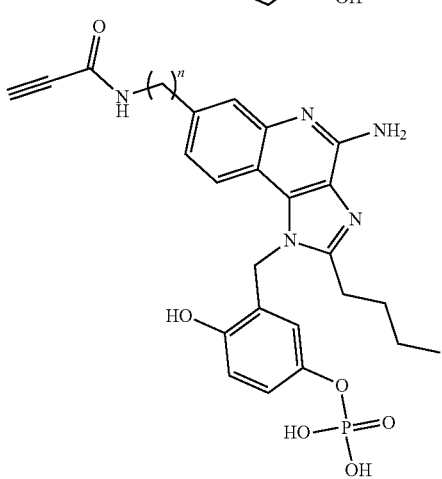

91
-continued
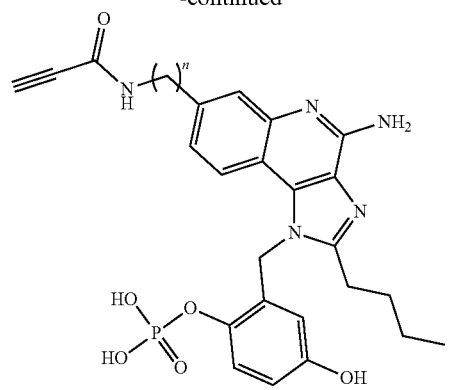
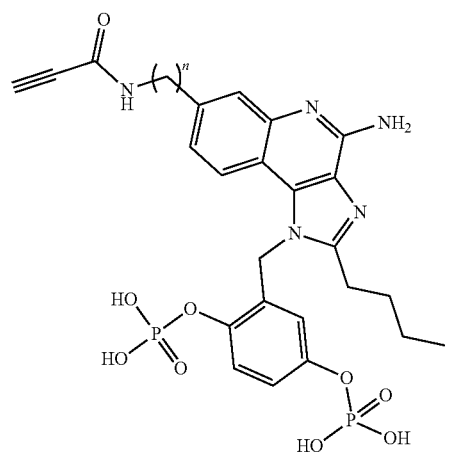
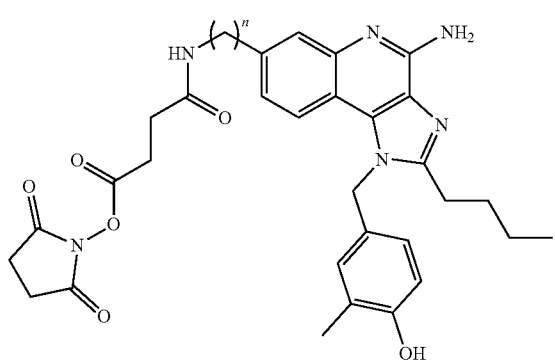
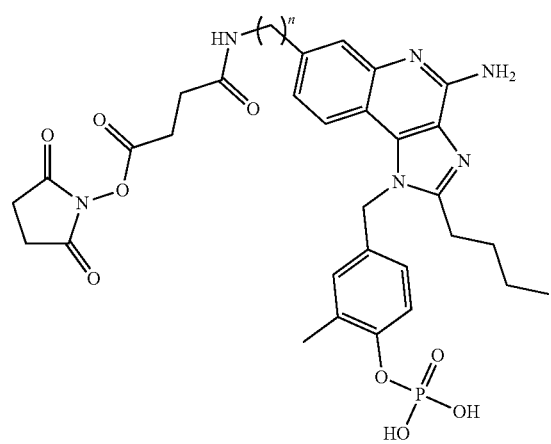
92
-continued
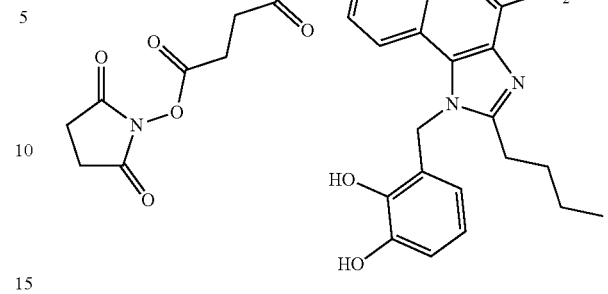
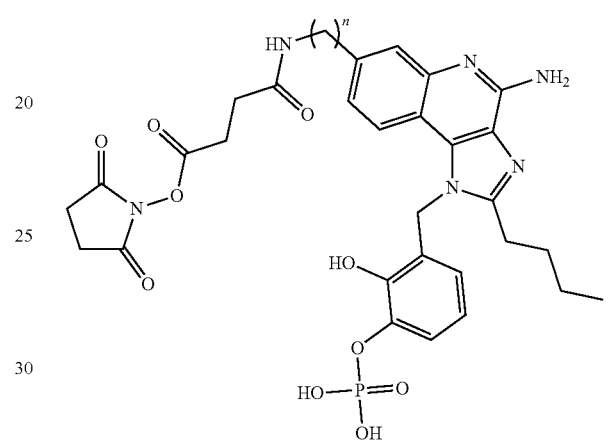
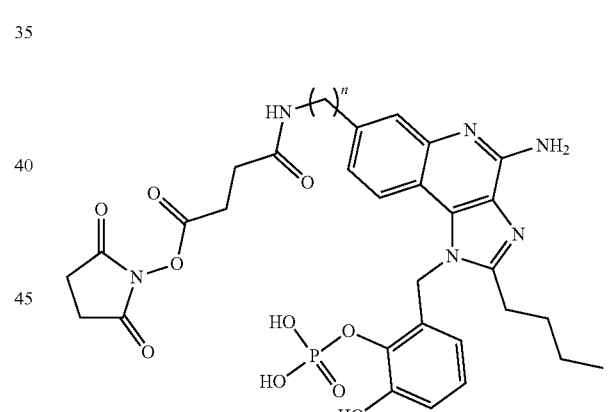
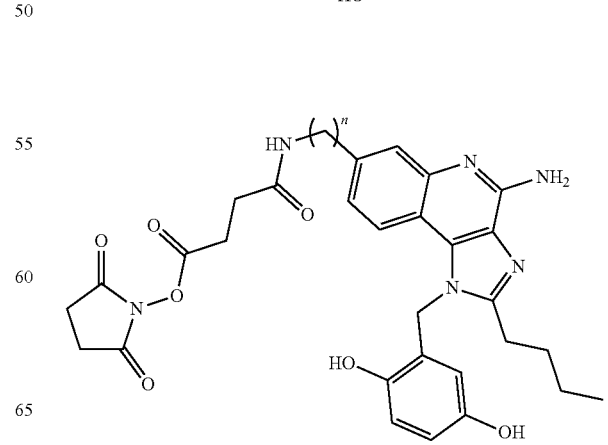

93
-continued
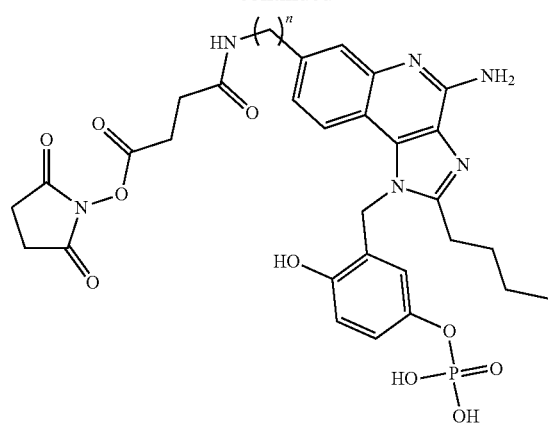
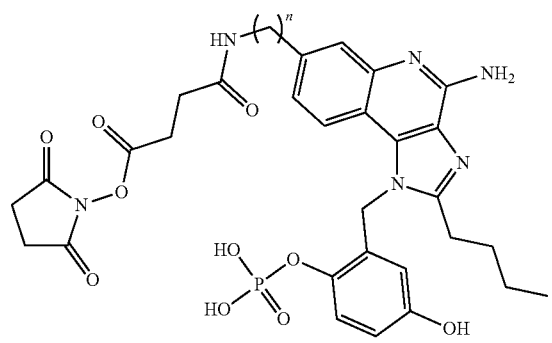
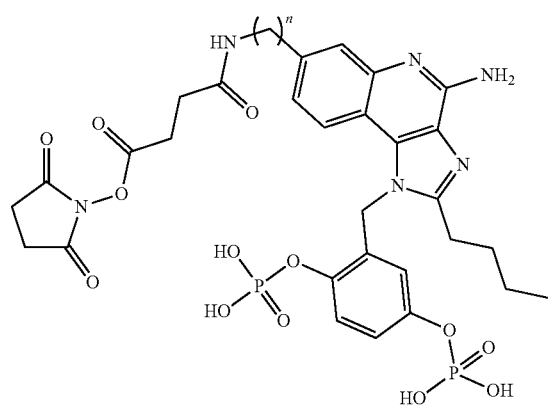
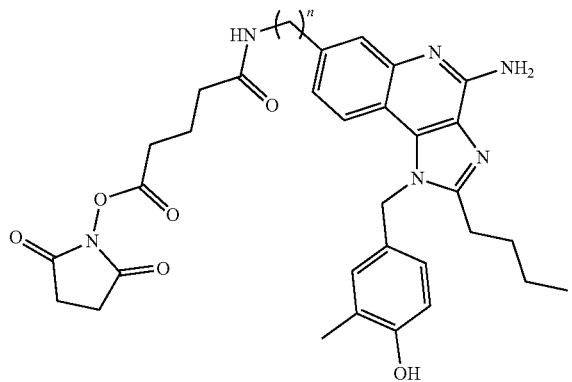
94
-continued
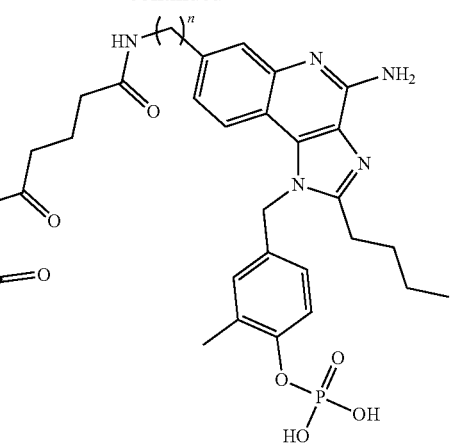
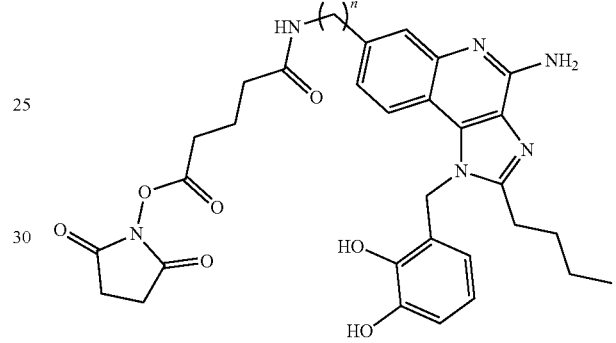
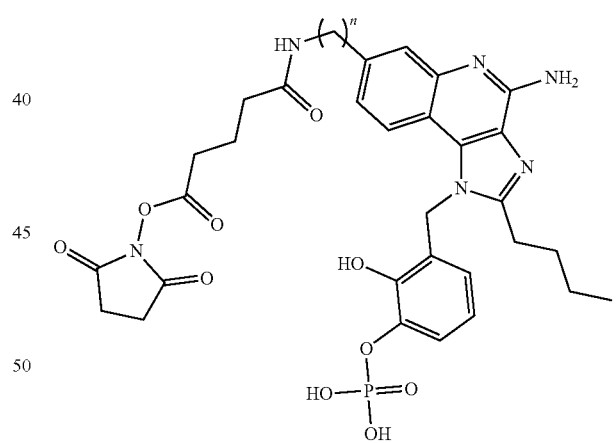
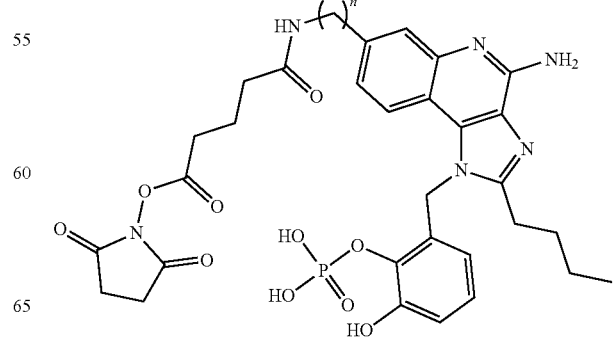

95
-continued
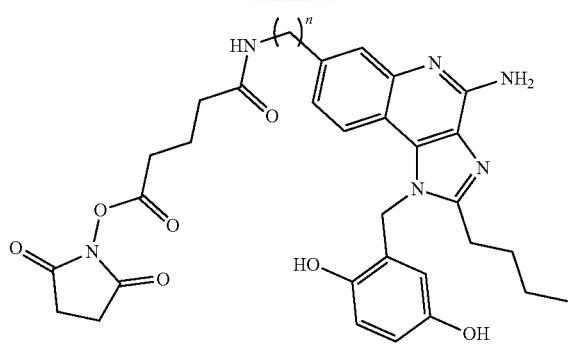
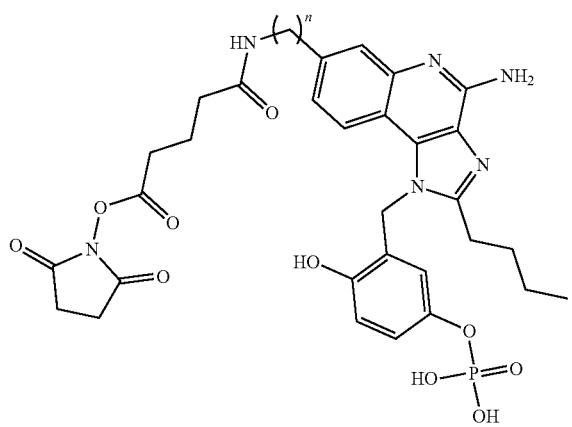
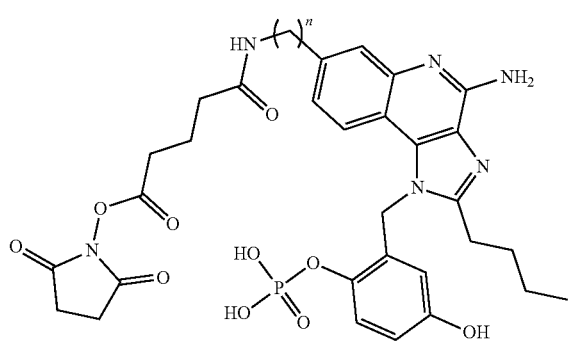
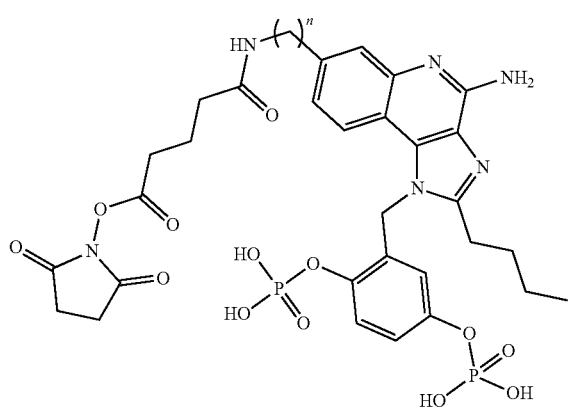
96
-continued
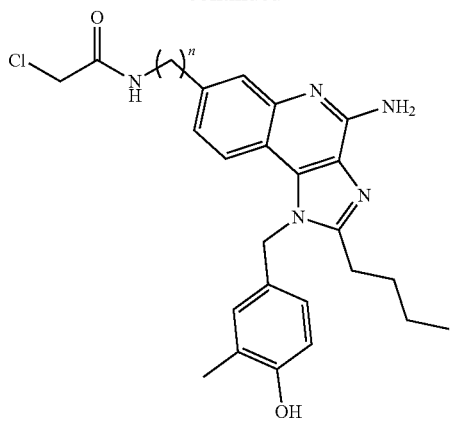
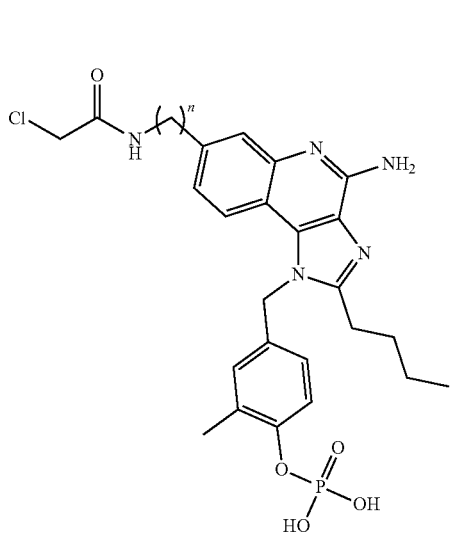
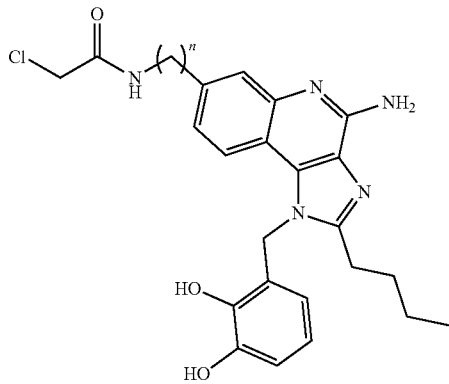

97
-continued
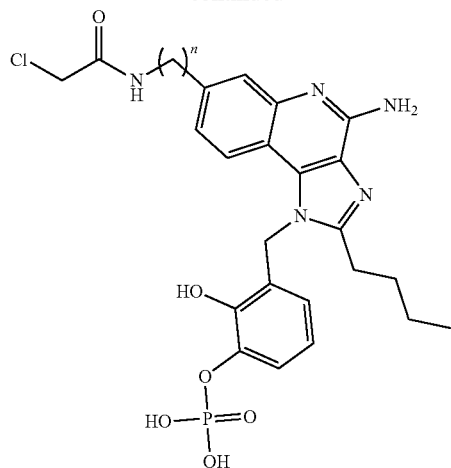
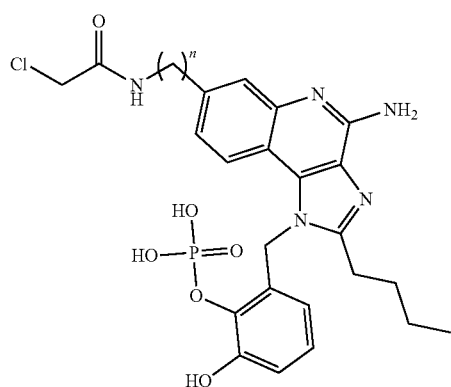
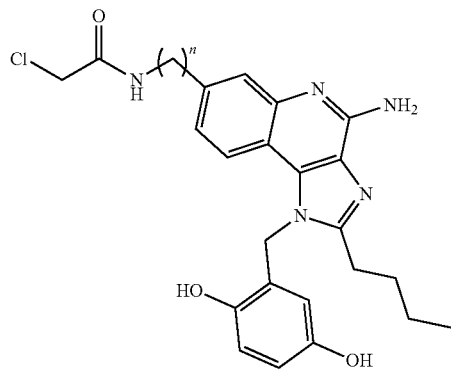
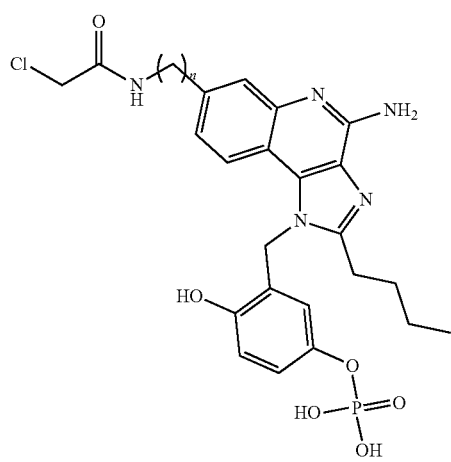
98
-continued
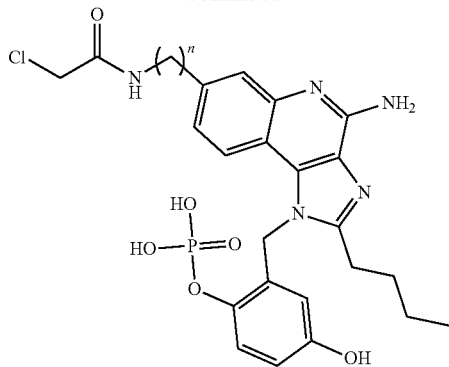
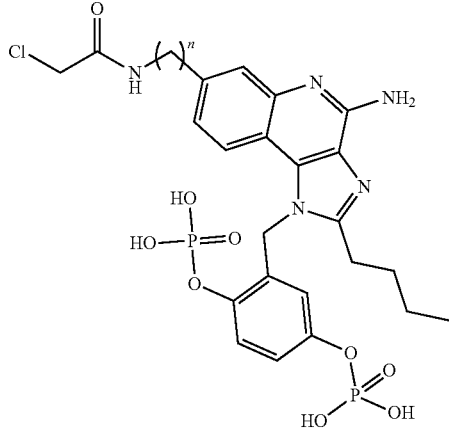
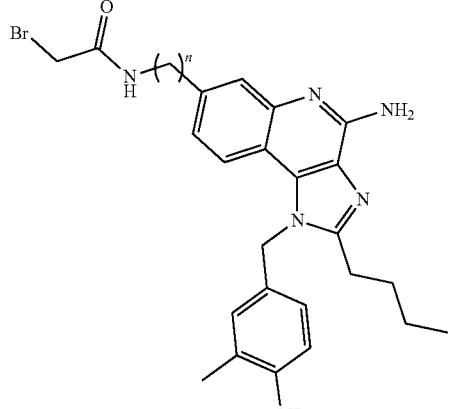
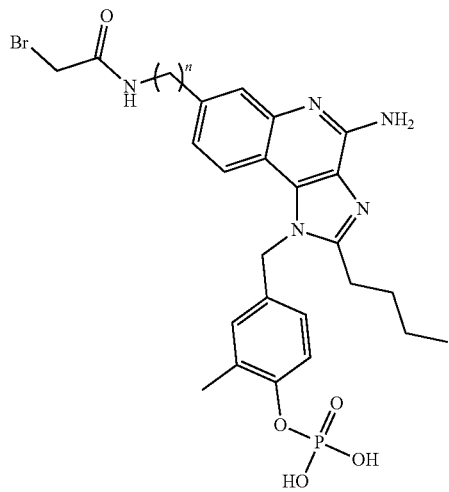

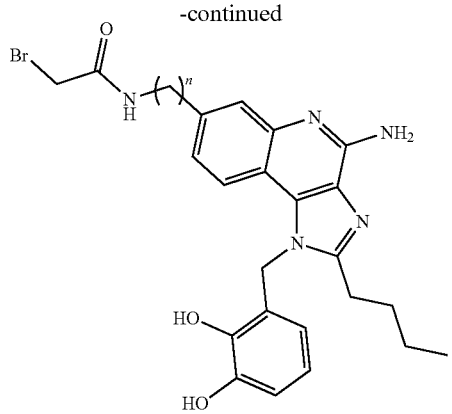
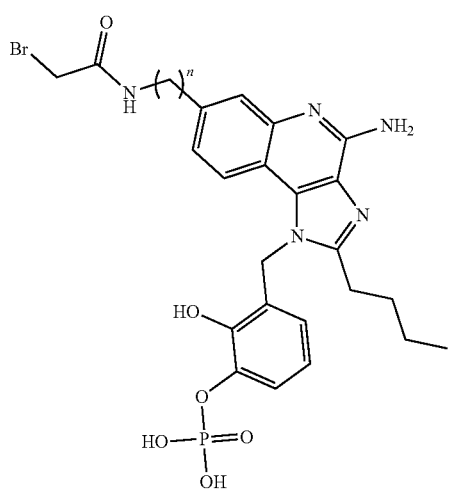
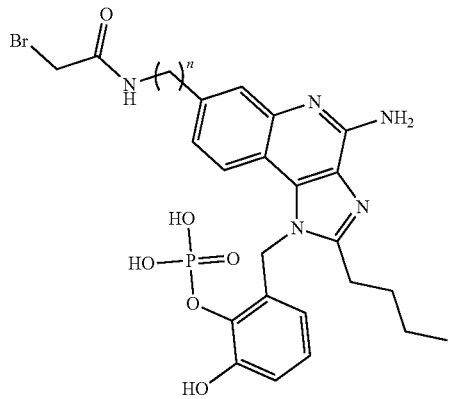
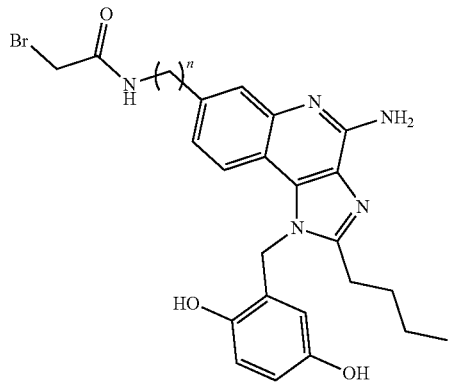
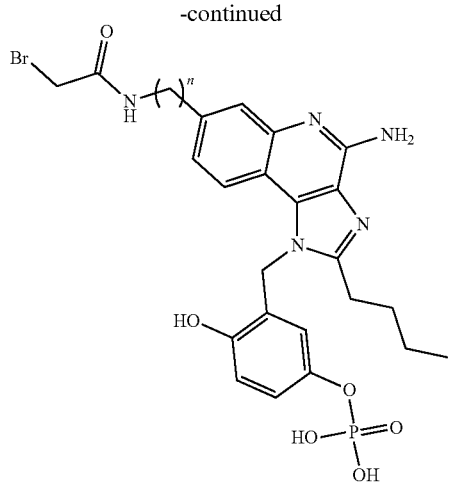
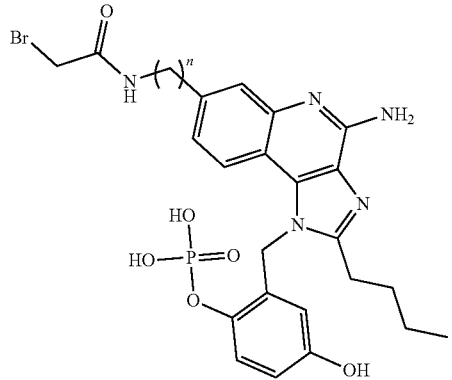
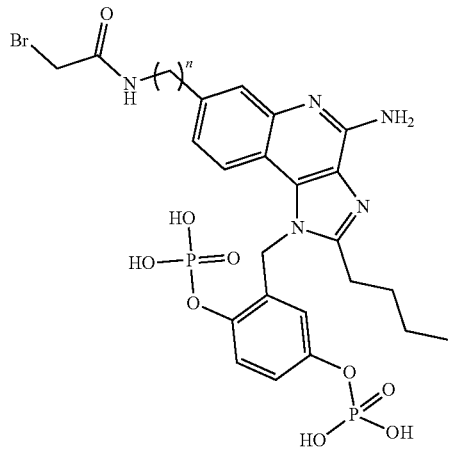
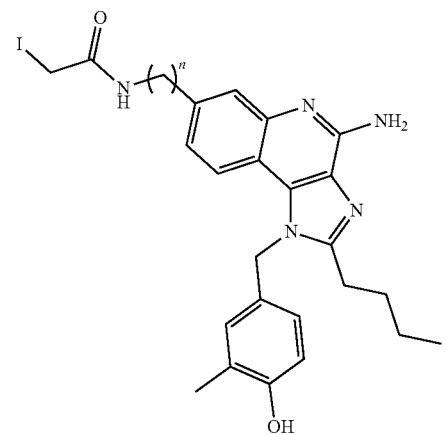

101
-continued
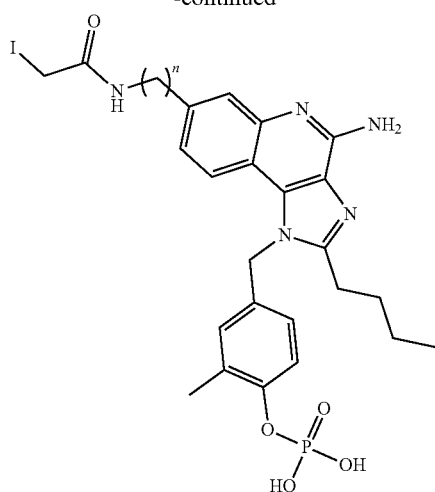
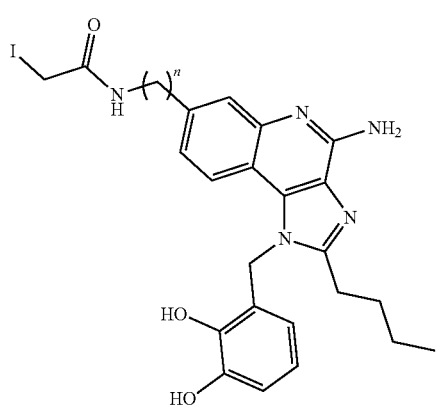
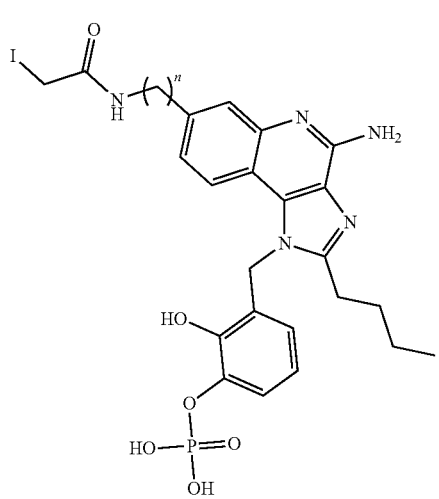
102
-continued
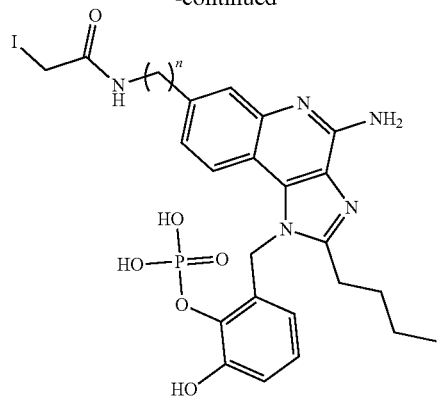
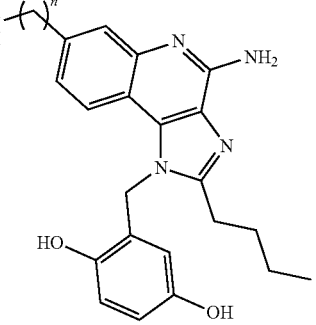
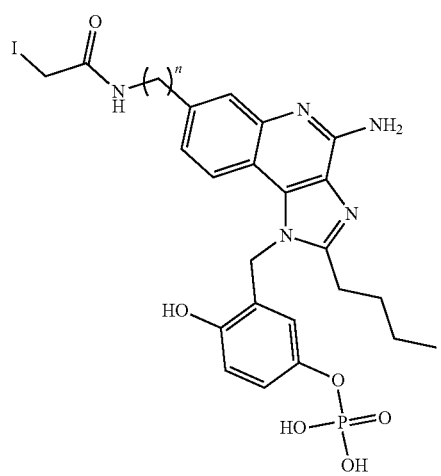
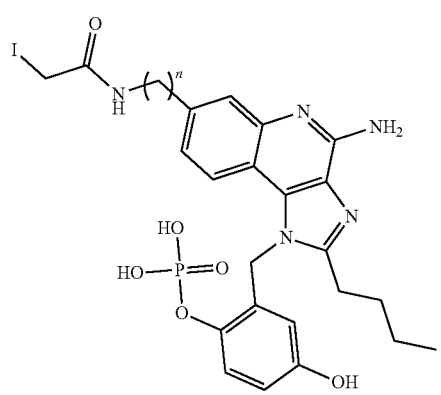

103
-continued

104
-continued

-continued
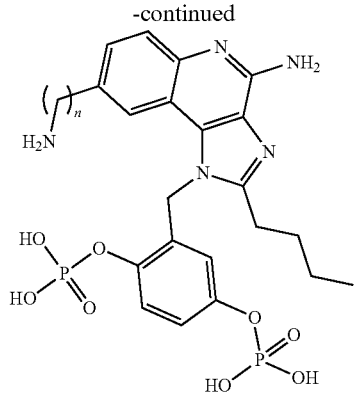
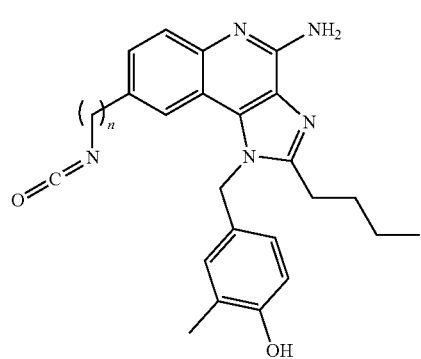
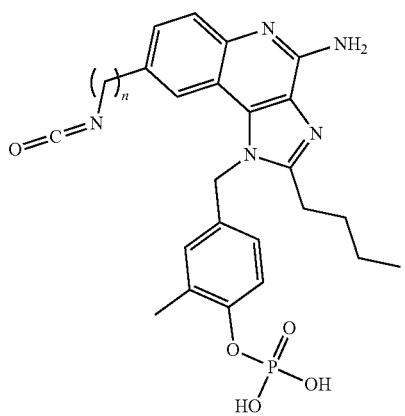
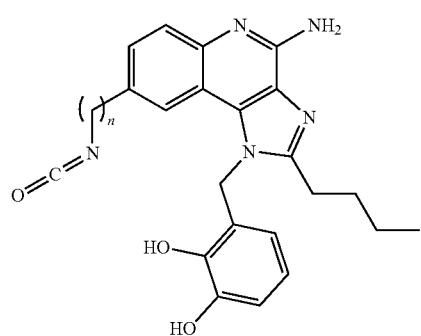
-continued
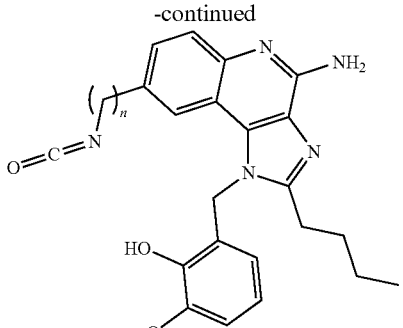
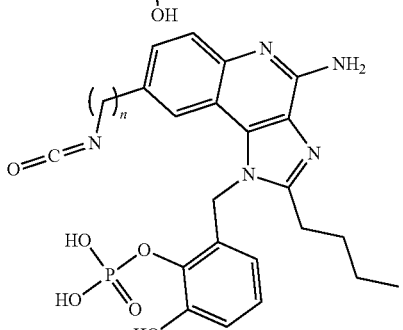
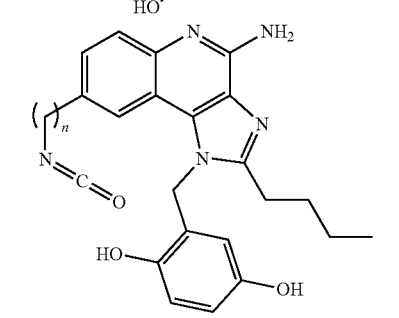
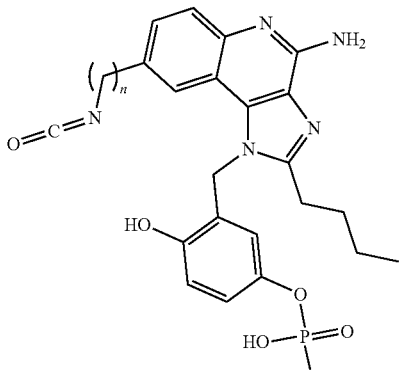
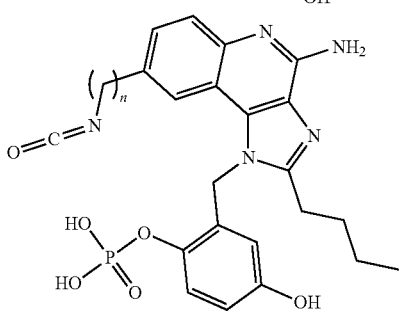

107
-continued
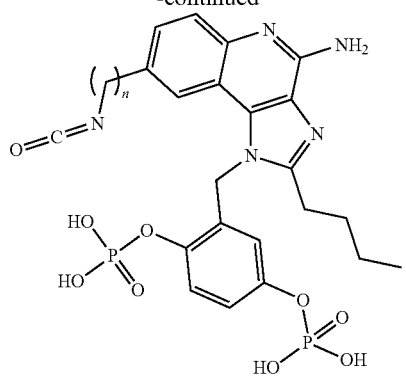
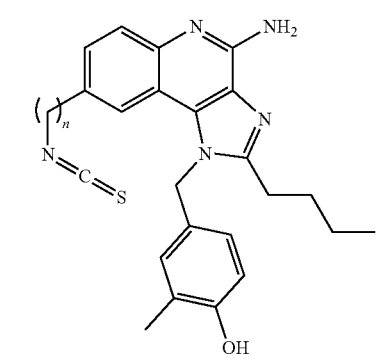
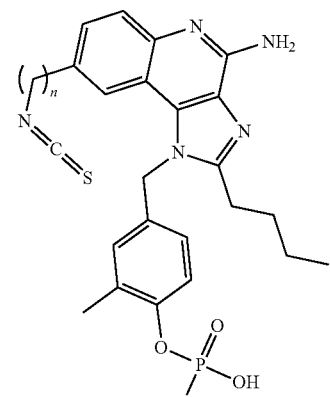
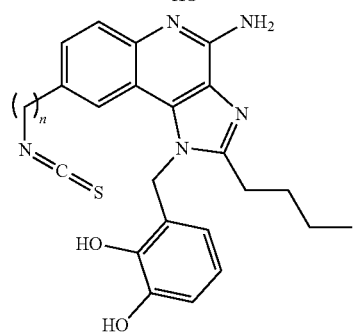
108
-continued
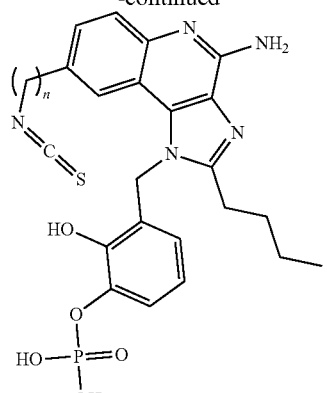
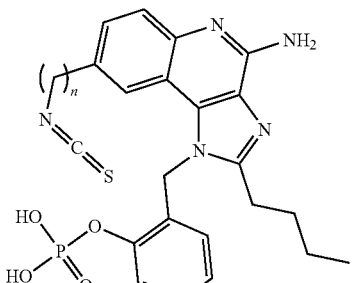
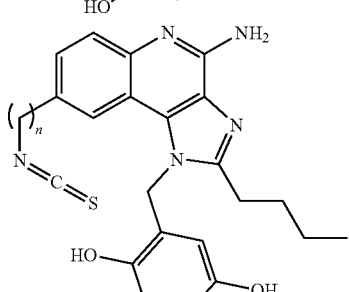
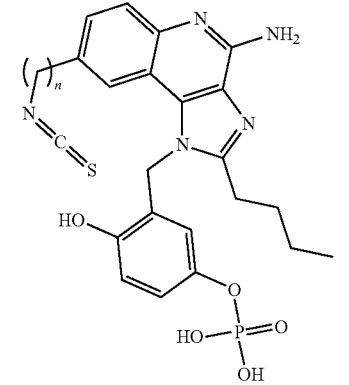
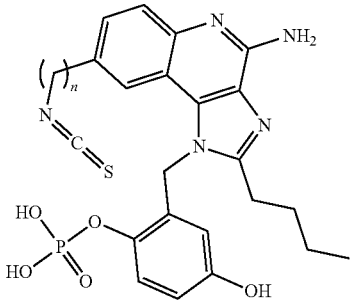

-continued
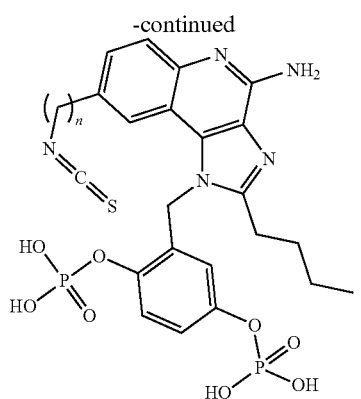
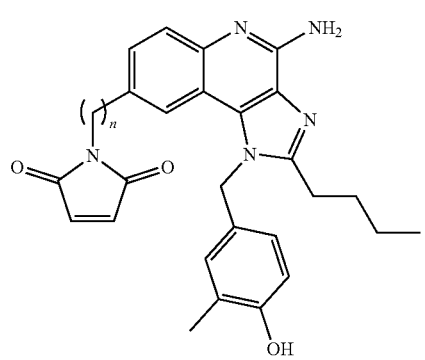
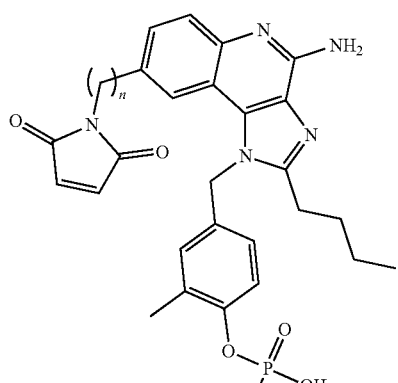
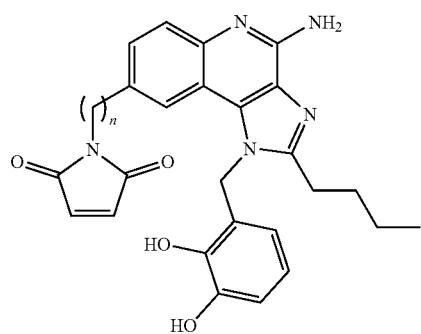
-continued
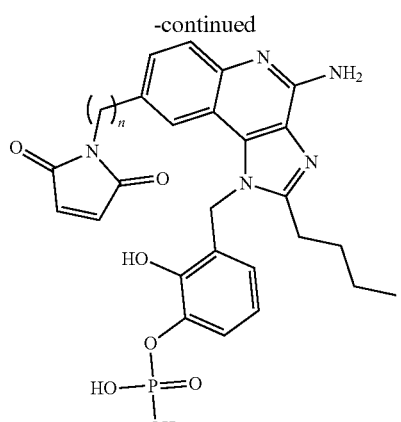
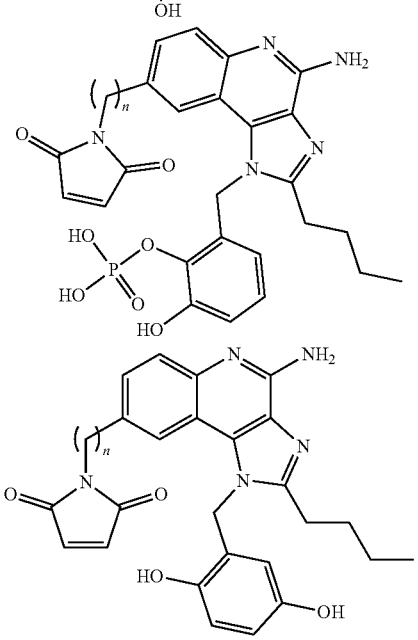
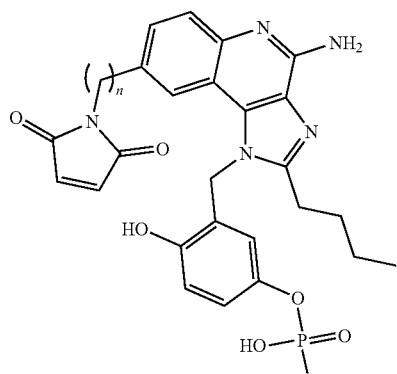
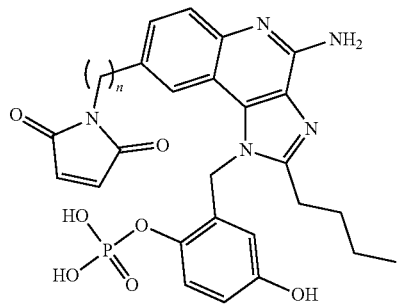

111
-continued
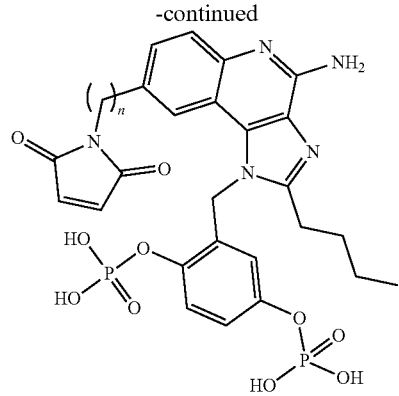
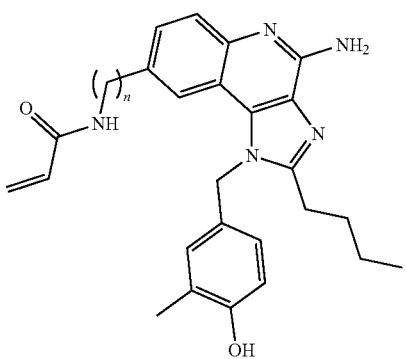
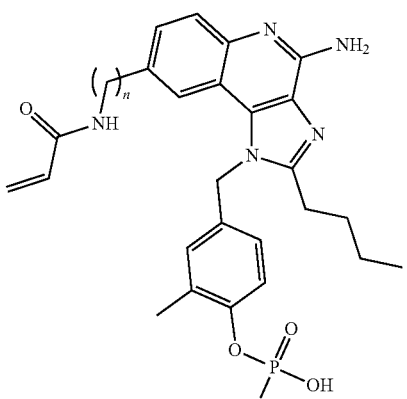
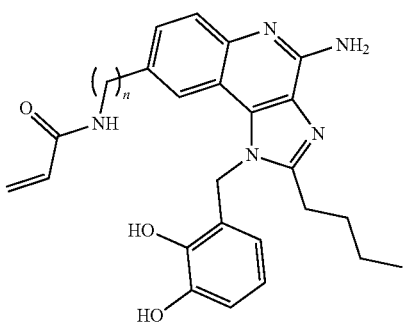
112
-continued
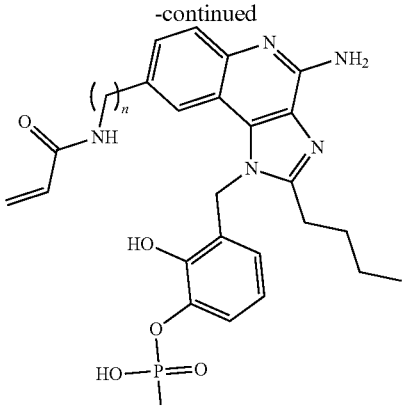
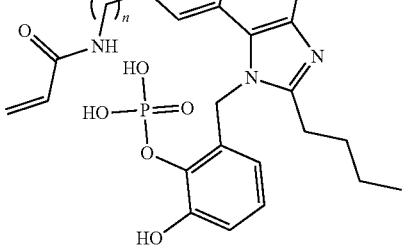
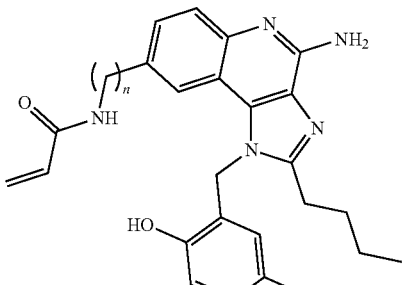
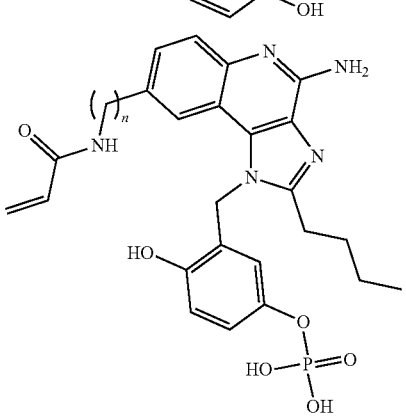
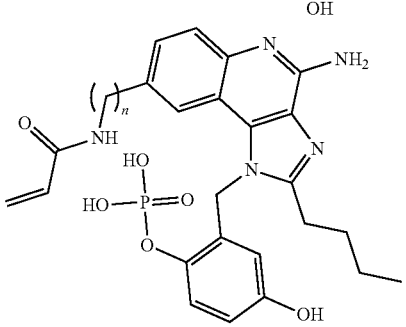

113
-continued
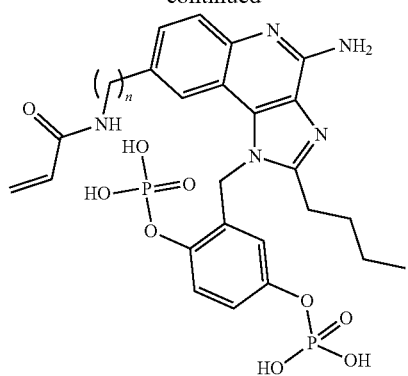
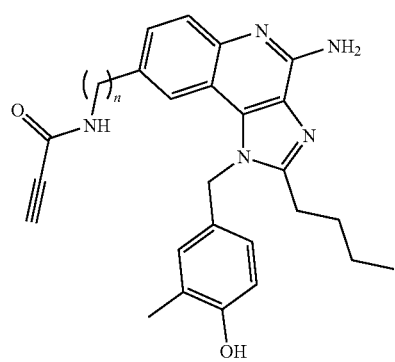
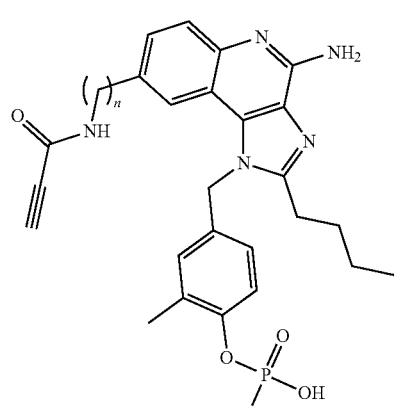
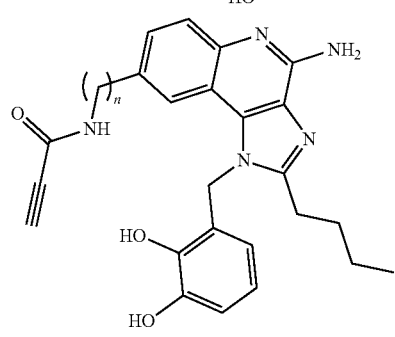
114
-continued
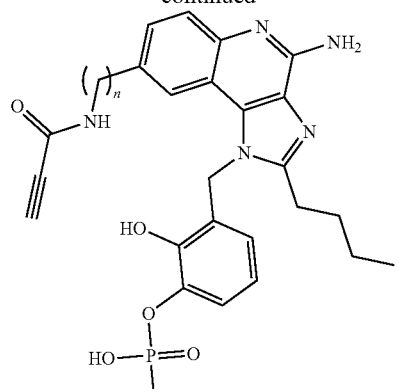
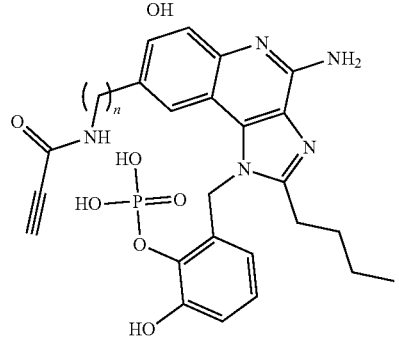
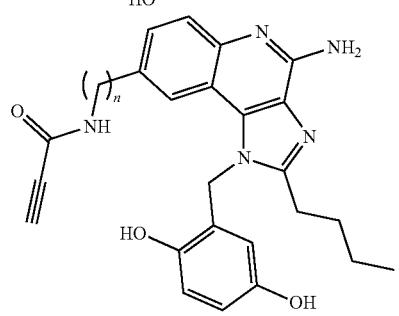
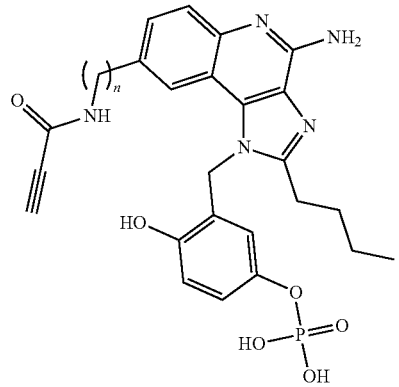
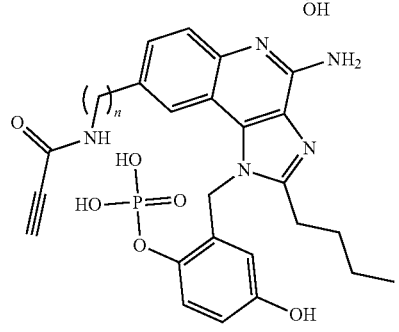

115
-continued
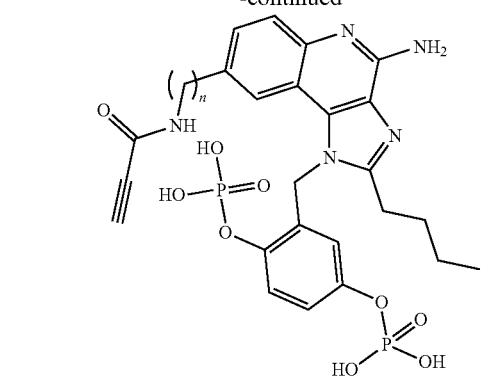
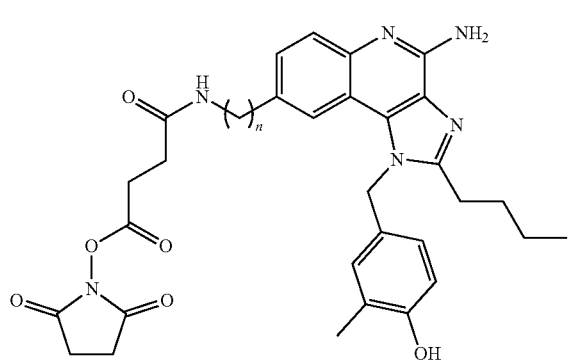
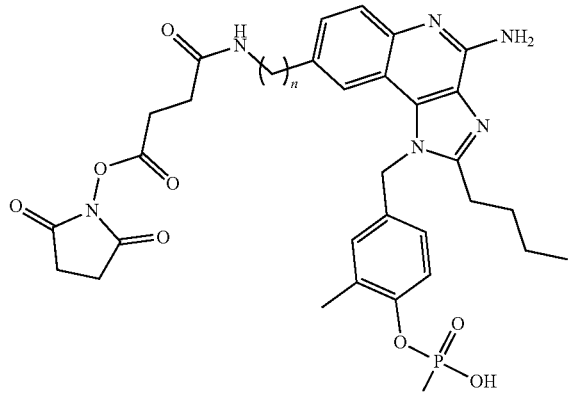
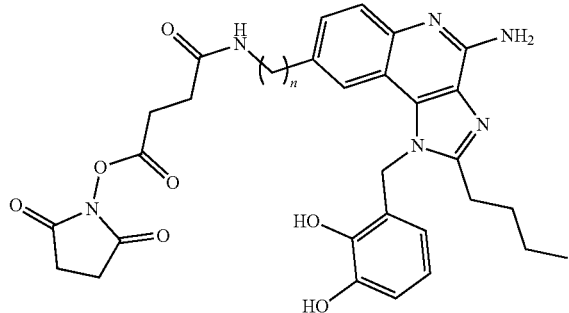
116
-continued
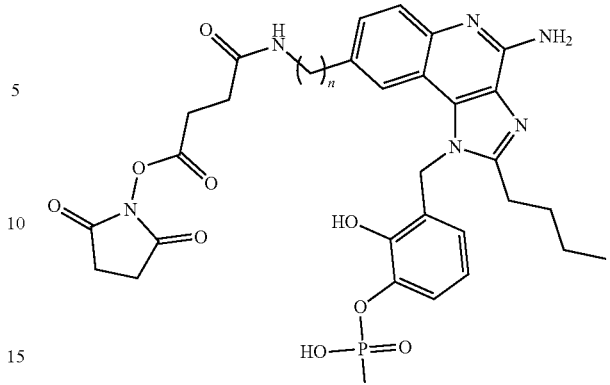
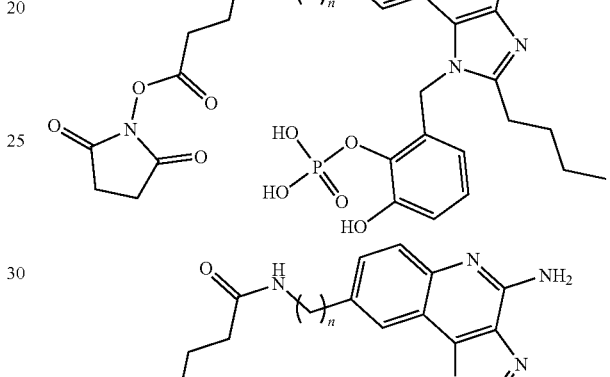
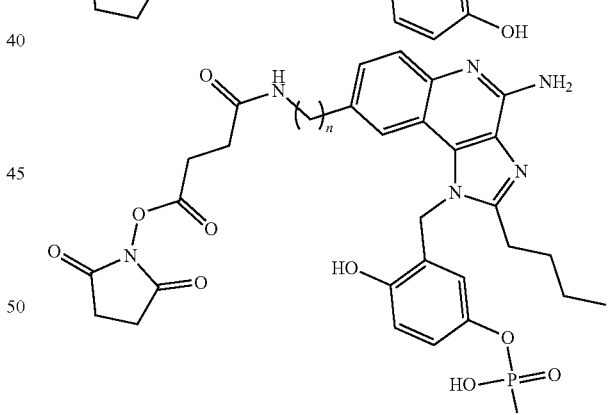
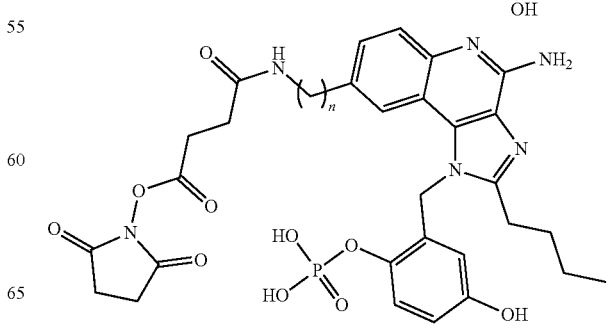

117
-continued
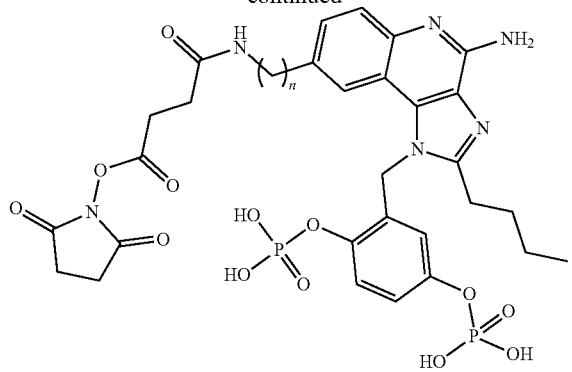
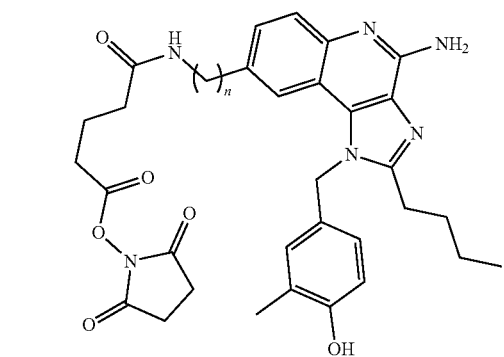
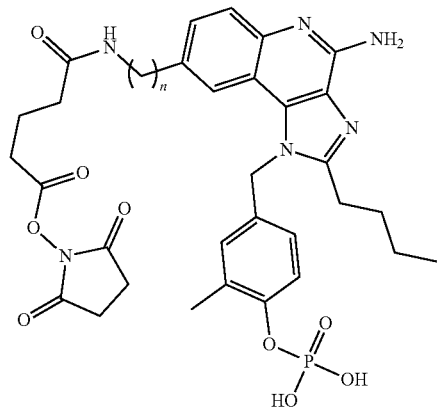
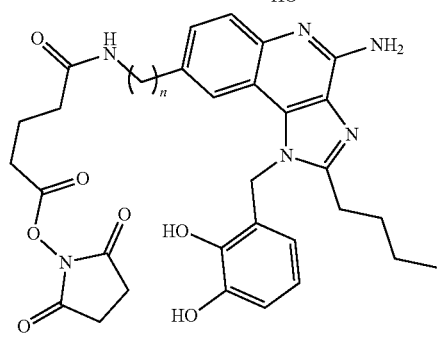
118
-continued
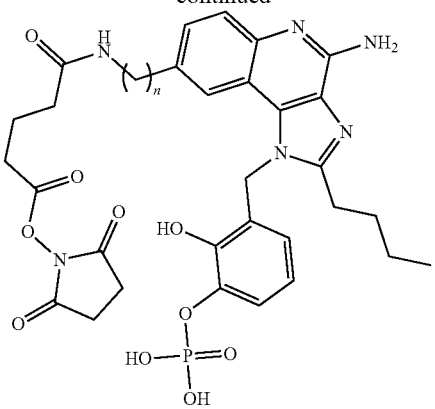
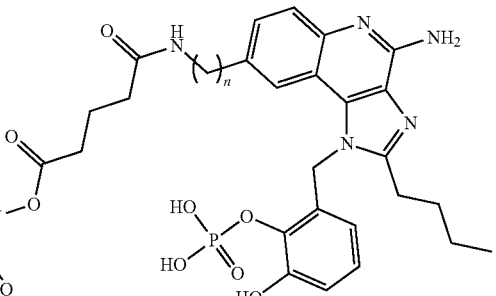
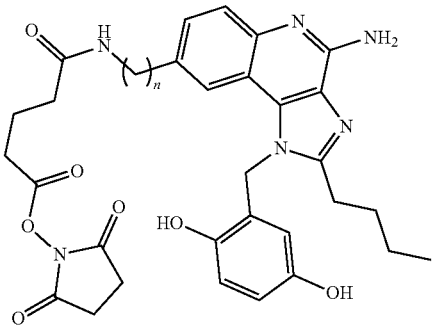
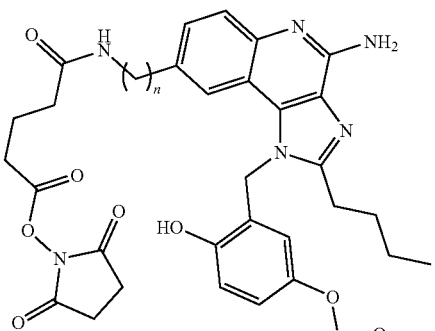
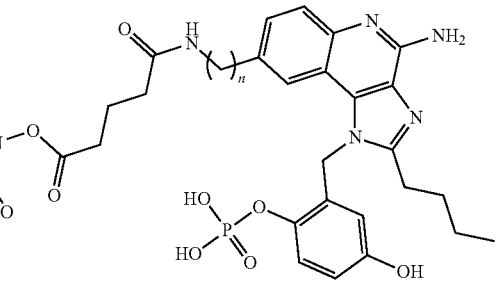

119
-continued
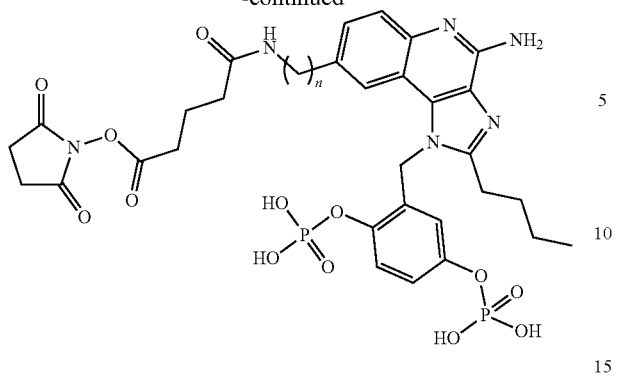
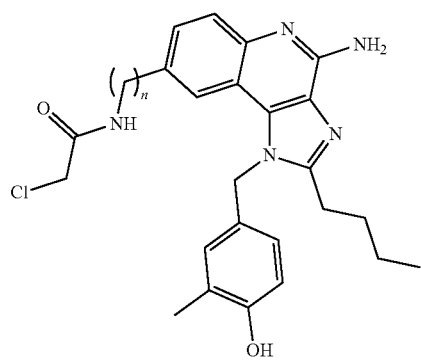
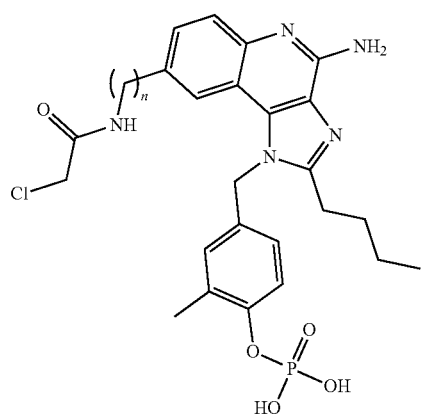
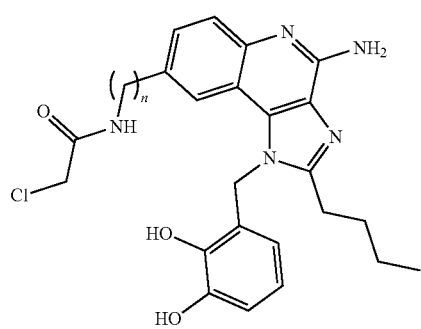
120
-continued
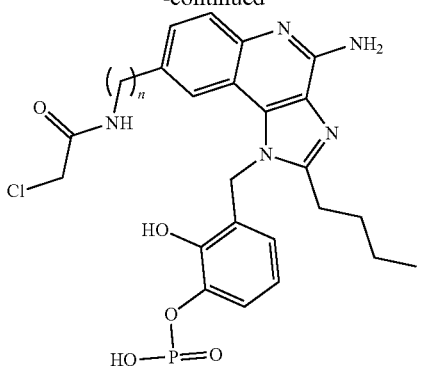
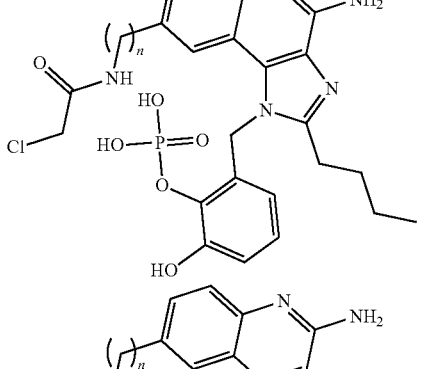
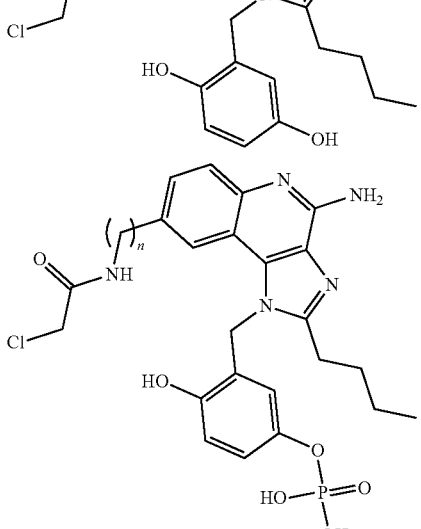
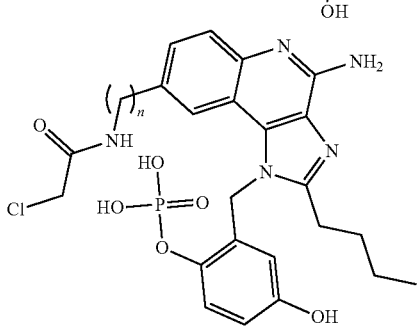

121
-continued
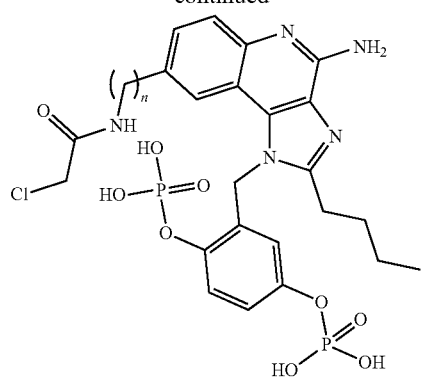
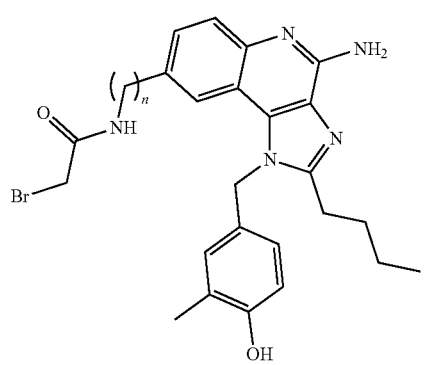
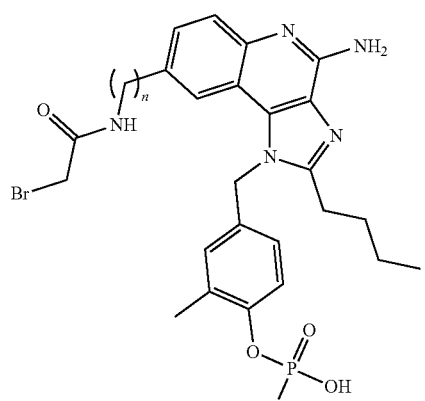
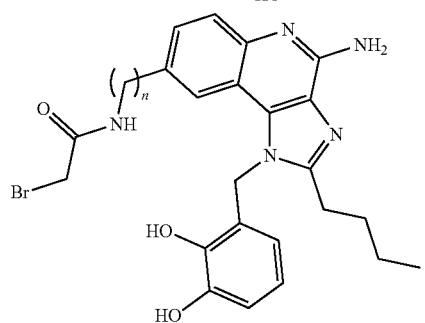
122
-continued
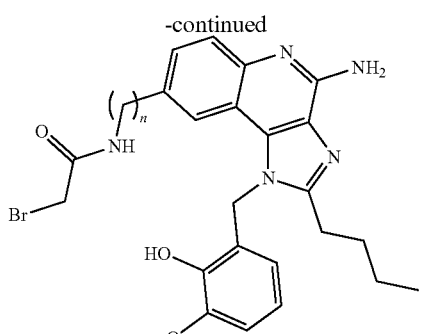
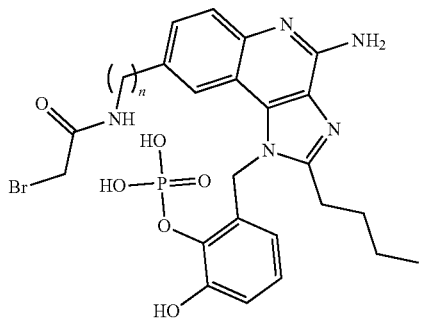
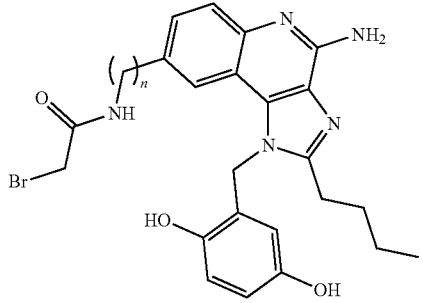
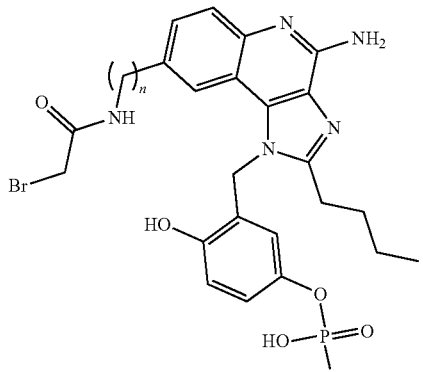
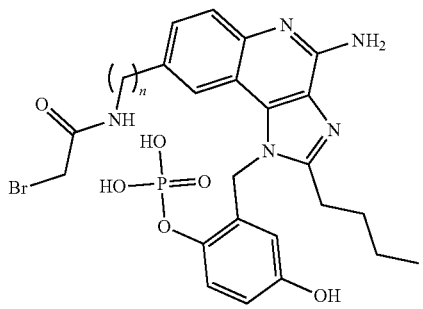

123
-continued
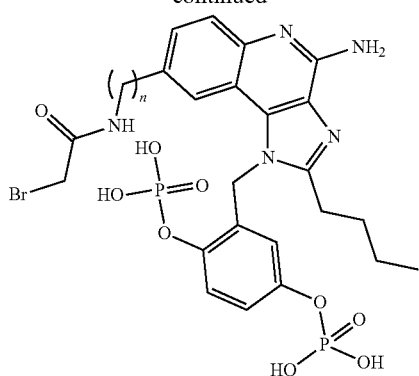
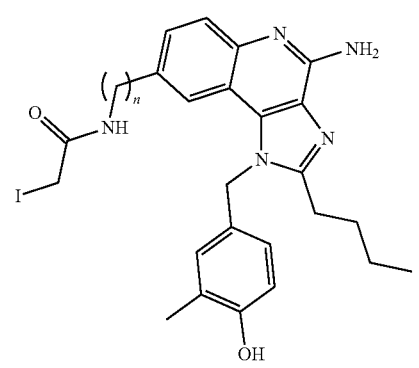
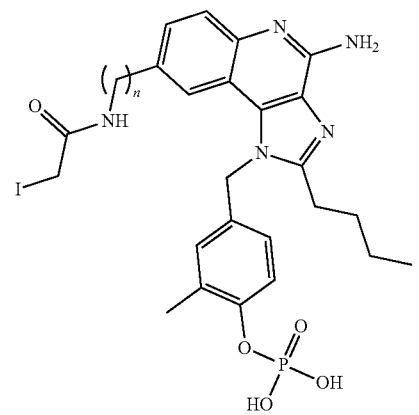
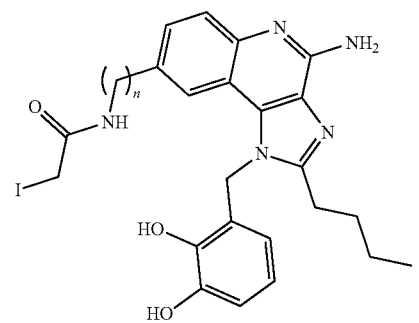
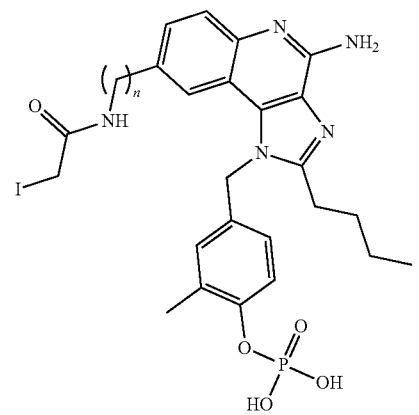
124
-continued
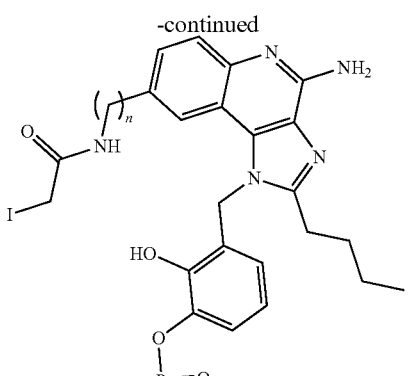
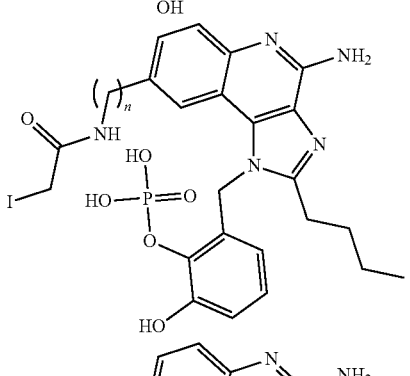
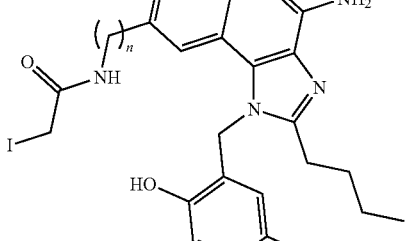
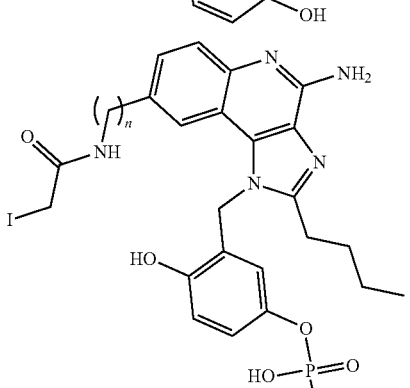
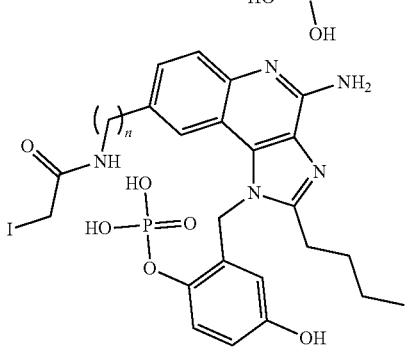

125
-continued
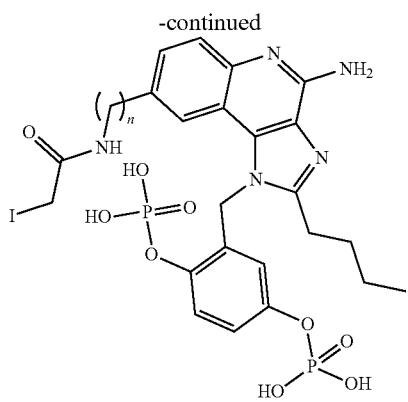
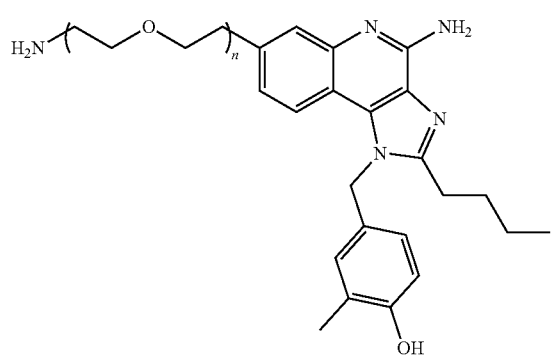
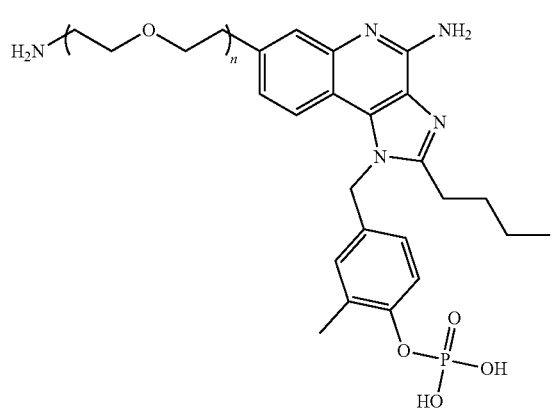
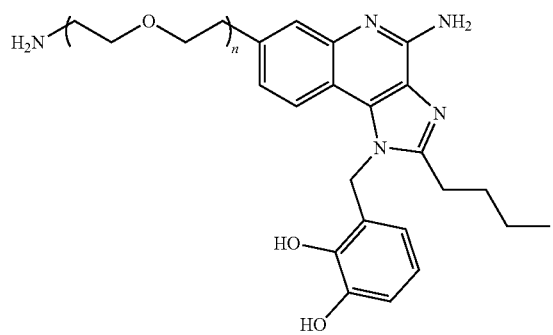
126
-continued
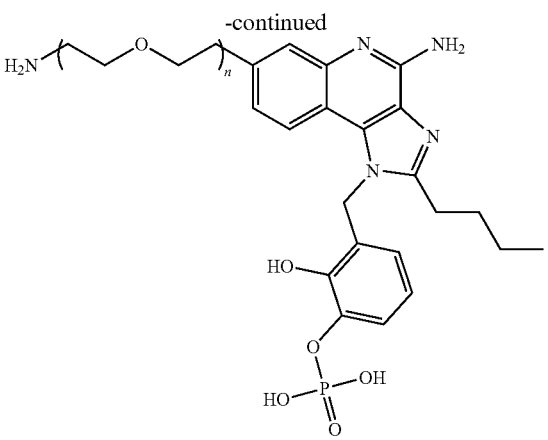
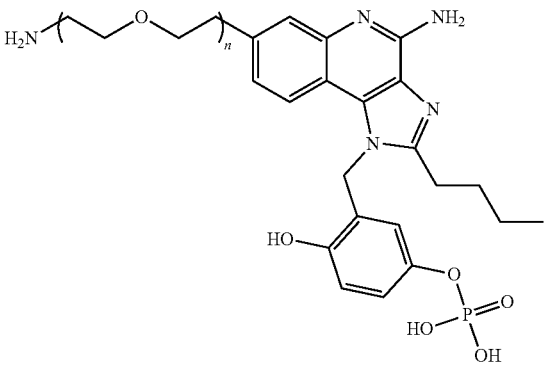

127
-continued
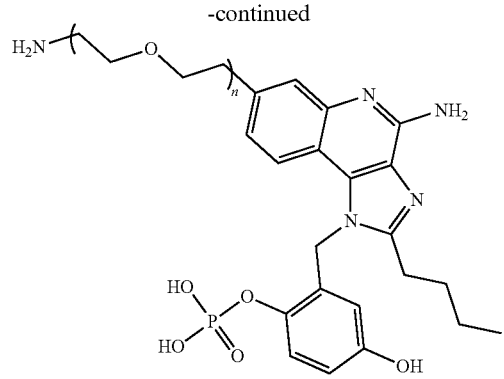
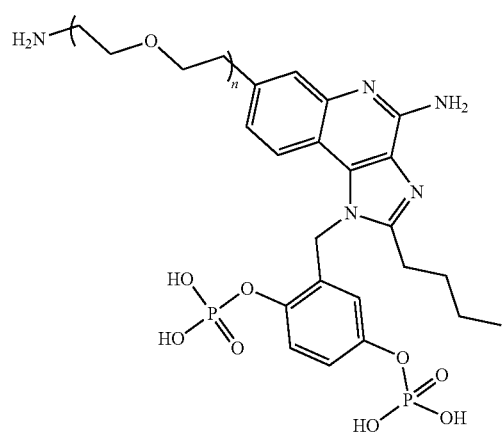
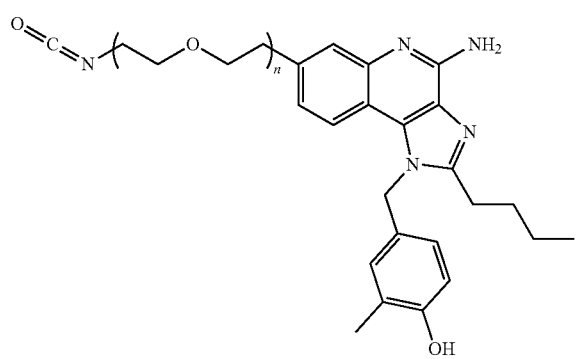
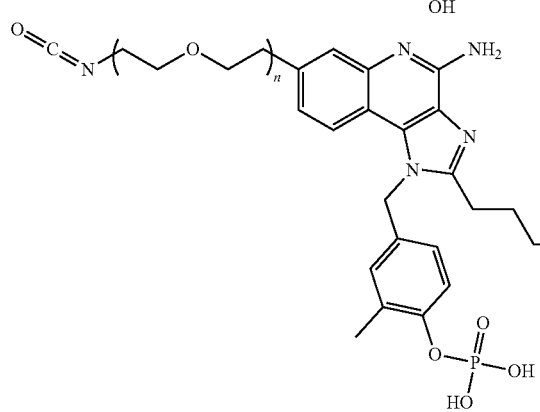
128
-continued
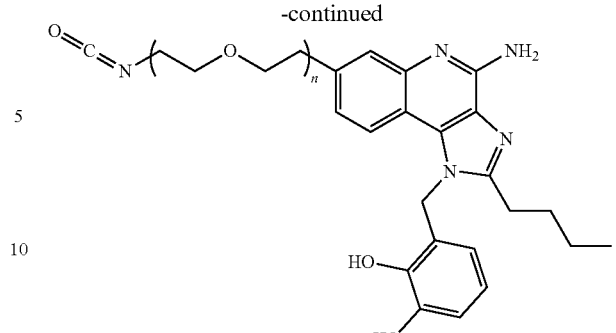
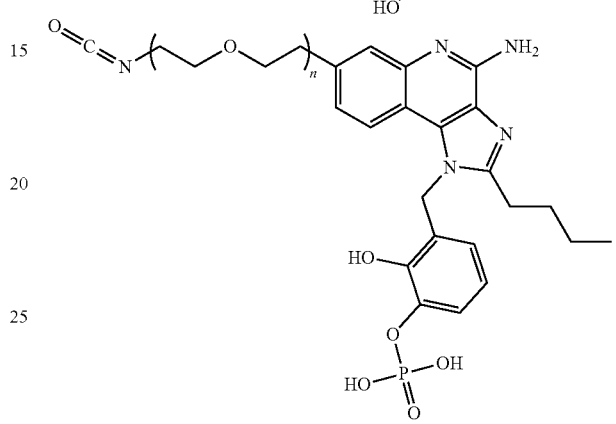
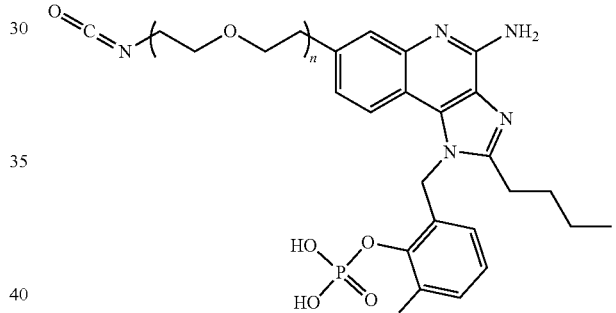
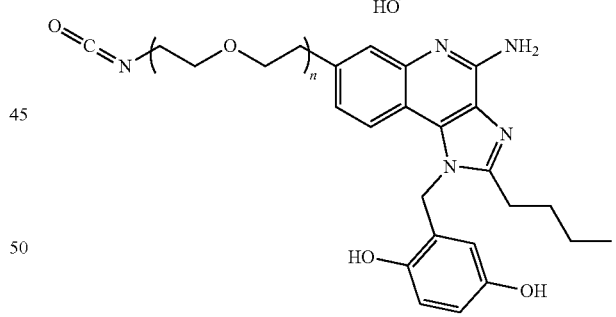
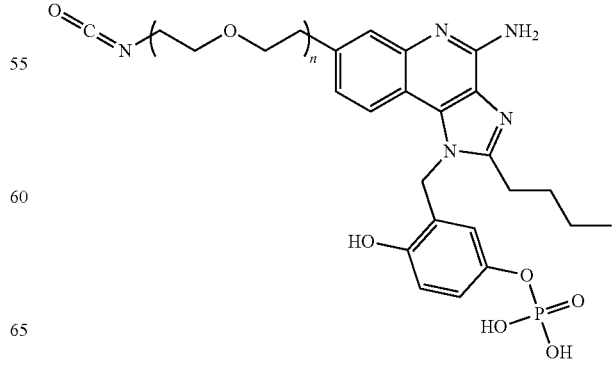

129
-continued
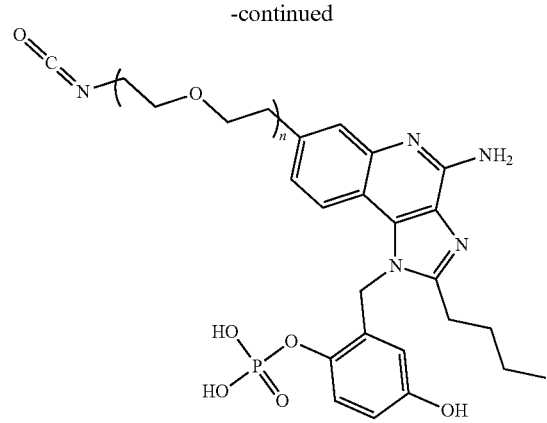
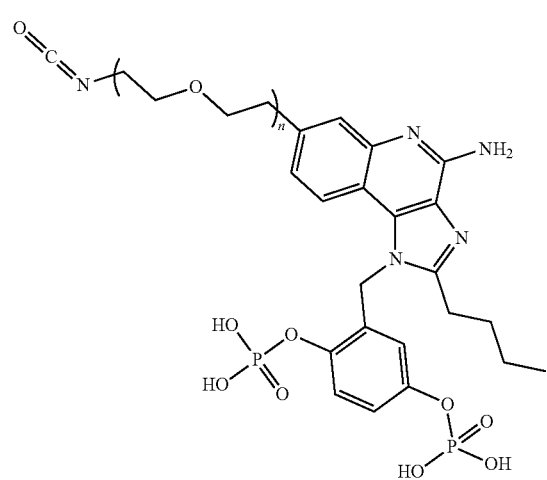
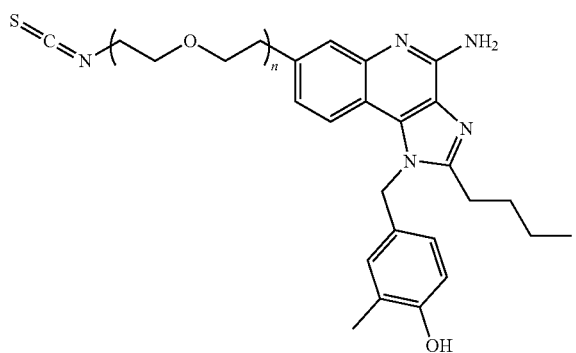
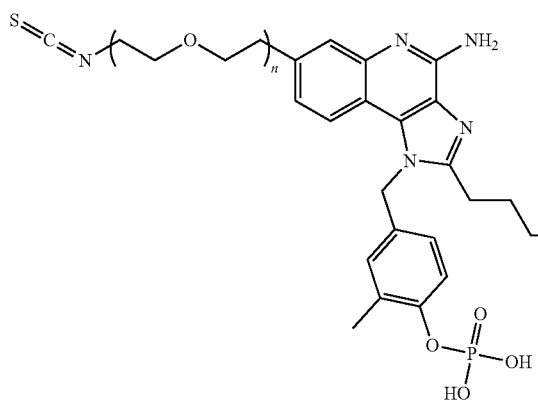
130
-continued
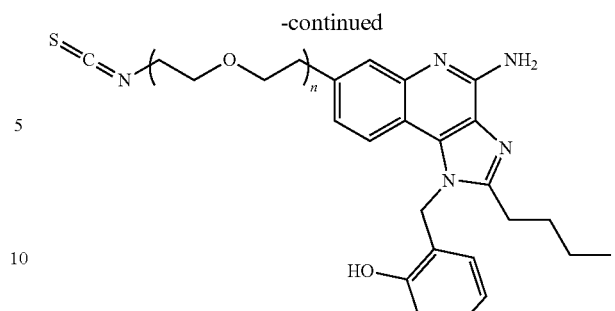
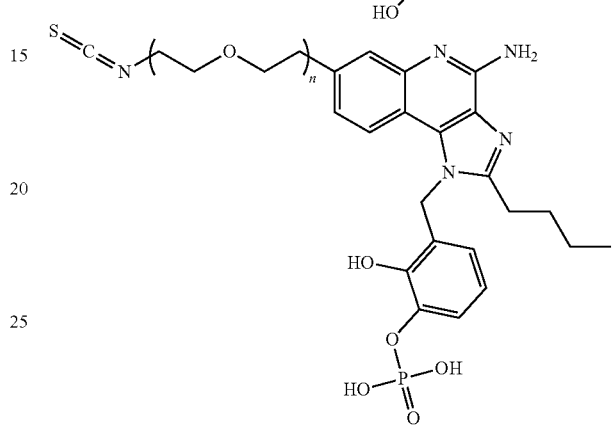
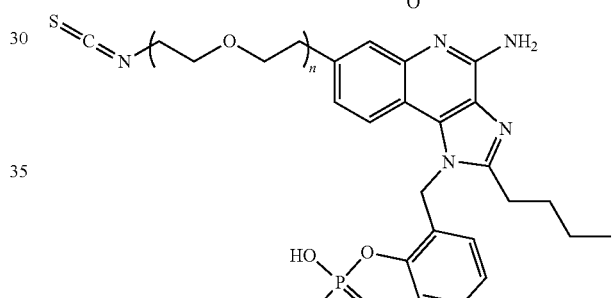
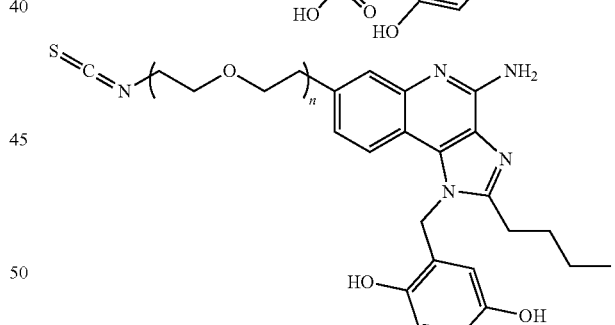
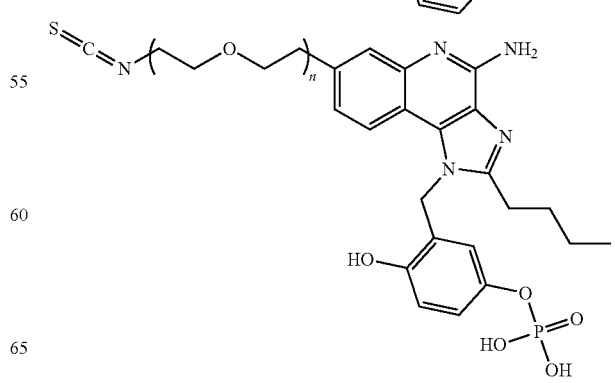

131
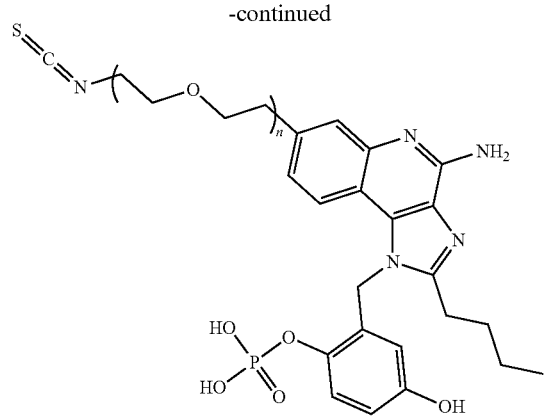
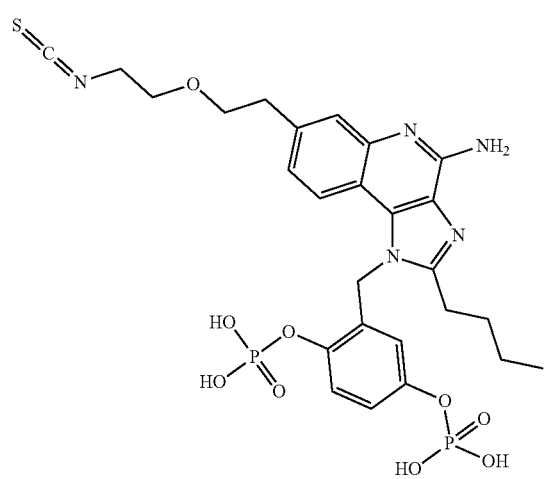
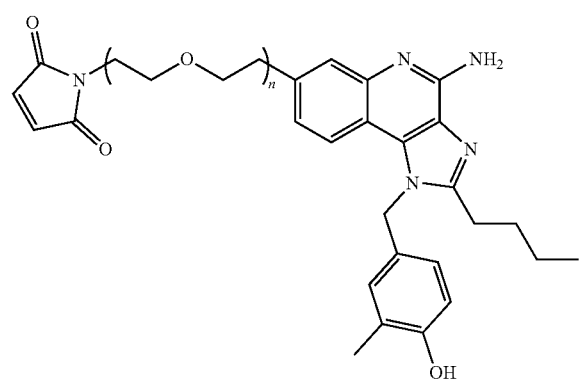
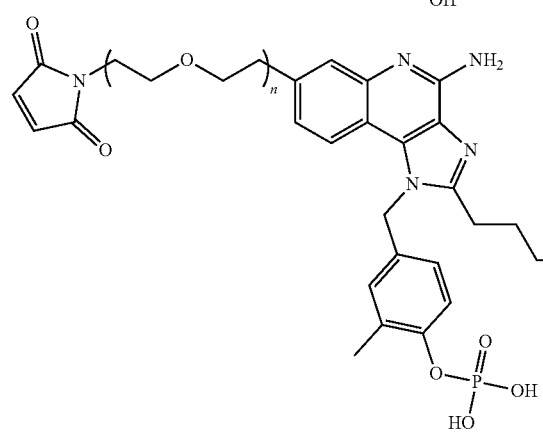
132
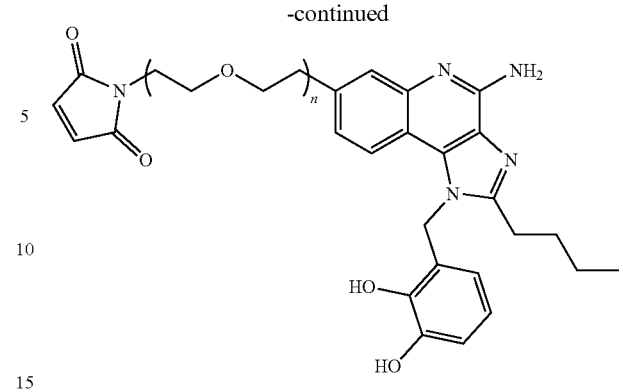
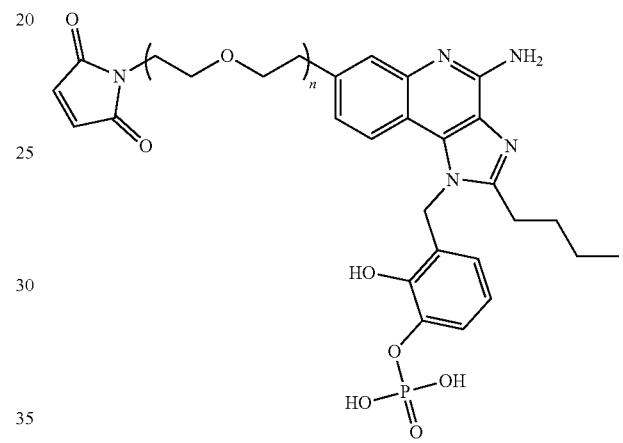
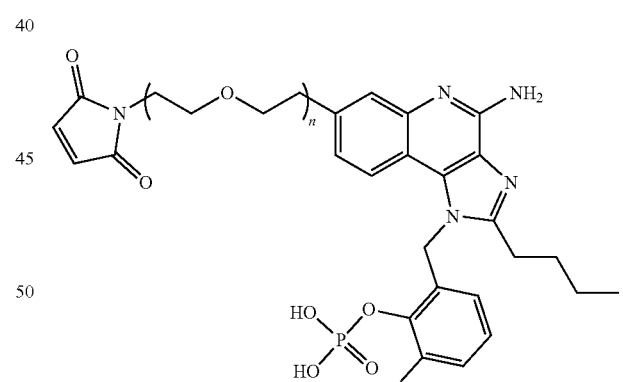
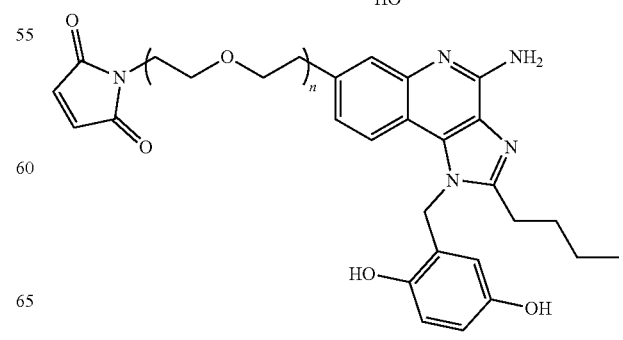

133
-continued
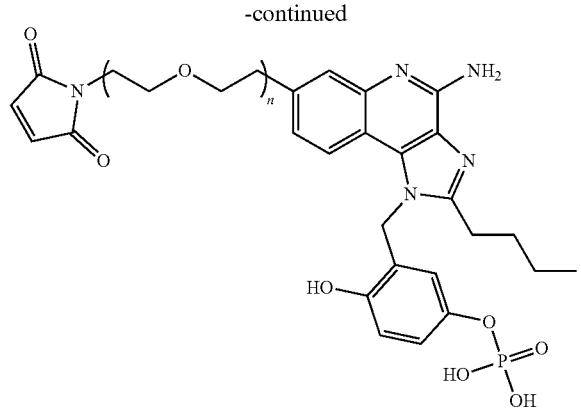
134
-continued
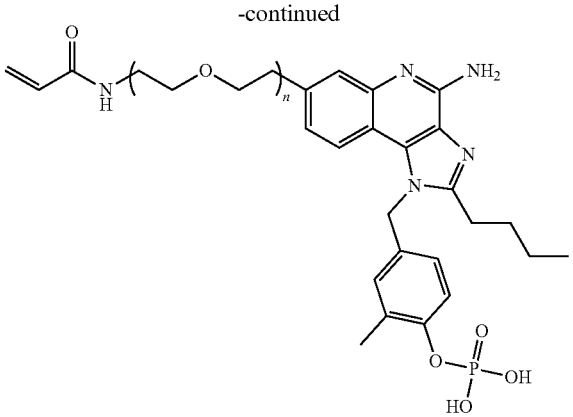
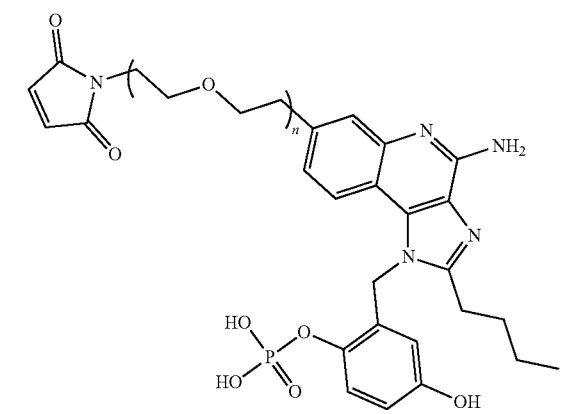
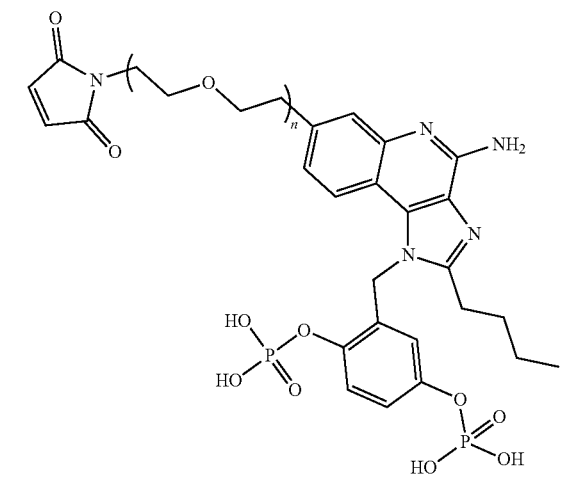
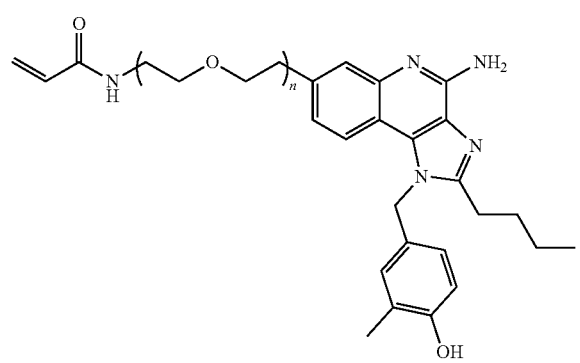

135
-continued
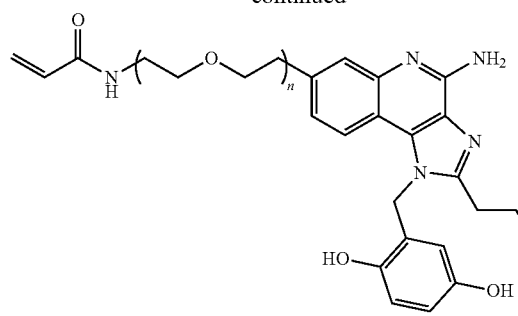
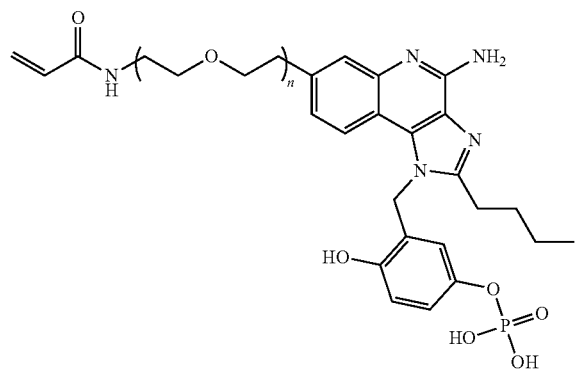
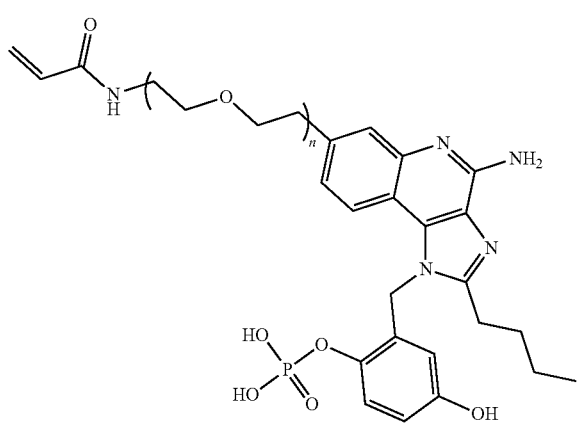
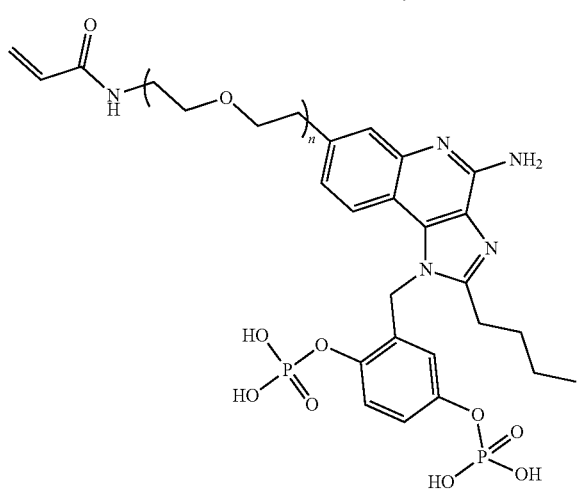
136
-continued
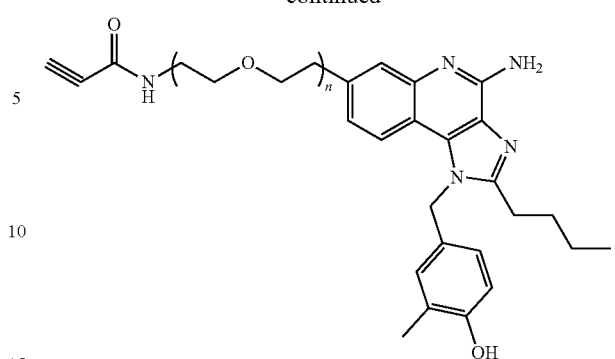
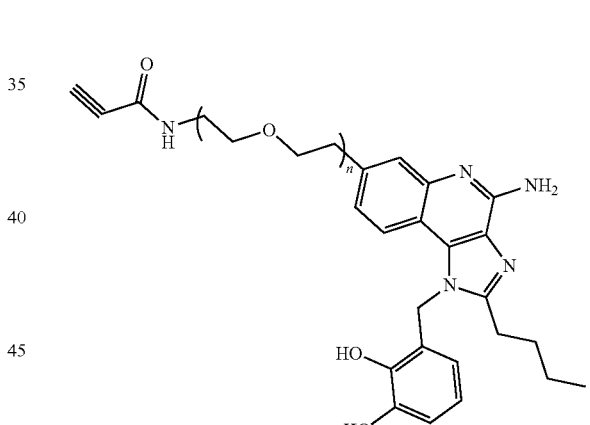
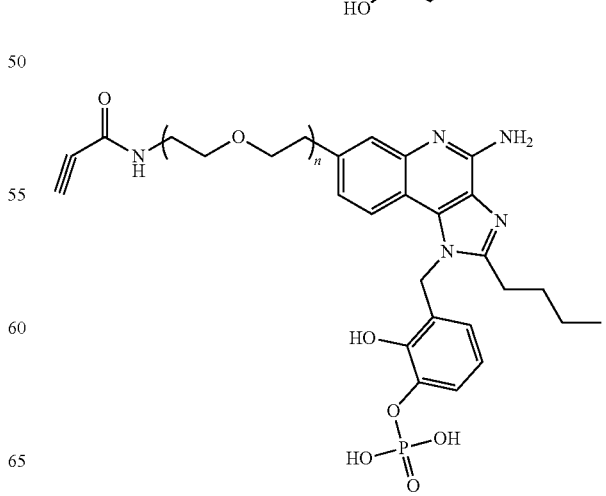

137
-continued
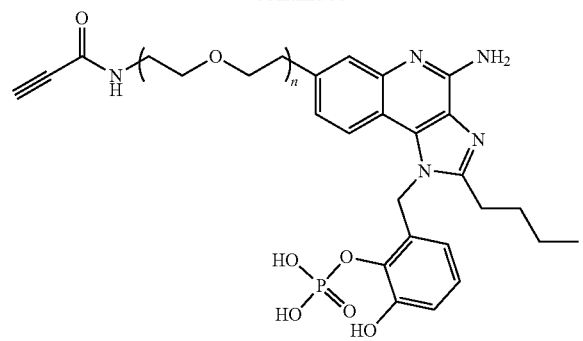
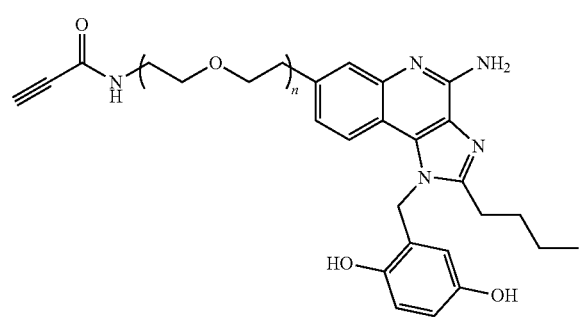
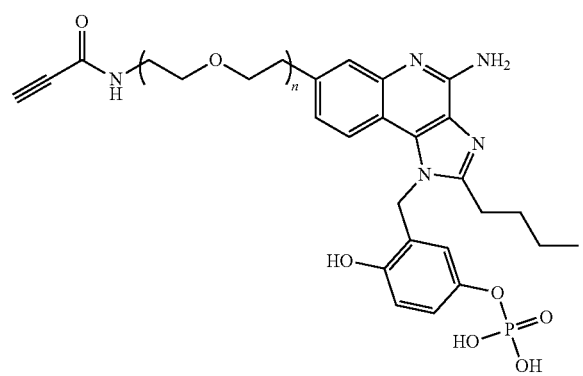
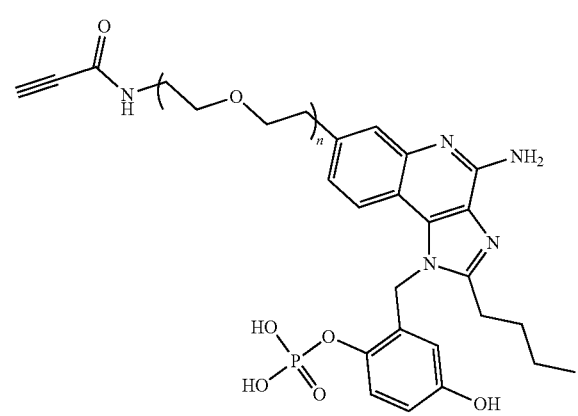
138
-continued
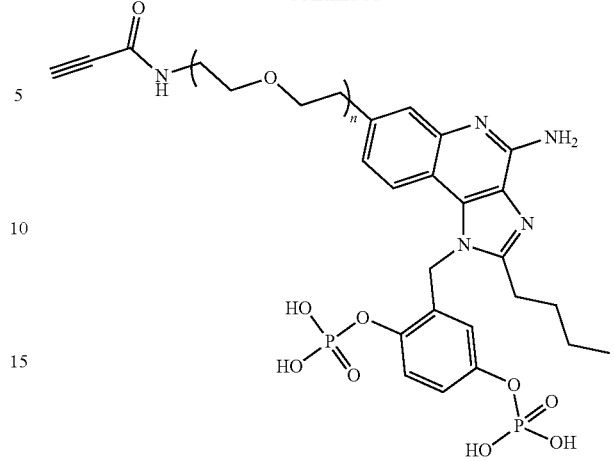
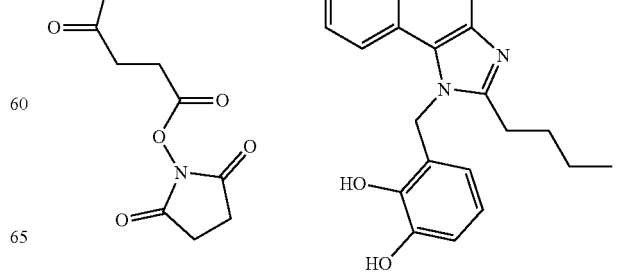

139 -continued
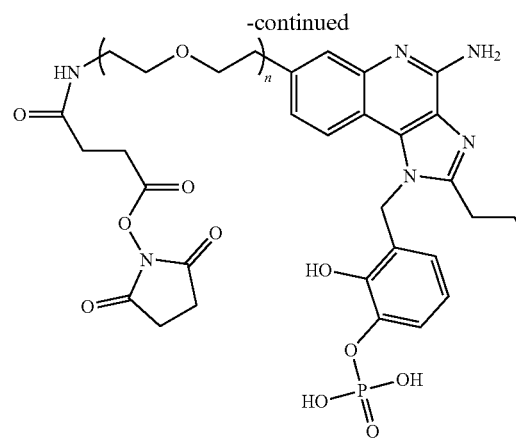
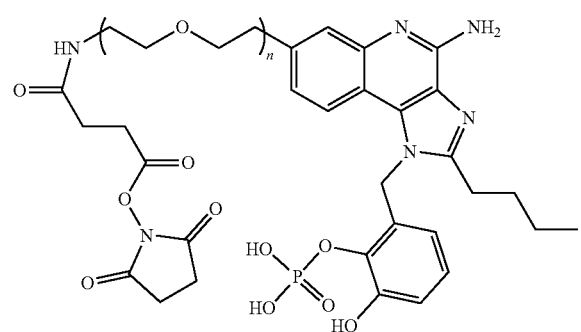
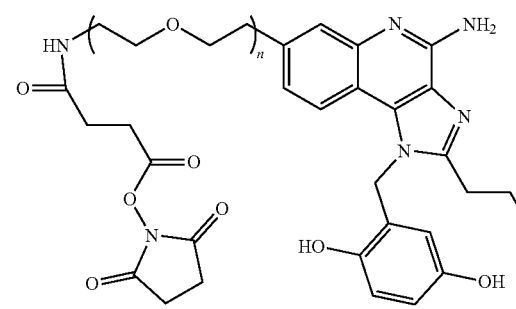
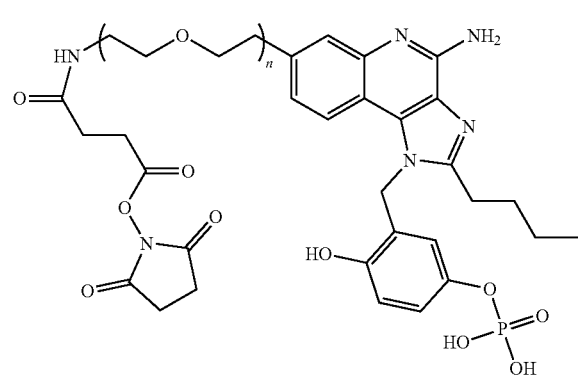
140 -continued
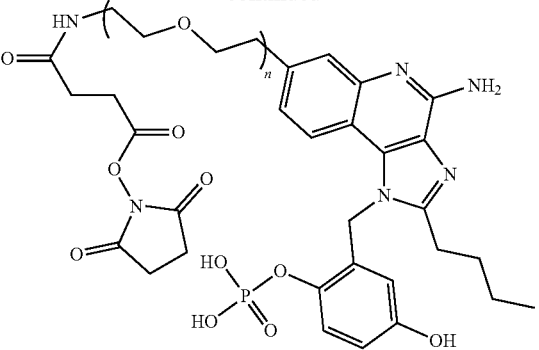
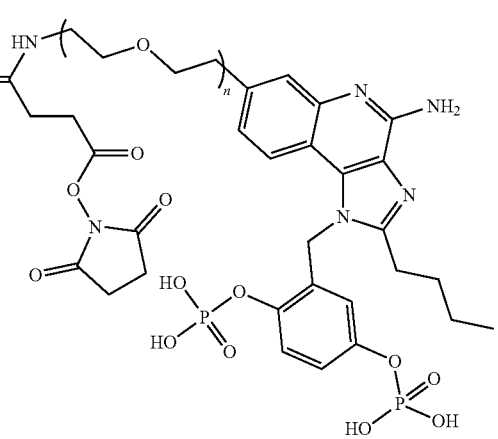
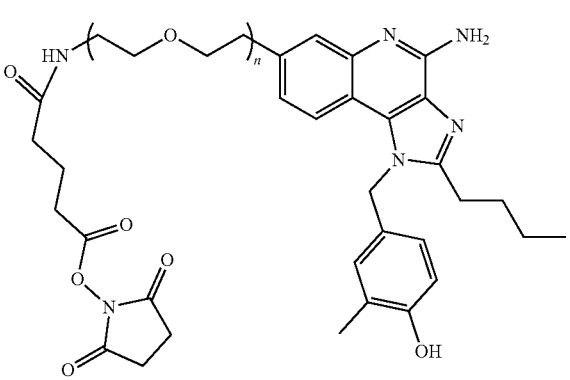
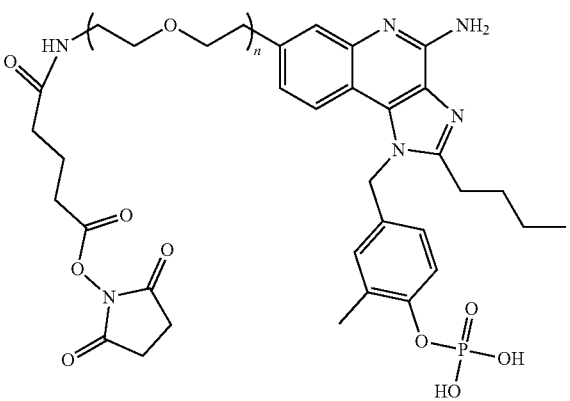

141
-continued
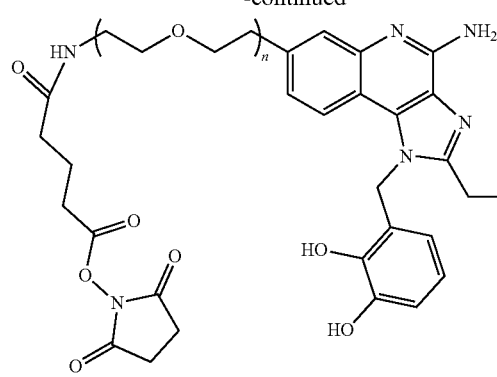
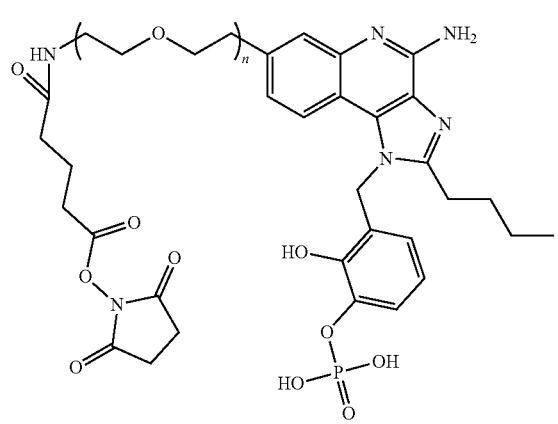
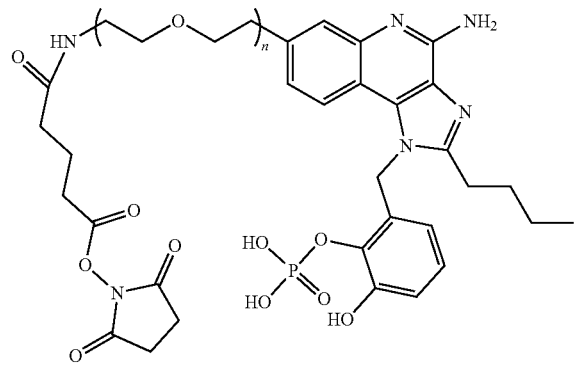
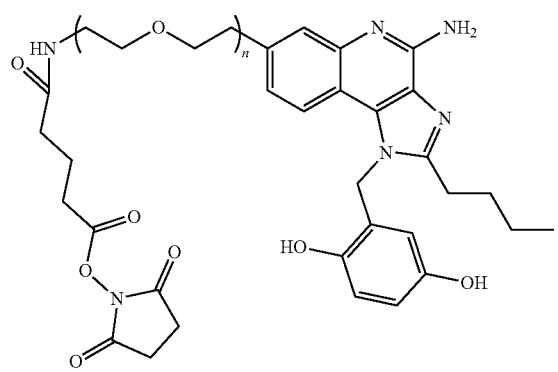
142
-continued
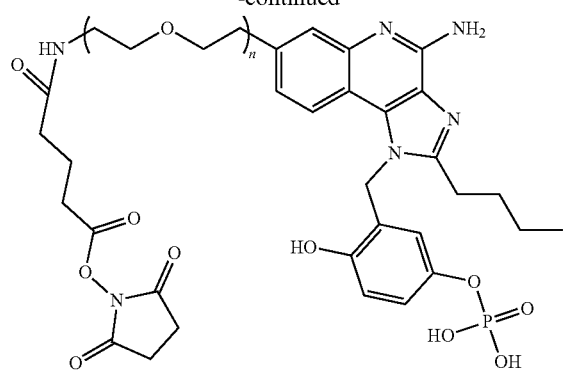
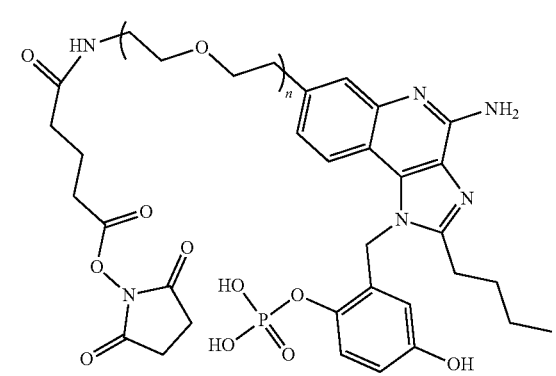
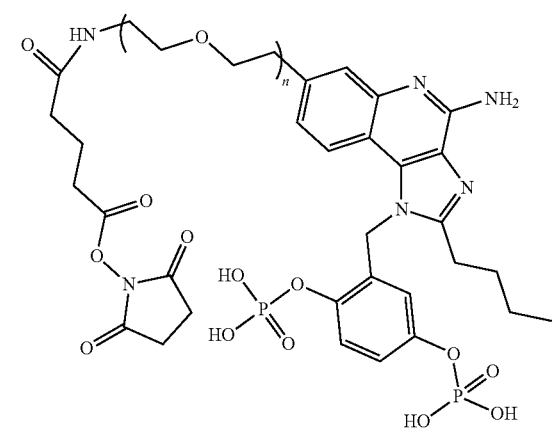
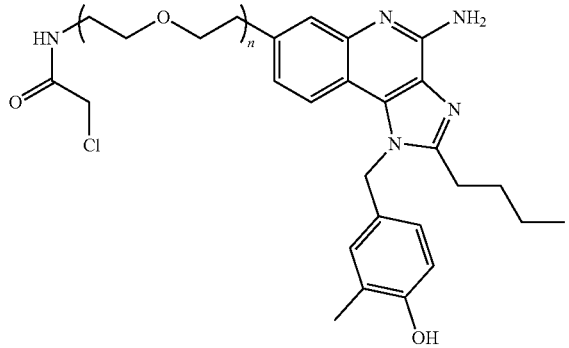

143
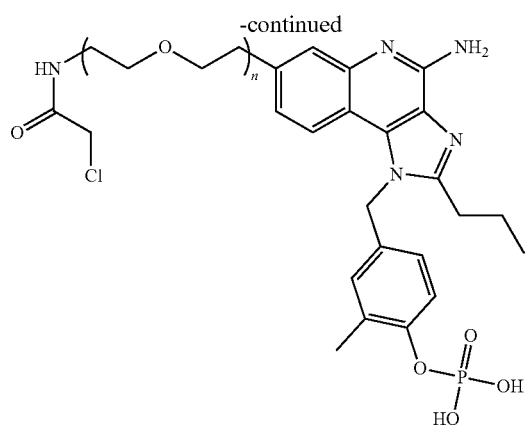
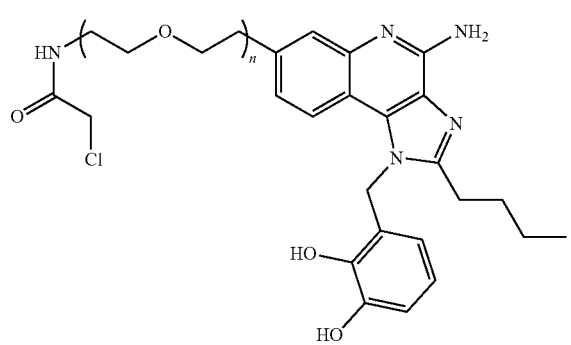
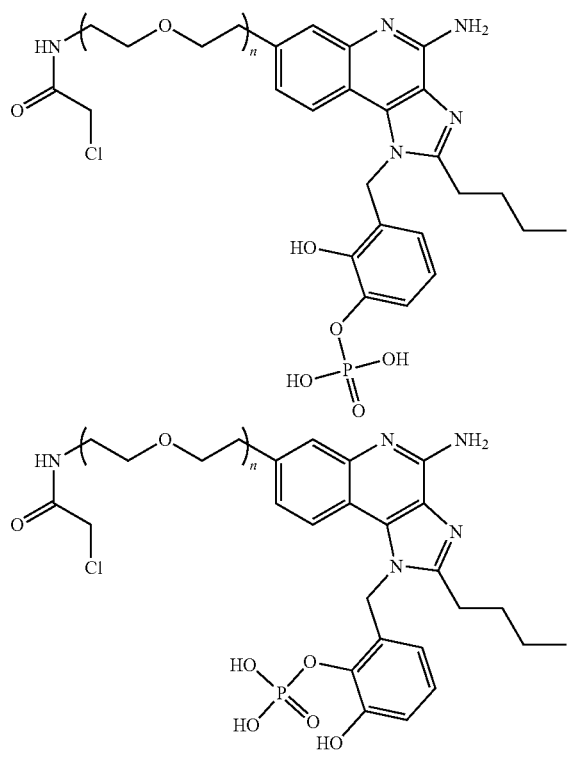
144
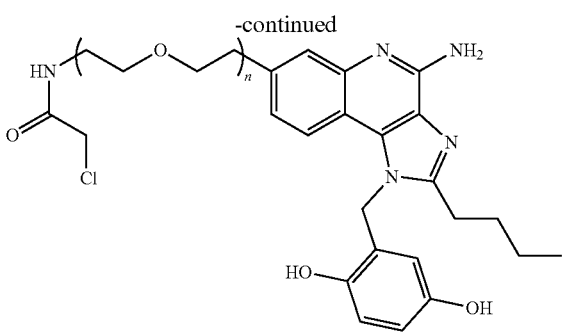
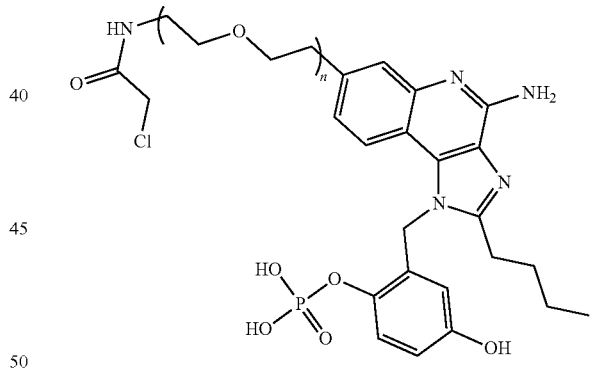
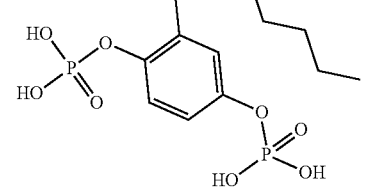

145
-continued
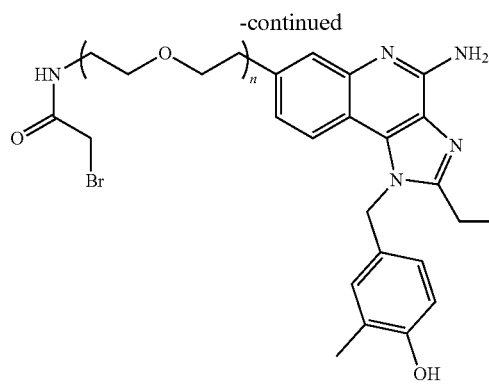
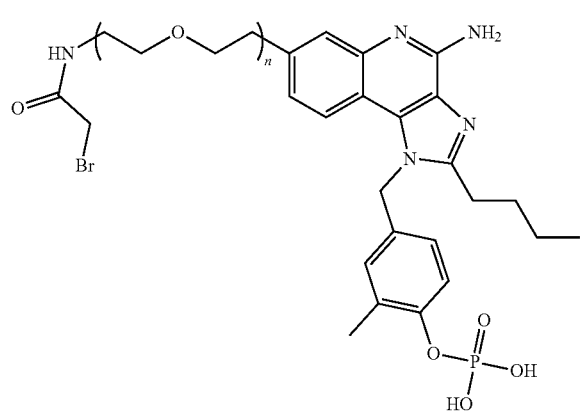
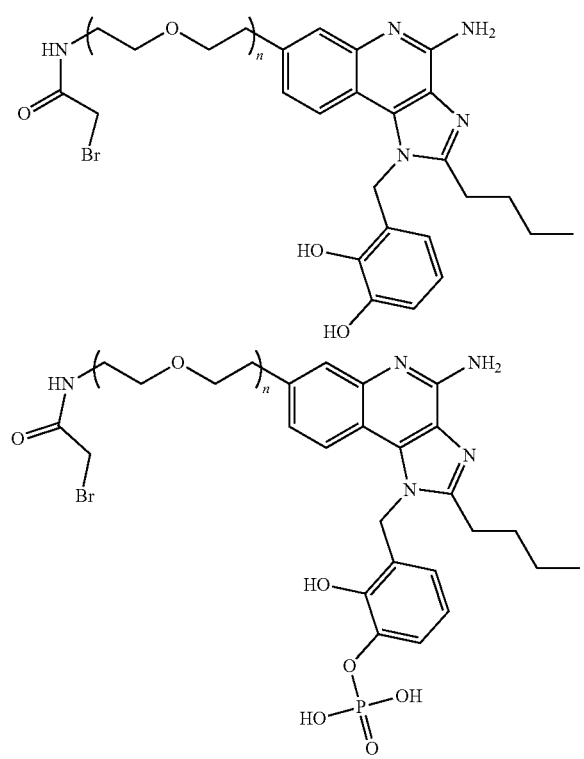
146
-continued
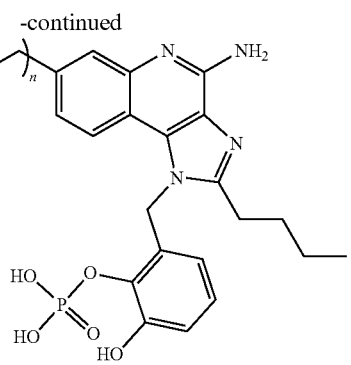
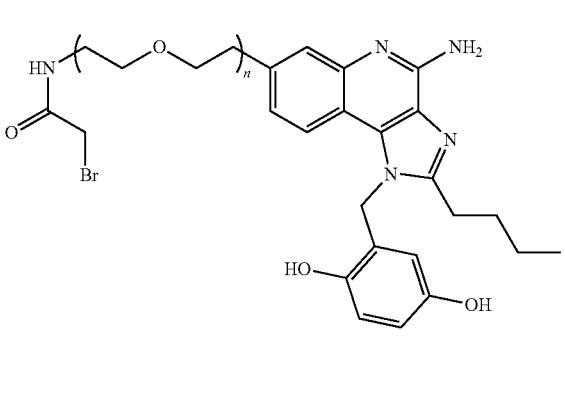
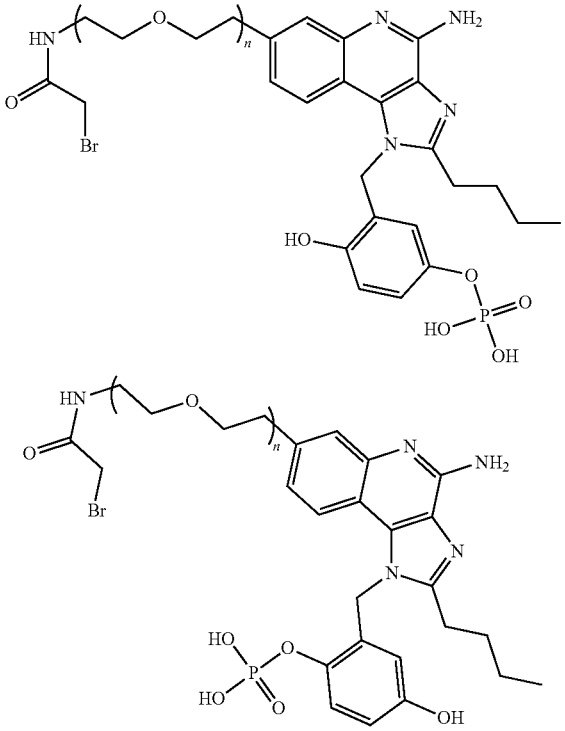

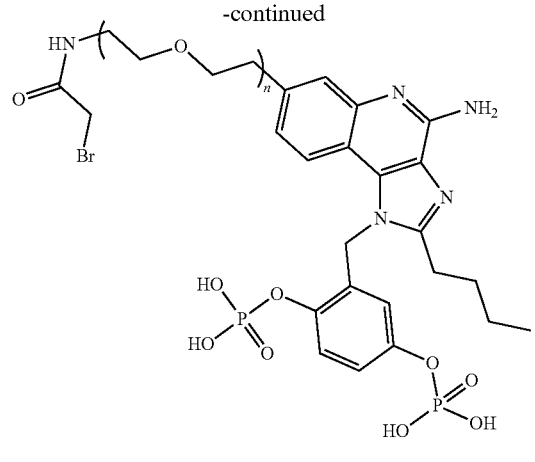
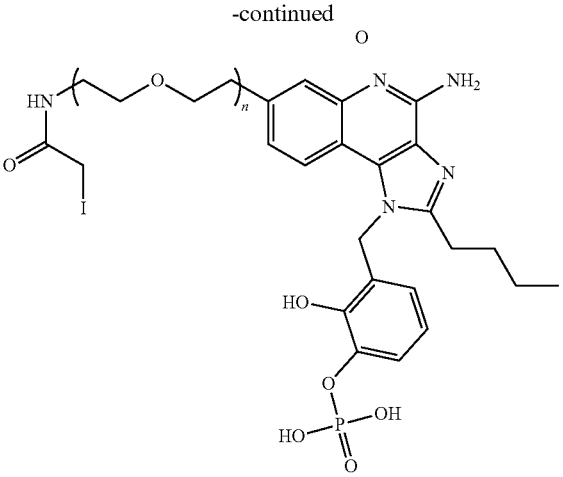

149
-continued
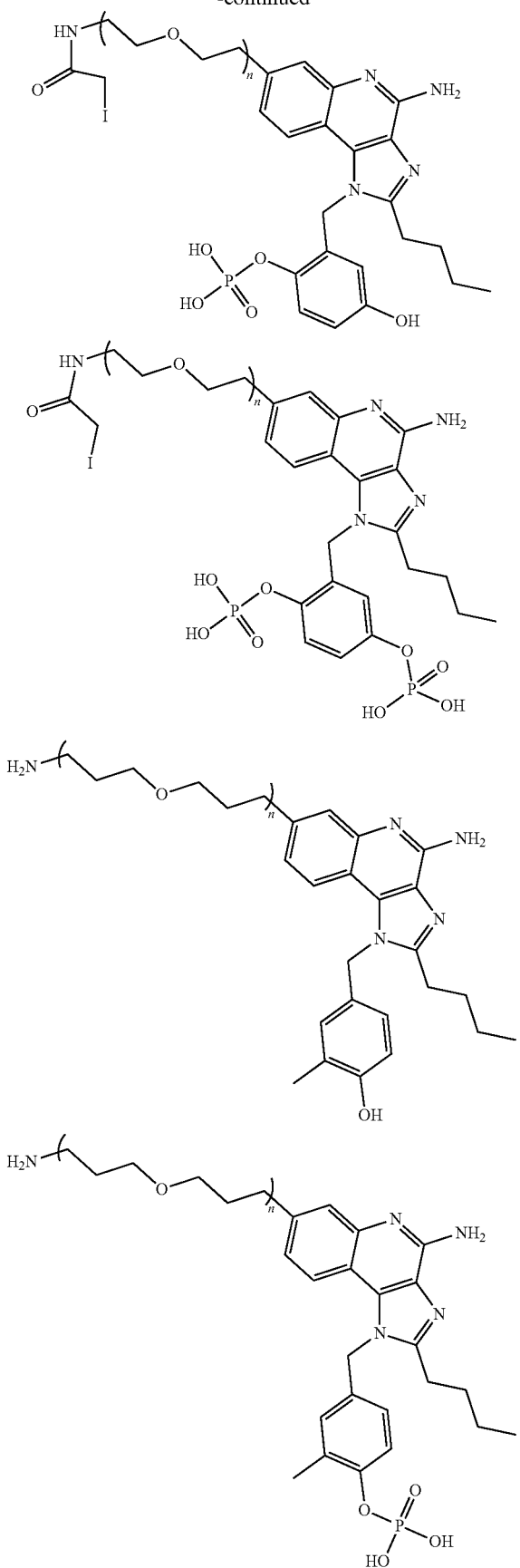
150
-continued
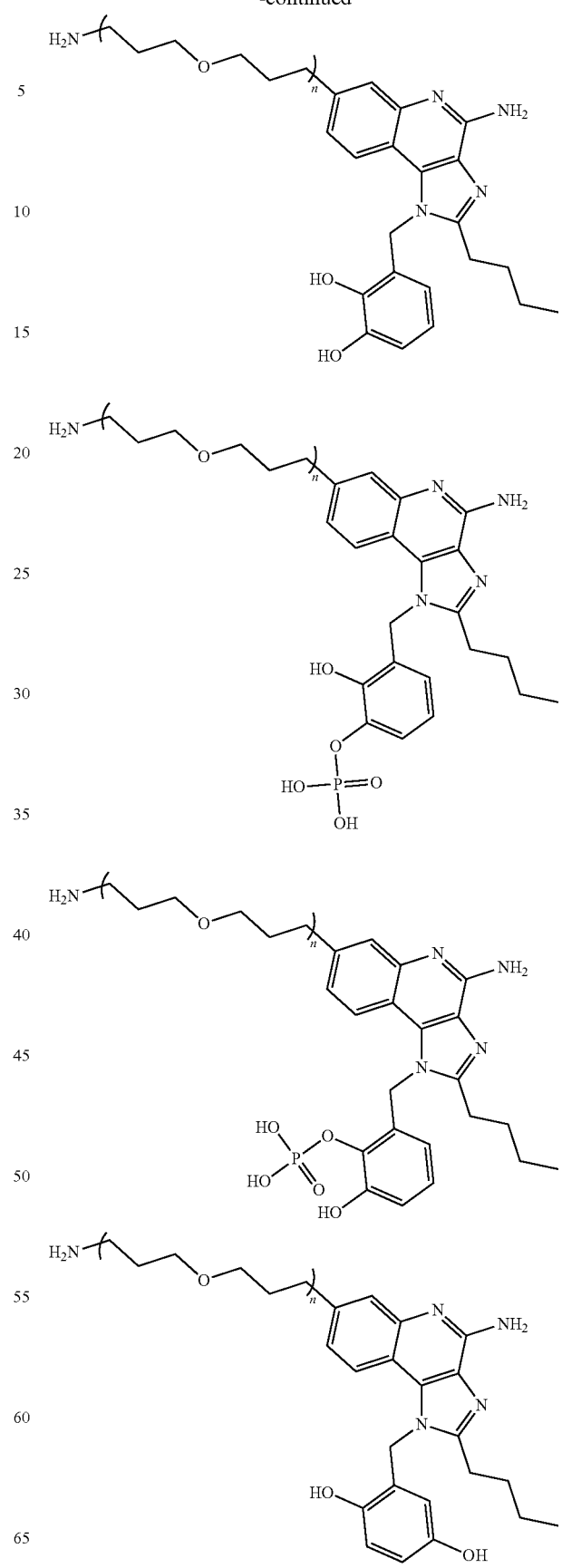

151
-continued
152
-continued
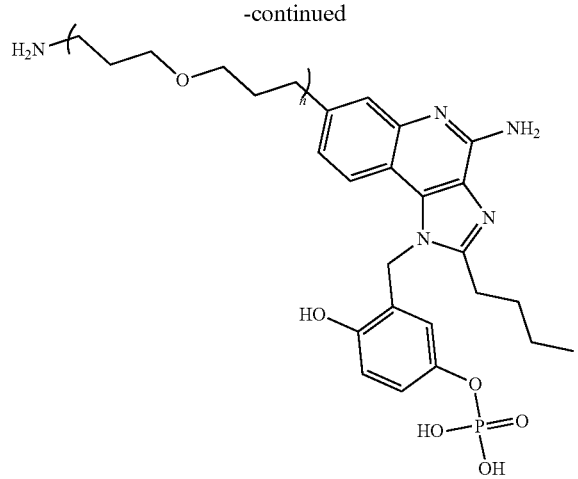
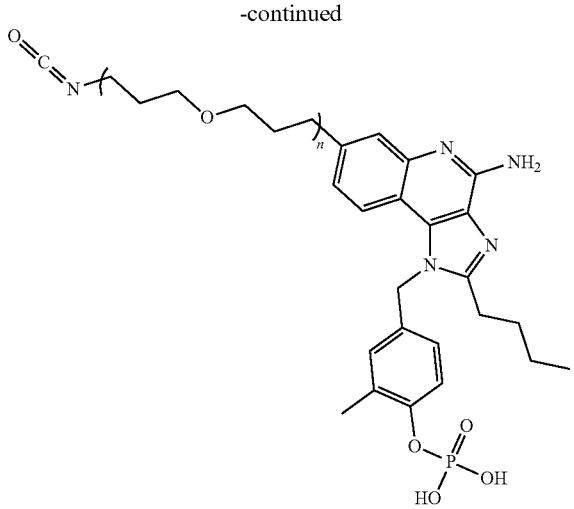
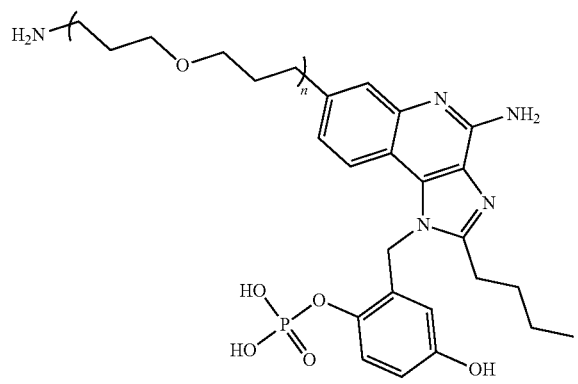
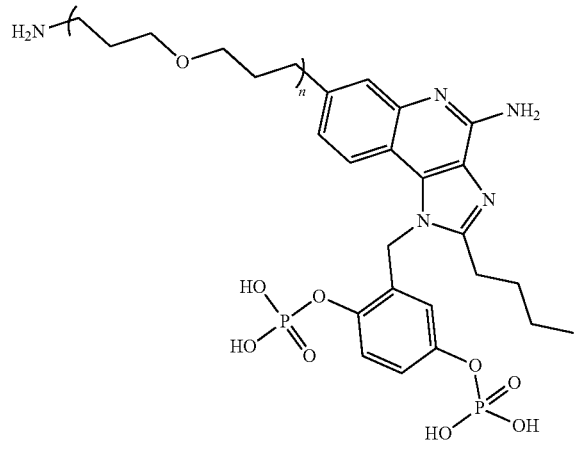
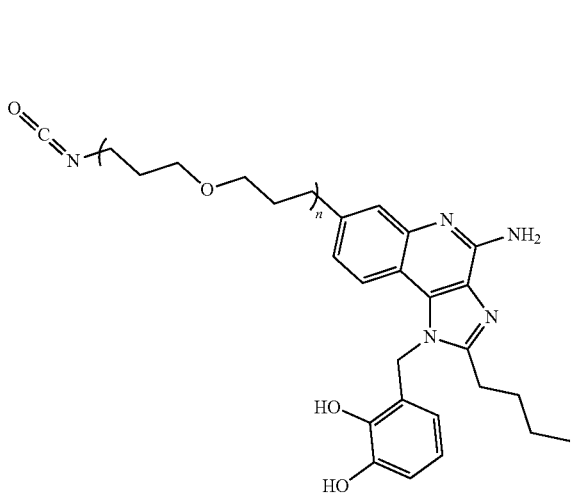
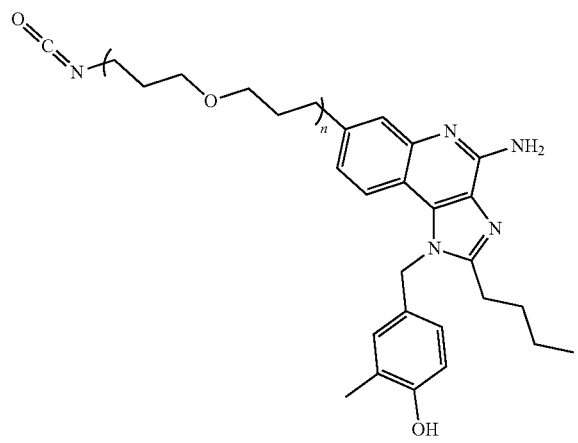
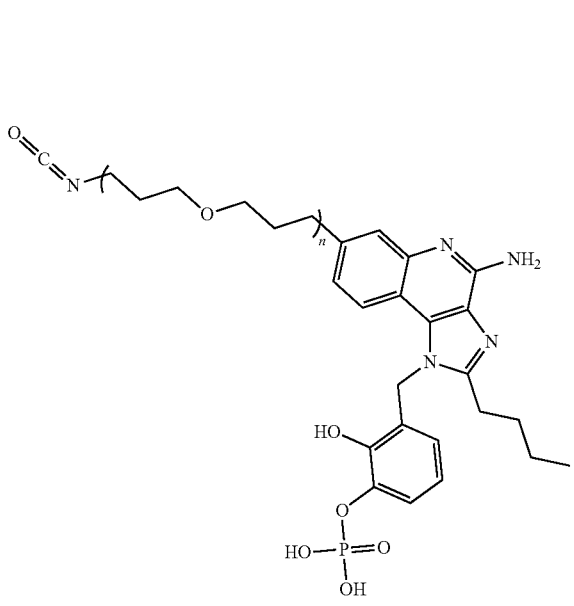

153
-continued
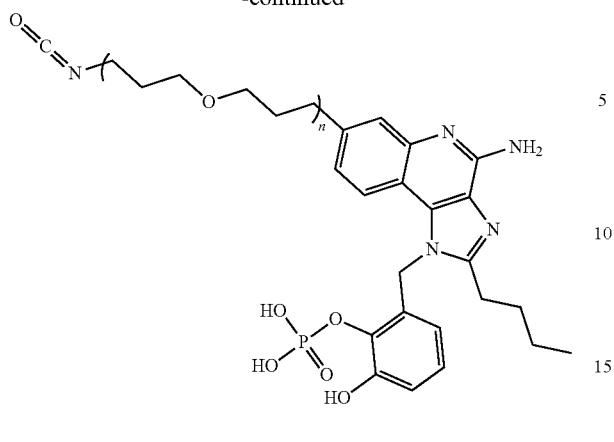
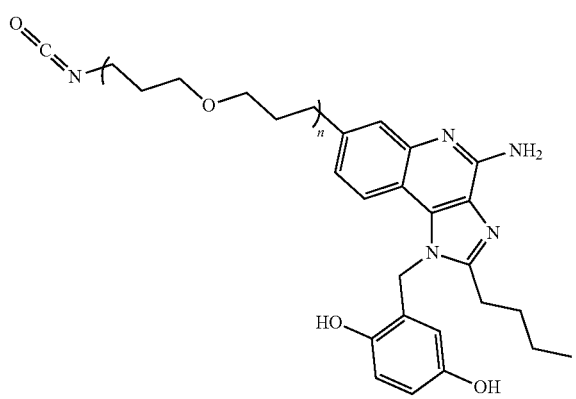
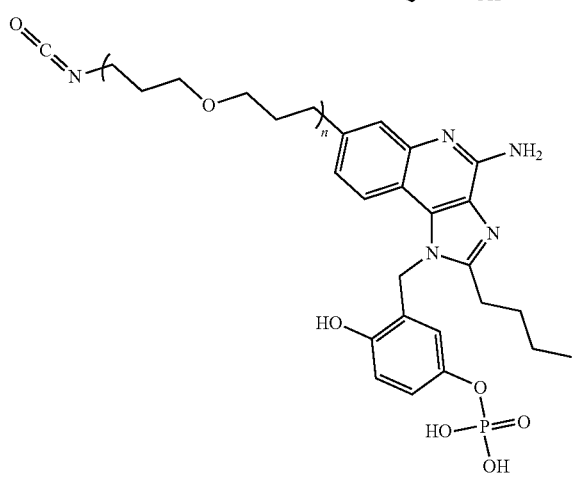
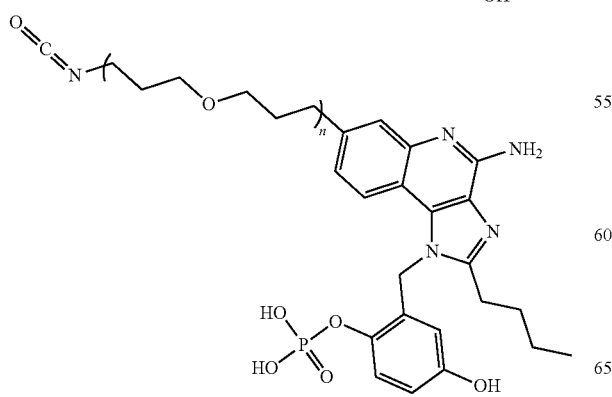
154
-continued
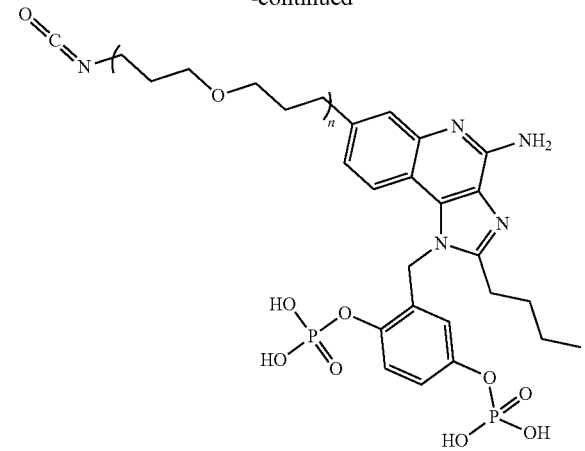
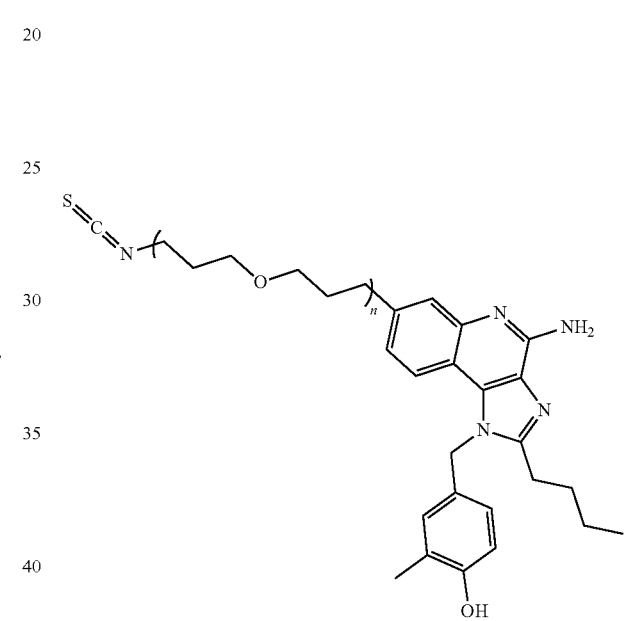
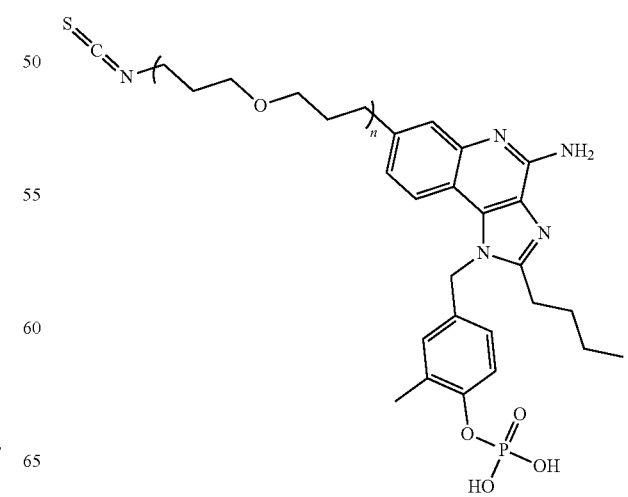

155
-continued
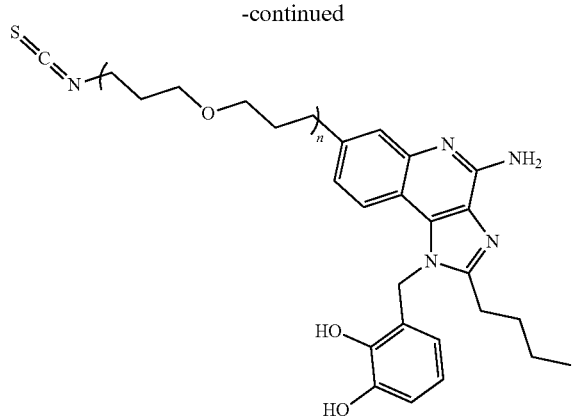
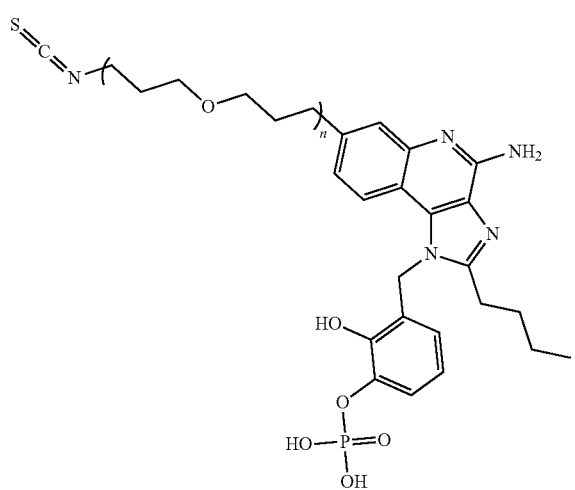
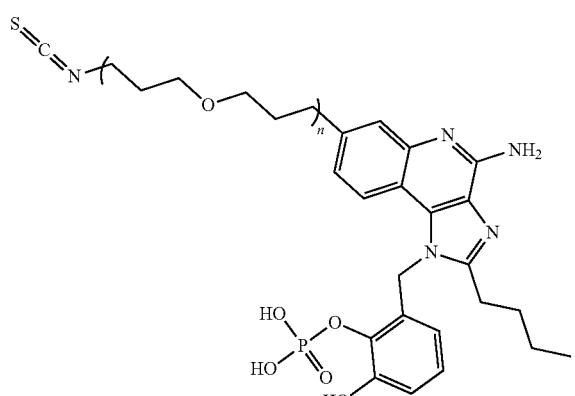
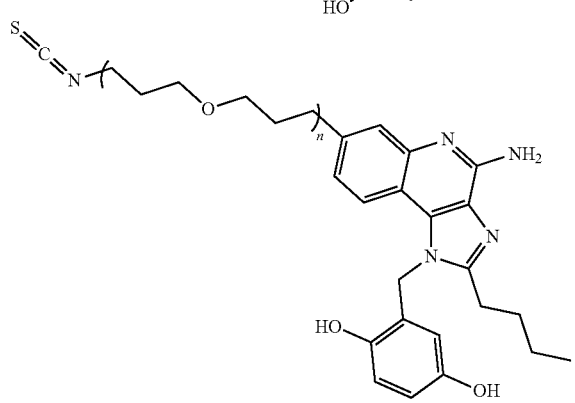
156
-continued
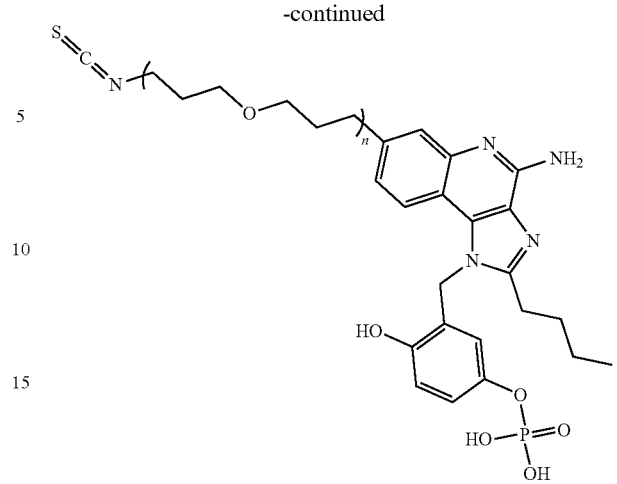
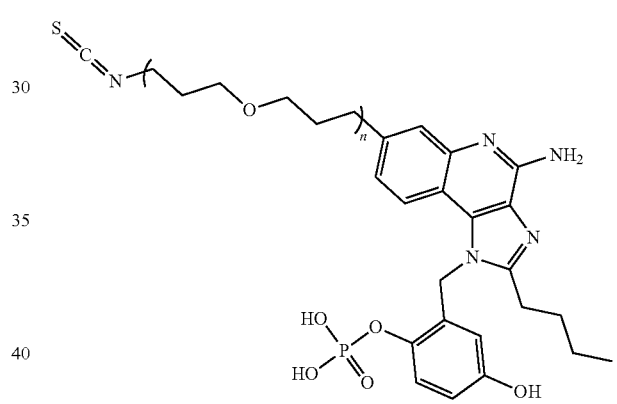
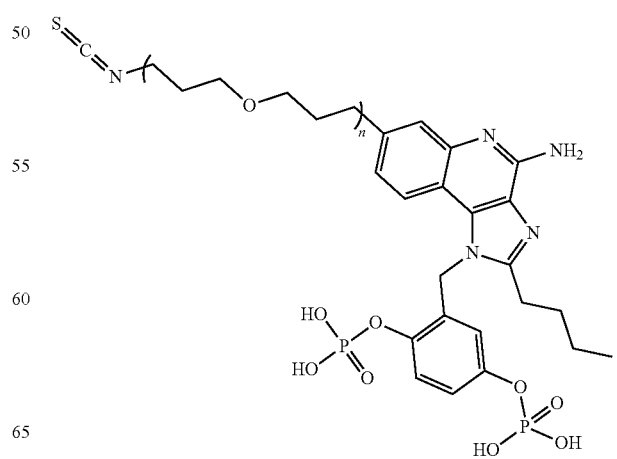

157
-continued
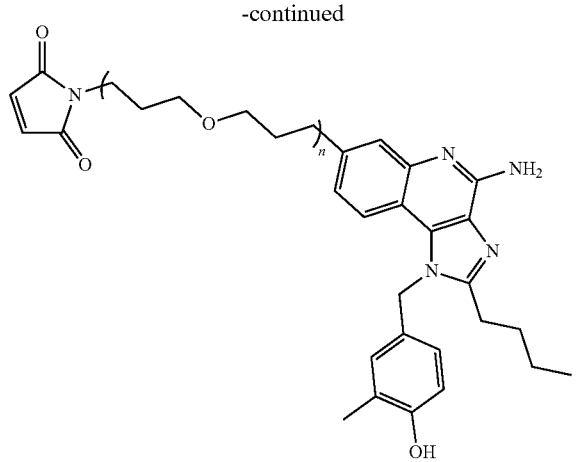
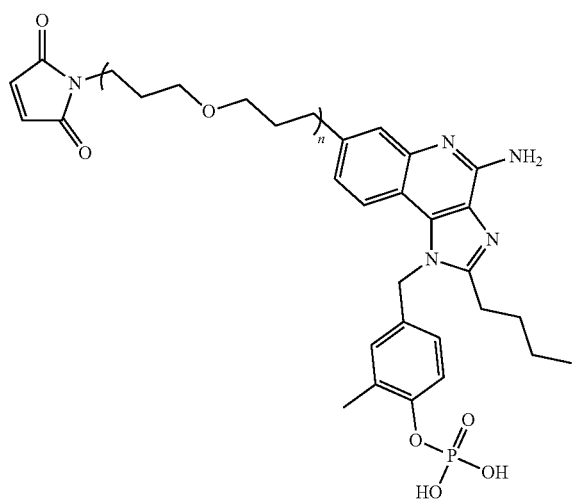
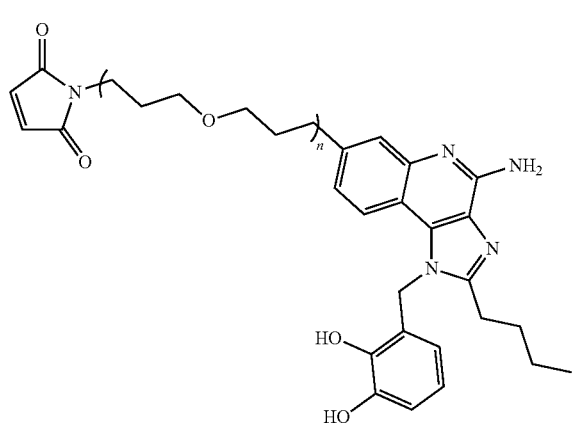
158
-continued
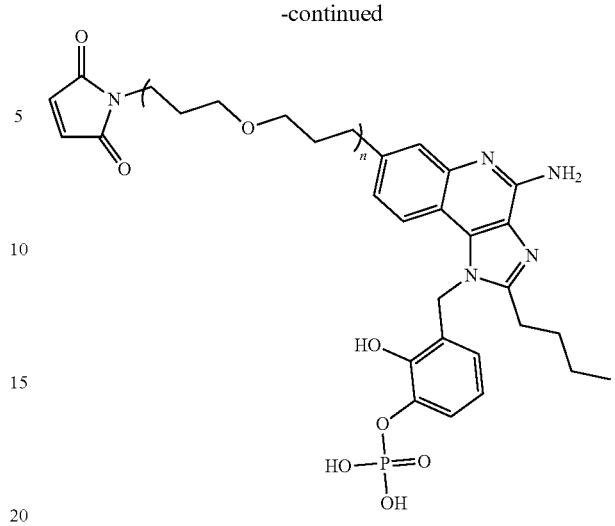
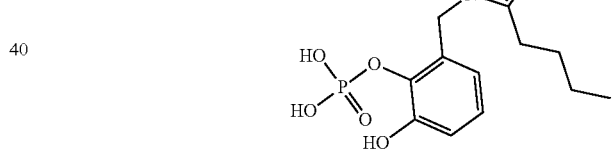
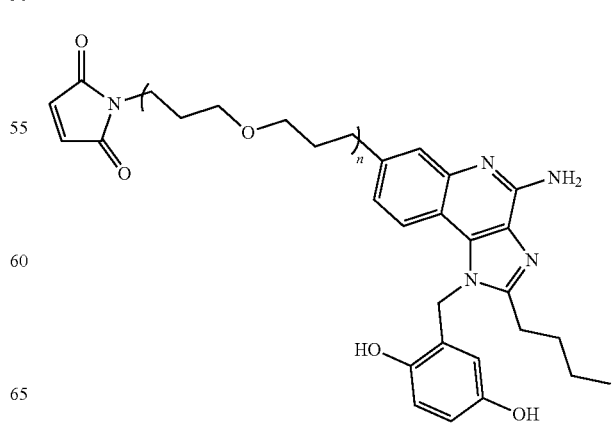

159
-continued
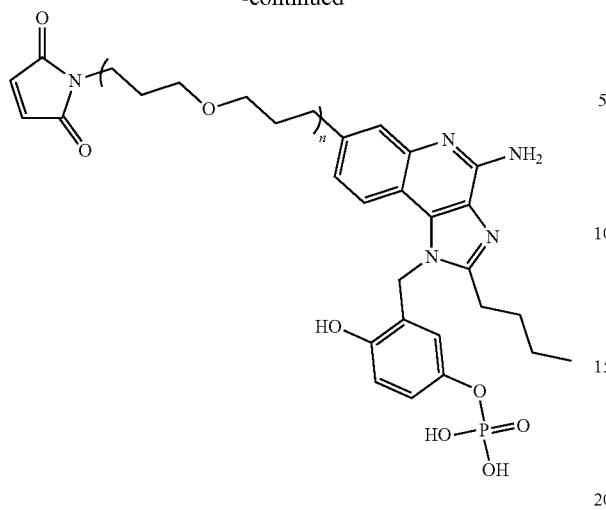
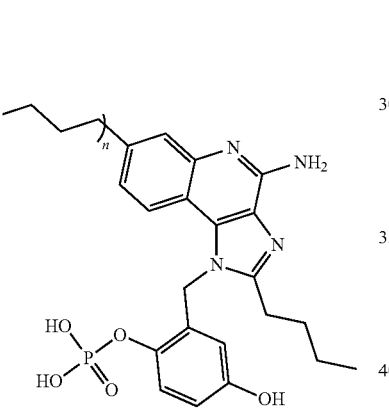
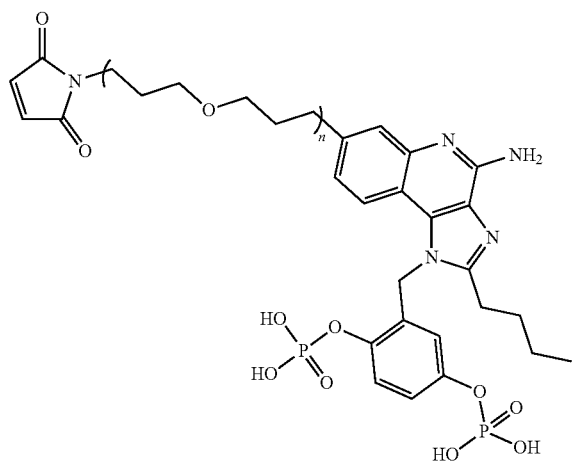
160
-continued
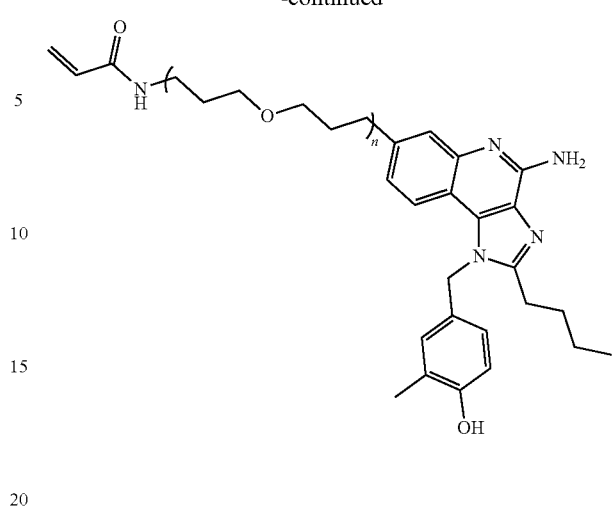
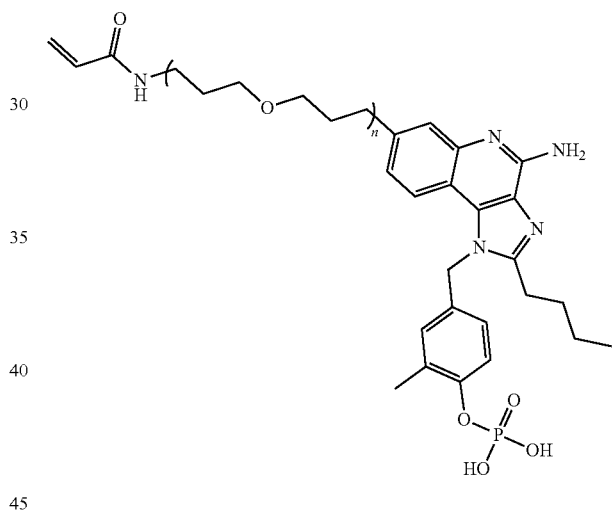
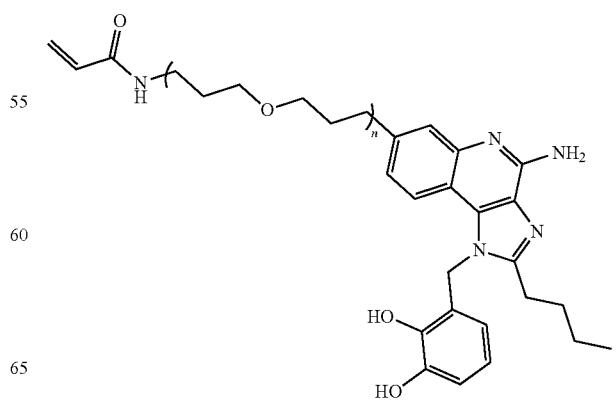

161
-continued
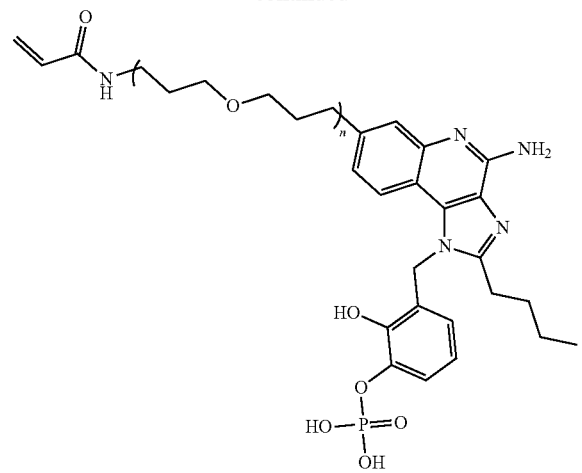
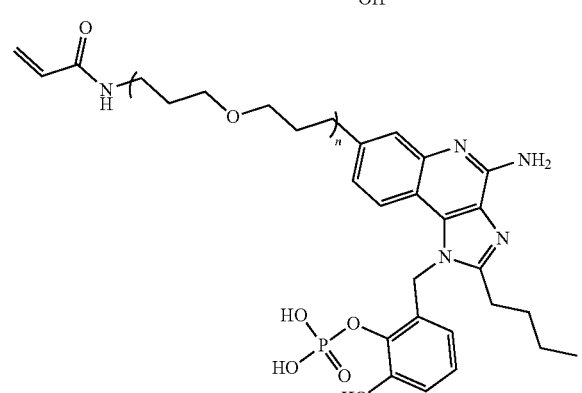
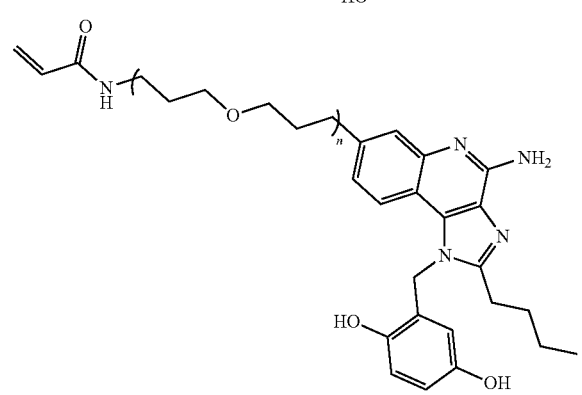
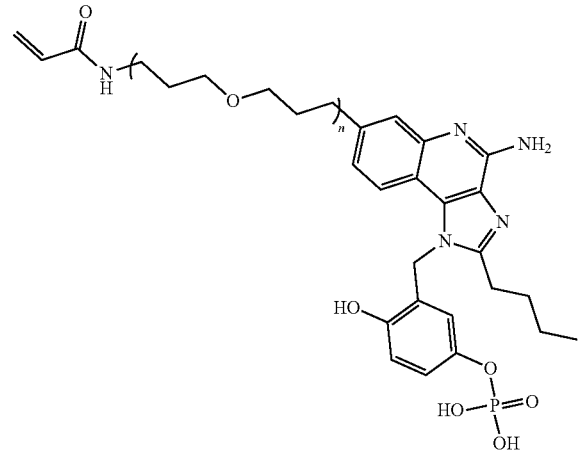
162
-continued
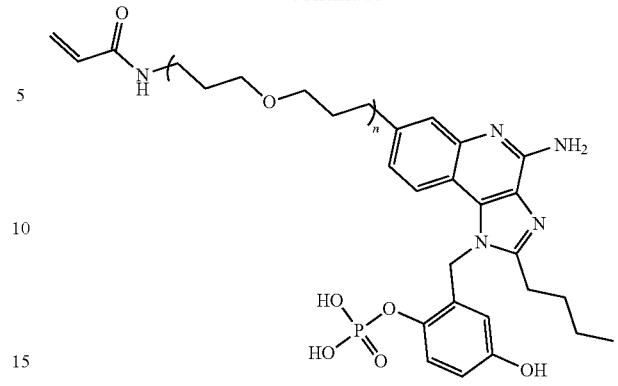
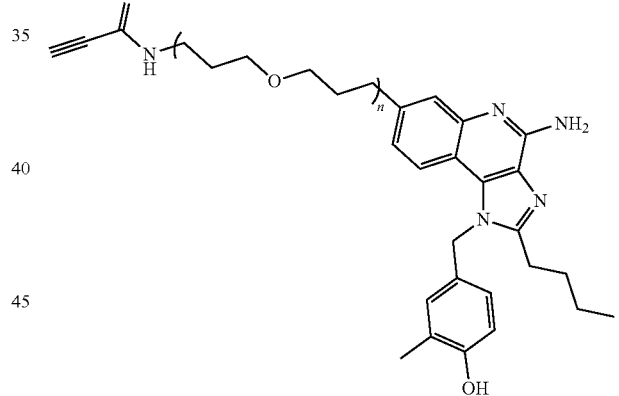
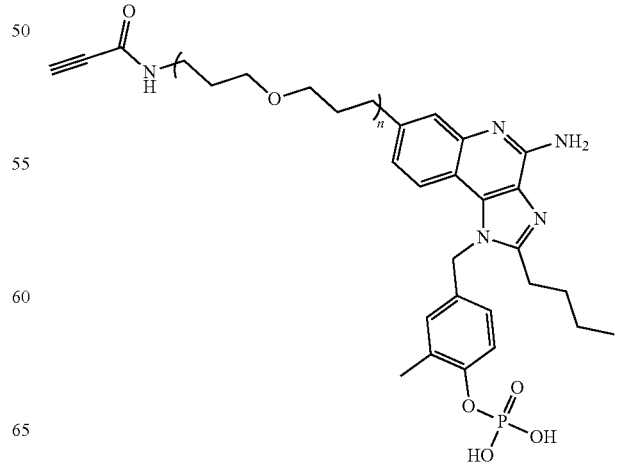

163
-continued
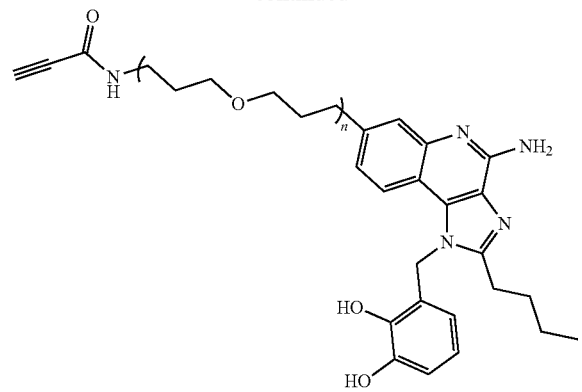
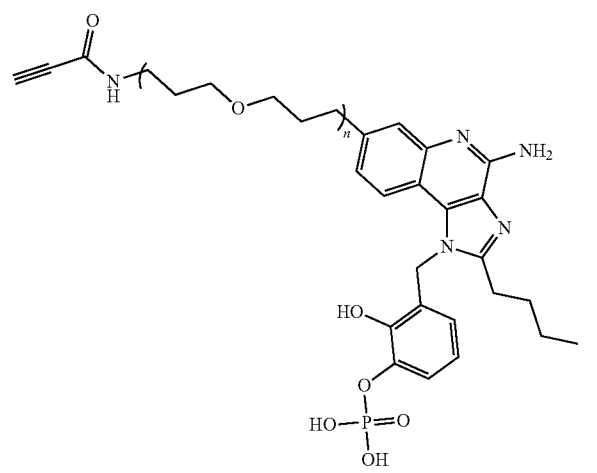
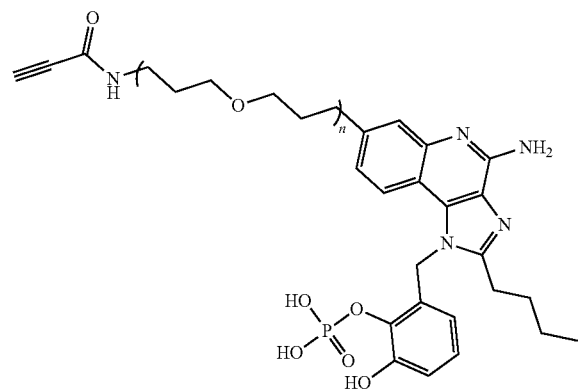
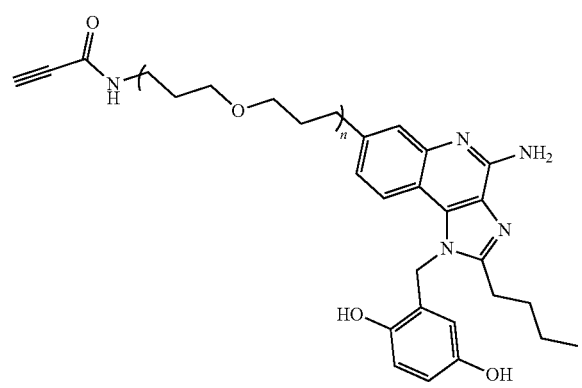
164
-continued
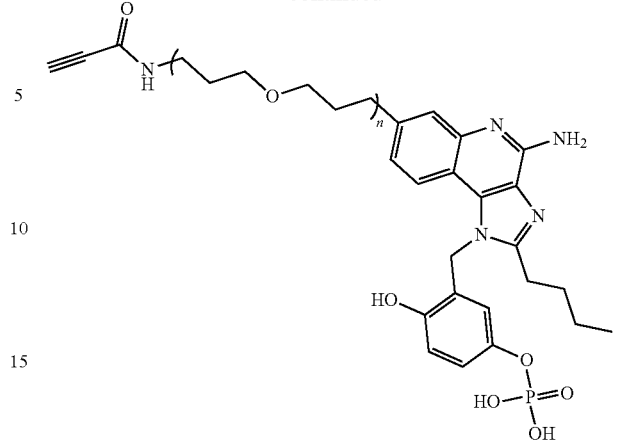
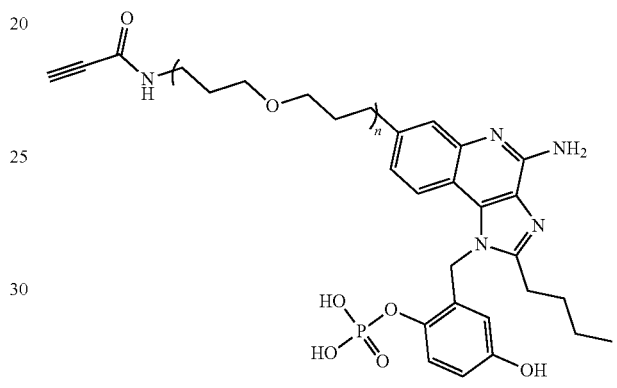
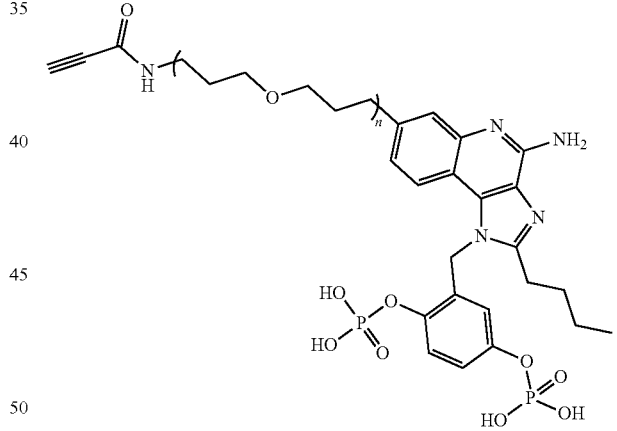
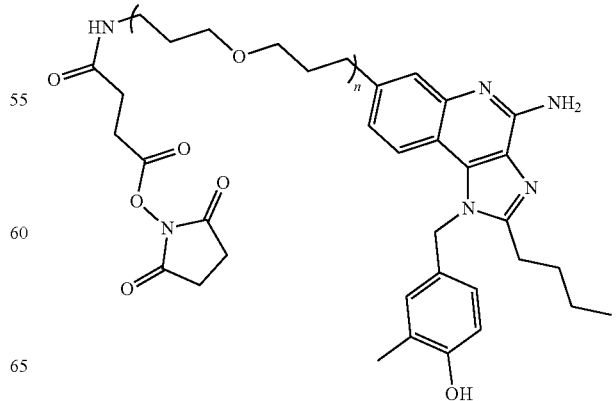

165
-continued
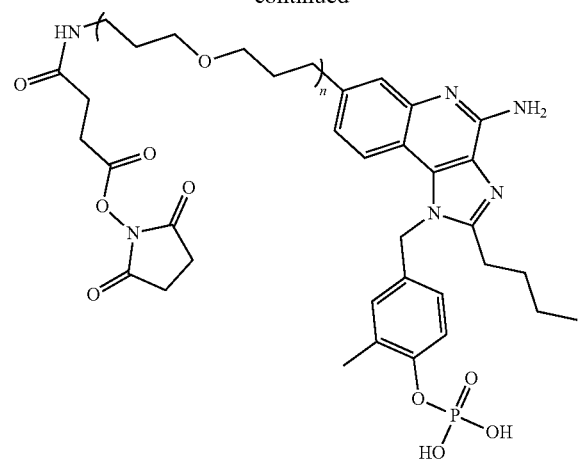
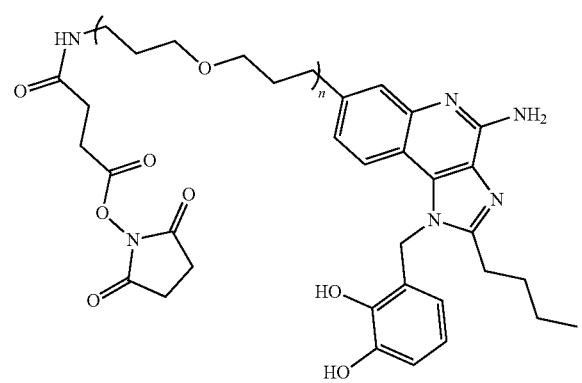
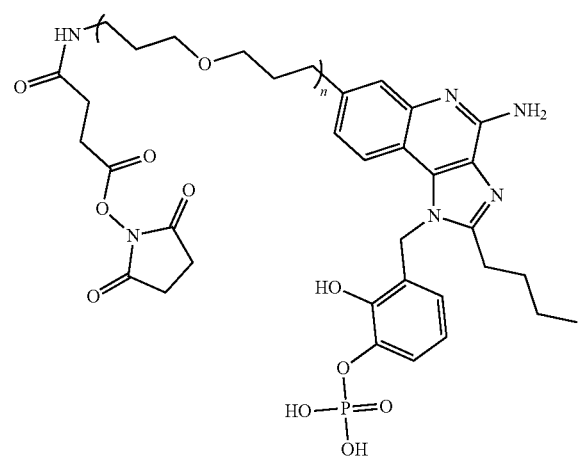
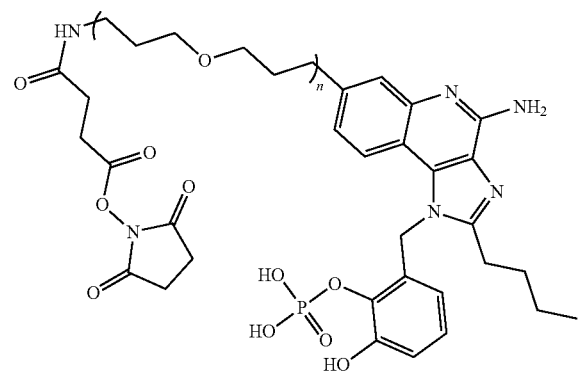
166
-continued
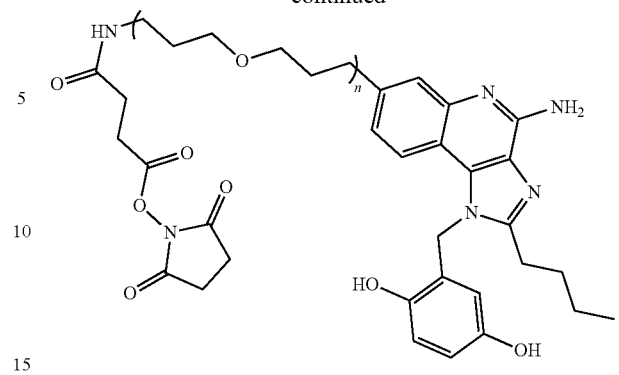
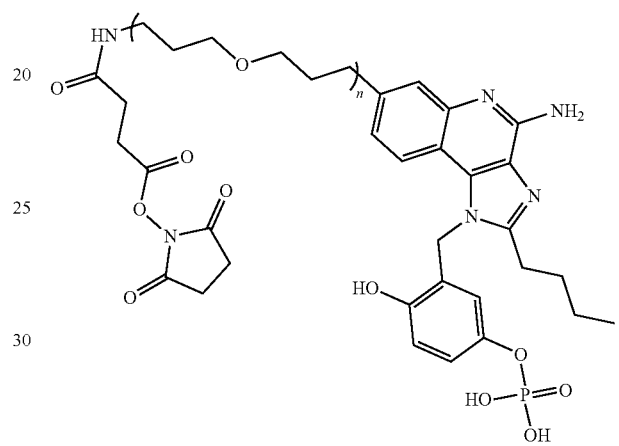
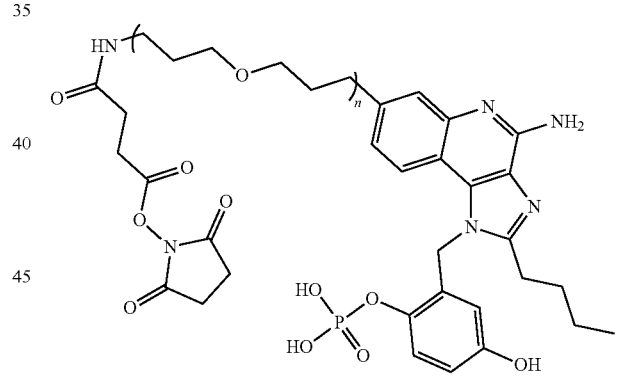
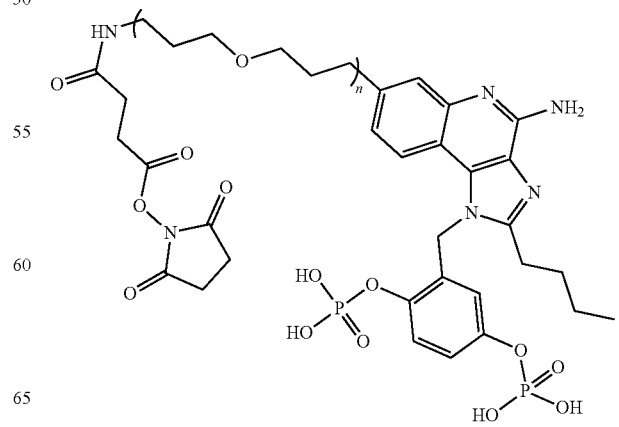

167
-continued
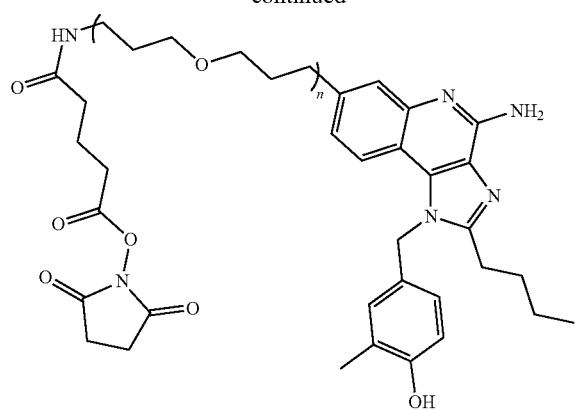
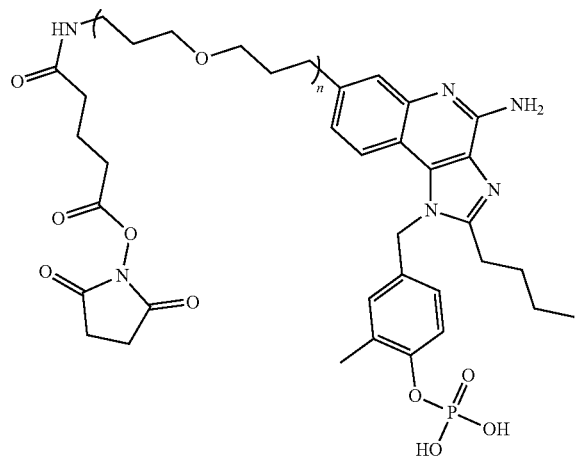
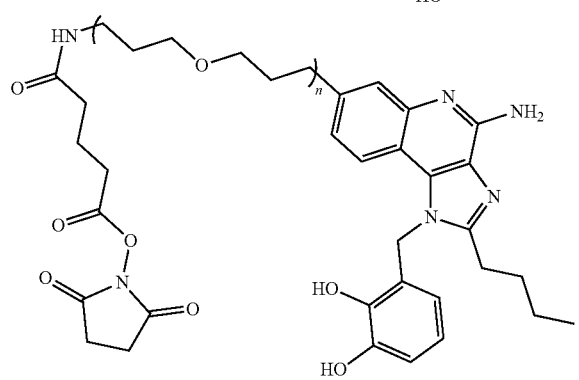
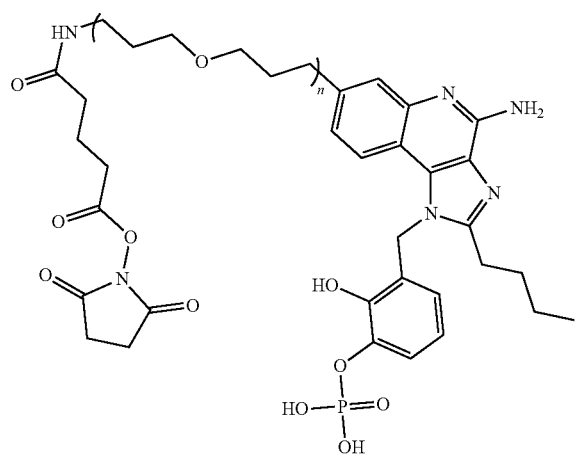
168
-continued
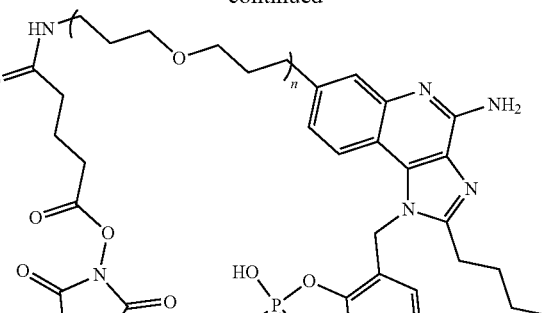
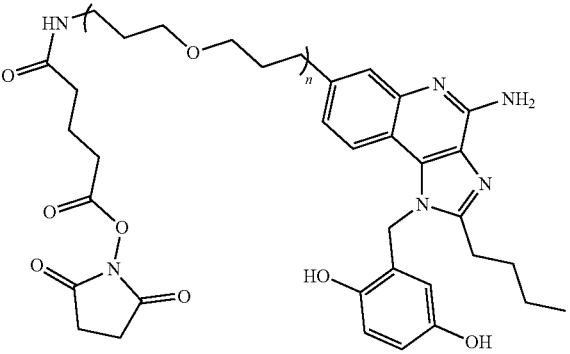
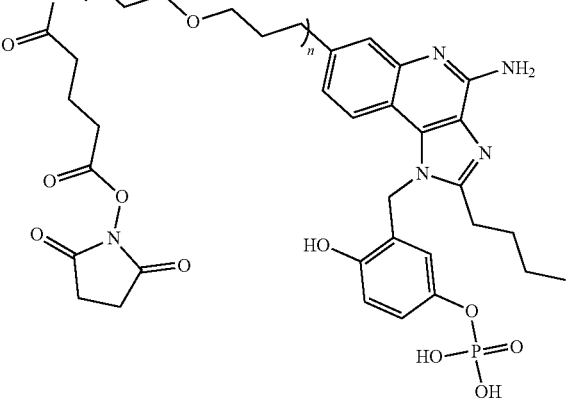
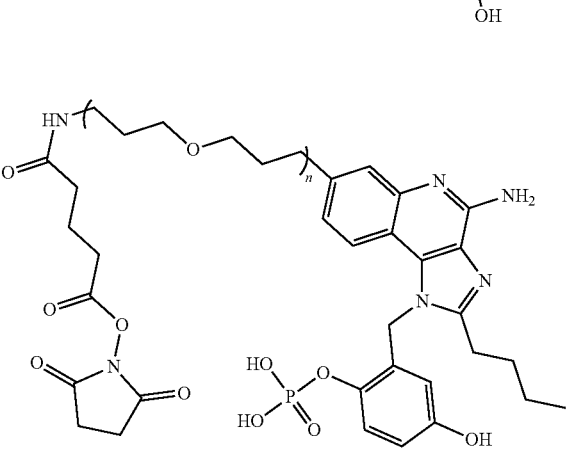

169
-continued
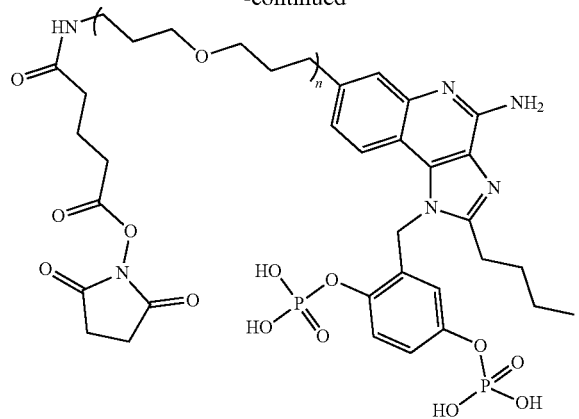
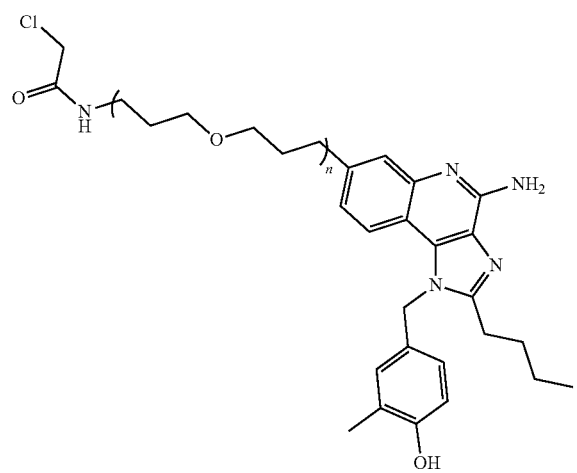
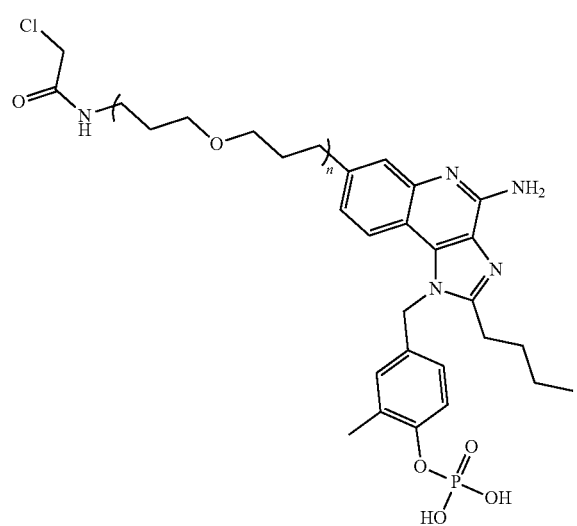
170
-continued
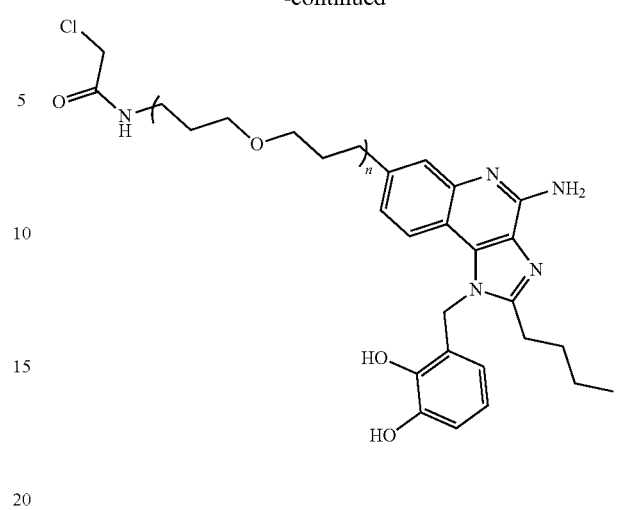
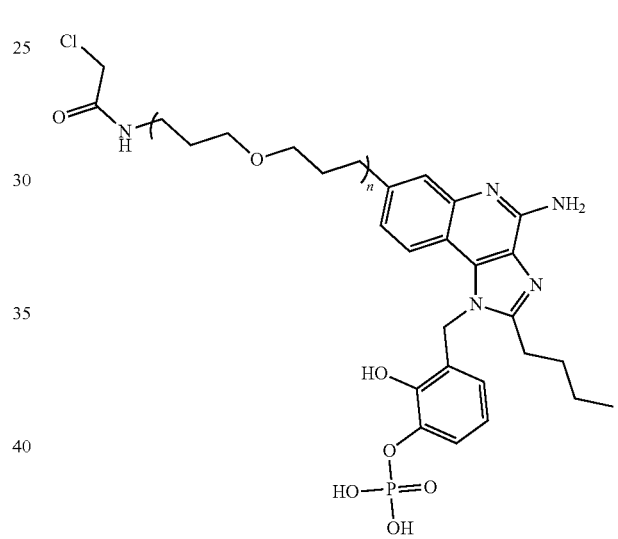
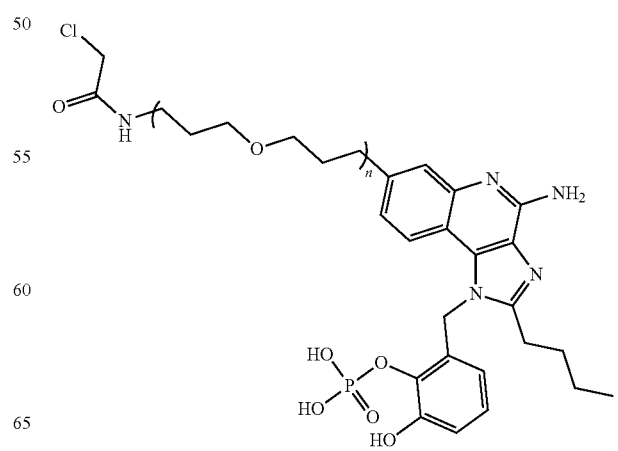

171
-continued
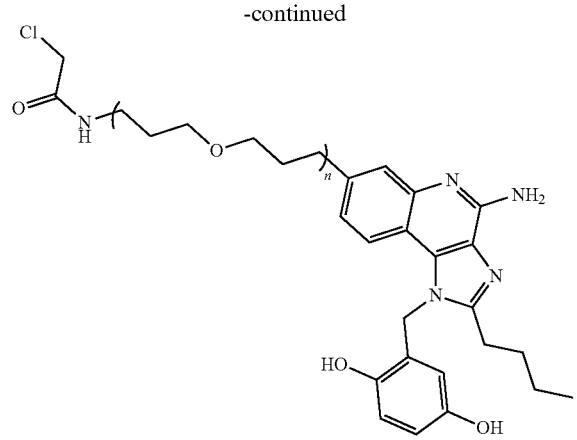
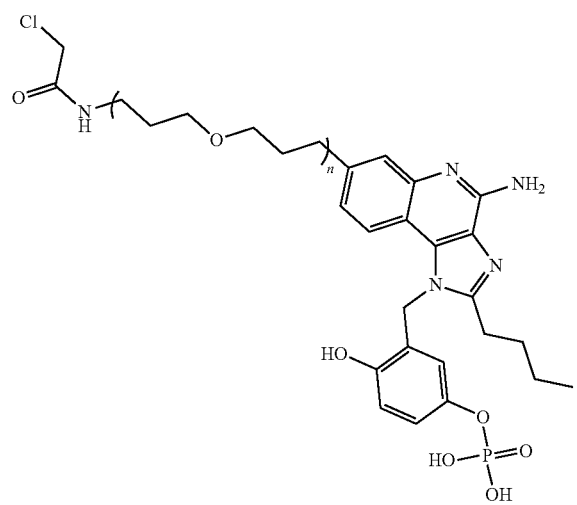
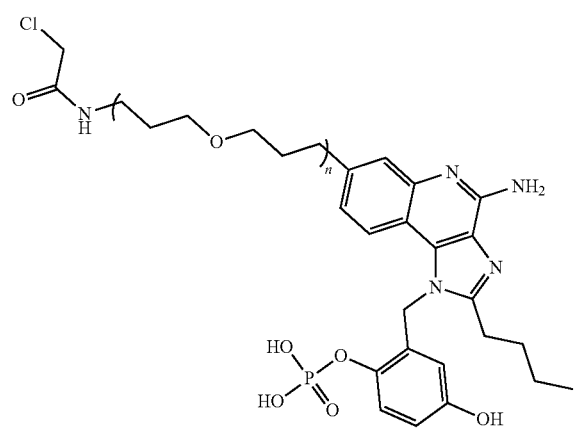
172
-continued
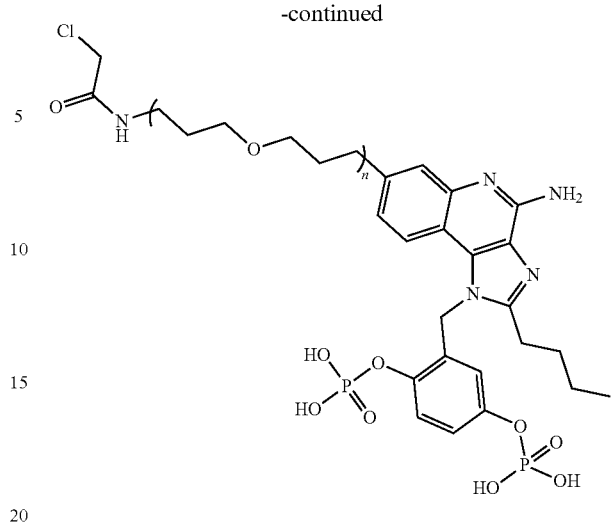
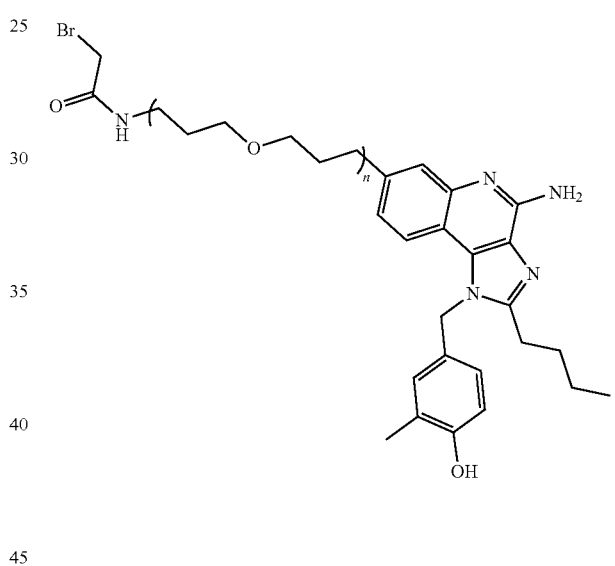
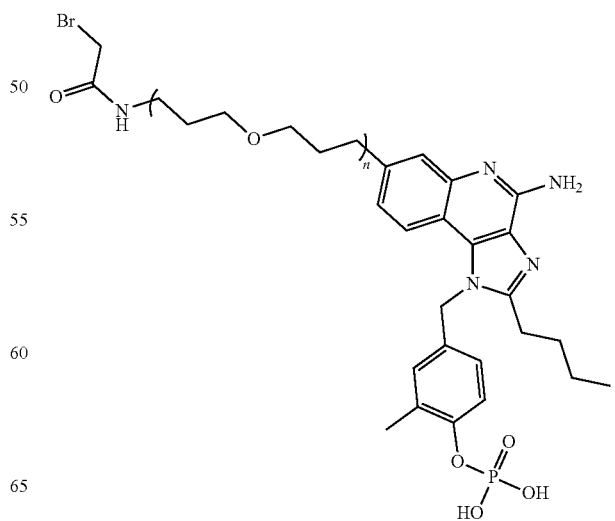

173
-continued
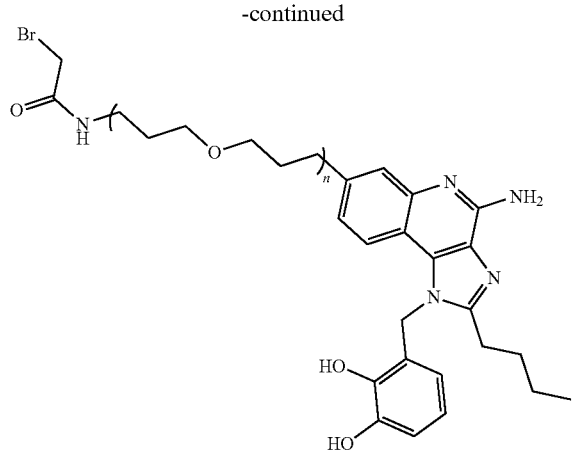
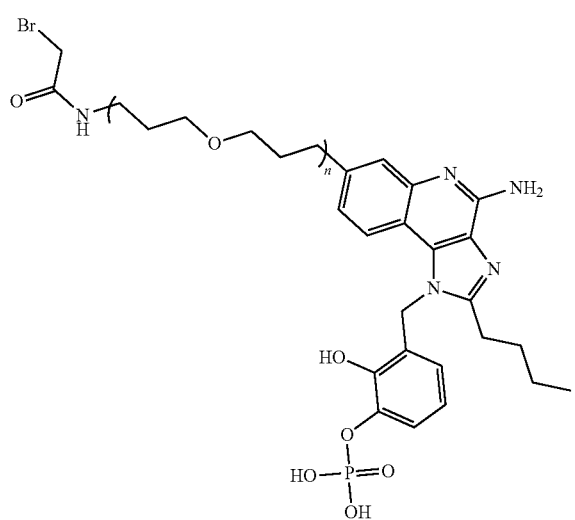
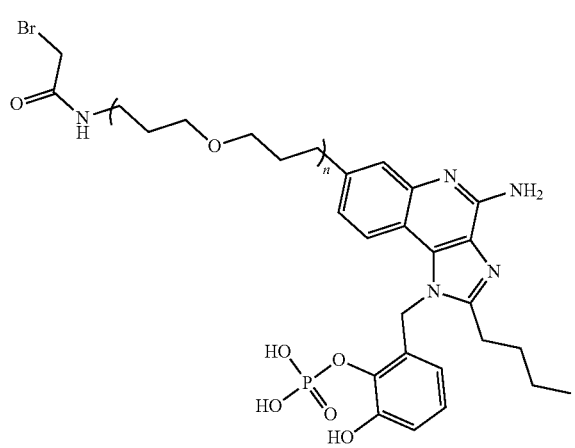
174
-continued
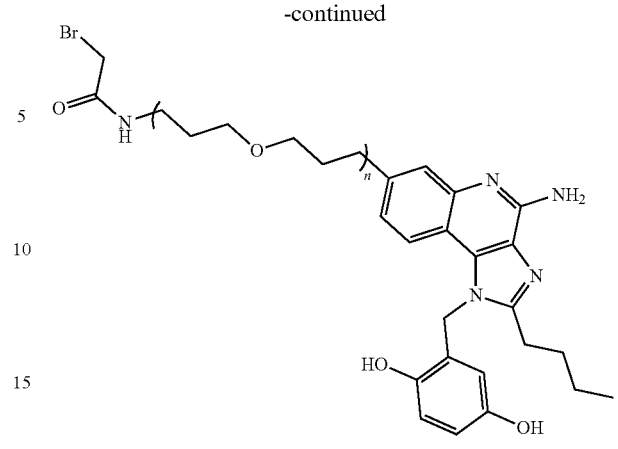
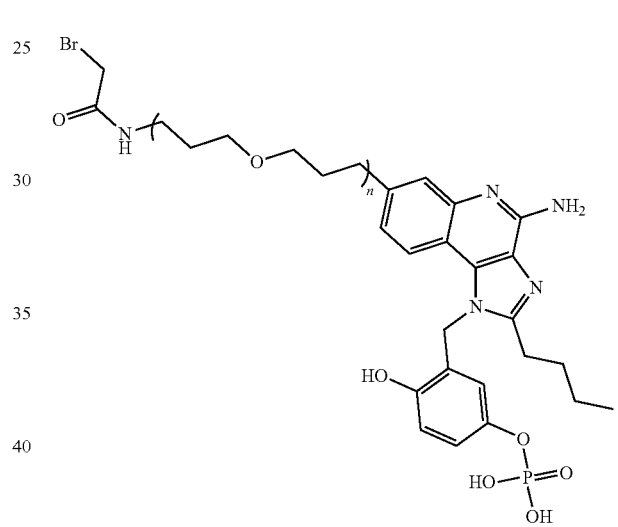
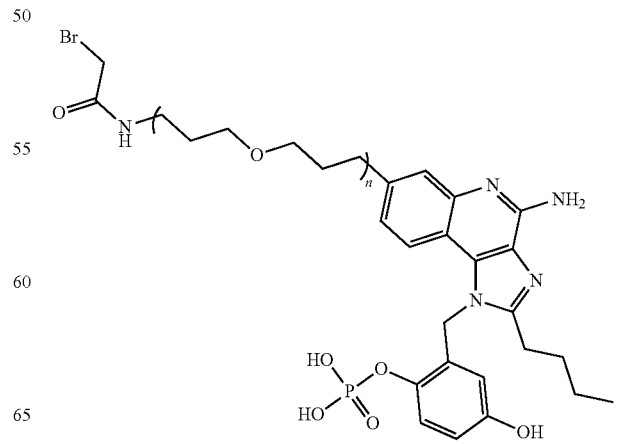

175
-continued
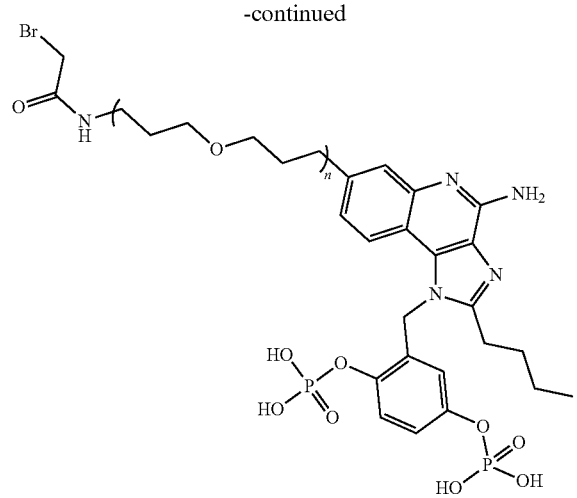
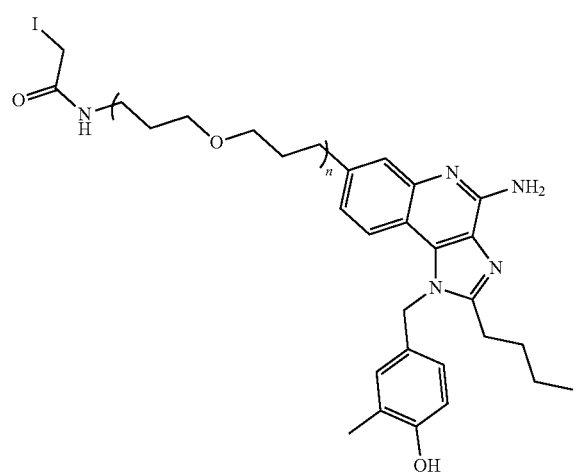
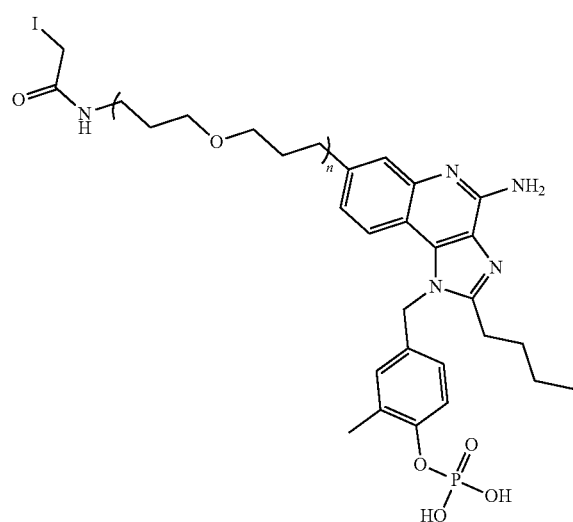
176
-continued
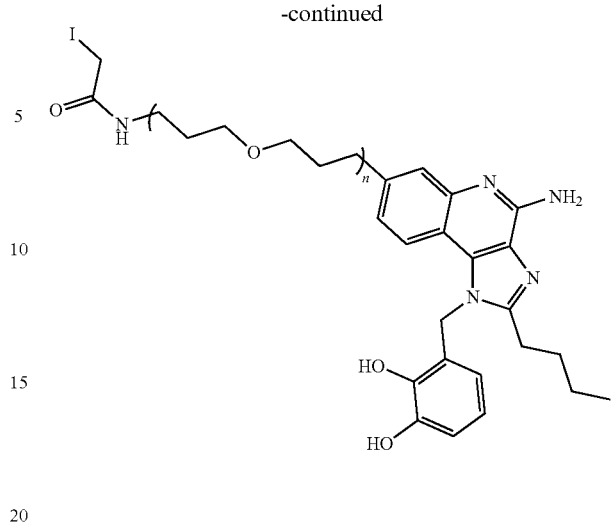
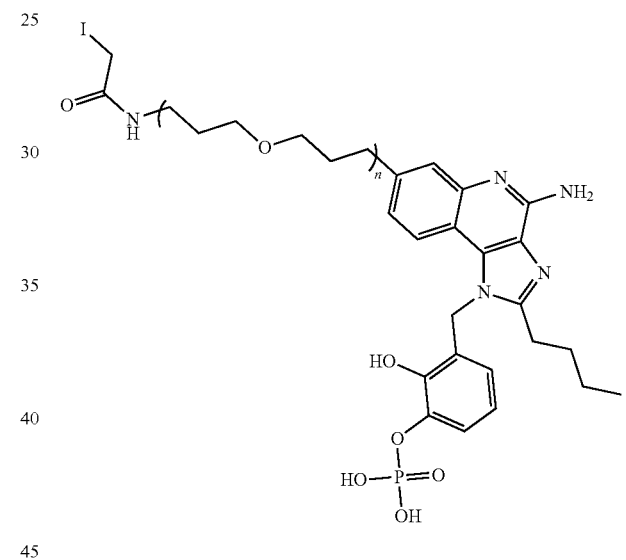
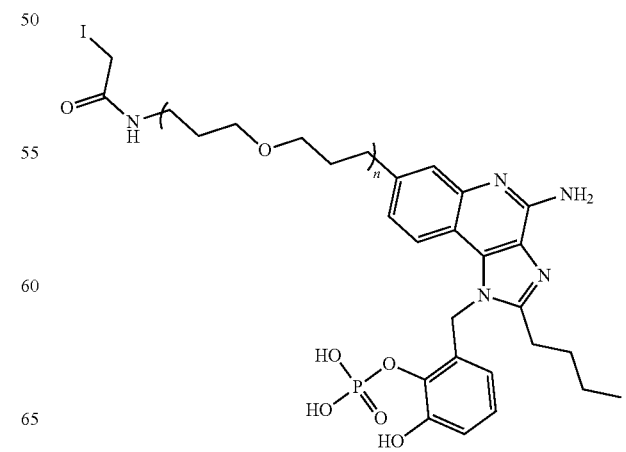

177
-continued
178
-continued
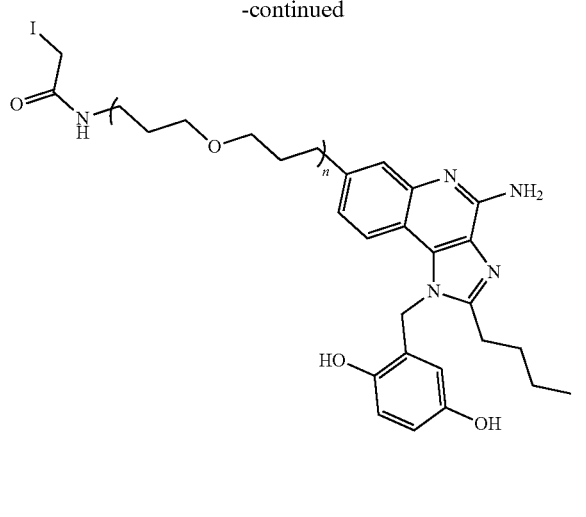
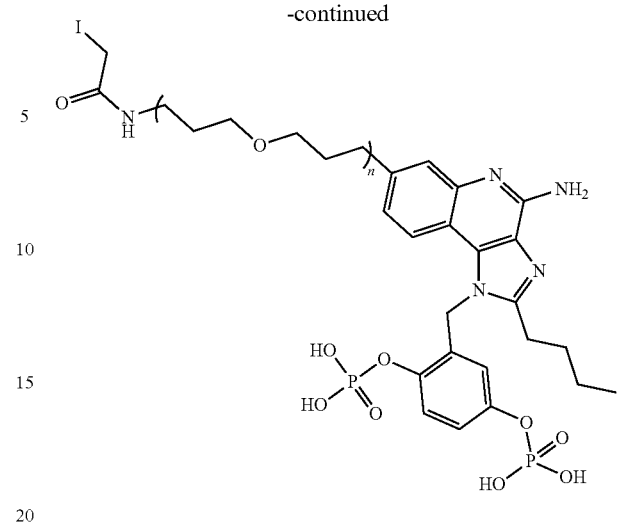
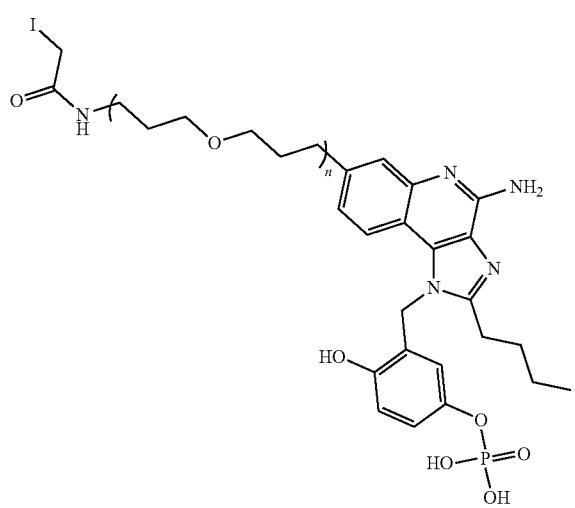
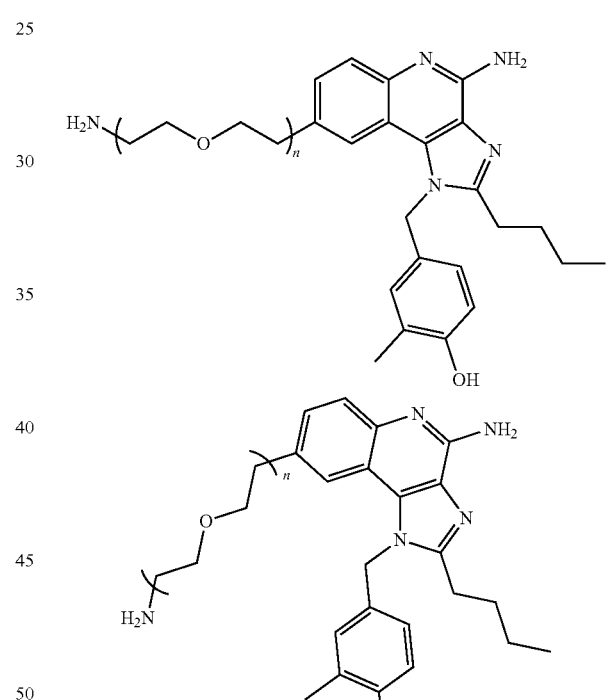
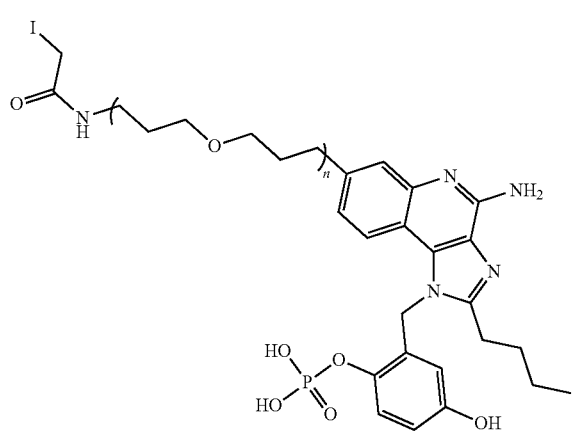
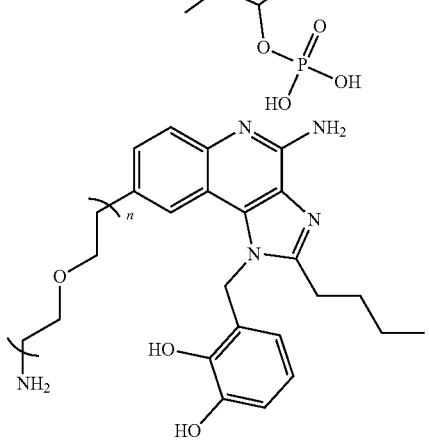

179
-continued
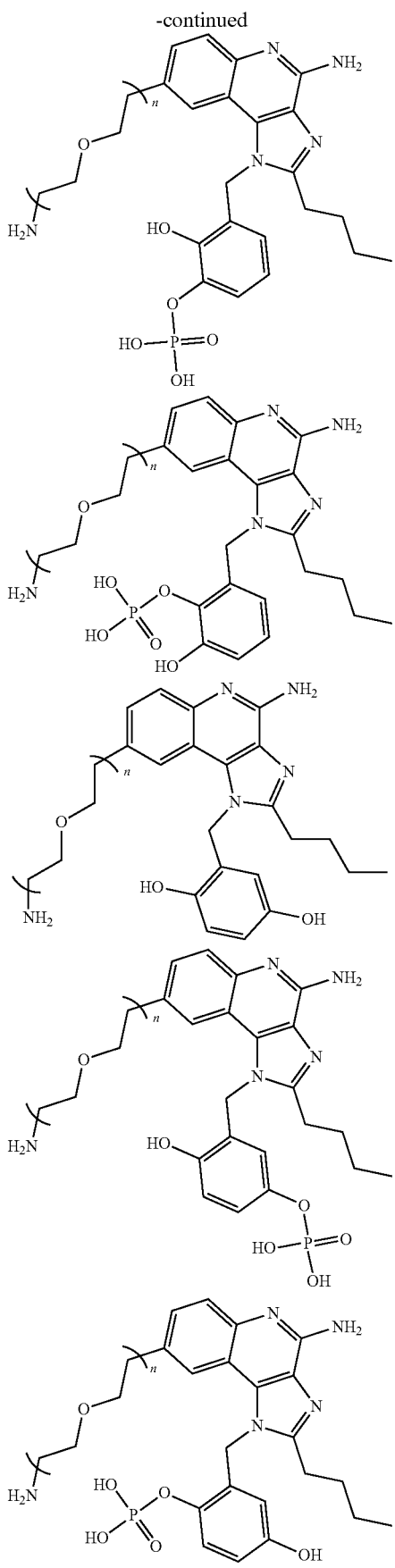
180
-continued
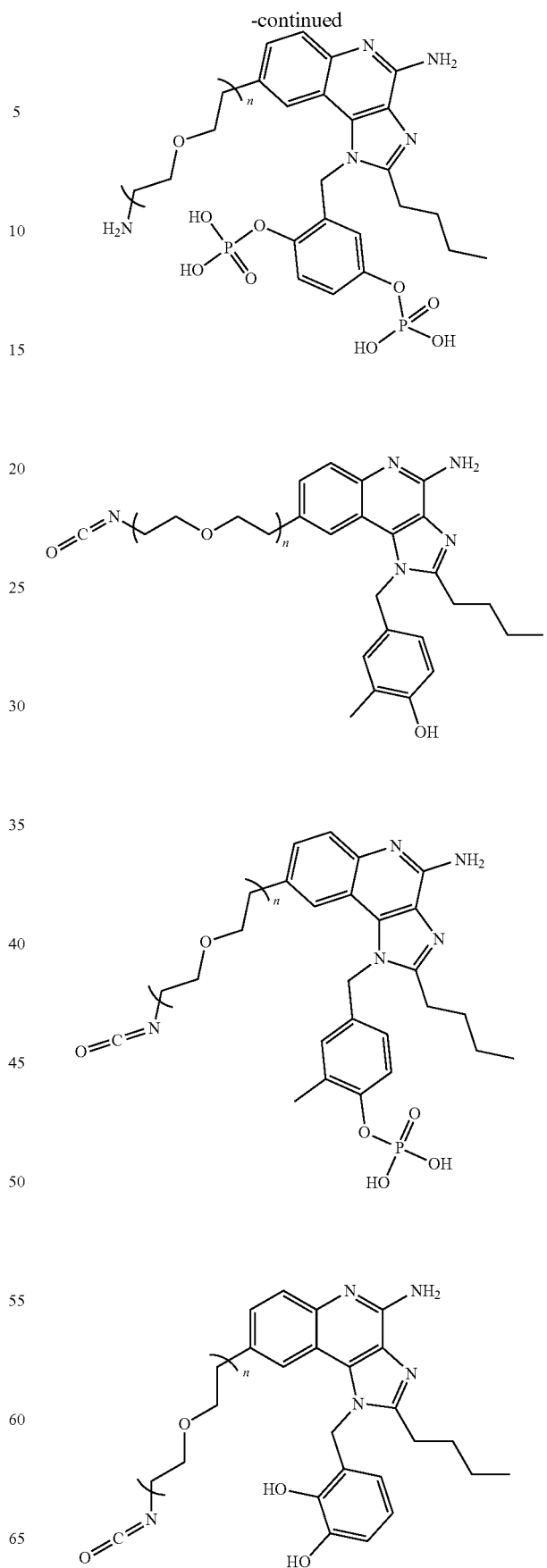

181
-continued
182
-continued
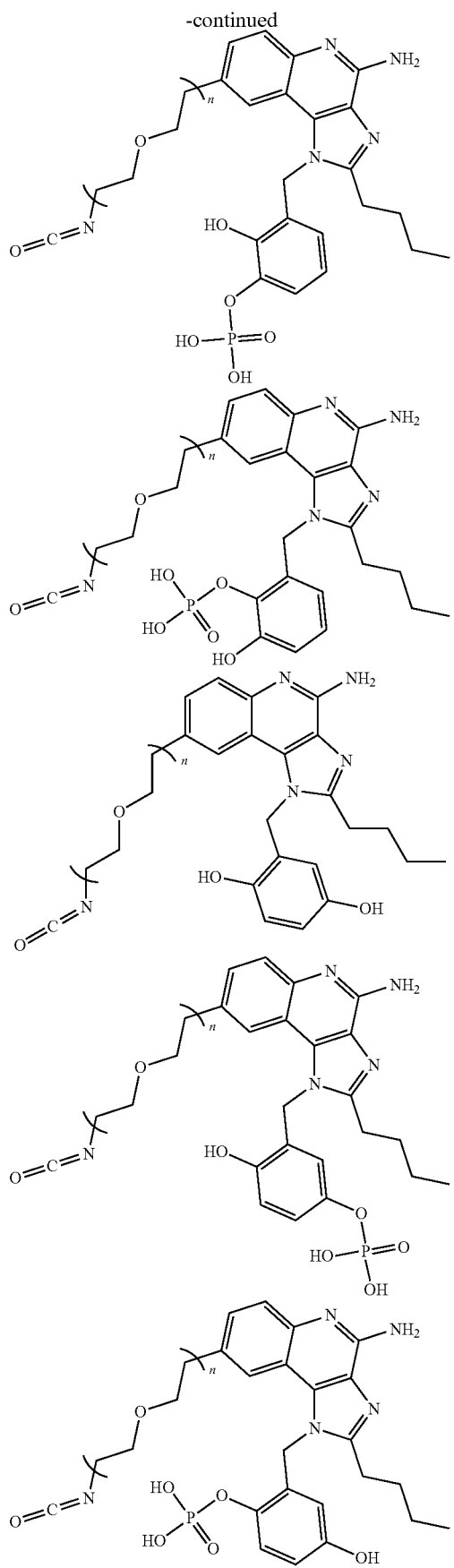
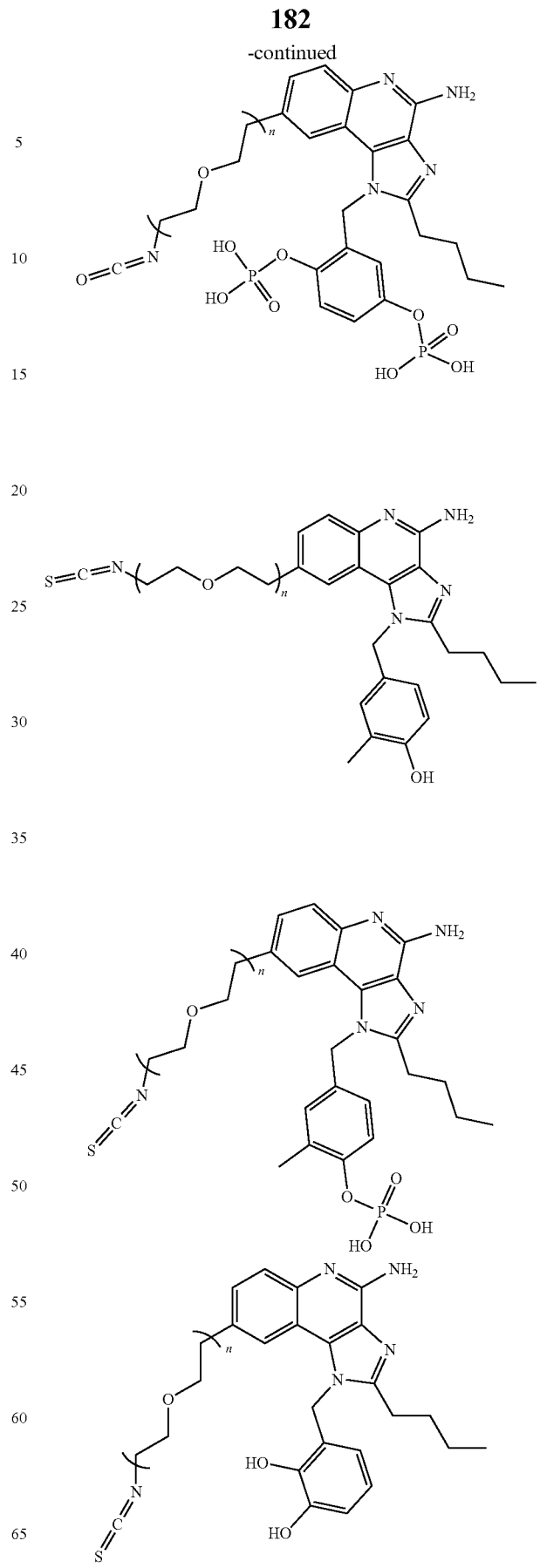

183
-continued
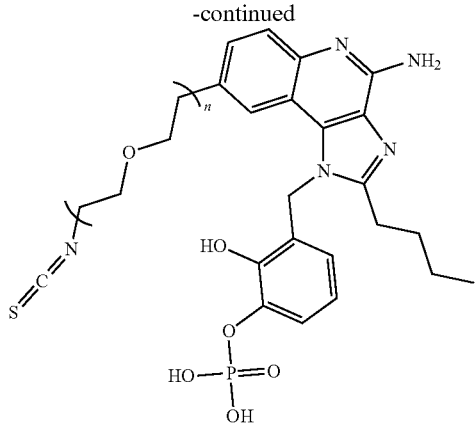
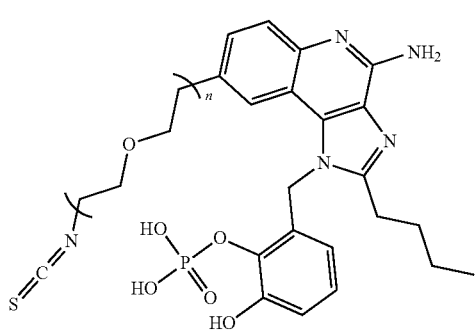
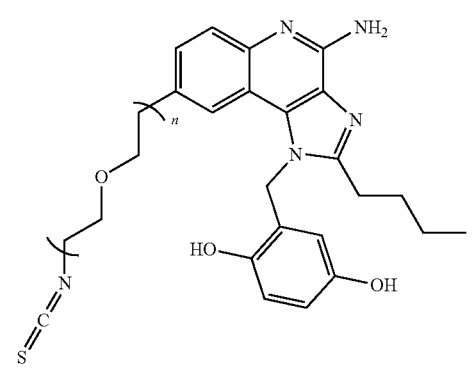
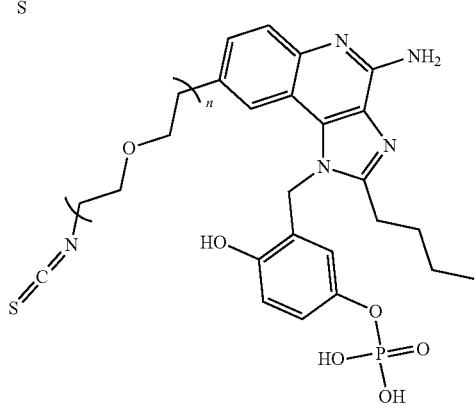
184
-continued
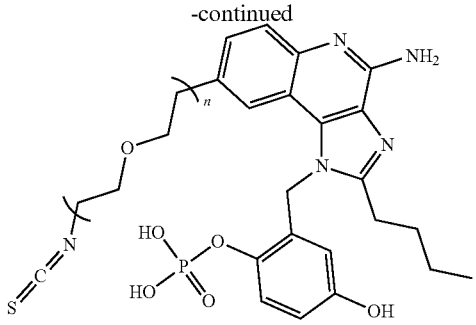
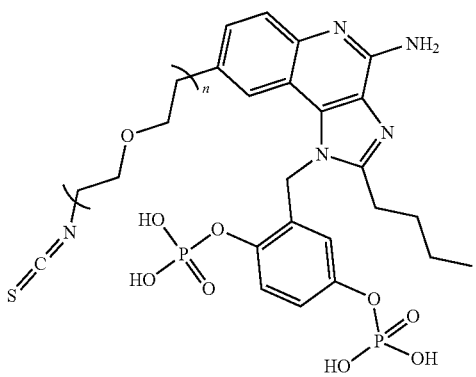
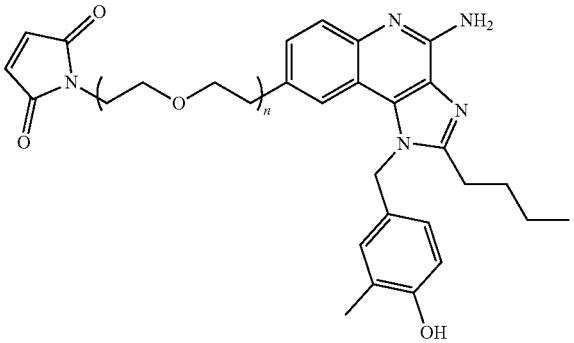
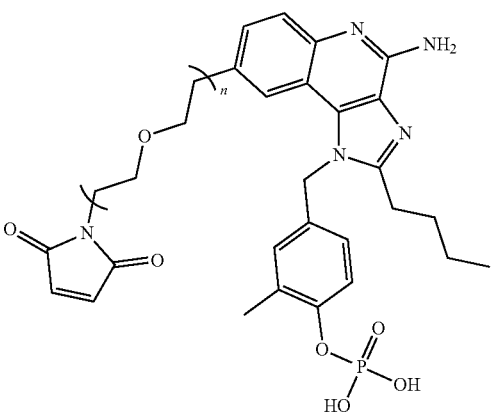

185
-continued
186
-continued
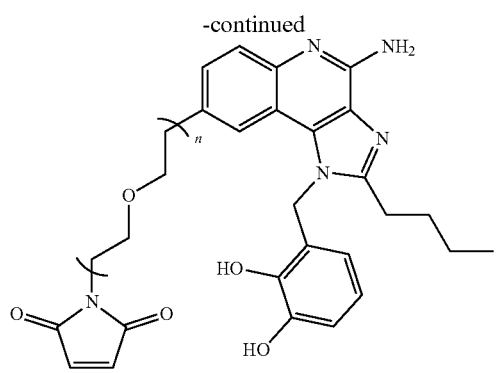
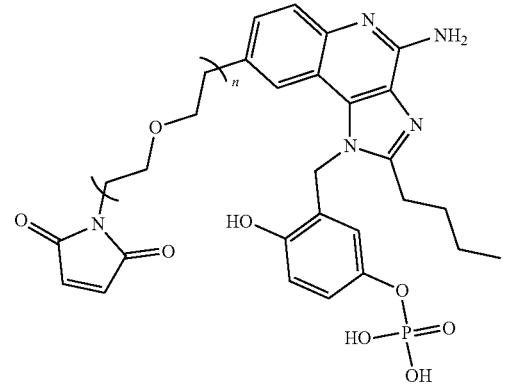

187
-continued
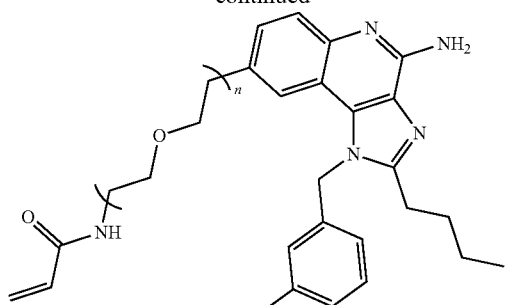
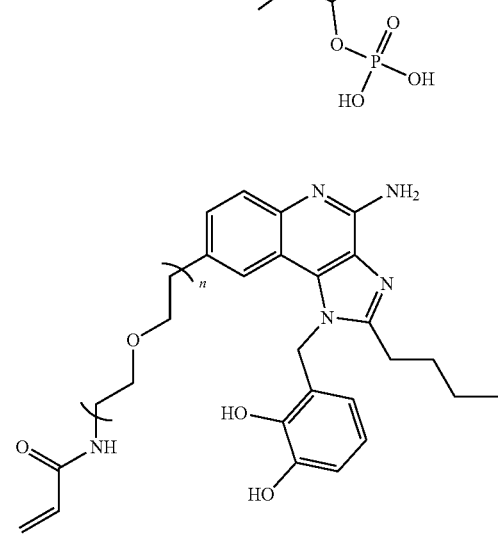
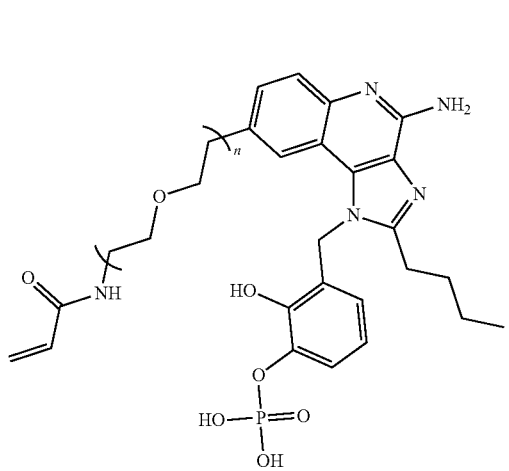
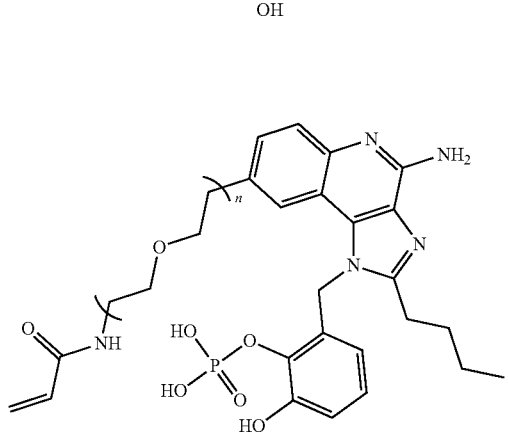
188
-continued
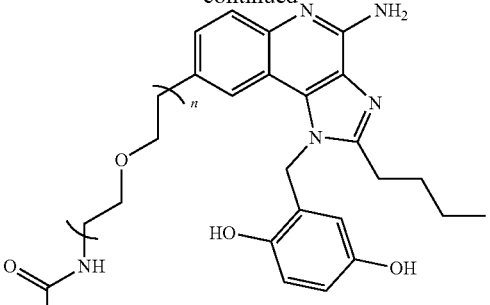
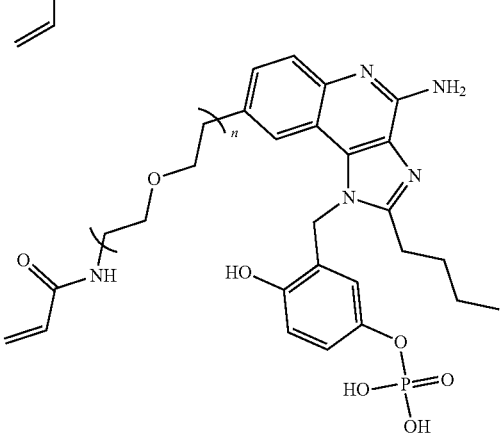
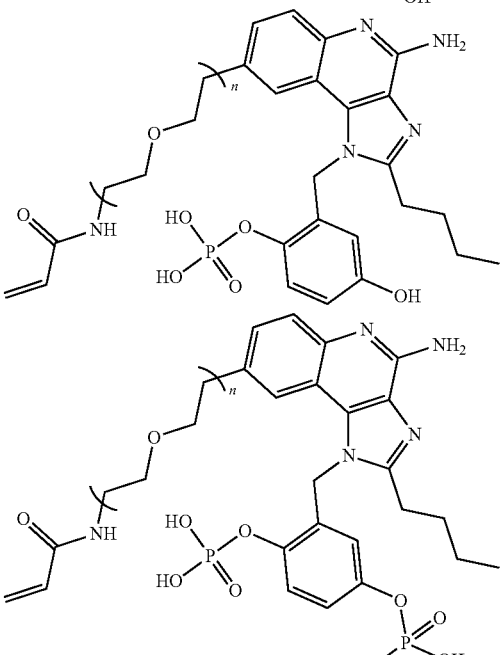
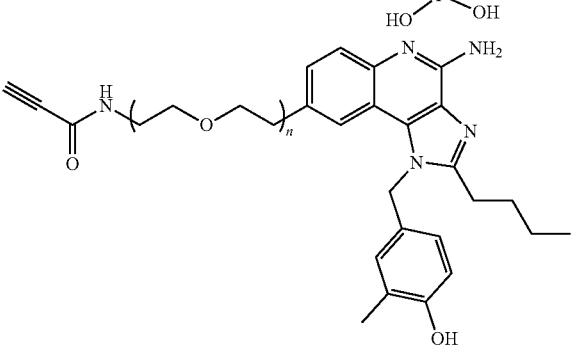

189
-continued
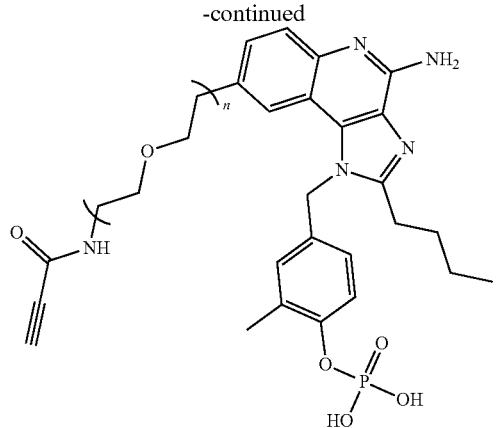
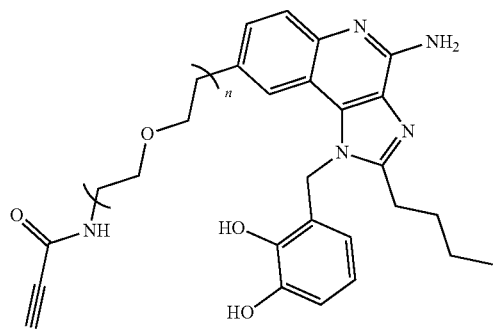
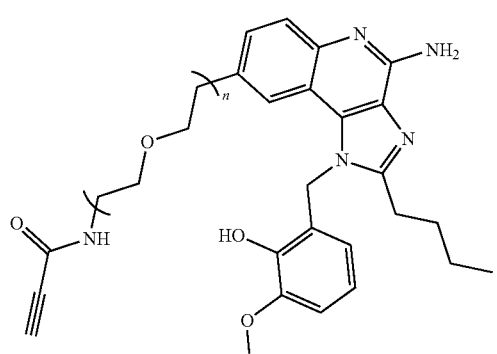
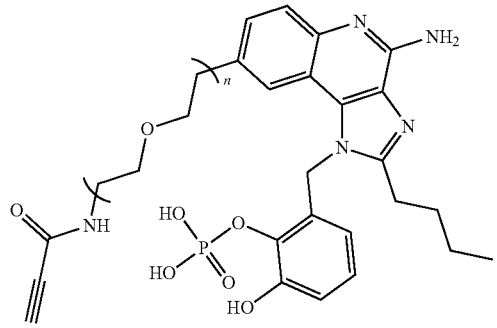
190
-continued
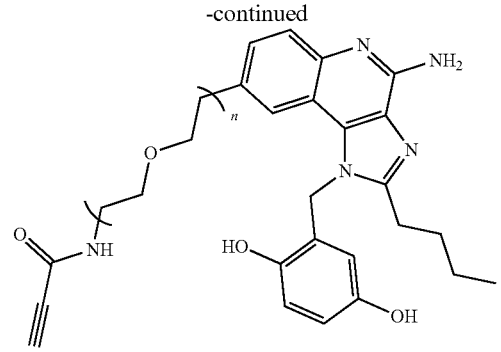
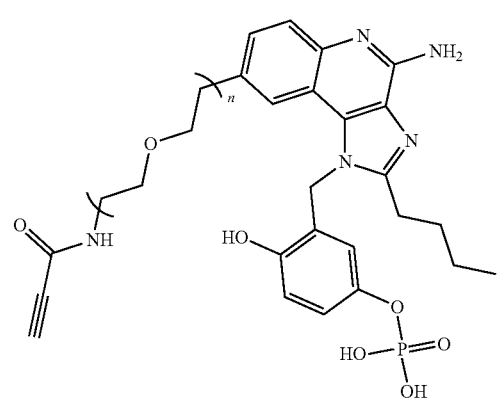
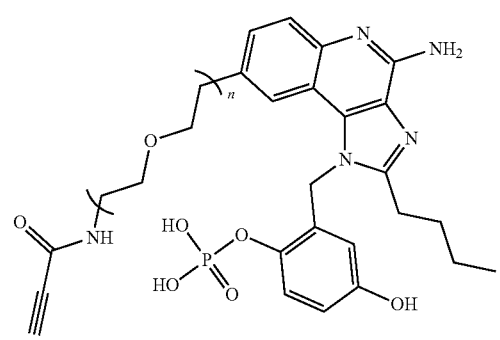
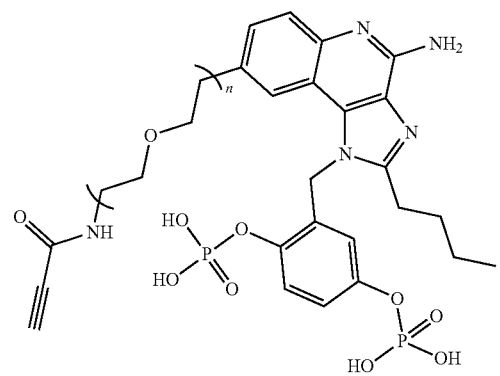

191
-continued
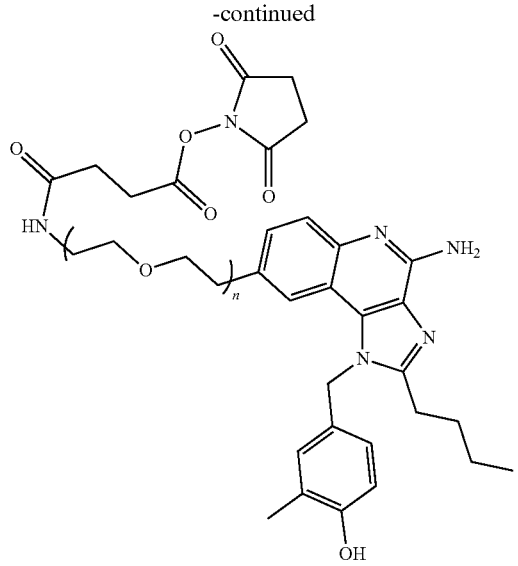
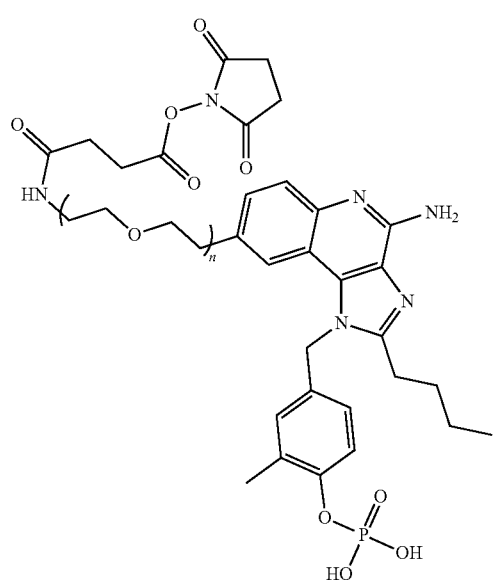
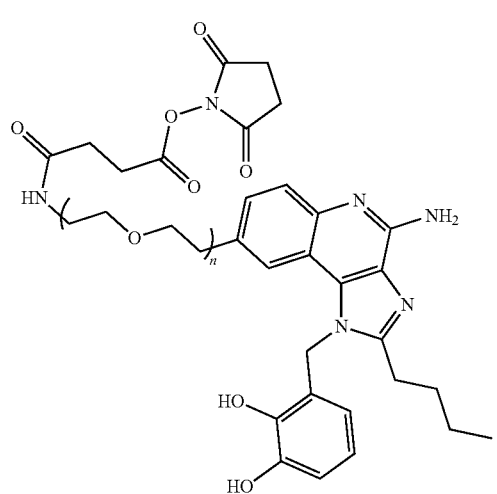
192
-continued
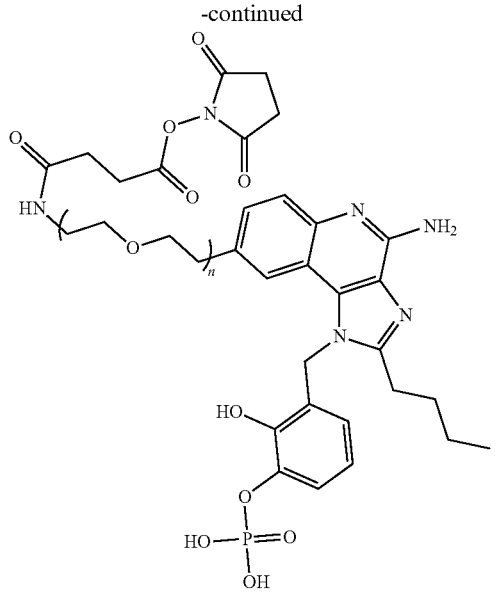
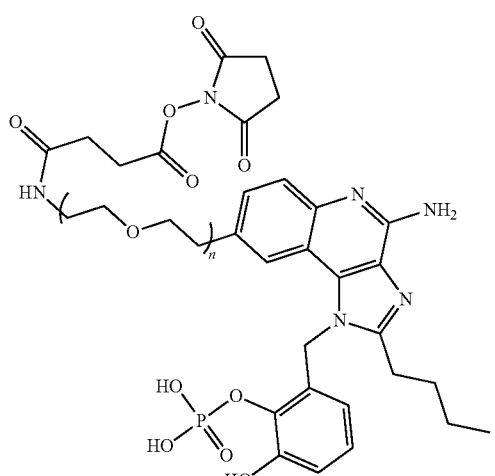
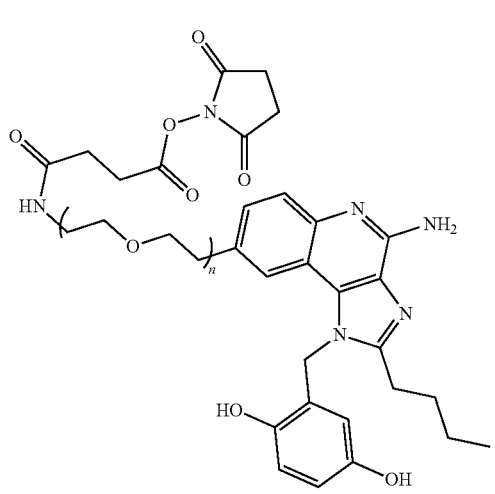

193
-continued
194
-continued
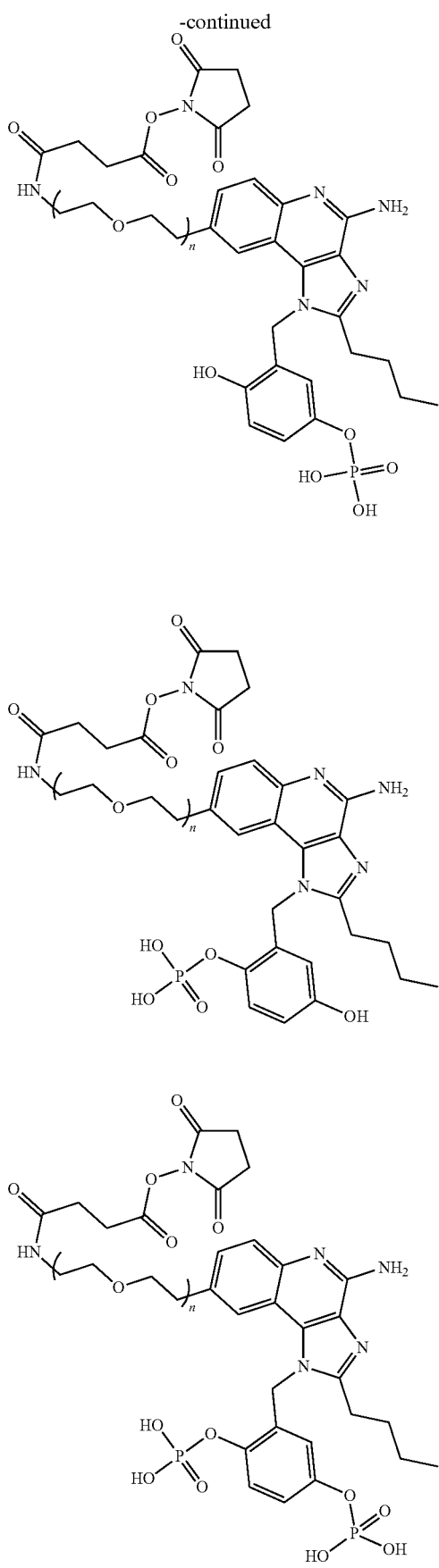

195
-continued
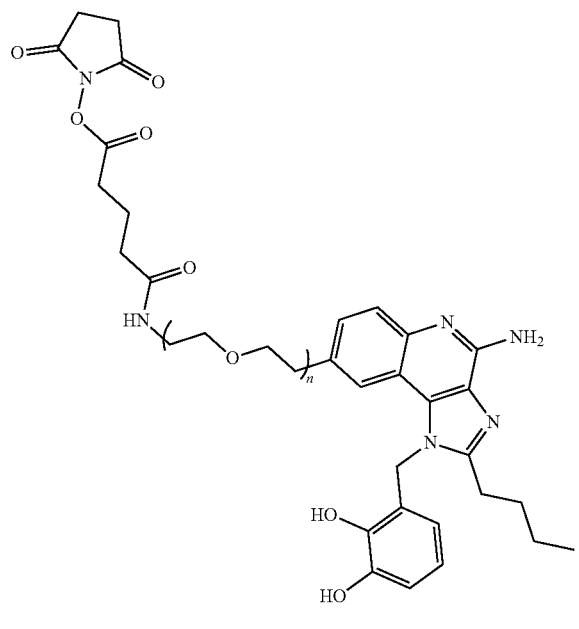
196
-continued
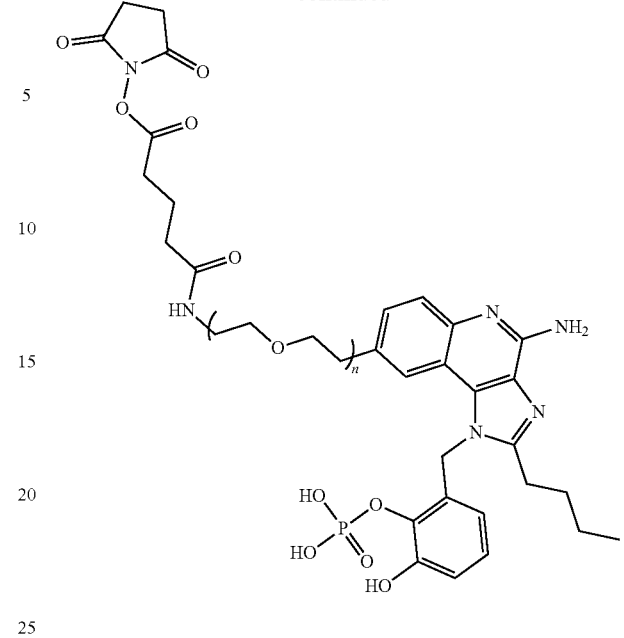
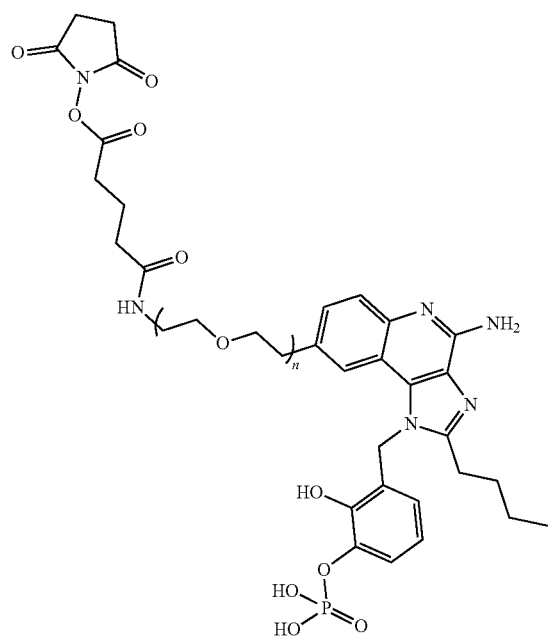
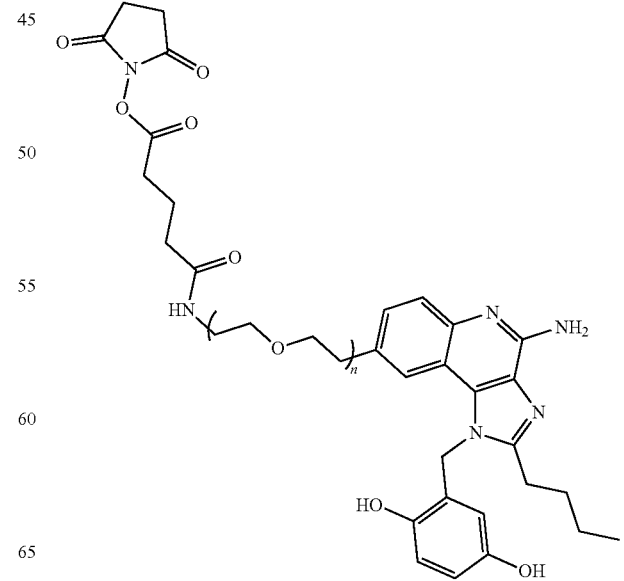

197
-continued
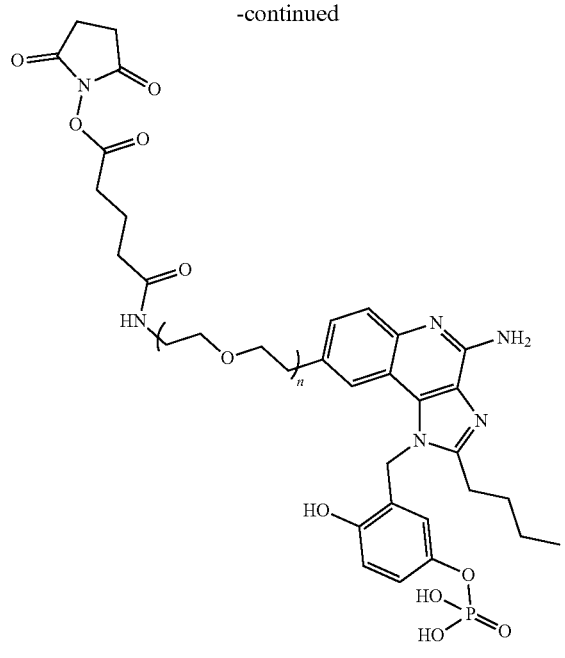
198
-continued
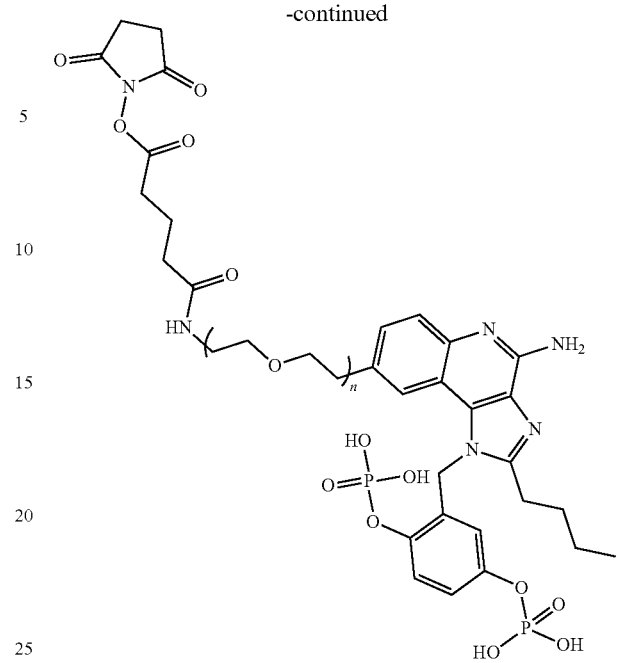
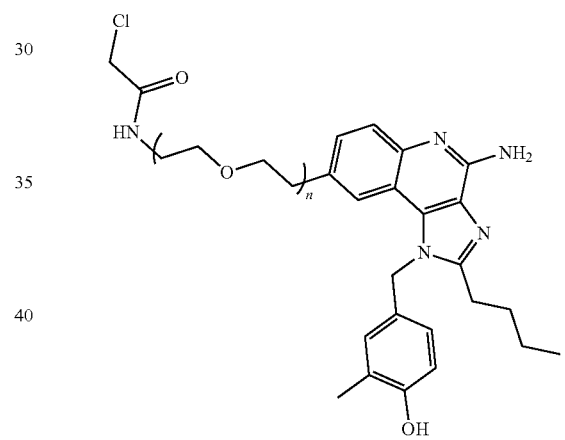
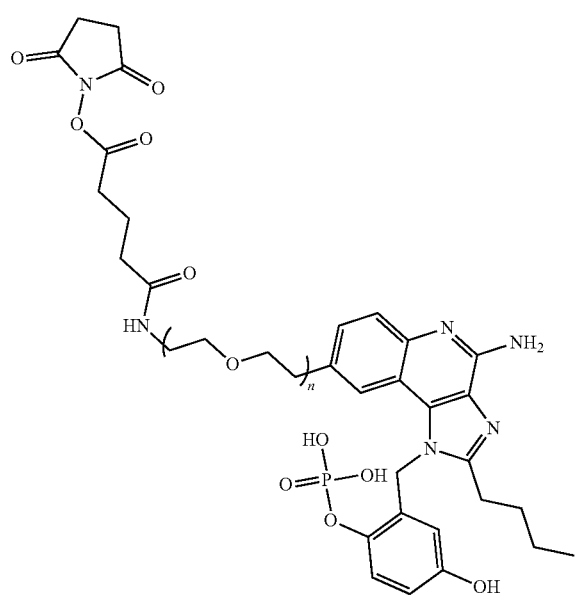
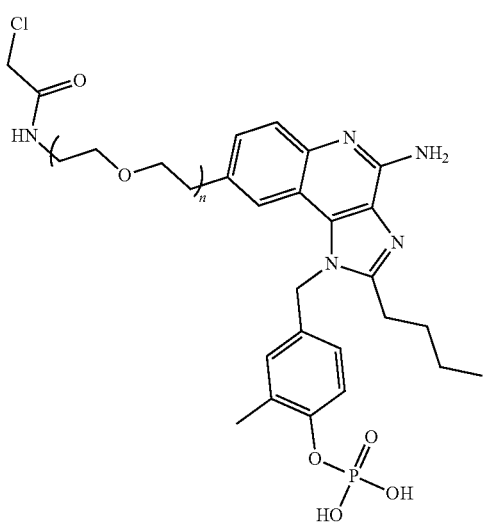

199
-continued
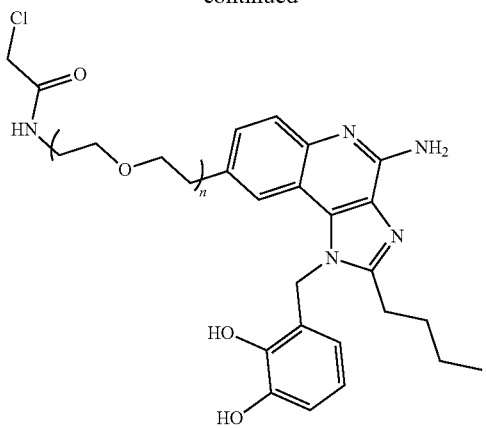
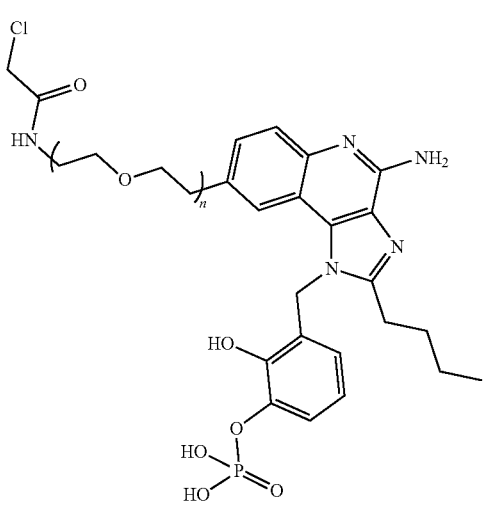
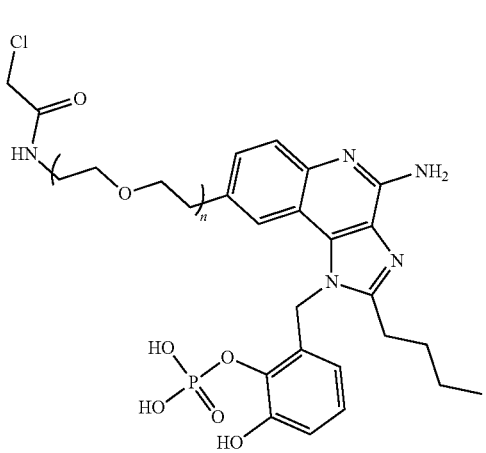
200
-continued
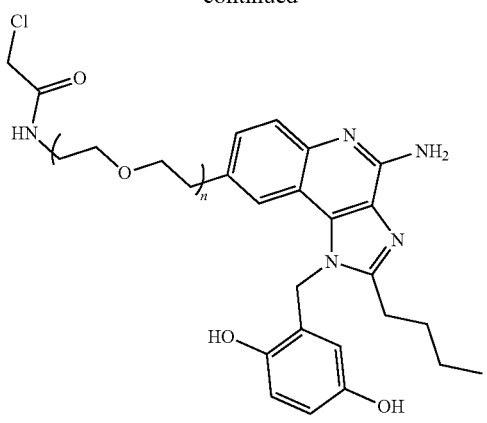
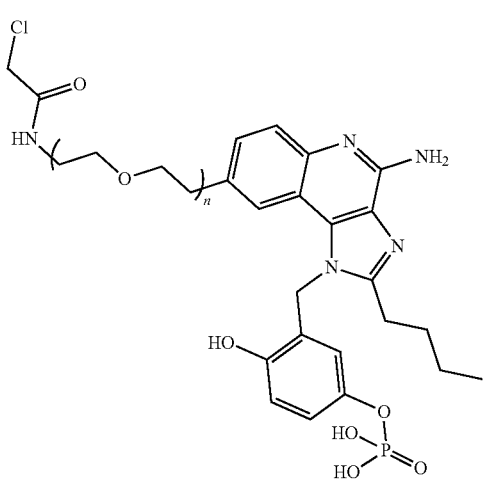
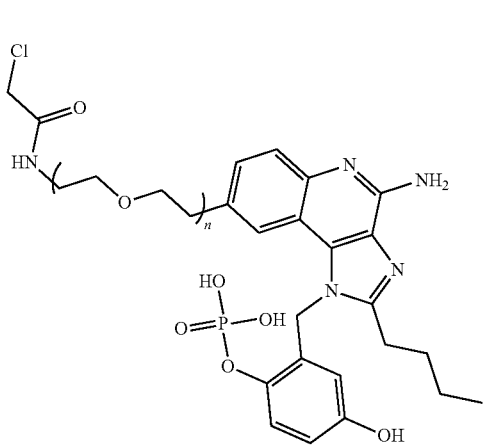

201
-continued
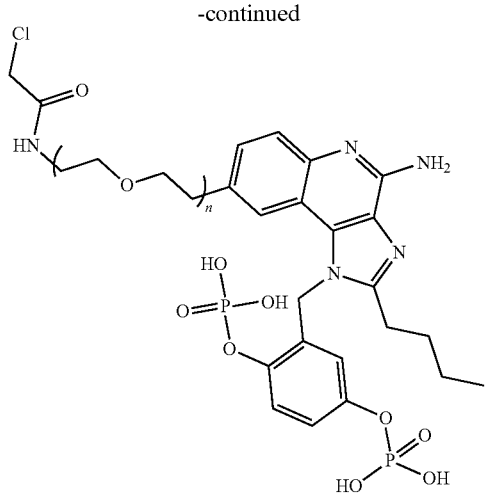
202
-continued
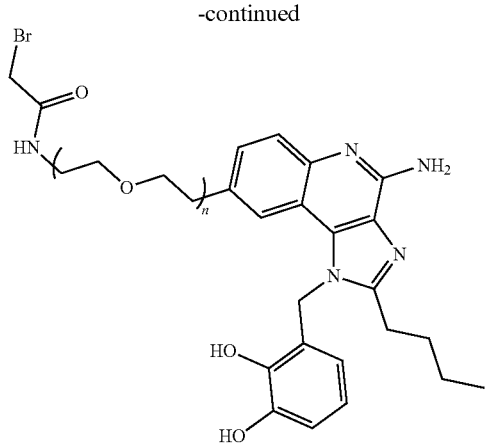
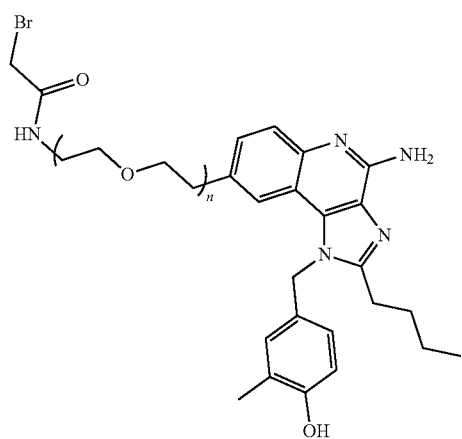
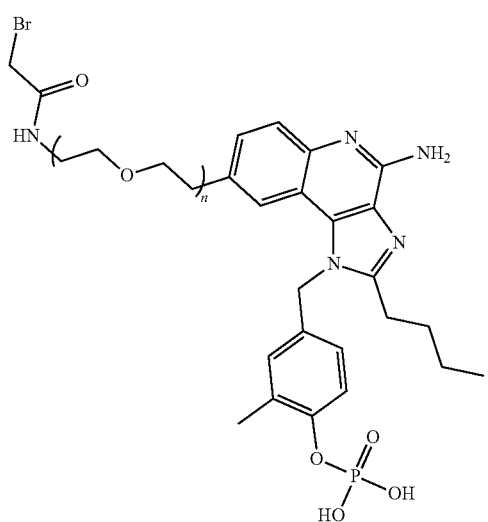
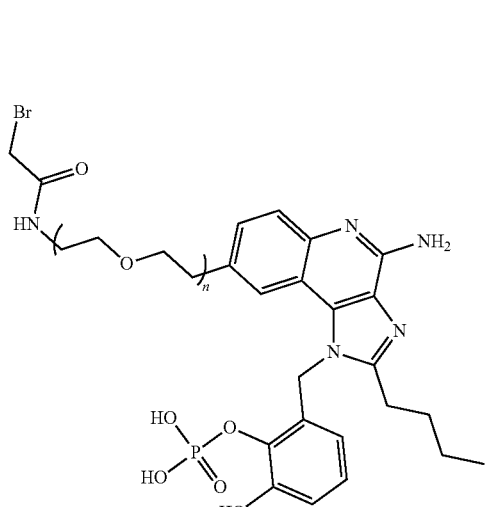

203
-continued
204
-continued
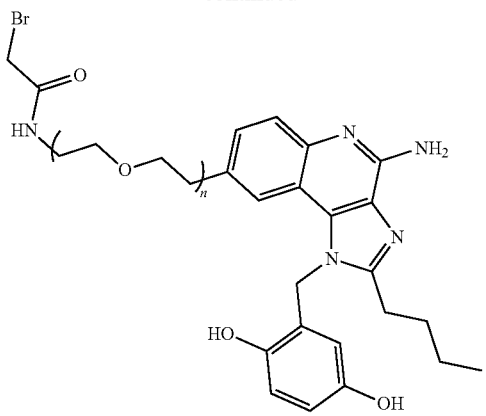
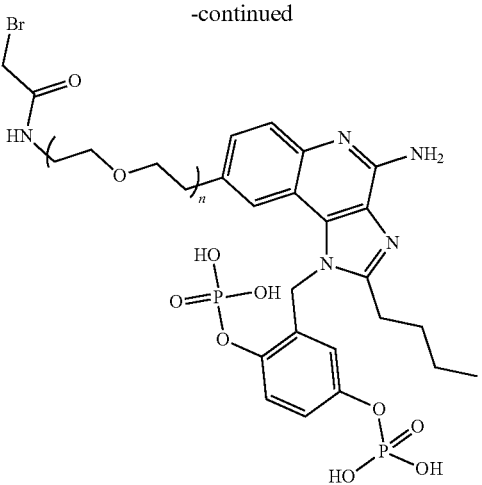
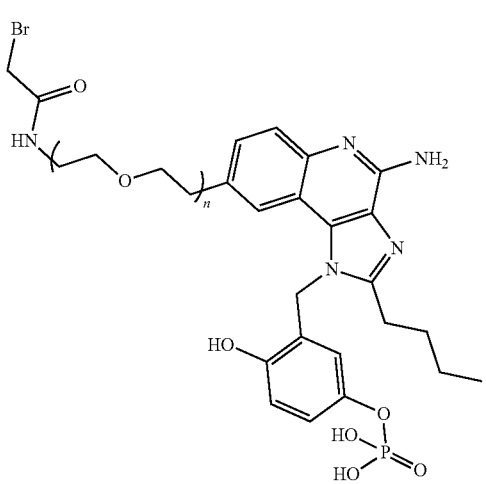
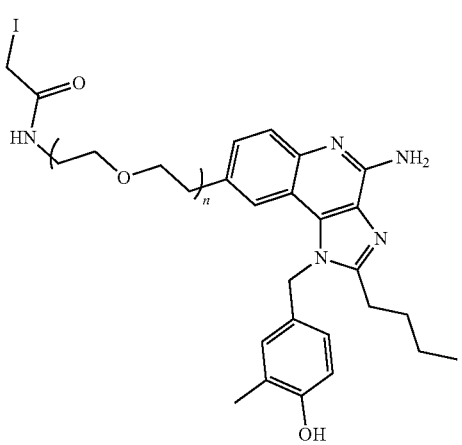
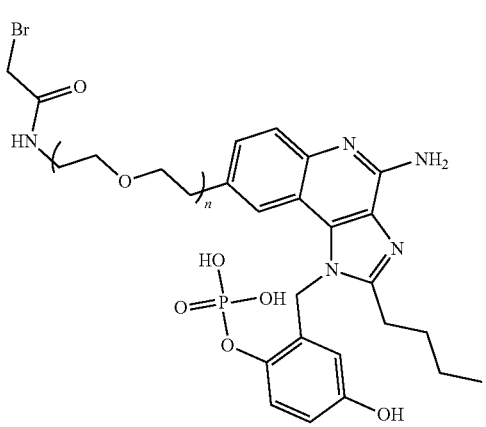
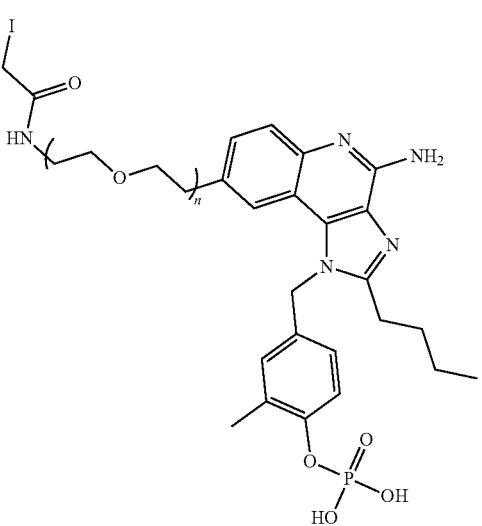

205
-continued
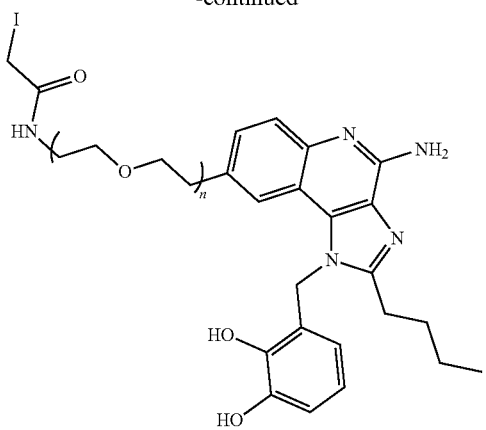
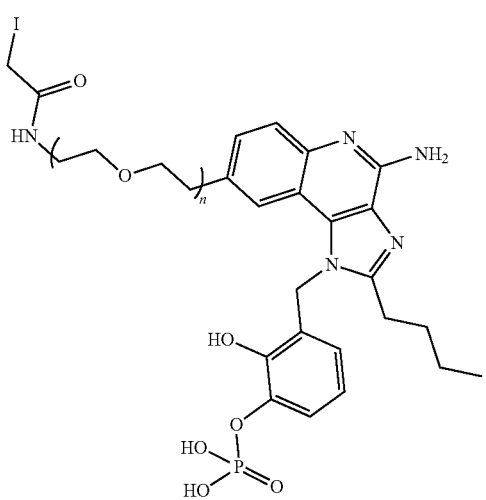
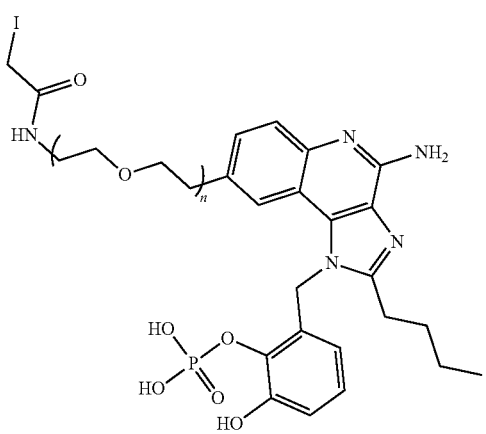
206
-continued
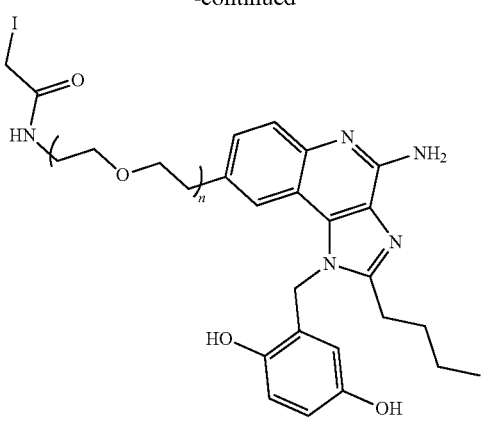
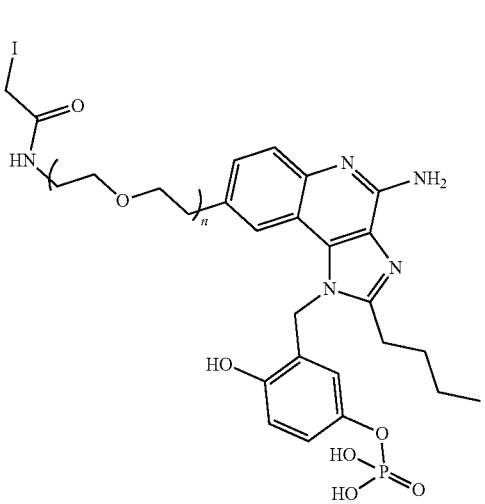
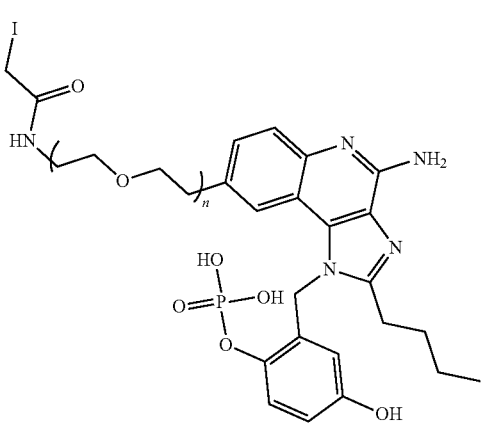

207
-continued
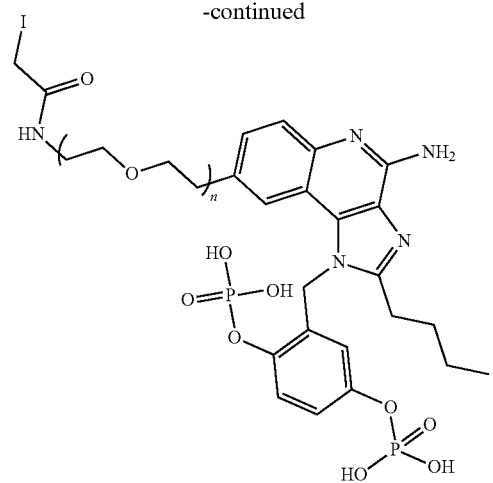
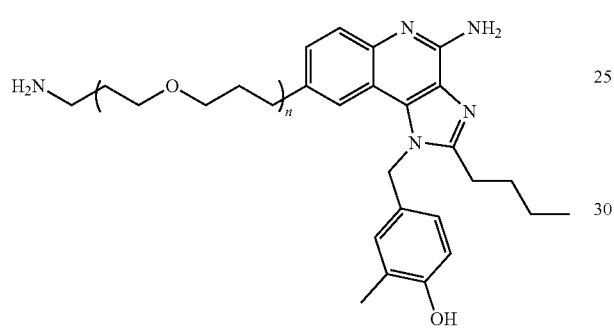
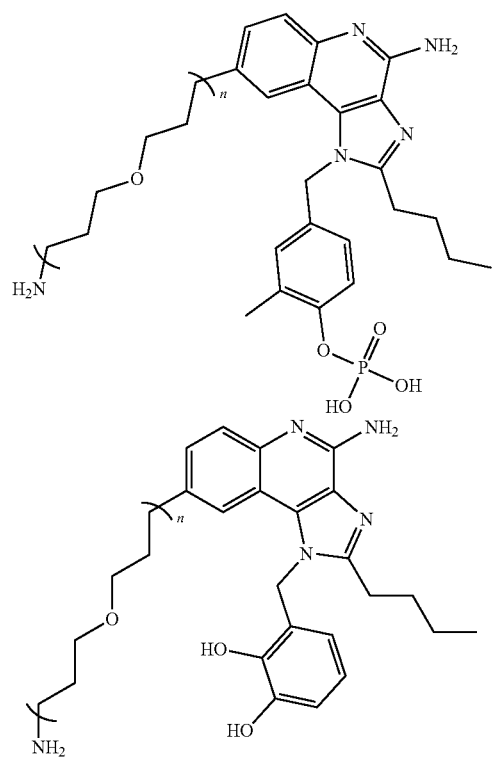
208
-continued
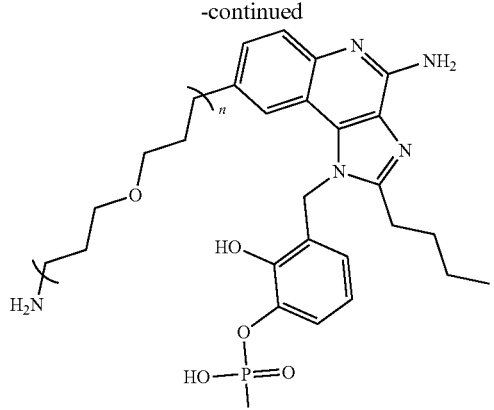
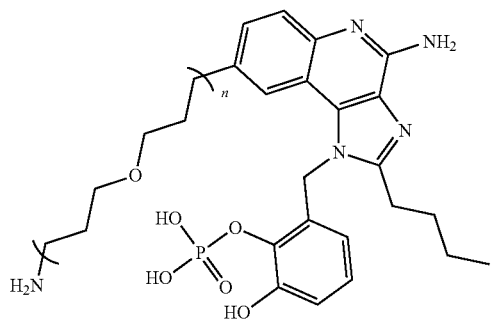
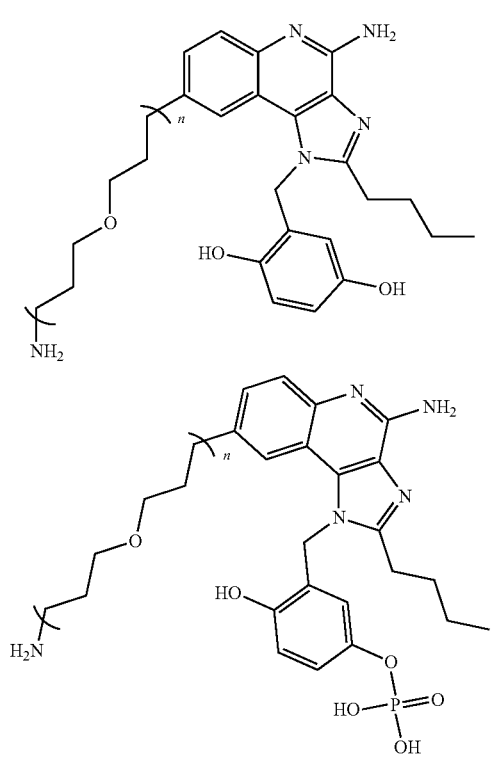

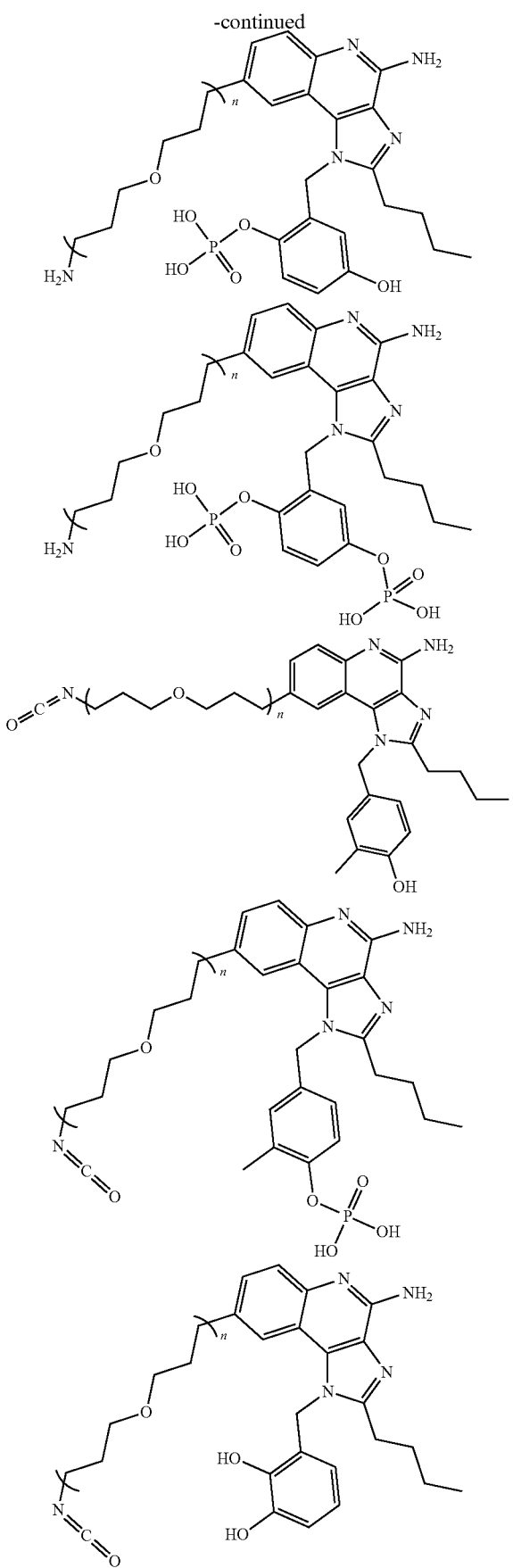
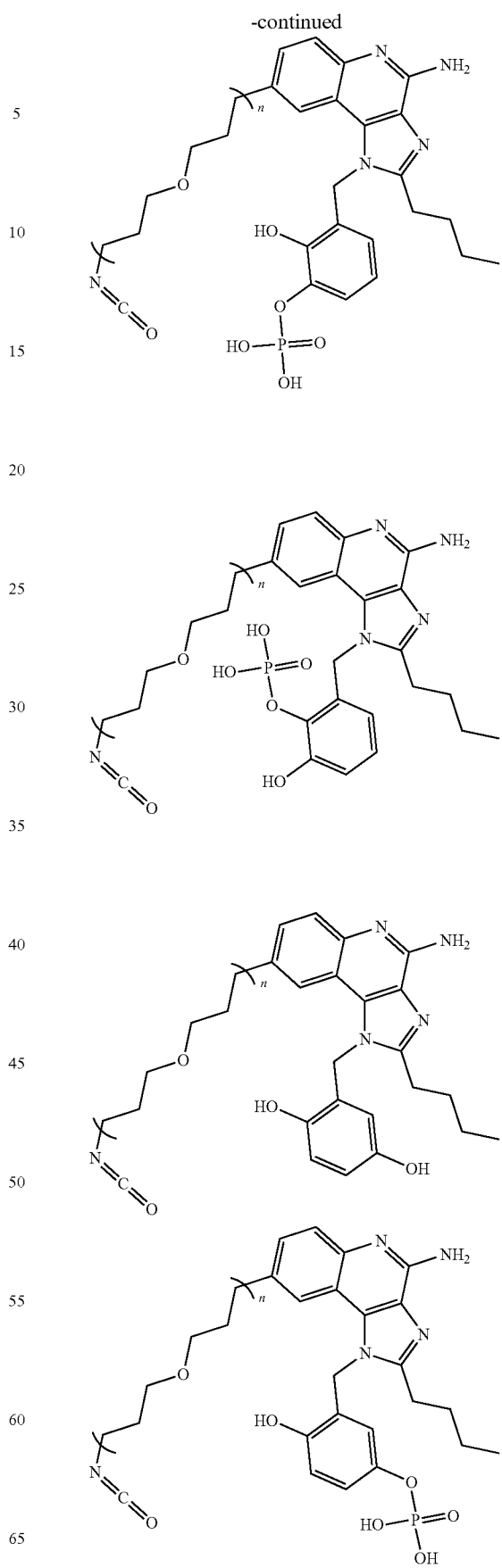

211
-continued
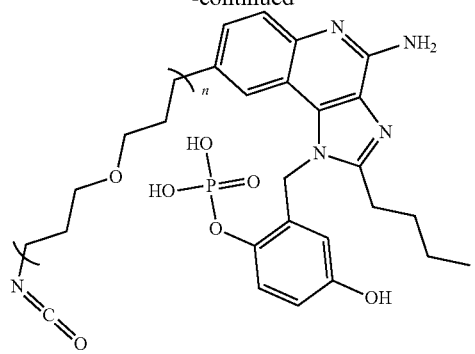
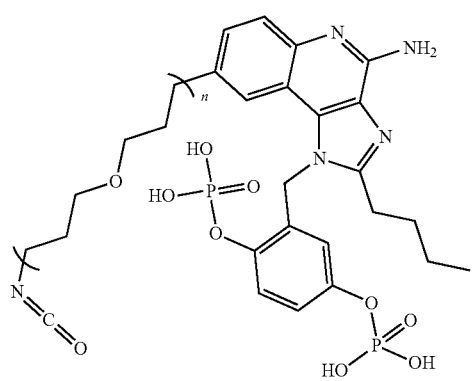
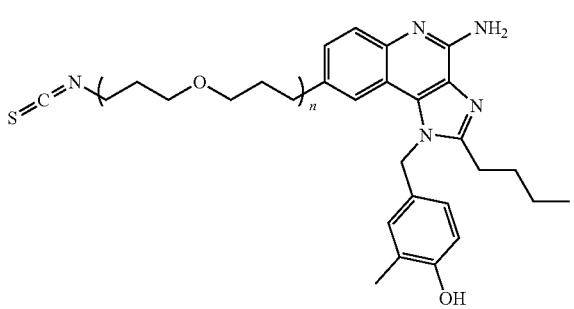
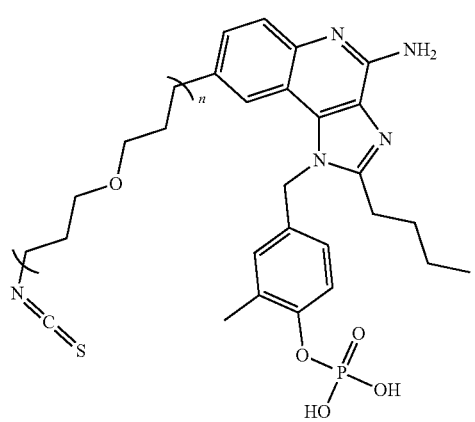
212
-continued
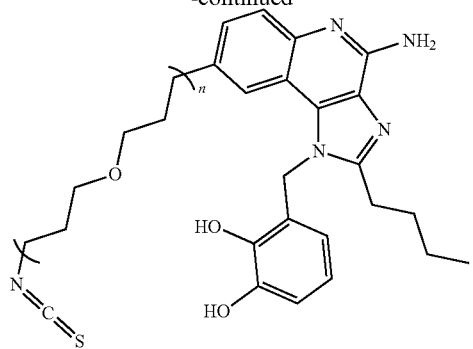
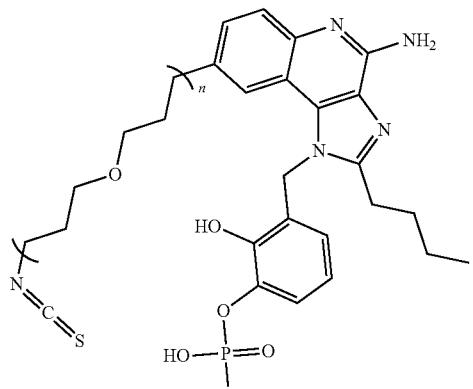
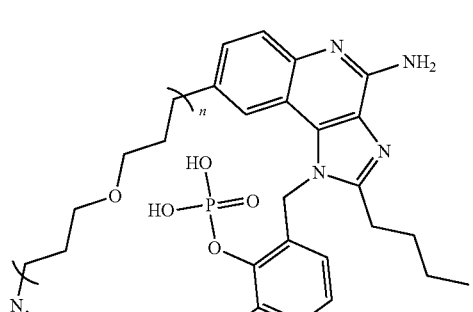
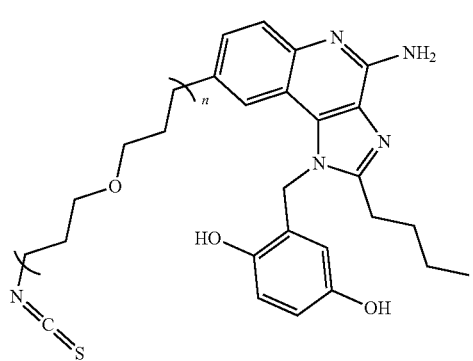

213
-continued
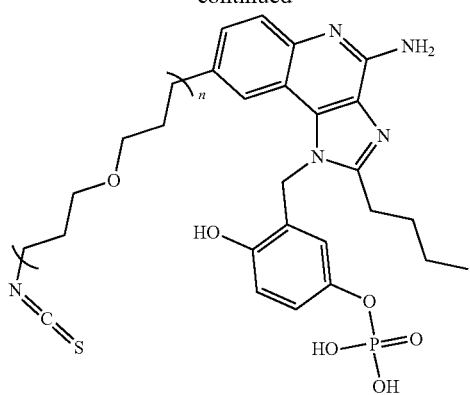
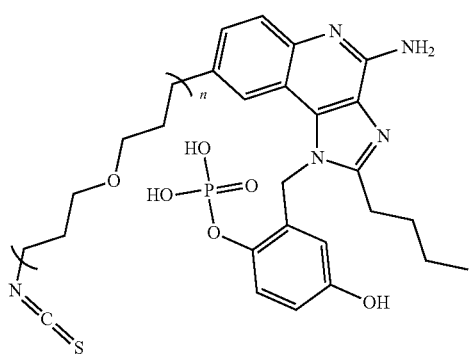
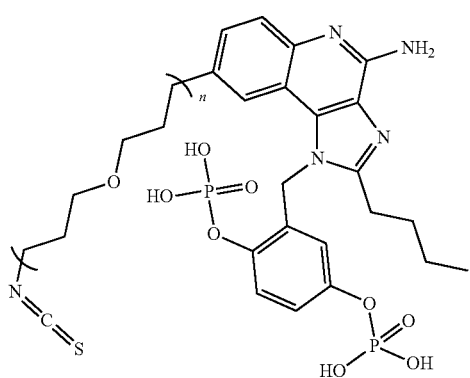
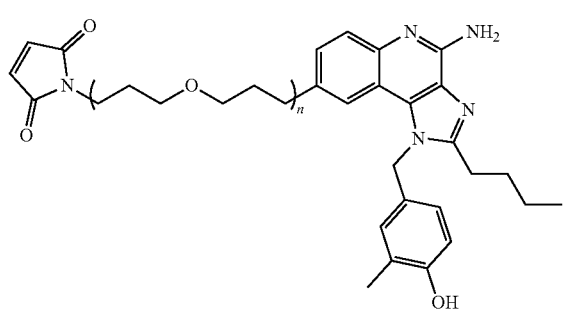
214
-continued
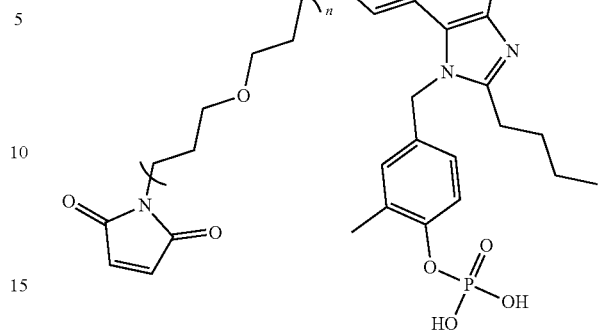
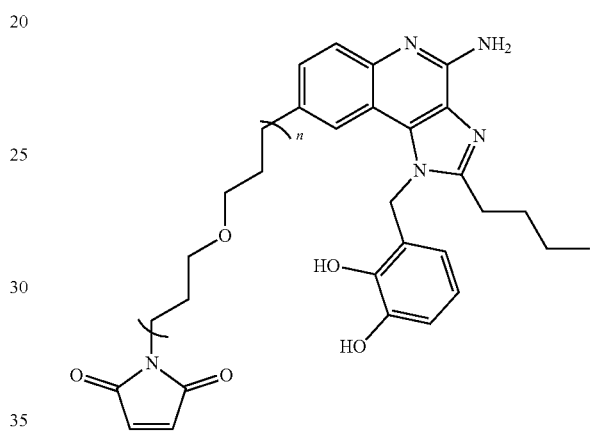
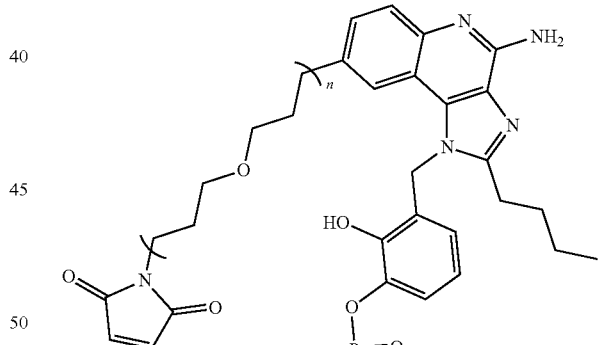
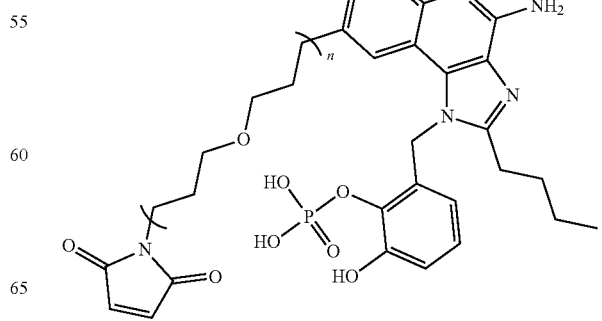

215
-continued
216
-continued
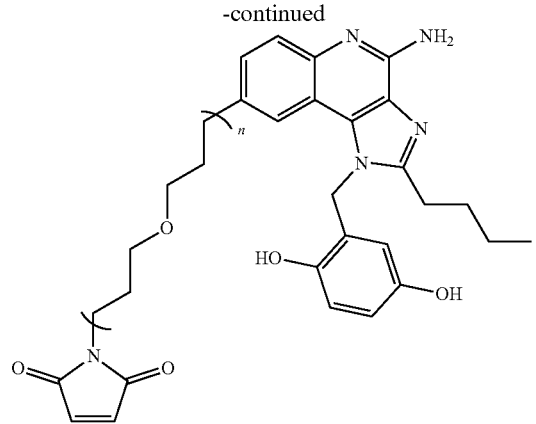
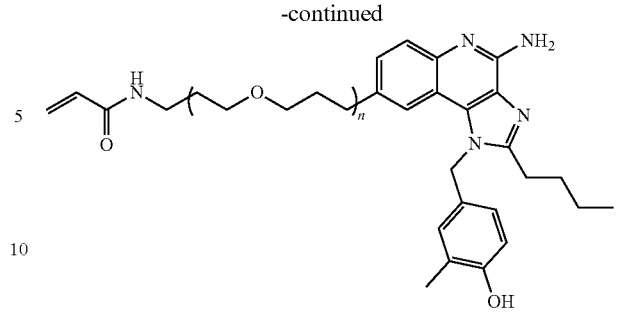
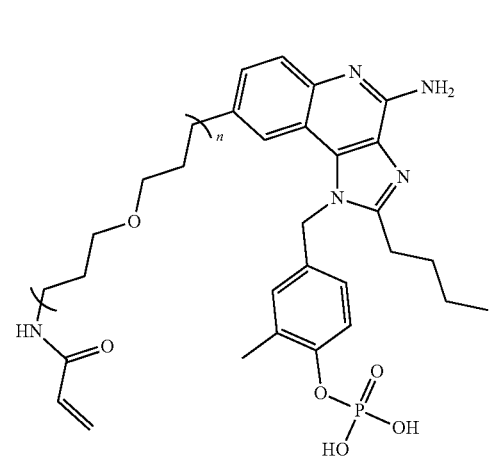
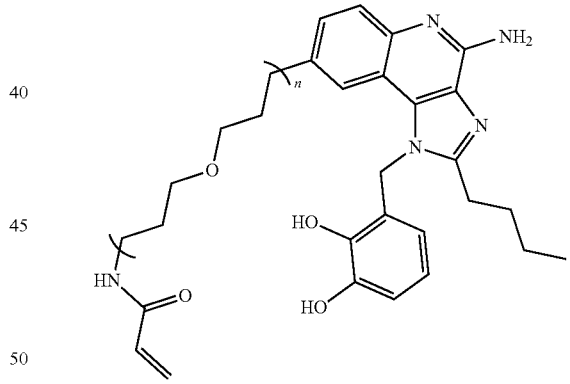
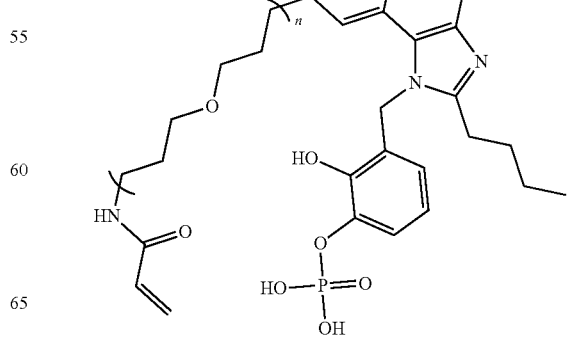

217
-continued
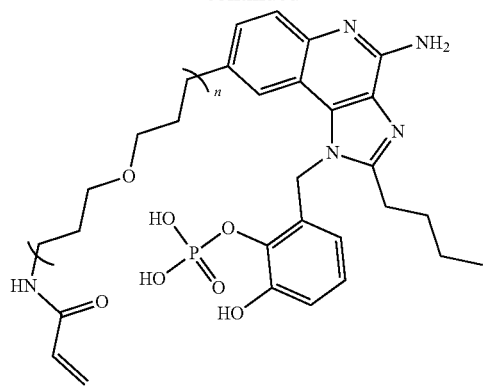
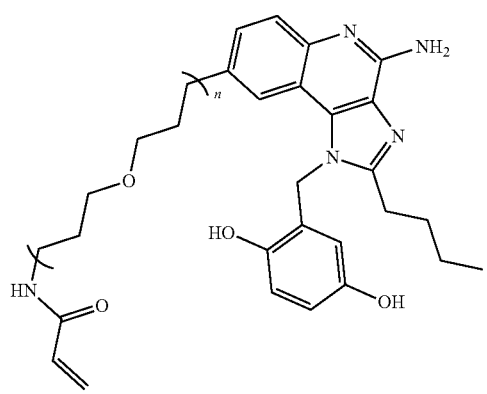
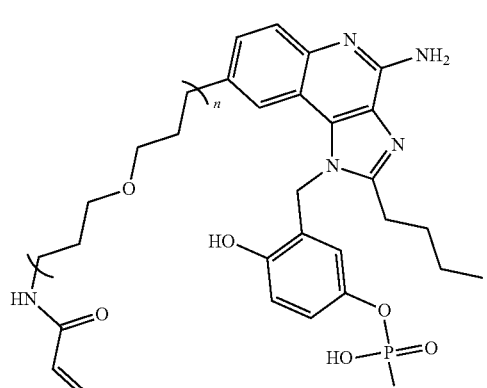
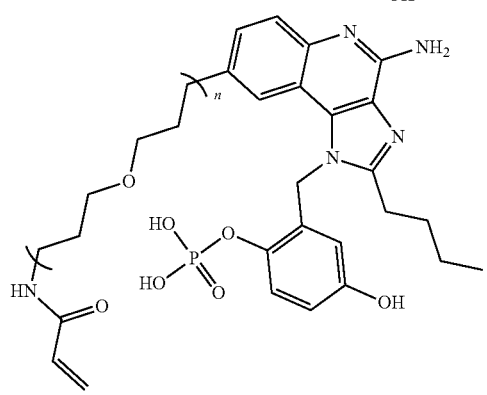
218
-continued
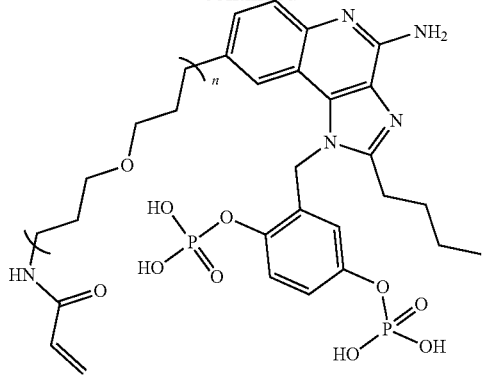
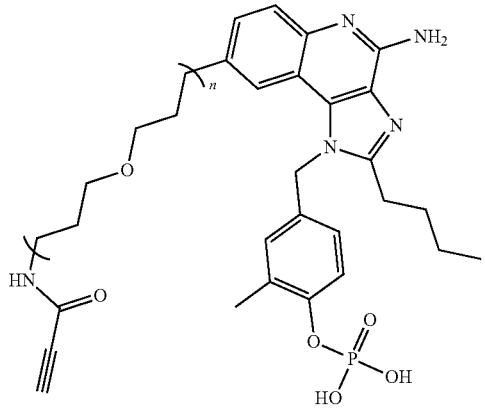
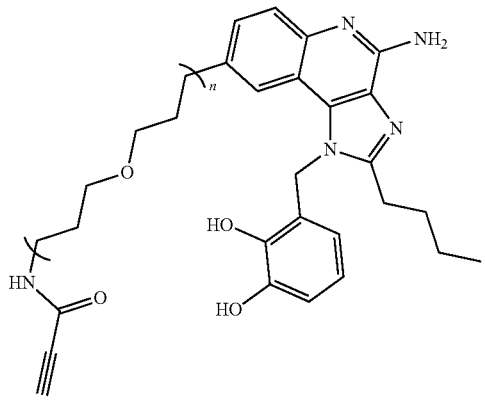

219
-continued
220
-continued
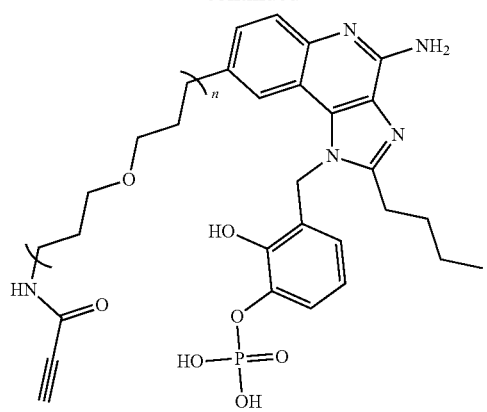
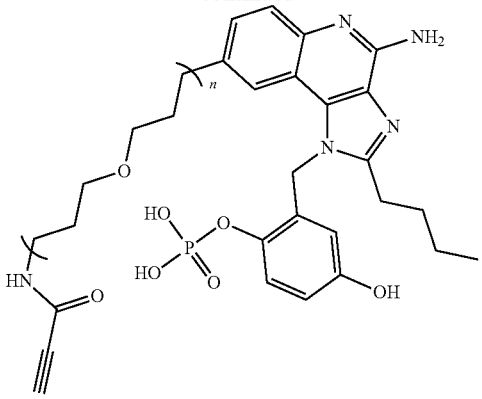
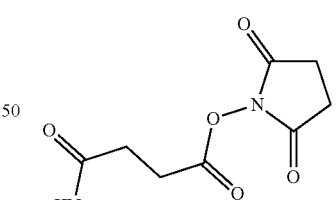
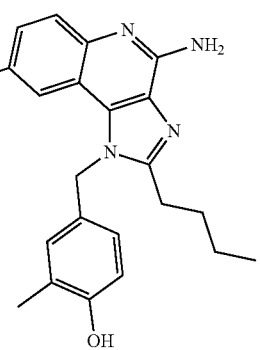

221
-continued
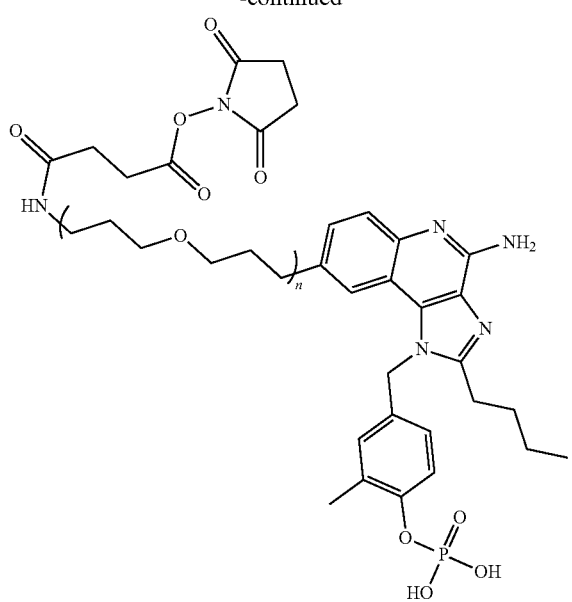
222
-continued
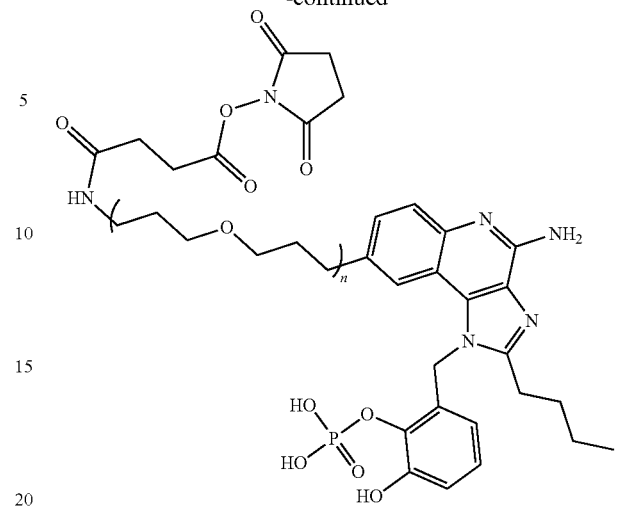
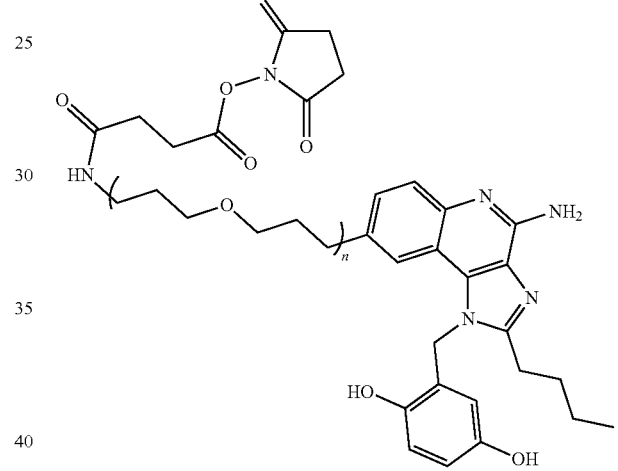
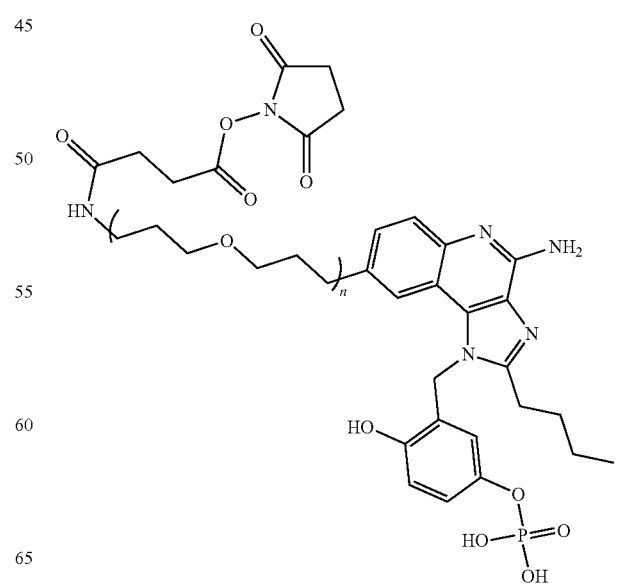

223
-continued
224
-continued
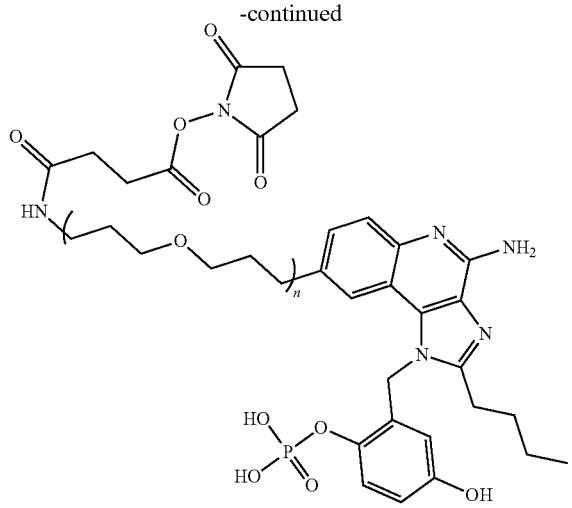
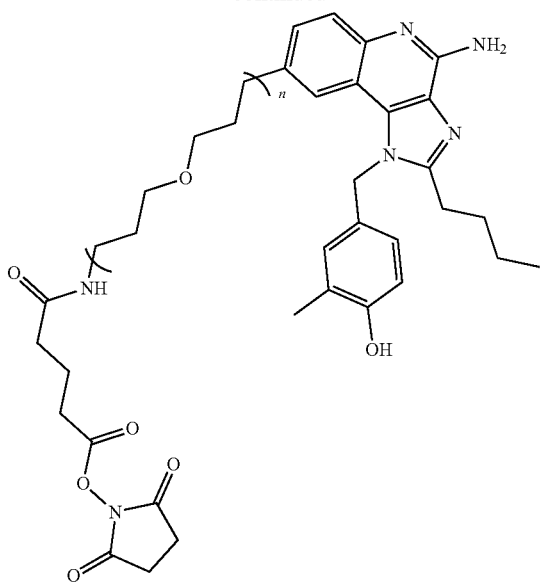

225
-continued
226
-continued
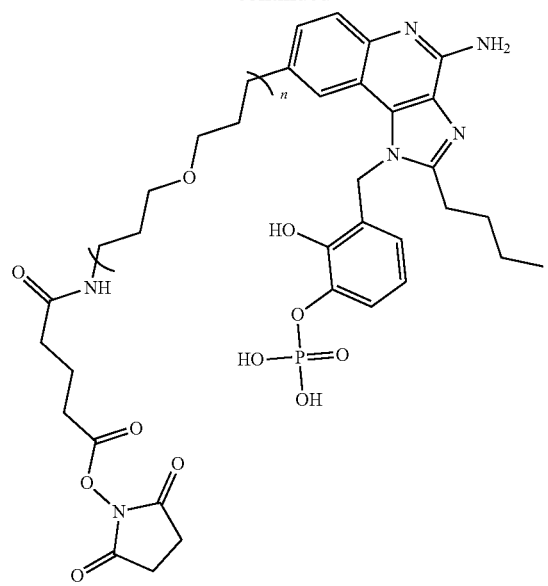
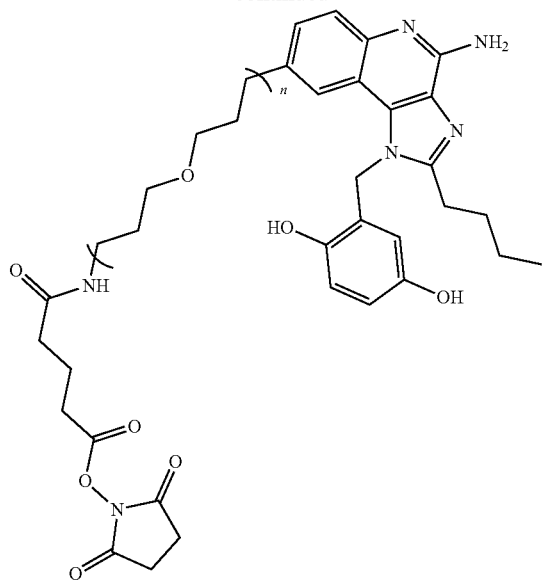

227
-continued
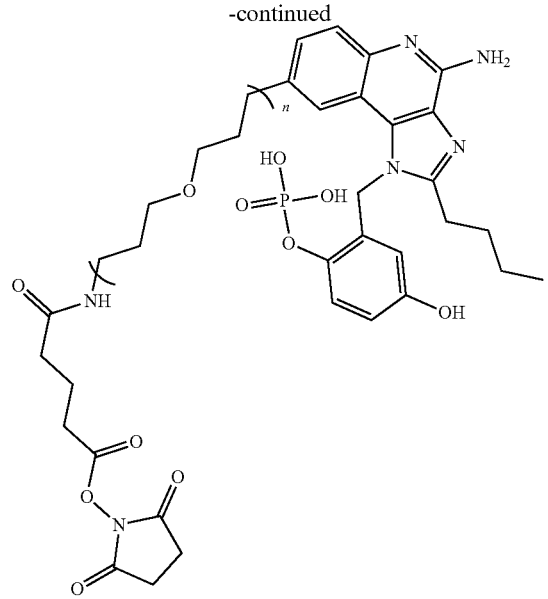
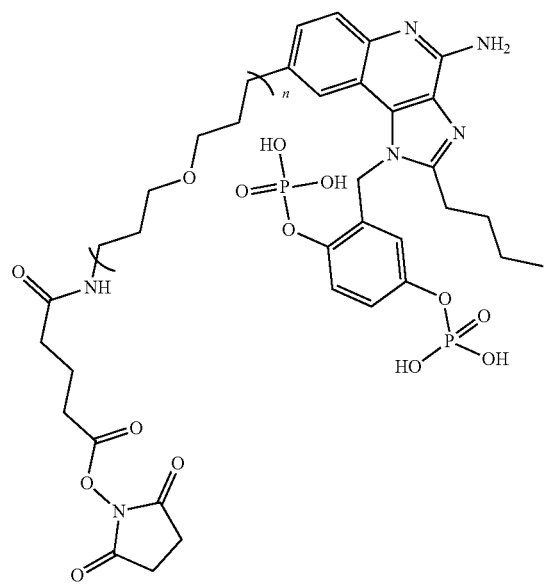
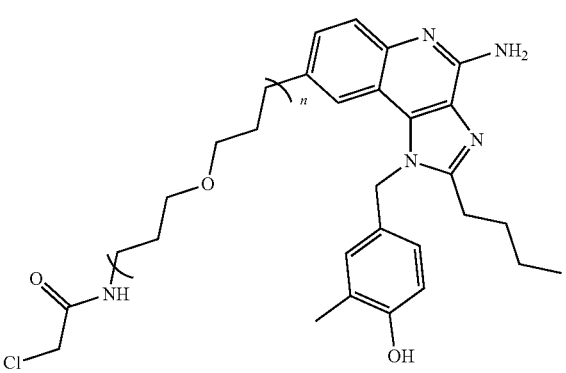
228
-continued
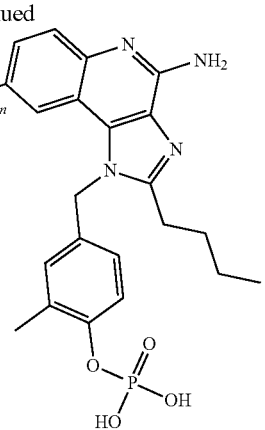
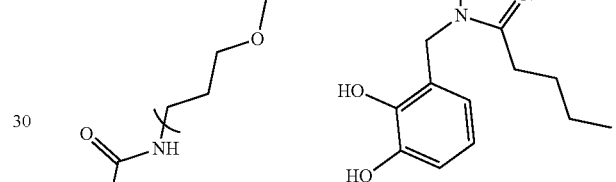
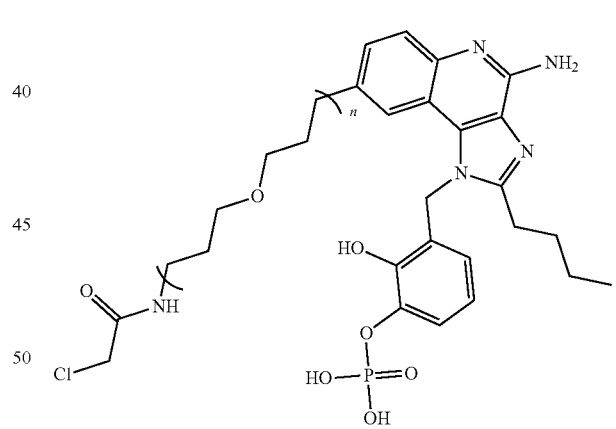
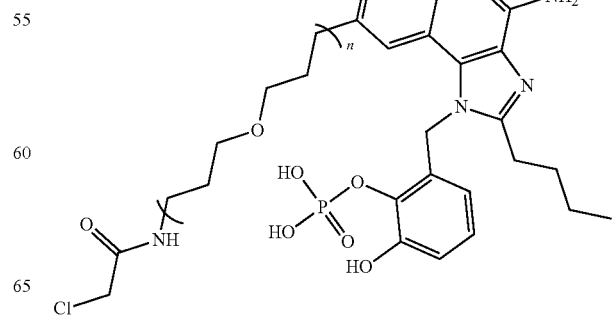

229
-continued
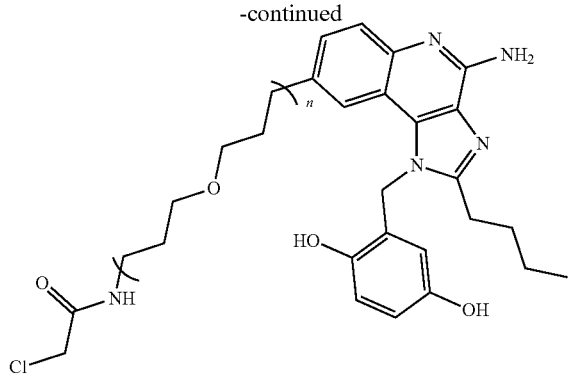
230
-continued
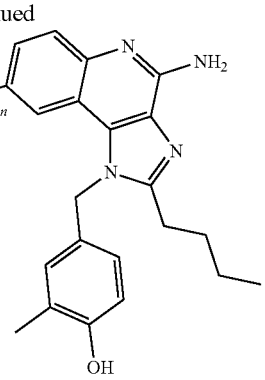
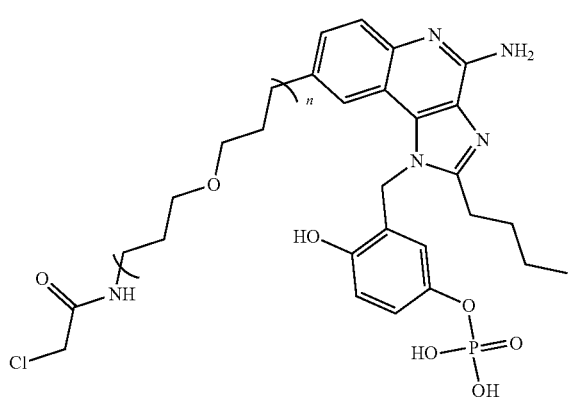
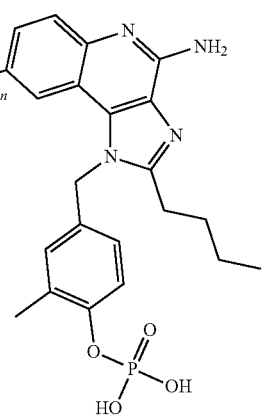
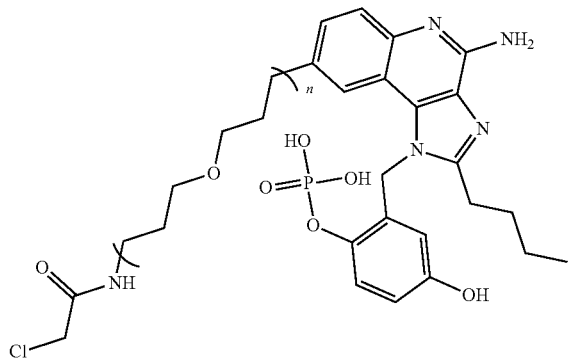
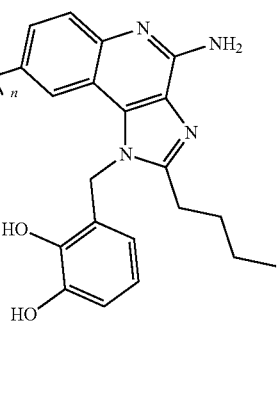
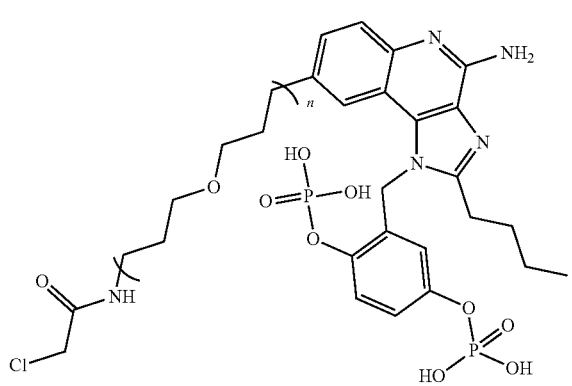
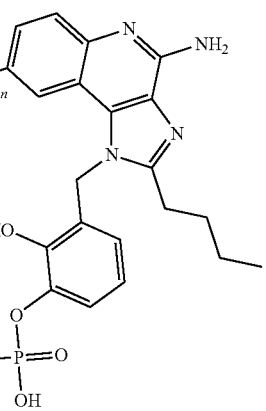

231
-continued
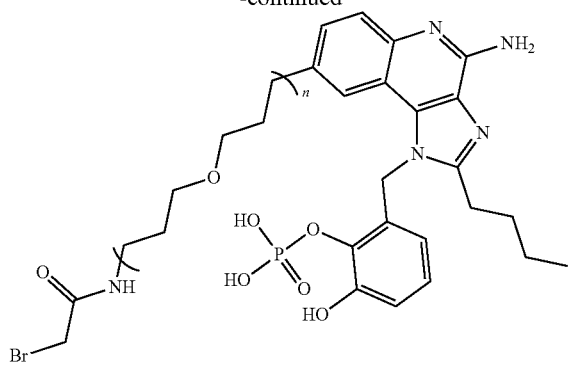
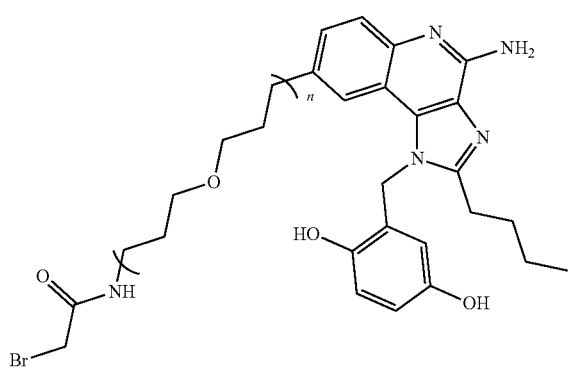
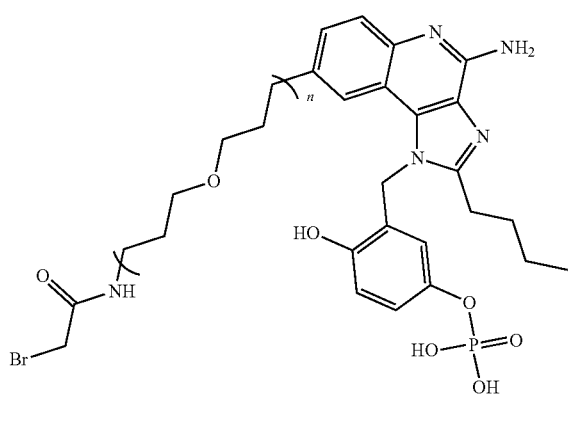
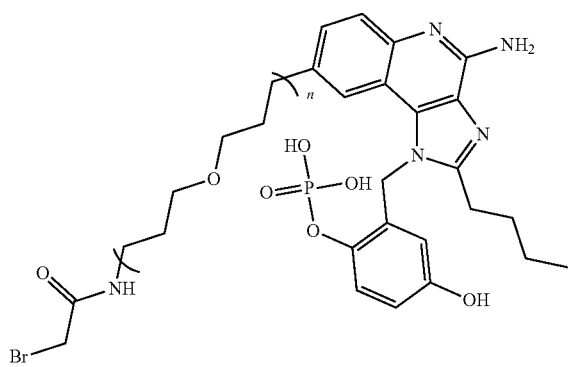
232
-continued
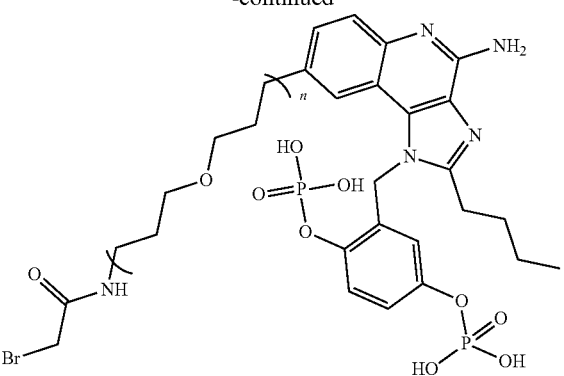
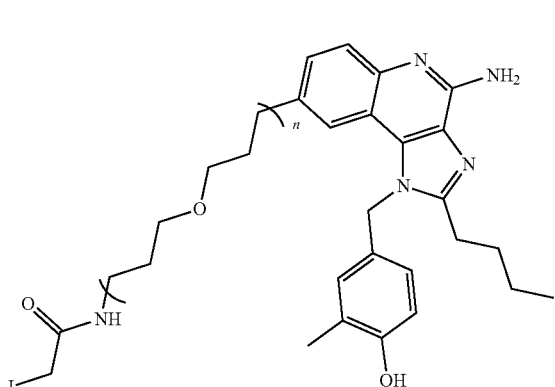
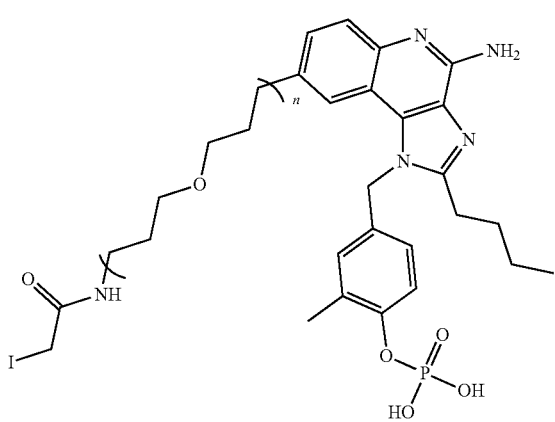
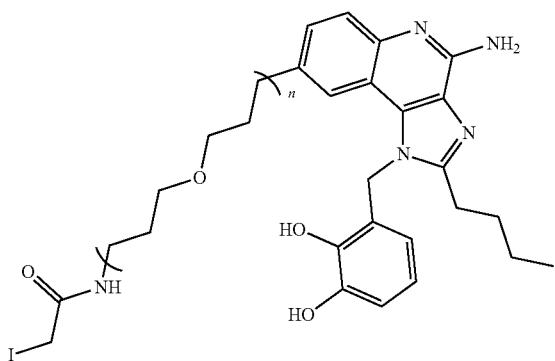

233

-continued

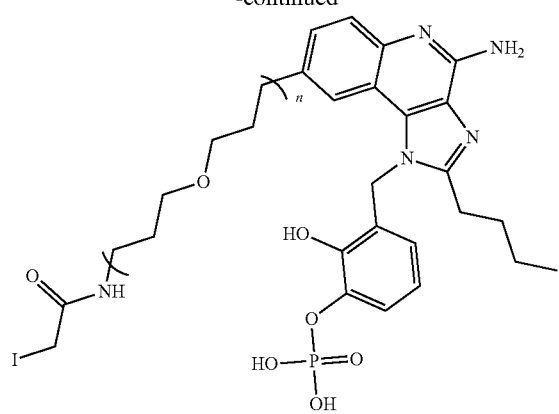

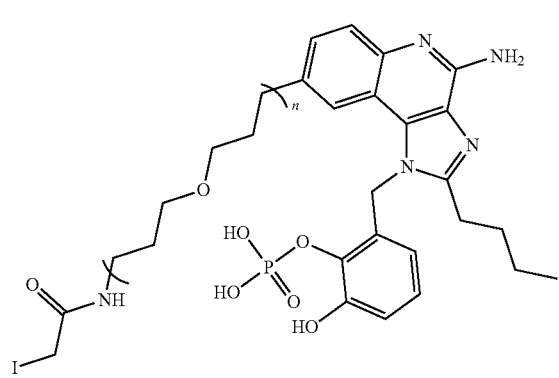

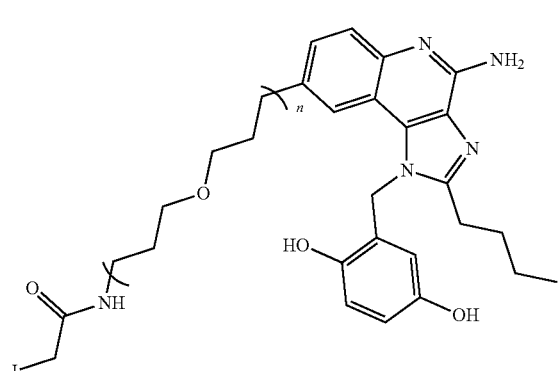

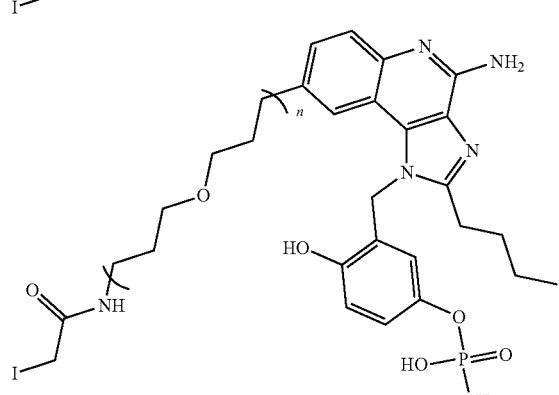

234

-continued

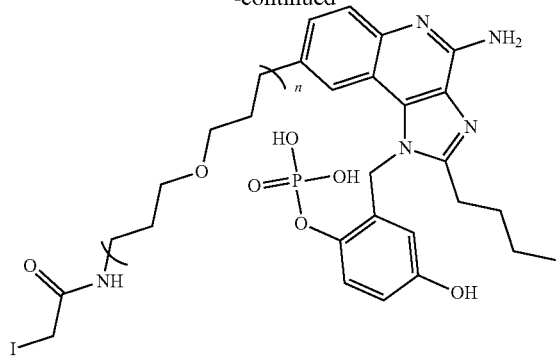

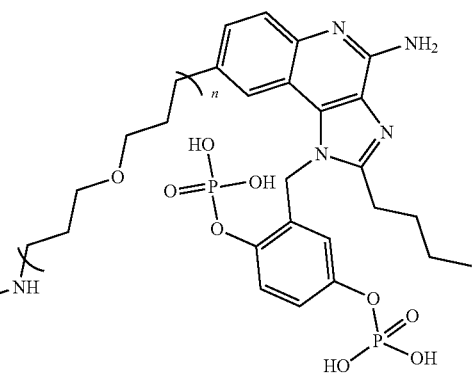

where n = 1-9 or

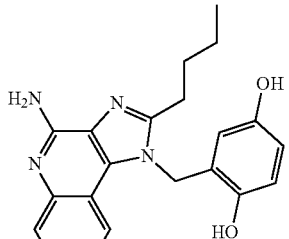

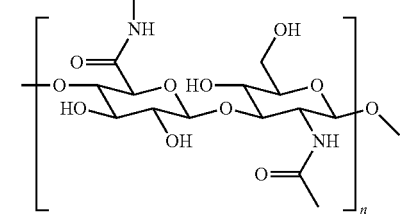

or a salt therof.

The biological activity of compounds of the invention can be evaluated using the following assays Example 13

Human TLR-7/-8 reporter gene assays (NF-κB Induction). The induction of NF-κB is quantified using HEK-Blue-7 (hTLR7-specific) and HEK-Blue-8 (hTLR8-specific) cells using known method. HEK293 cells stably co-transfected with human TLR7 or human TLR8 and secreted alkaline phosphatase (sAP), are maintained in HEK-Blue™ Selection medium containing zeocin and normocin. Stable expression of secreted alkaline phosphatase (sAP) under control of NF-κB/AP-1 promoters is inducible by appropriate TLR agonists, and extracellular sAP in the supernatant is proportional to NF-κB induction. HEK-Blue cells are incubated at a density of ~10' cells/ml in a volume of 80 μl/well, in 384-well, flat-bottomed, cell culture-treated microtiter plates until confluency is achieved, and subsequently stimulated with graded concentrations of stimuli. sAP is assayed spectrophotometrically using an alkaline phosphatase-specific chromogen (present in HEK-detection medium as supplied by the vendor) at 620 nm.

Example 14

IFN-α/β, IFN-γ, and TNF-α/IL-1β Whole Blood Reporter Gene Assays. Whole heparinized blood is collected from consenting individuals, as approved by the University of Minnesota Institutional Review Board, and is diluted 1:2 in RPMI supplemented with 10% fetal bovine serum (FBS). Forty microliters is added to 384-well, flat-bottomed, cell culture-treated microtiter plates containing serial dilutions of compounds. Following incubation at 37° C. for 24 h, 40 μL of supernatant is transferred to separate 384-well plates using a liquid handler equipped with liquid level sensing in order to avoid disturbing the erythrocyte-rich pellet. Forty microliters of HEK-IFNα/β, HEK-IFNγ, or HEK-TNFα/IL-β cytokine reporter cells (InvivoGen, San Diego, CA) harvested at a density of 1×106 cells/mL in DMEM with 10% FBS is added to the supernatant plates and incubated at 37° C. for 24 h. The plates are washed in sterile PBS using a plate washer (BioTek, Winooski, VT), and 40 μL of HEK Blue Detection Media (InvivoGen, San Diego, CA) is added and incubated for 16 h at 37° C. sAP is assayed spectrophotometrically using an alkaline phosphatase-specific chromogen (present in HEKdetection medium as supplied by InvivoGen) at 620 nm. In order to calibrate the assays, human serum (or plasma) is "spiked" with graded concentrations of human IFN-α, IFN-γ, or TNF-α, and cytokine reporter assays are performed as described above. Sigmoidal dose-response profiles for each cytokine are observed (Beesu M. et al. *J. Med. Chem.* 2017, 2084), from which threshold cytokine concentrations corresponding to maximal responses for each cytokine reporter cell line are recorded. Compound concentrations eliciting maximal cytokine responses are defined as effective concentrations eliciting maximal responses (ECMR100).

Example 15

Size exclusion chromatography (SEC). A Shimadzu analytical HPLC system is used with HiPrep 16/60 Sephacryl S-200 HR (GE Healthcare, PA, USA.) size exclusion chromatography (SEC) column for analytical characterization. Samples of the conjugates (1 mg/mL, 50 μL) are injected using PBS (pH 7.4) buffer containing 0.05% NaN₃ as a mobile phase at a flow rate of 1.5 mL/min.

Example 16

Mouse immunizations and in vivo imaging. Cohorts of IFN-β mice (n=4 per cohort), which are described previously (Nuhn, L. et al. *PNAS*, 2016, 8098), are housed in specific-pathogen-free conditions in accordance with institutional guidelines (University of Minnesota IACUC Protocols #1607-33991A/1601-33398A and University of Ghent IACUC Protocols). Mice are injected in the hock or footpad with either 10 μg of imidazoquinoline or an equivalent dose of HA conjugate (10 μg of TLR ligand based on w/w %) in 20 μL of saline. Each mouse is injected subcutaneously in the scruff of the neck with 4.5 mg of VivoGlo™ luciferin (Promega, Madison, WI) in 150 μL of saline 10 minutes prior to luminescence imaging at each of the following time points: 0, 4, 8, 12, 24, 48, 72, and 96 hours. Mice are anesthetized in an induction box with isoflurane using an isoflurane vaporizer and maintained under isoflurane during the course of imaging. Bioluminescent imaging is performed with a either a Xenogen IVIS 100 in vivo imaging system or a Bruker In-Vivo Xtreme II.

Example 17

The following illustrate representative pharmaceutical dosage forms, containing a compound of formula I ('Compound X'), for therapeutic or prophylactic use in humans

|  | mg/ml |
|---|---|
| (i) Injection 1 (1 mg/ml) | |
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |
| (ii) Injection 2 (10 mg/ml) | |
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

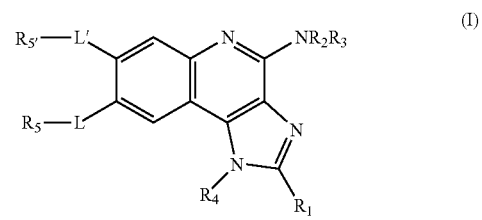

wherein:
R₁ is H, (C₁-C₆)alkyl, (C₂-C₆)alkenyl, (C₂-C₆)alkynyl, (C₁-C₆)alkanoyl, (C₁-C₆)alkoxycarbonyl, (C₁-C₆)alkanoyloxy, or (C₃-C₆)cycloalkyl, wherein any (C₁-C₆)alkyl, (C₂-C₆)alkenyl, (C₂-C₆)alkynyl, (C₁-C₆) alkanoyl, (C₁-C₆)alkoxycarbonyl, (C₁-C₆)

alkanoyloxy, or (C$_3$-C$_6$)cycloalkyl, is optionally substituted with one or more groups independently selected from hydroxy, halo, oxo, (C$_3$-C$_8$)cycloalkyl, and (C$_1$-C$_6$)alkoxy;

each R$_2$ and R$_3$ is independently H, or (C$_1$-C$_6$)alkyl that is optionally substituted with one or more groups independently selected from hydroxy, halo, (C$_3$-C$_8$) cycloalkyl, and (C$_1$-C$_6$)alkoxy;

R$_4$ is (C$_1$-C$_6$)alkyl that is substituted with aryl, wherein the aryl is substituted with one —OR$^z$ and is optionally substituted with one or more groups independently selected from the group consisting of halogen, (C$_3$-C$_8$)cycloalkyl, —OR$^h$, isothiocyanate, —NR$^a$R$^b$, —NR$^c$C(=O)R$^d$, —NR$^c$C(=S)—NR$^f$R$^g$, and (C$_1$-C$_6$)alkyl optionally substituted with one or more groups independently selected from the group consisting of halogen, (C$_3$-C$_8$)cycloalkyl, —OR$^h$, isothiocyanate, —NR$^a$R$^b$, —NR$^c$C(=O)R$^d$, and —NR$^e$C(=S)—NR$^f$R$^g$;

L is absent or is a divalent, branched or unbranched hydrocarbon chain, having from 1 to 20 carbon atoms, wherein one or more (e.g. 1, 2, 3, or 4) of the carbon atoms is optionally replaced by a non-peroxide (—O—);

R$_5$ is H, an activated group, or NR$^x$R$^y$;

L' is absent or is a divalent, branched or unbranched hydrocarbon chain, having from 1 to 20 carbon atoms, wherein one or more (e.g. 1, 2, 3, or 4) of the carbon atoms is optionally replaced by a non-peroxide (—O—);

R$_{5'}$ is H, an activated group, or NR$^x$R$^y$;

provided that either -L-R$_5$ taken together or -L'-R$^{5'}$ taken together is H;

each R$^a$ and R$^b$ is independently selected from the group consisting of H, (C$_1$-C$_6$)alkyl, (C$_3$-C$_6$)cycloalkyl, (C$_1$-C$_6$)alkoxy and X-Y; or R$^a$ and R$^b$ together with the nitrogen to which they are attached form a aziridino, azetidino, morpholino, piperazino, pyrrolidino or piperidino;

each R$^c$ and R$^d$ is independently selected from the group consisting of H, (C$_1$-C$_6$)alkyl, (C$_3$-C$_6$)cycloalkyl, and (C$_1$-C$_6$)alkoxy;

each R$^e$ is independently selected from the group consisting of H, (C$_1$-C$_6$)alkyl, (C$_3$-C$_6$)cycloalkyl, and (C$_1$-C$_6$)alkoxy;

each R$^f$ and R$^g$ is independently selected from the group consisting of H, (C$_3$-C$_6$)cycloalkyl, (C$_1$-C$_6$)alkoxy and (C$_1$-C$_6$)alkyl that is optionally substituted with NR$^k$R$^m$; or R$^f$ and R$^g$ together with the nitrogen to which they are attached form a aziridino, azetidino, morpholino, piperazino, pyrrolidino or piperidino;

each R$^k$ and R$^m$ is independently selected from the group consisting of H, (C$_1$-C$_6$)alkyl, and (C$_3$-C$_6$) cycloalkyl; or R$^k$ and R$^m$ together with the nitrogen to which they are attached form a aziridino, azetidino, morpholino, piperazino, pyrrolidino or piperidino;

each R$^z$ and R$^h$ is independently selected from the group consists of H, (C$_1$-C$_6$)alkyl, (C$_2$-C$_6$)alkenyl, (C$_2$-C$_6$)alkynyl, (C$_3$-C$_8$)cycloalkyl —P(=O)OH)$_2$, or W—Z;

R$^x$ is H;

R$^y$ is a residue of hyaluronic acid;

each W is independently a linking group or is absent;

each Z is independently an antigen;

each X is independently a linking group or is absent; and each Y is independently a residue of hyaluronic acid;

or a salt thereof.

2. The compound or salt of claim 1, wherein R$_1$ is H, (C$_1$-C$_6$)alkyl, (C$_2$-C$_6$)alkenyl, (C$_2$-C$_6$)alkynyl, (C$_1$-C$_6$)alkanoyl, (C$_1$-C$_6$)alkoxycarbonyl, (C$_1$-C$_6$)alkanoyloxy, or (C$_3$-C$_6$)cycloalkyl, wherein any (C$_1$-C$_6$)alkyl, (C$_2$-C$_6$)alkenyl, (C$_2$-C$_6$)alkynyl, (C$_1$-C$_6$)alkanoyl, (C$_1$-C$_6$)alkoxycarbonyl, (C$_1$-C$_6$)alkanoyloxy, or (C$_3$-C$_6$)cycloalkyl, is optionally substituted with one or more groups independently selected from hydroxy, halo, oxo, (C$_3$-C$_8$)cycloalkyl, and (C$_1$-C$_6$)alkoxy;

each R$_2$ and R$_3$ is independently H, or (C$_1$-C$_6$)alkyl, that is optionally substituted with one or more groups independently selected from hydroxy, halo, (C$_3$-C$_8$) cycloalkyl, and (C$_1$-C$_6$)alkoxy;

R$_4$ is (C$_1$-C$_6$)alkyl that is substituted with aryl, wherein the aryl is substituted with one —OR$^z$ and is optionally substituted with one or more groups independently selected from the group consisting of halogen, (C$_3$-C$_8$) cycloalkyl, —OR$^h$, isothiocyanate, —NR$^a$R$^b$, —NR$^c$C(=O)R$^d$, —NR$^e$C(=S)—NR$^f$R$^g$, and (C$_1$-C$_6$)alkyl optionally substituted with one or more groups independently selected from the group consisting of halogen, (C$_3$-C$_8$)cycloalkyl, —OR$^h$, isothiocyanate, —N$^a$R$^b$, —NR$^c$C(=O)R$^d$, and —NR$^c$C(=S)—NR$^f$R$^g$;

each R$^a$ and R$^b$ is independently selected from the group consisting of H, (C$_1$-C$_6$)alkyl, (C$_3$-C$_6$)cycloalkyl, and (C$_1$-C$_6$)alkoxy; or R$^a$ and R$^b$ together with the nitrogen to which they are attached form a aziridino, azetidino, morpholino, piperazino, pyrrolidino or piperidino;

each R$^c$ and R$^d$ is independently selected from the group consisting of H, (C$_1$-C$_6$)alkyl, (C$_3$-C$_6$)cycloalkyl, and (C$_1$-C$_6$)alkoxy;

R$^e$ is independently selected from the group consisting of H, (C$_1$-C$_6$)alkyl, (C$_3$-C$_6$)cycloalkyl, and (C$_1$-C$_6$) alkoxy;

each R$^f$ and R$^g$ is independently selected from the group consisting of H, (C$_3$-C$_6$)cycloalkyl, (C$_1$-C$_6$)alkoxy and (C$_1$-C$_6$)alkyl that is optionally substituted with NR$^k$R$^m$; or R$^f$ and R$^g$ together with the nitrogen to which they are attached form a aziridino, azetidino, morpholino, piperazino, pyrrolidino or piperidino;

each R$^k$ and R$^m$ is independently selected from the group consisting of H, (C$_1$-C$_6$)alkyl, (C$_3$-C$_6$)cycloalkyl, and (C$_1$-C$_6$)alkoxy; or R$^k$ and R$^m$ together with the nitrogen to which they are attached form a aziridino, azetidino, morpholino, piperazino, pyrrolidino or piperidino;

each R$^z$ and R$^h$ is selected from the group consists of H, (C$_1$-C$_6$)alkyl, (C$_2$-C$_6$)alkenyl, (C$_2$-C$_6$)alkynyl, or (C$_3$-C$_8$)cycloalkyl;

or a salt thereof.

3. The compound or salt of claim 1, wherein R$_4$ is benzyl, wherein the benzyl is substituted with one —OR$^z$ and is optionally substituted with one or more groups independently selected from the group consisting of halogen, (C$_3$-C$_8$)cycloalkyl, —OR$^h$, isothiocyanate, —N$^a$R$^b$, —NR$^c$C(=O)R$^d$, —NR$^c$C(=S)—NR$^f$R$^g$, and (C$_1$-C$_6$)alkyl optionally substituted with one or more groups independently selected from the group consisting of halogen, (C$_3$-C$_8$)cycloalkyl, —OR$^h$, isothiocyanate, —NR$^a$R$^b$, —NR$^c$C(=O)R$^d$, and —NR$^e$C(=S)—NR$^f$R$^g$.

4. The compound or salt of claim 1, wherein $R_4$ is selected from the group consisting of:
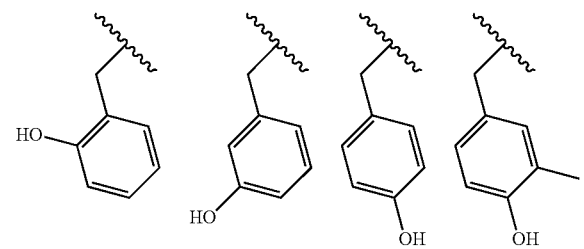
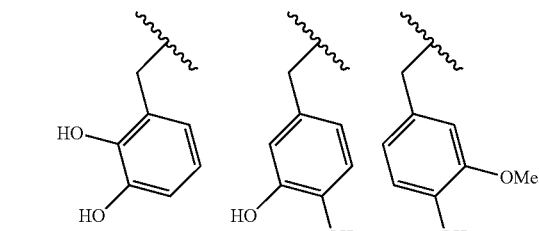
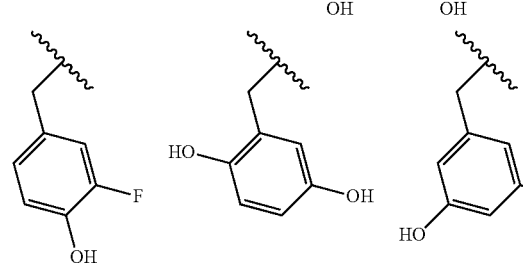
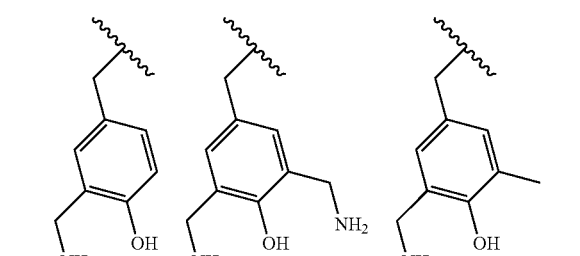
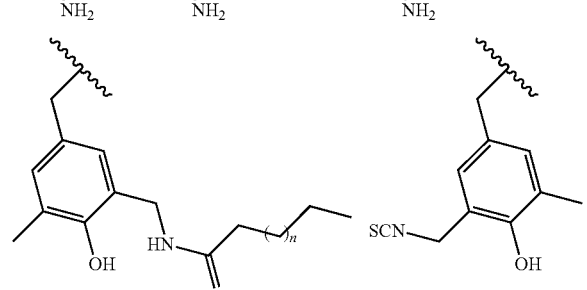
n = 0 to 18
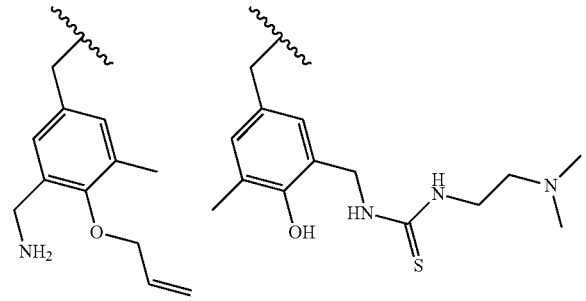
-continued
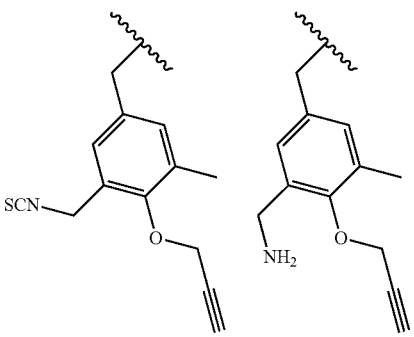
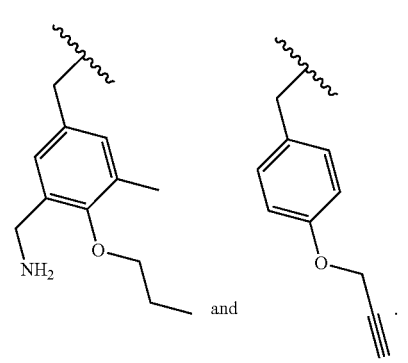
and
5. The compound or salt of claim 1, wherein at least one $R^a$ is X-Y.
6. The compound of salt of claim 1, wherein Y is
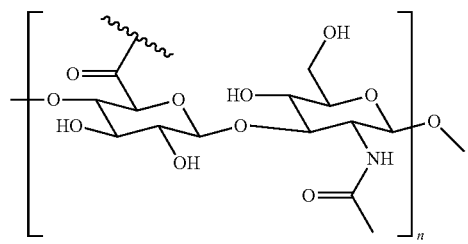
where n=1-1,000,000.
7. The compound or salt of claim 1, wherein at least one $R^z$ or $R^h$ is W—Z.
8. The compound or salt of a claim 7, wherein W is
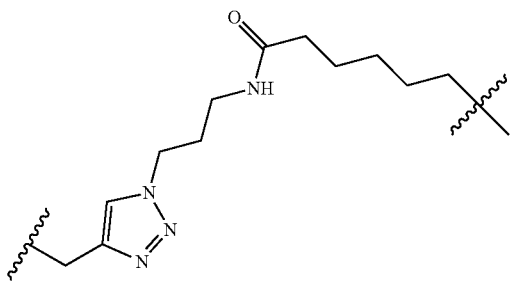

9. The compound of claim 1 which is:
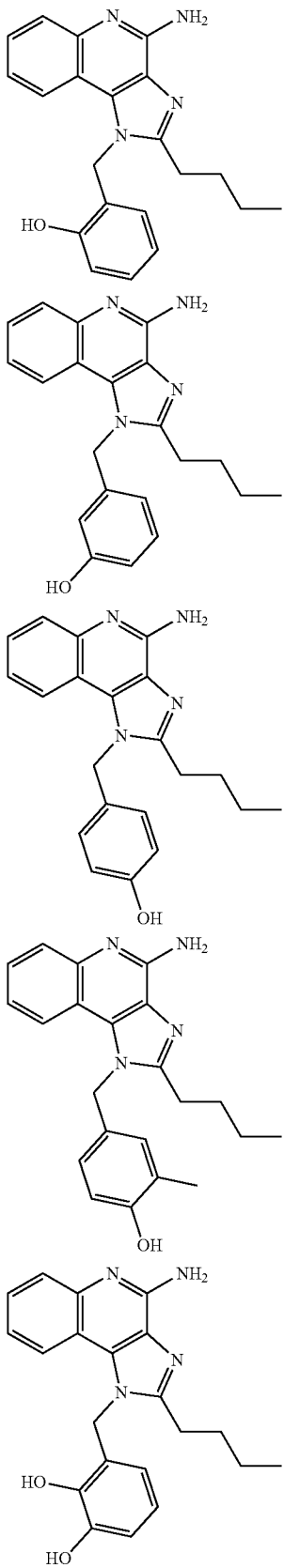
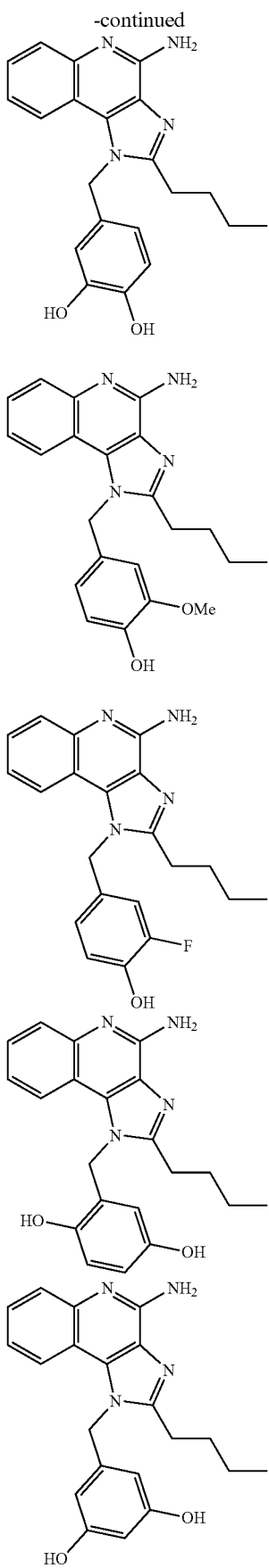

243
-continued
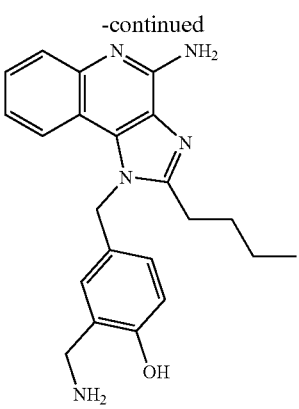
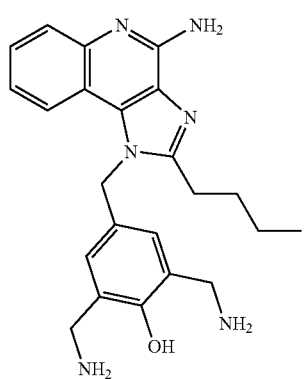
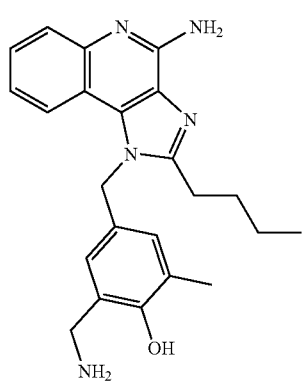
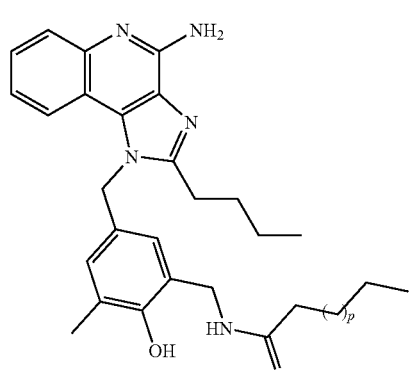
p = 0 to 18
244
-continued
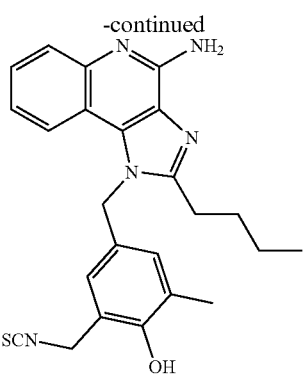
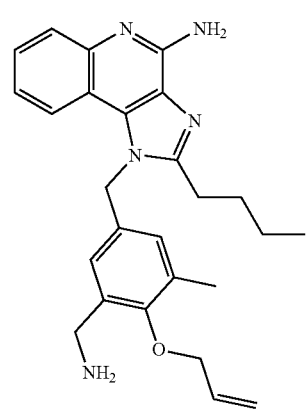
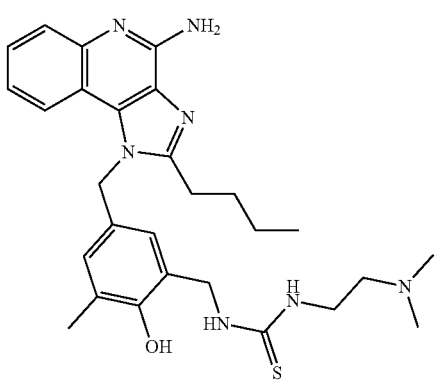
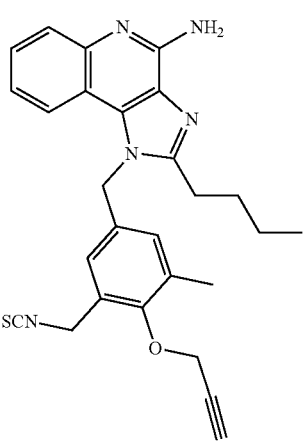

245
-continued
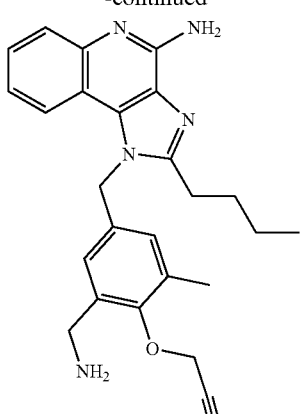
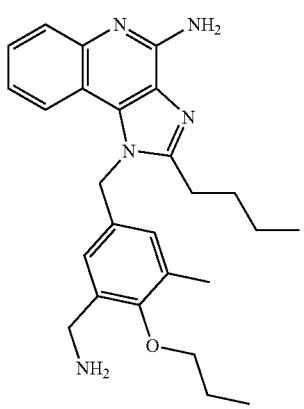
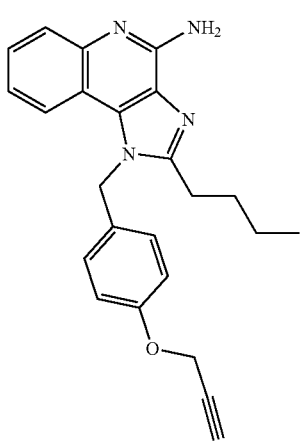
246
-continued
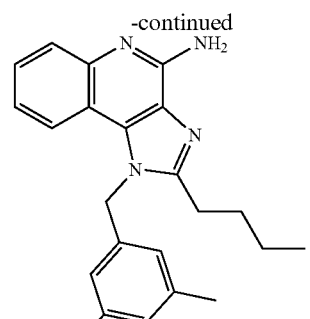
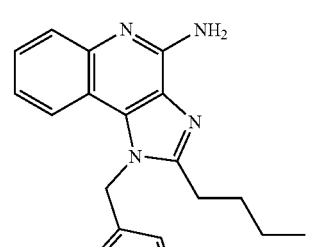
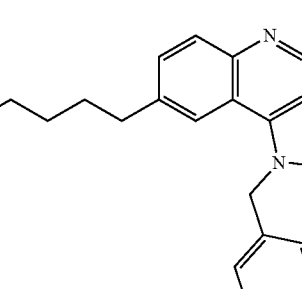

-continued

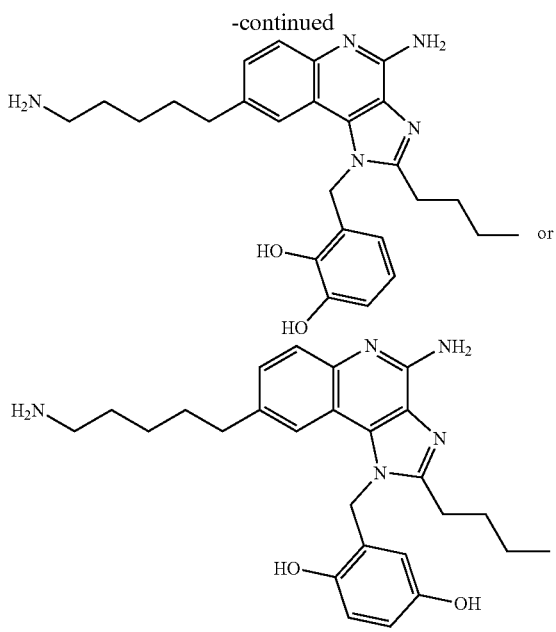

where each n is 1-1,000,000
or a salt thereof.

10. The compound of claim 1, which is a compound of formula (Iu):

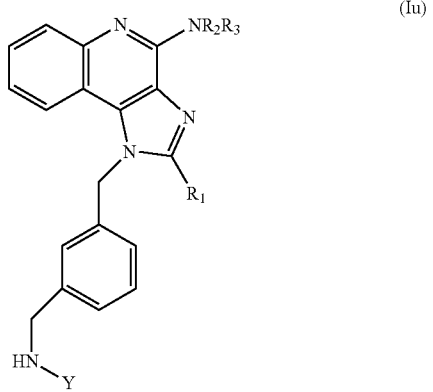

(Iu)

wherein:
R$_1$ is H, (C$_1$-C$_6$)alkyl, (C$_2$-C$_6$)alkenyl, (C$_2$-C$_6$)alkynyl, (C$_1$-C$_6$)alkanoyl, (C$_1$-C$_6$)alkoxycarbonyl, (C$_1$-C$_6$)alkanoyloxy, or (C$_3$-C$_6$)cycloalkyl, wherein any (C$_1$-C$_6$)alkyl, (C$_2$-C$_6$)alkenyl, (C$_2$-C$_6$)alkynyl, (C$_1$-C$_6$) alkanoyl, (C$_1$-C$_6$)alkoxycarbonyl, (C$_1$-C$_6$) alkanoyloxy, or (C$_3$-C$_6$)cycloalkyl, is optionally substituted with one or more groups independently selected from hydroxy, halo, oxo, (C$_3$-C$_5$)cycloalkyl, and (C$_1$-C$_6$)alkoxy;

each R$_2$ and R$_3$ is independently H, or (C$_1$-C$_6$)alkyl that is optionally substituted with one or more groups independently selected from hydroxy, halo, (C$_3$-C$_8$) cycloalkyl, and (C$_1$-C$_6$)alkoxy;

the benzyl ring is substituted with one —OR$^z$ and is optionally substituted with one or more groups independently selected from the group consisting of halogen, (C$_3$-C$_8$)cycloalkyl, —OR$^h$, isothiocyanate, —N$^a$R$^b$, —NR$^c$C(=O)R$^d$, —NR$^c$C(=S)—NR$^f$R$^g$, and (C$_1$-C$_6$)alkyl optionally substituted with one or more groups independently selected from the group consisting of halogen, (C$_3$-C$_8$)cycloalkyl, —OR$^h$, isothiocyanate, —NR$^a$R$^b$, —NR$^c$C(=O)R$^d$, and —NR$^e$C(=S)—NR$^f$R$^g$;

each R$^a$ and R$^b$ is independently selected from the group consisting of H, (C$_1$-C$_6$)alkyl, (C$_3$-C$_6$)cycloalkyl, (C$_1$-C$_6$)alkoxy and X-Y; or R$^a$ and R$^b$ together with the nitrogen to which they are attached form a aziridino, azetidino, morpholino, piperazino, pyrrolidino or piperidino;

each R$^c$ and R$^d$ is independently selected from the group consisting of H, (C$_1$-C$_6$)alkyl, (C$_3$-C$_6$)cycloalkyl, and (C$_1$-C$_6$)alkoxy;

each R is independently selected from the group consisting of H, (C$_1$-C$_6$)alkyl, (C$_3$-C$_6$cycloalkyl, and (C$_1$-C$_6$)alkoxy;

each R$^f$ and R$^g$ is independently selected from the group consisting of H, (C$_3$-C$_6$)cycloalkyl, (C$_1$-C$_6$)alkoxy and (C$_1$-C$_6$)alkyl that is optionally substituted with NR$^k$R$^m$; or R$^f$ and R$^g$ together with the nitrogen to which they are attached form a aziridino, azetidino, morpholino, piperazino, pyrrolidino or piperidino;

each R$^h$ is independently selected from the group consists of H, (C$_1$-C$_6$)alkyl, (C$_2$-C$_6$)alkenyl, (C$_2$-C$_6$) alkynyl, (C$_3$-C$_8$)cycloalkyl —P(=O)OH)$_2$, or W—Z;

each R$^z$ is independently selected from the group consists of H, (C$_1$-C$_6$)alkyl, (C$_2$-C$_6$)alkenyl, (C$_2$-C$_6$) alkynyl, (C$_3$-C$_8$)cycloalkyl —P(=O)OH)$_2$, or W—Z;

each W is independently a linking group or is absent;
each Z is independently Z is an antigen; and
Y is a residue of hyaluronic acid;
or a salt thereof.

11. The compound of claim 1, which is a compound of formula (Ib)

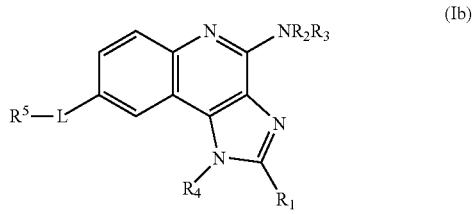

(Ib)

wherein:
R$_1$ is H, (C$_1$-C$_6$)alkyl, (C$_2$-C$_6$)alkenyl, (C$_2$-C$_6$)alkynyl, (C$_1$-C$_6$)alkanoyl, (C$_1$-C$_6$)alkoxycarbonyl, (C$_1$-C$_6$)alkanoyloxy, or (C$_3$-C$_6$)cycloalkyl, wherein any (C$_1$-C$_6$)alkyl, (C$_2$-C$_6$)alkenyl, (C$_2$-C$_6$)alkynyl, (C$_1$-C$_6$) alkanoyl, (C$_1$-C$_6$)alkoxycarbonyl, (C$_1$-C$_6$) alkanoyloxy, or (C$_3$-C$_6$)cycloalkyl, is optionally substituted with one or more groups independently selected from hydroxy, halo, oxo, (C$_3$-C$_8$)cycloalkyl, and (C$_1$-C$_6$)alkoxy;

each R$_2$ and R$_3$ is independently H, or (C$_1$-C$_6$)alkyl that is optionally substituted with one or more groups independently selected from hydroxy, halo, (C$_3$-C$_8$) cycloalkyl, and (C$_1$-C$_6$)alkoxy;

R$_4$ is (C$_1$-C$_6$)alkyl that is substituted with aryl, wherein the aryl is substituted with one —OR$^z$ and is optionally substituted with one or more groups independently selected from the group consisting of halogen, $(C_3-C_8)$cycloalkyl, —$OR^h$, isothiocyanate, —$NR^aR^b$, —$NR^cC(=O)R^d$ —$NR^eC(=S)$—$NR^fR^g$, and $(C_1-C_6)$alkyl optionally substituted with one or more groups independently selected from the group consisting of halogen, $(C_3-C_8)$cycloalkyl, —$OR^h$, isothiocyanate, —$N^aR^b$, —$NR^cC(=O)R^d$, and —$NR^cC(=S)$—$NR^fR^g$;

L is absent or is a divalent, branched or unbranched hydrocarbon chain, having from 1 to 8 carbon atoms, wherein one or more (e.g. 1, 2, 3, or 4) of the carbon atoms is optionally replaced by a non-peroxide (—O—);

$R_5$ is H or an activated group; each $R^a$ and $R^b$ is independently selected from the group consisting of H, $(C_1-C_6)$alkyl, $(C_3-C_6)$cycloalkyl, $(C_1-C_6)$alkoxy and X-Y; or $R^a$ and $R^b$ together with the nitrogen to which they are attached form a aziridino, azetidino, morpholino, piperazino, pyrrolidino or piperidino;

each $R^c$ and $R^d$ is independently selected from the group consisting of H, $(C_1-C_6)$alkyl, $(C_3-C_6)$cycloalkyl, and $(C_1-C_6)$alkoxy;

each $R^e$ is independently selected from the group consisting of H, $(C_1-C_6)$alkyl, $(C_3-C_6)$cycloalkyl, and $(C_1-C_6)$alkoxy;

each $R^f$ and $R^g$ is independently selected from the group consisting of H, $(C_3-C_6)$cycloalkyl, $(C_1-C_6)$alkoxy and $(C_1-C_6)$alkyl that is optionally substituted with $NR^kR^m$; or $R^f$ and $R^g$ together with the nitrogen to which they are attached form a aziridino, azetidino, morpholino, piperazino, pyrrolidino or piperidino;

each $R^k$ and $R^m$ is independently selected from the group consisting of H, $(C_1-C_6)$alkyl, and $(C_3-C_6)$cycloalkyl; or $R^k$ and $R^m$ together with the nitrogen to which they are attached form a aziridino, azetidino, morpholino, piperazino, pyrrolidino or piperidino;

at least one of $R^z$ and $R^h$ is present and is W—Z any each of any remaining $R^z$ and $R^h$ is independently selected from the group consists of H, $(C_1-C_6)$alkyl, $(C_2-C_6)$alkenyl, $(C_2-C_6)$alkynyl, $(C_3-C_8)$cycloalkyl —$P(=O)OH)_2$, or W—Z;

each W is independently a linking group or is absent;

each Z is independently Z is an antigen;

each X is independently a linking group or is absent; and each Y is independently a residue of hyaluronic acid; or a salt thereof.

12. A pharmaceutical composition comprising a compound as described in claim 1, or a pharmaceutically acceptable salt thereof, and a pharmaceutically acceptable excipient.

13. A compound of formula I as described in claim 1, or a pharmaceutically acceptable salt thereof wherein Y is a residue of hyaluronic acid.

14. A composition comprising an antigen and a compound of formula I as described in claim 1 or a pharmaceutically acceptable salt thereof.

\* \* \* \* \*

UNITED STATES PATENT AND TRADEMARK OFFICE
CERTIFICATE OF CORRECTION

PATENT NO. : 12,060,350 B2
APPLICATION NO. : 17/256933
DATED : August 13, 2024
INVENTOR(S) : Sunil A. David et al.

Page 1 of 1

It is certified that error appears in the above-identified patent and that said Letters Patent is hereby corrected as shown below:

In the Claims

Column 237, Line 32, Claim 1, please delete "-L'-$R^{5'}$" and insert -- -L'-$R_{5'}$ --;

Column 237, Line 60, Claim 1, please delete "($C_3$-$C_8$)cycloalkyl -P(=O)$OH)_2$" and insert -- ($C_3$-$C_8$)cycloalkyl, -P(=O)$(OH)_2$ --;

Column 238, Line 27, Claim 1, please delete "-$NR^cC(=S)NR^fR^g$" and insert -- -$NR^cC(=S)NR^fR^g$ --;

Column 238, Line 63, Claim 3, please delete "-$NR^cC(=S)NR^fR^g$" and insert -- -$NR^cC(=S)NR^fR^g$ --;

Column 247, Line 67, Claim 10, please delete "-$NR^cC(=S)NR^fR^g$" and insert -- -$NR^cC(=S)NR^fR^g$ --;

Column 248, Line 15, Claim 10, please delete "each R is" and insert -- each $R^e$ is --;

Column 248, Line 26, Claim 10, please delete "($C_3$-$C_8$)cycloalkyl -P(=O)$OH)_2$" and insert -- ($C_3$-$C_8$)cycloalkyl, -P(=O)$(OH)_2$ --;

Column 248, Line 30, Claim 10, please delete "($C_3$-$C_8$)cycloalkyl -P(=O)$OH)_2$" and insert -- ($C_3$-$C_8$)cycloalkyl, -P(=O)$(OH)_2$ --;

Column 249, Line 7, Claim 11, please delete "-$NR^cC(=S)NR^fR^g$" and insert -- -$NR^cC(=S)NR^fR^g$ --; and Column 250, Lines 10 - 11, Claim 11, please delete "($C_3$-$C_8$)cycloalkyl -P(=O)$OH)_2$" and insert -- ($C_3$-$C_8$)cycloalkyl, -P(=O)$(OH)_2$ -- therefor.

Signed and Sealed this
Twenty-seventh Day of May, 2025

Coke Morgan Stewart
*Acting Director of the United States Patent and Trademark Office*